US011034975B2

(12) United States Patent
Gall et al.

(10) Patent No.: US 11,034,975 B2
(45) Date of Patent: *Jun. 15, 2021

(54) AFFENADENOVIRUS (GORILLA) OR ADENOVIRAL VECTORS AND METHODS OF USE

(71) Applicant: GenVec, Inc., Gaithersburg, MD (US)

(72) Inventors: Jason G. D. Gall, Germantown, MD (US); Duncan McVey, Derwood, MD (US); Douglas E. Brough, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/282,924

(22) Filed: Feb. 22, 2019

(65) Prior Publication Data
US 2019/0316152 A1  Oct. 17, 2019

Related U.S. Application Data

(60) Continuation of application No. 15/650,289, filed on Jul. 14, 2017, now Pat. No. 10,260,074, which is a continuation of application No. 14/992,152, filed on Jan. 11, 2016, now Pat. No. 9,725,738, which is a division of application No. 14/349,421, filed as application No. PCT/US2012/058956 on Oct. 5, 2012, now Pat. No. 9,233,153.

(60) Provisional application No. 61/543,638, filed on Oct. 5, 2011.

(51) Int. Cl.
| C12N 15/86 | (2006.01) |
| C07K 14/005 | (2006.01) |
| A61K 39/155 | (2006.01) |
| C12N 7/00 | (2006.01) |
| A61K 48/00 | (2006.01) |

(52) U.S. Cl.
CPC ............ *C12N 15/86* (2013.01); *A61K 39/155* (2013.01); *C07K 14/005* (2013.01); *C12N 7/00* (2013.01); *A61K 48/00* (2013.01); *C12N 2710/10043* (2013.01); *C12N 2710/10322* (2013.01); *C12N 2710/10333* (2013.01); *C12N 2710/10343* (2013.01)

(58) Field of Classification Search
CPC .................. C07K 14/005; C12N 15/86; C12N 2710/10322; C12N 2710/10333; C12N 2710/10343; C12N 7/00; C12N 2710/10043; A61K 39/155; A61K 48/00; A61P 31/12
See application file for complete search history.

(56) References Cited

U.S. PATENT DOCUMENTS

| 5,837,511 A | 11/1998 | Falck-Pedersen et al. |
| 5,851,806 A | 12/1998 | Kovesdi et al. |
| 5,994,106 A | 11/1999 | Kovesdi et al. |
| 5,994,128 A | 11/1999 | Fallaux et al. |
| 5,998,205 A | 12/1999 | Hallenbeck et al. |
| 6,033,908 A | 3/2000 | Bout et al. |
| 6,127,175 A | 10/2000 | Vigne et al. |
| 6,225,289 B1 | 5/2001 | Kovesdi et al. |
| 6,482,616 B1 | 11/2002 | Kovesdi et al. |
| 6,514,943 B2 | 2/2003 | Kovesdi et al. |
| 6,551,586 B1 | 4/2003 | Davidson et al. |
| 6,677,156 B2 | 1/2004 | Brough et al. |
| 6,682,929 B2 | 1/2004 | Brough et al. |
| 7,195,896 B2 | 3/2007 | Kovesdi et al. |
| 8,940,290 B2 | 1/2015 | Roy et al. |
| 10,059,962 B2 | 8/2018 | Brough et al. |
| 2003/0165820 A1 | 9/2003 | Day et al. |
| 2004/0136963 A1 | 7/2004 | Wilson et al. |
| 2008/0233650 A1 | 9/2008 | Gall et al. |
| 2011/0123564 A1 | 5/2011 | Mayall et al. |
| 2011/0223135 A1 | 9/2011 | Roy et al. |
| 2011/0274654 A1 | 11/2011 | Bahadoor et al. |
| 2014/0248307 A1 | 9/2014 | Gall et al. |
| 2014/0248308 A1 | 9/2014 | McVey et al. |
| 2014/0271711 A1 | 9/2014 | Brough et al. |
| 2014/0314717 A1 | 10/2014 | Brough et al. |
| 2015/0140025 A1 | 5/2015 | Wei et al. |
| 2015/0152434 A1 | 6/2015 | Roy et al. |
| 2015/0157700 A1 | 6/2015 | Bruder et al. |

FOREIGN PATENT DOCUMENTS

| WO | WO 1994/028152 A1 | 12/1994 |
| WO | WO 1995/002697 A2 | 1/1995 |
| WO | WO 1995/016772 A1 | 6/1995 |

(Continued)

OTHER PUBLICATIONS

"Gorilla Adenovirus Vectors for Molecular Therapeutics and Vaccines." Douglas E. Brough, GenVec, Inc., USA. Presentation Nov. 3, 2015, Track B, 10:40-11:00 AM. Intl Conf on Vaccines R&D—2015: A New Era in Vaccine Discovery. Nov. 2-4, 2015, Baltimore, MD, USA.*

Bernstein et al., "N-methanocarbathymidine is more effective than acyclovir for treating neonatal herpes simplex virus infection in guinea pigs," *Antiviral Res.*, 92(2): 386-388 (2011).

Braitman et al., "Evaluation of SQ 34,514: Pharmacokinetics and Efficacy in Experimental Herpesvirus Infections in Mice," *Antimicrob. Agents Chemother.*, 35(7): 1464-1468 (1991).

(Continued)

*Primary Examiner* — Rachel B Gill
(74) *Attorney, Agent, or Firm* — Leydig Voit and Mayer Ltd

(57) ABSTRACT

The invention provides an adenovirus or adenoviral vector characterized by comprising one or more particular nucleic acid sequences or one or more particular amino acid sequences, or portions thereof, pertaining to, for example, an adenoviral pIX protein, DNA polymerase protein, penton protein, hexone protein, and/or fiber protein.

28 Claims, No Drawings
Specification includes a Sequence Listing.

(56) References Cited

FOREIGN PATENT DOCUMENTS

| WO | WO 1995/034671 A1 | 12/1995 |
|---|---|---|
| WO | WO 1996/022378 A1 | 7/1996 |
| WO | WO 1997/000326 A1 | 1/1997 |
| WO | WO 1997/012986 A2 | 4/1997 |
| WO | WO 1997/021826 A2 | 6/1997 |
| WO | WO 2000/000628 A1 | 1/2000 |
| WO | WO 2000/034444 A2 | 6/2000 |
| WO | WO 01/58940 A2 | 8/2001 |
| WO | WO 2003/020879 A2 | 3/2003 |
| WO | WO 2003/022311 A1 | 3/2003 |
| WO | WO 2005/075506 A1 | 8/2005 |
| WO | WO 2006/065827 A2 | 6/2006 |
| WO | WO 2007/027860 A2 | 3/2007 |
| WO | WO 2008/011609 A2 | 1/2008 |
| WO | WO 2010/051367 A1 | 5/2010 |
| WO | WO 2010/086189 A2 | 8/2010 |
| WO | WO 2011/057248 A2 | 5/2011 |
| WO | WO 2012/021730 A2 | 2/2012 |

OTHER PUBLICATIONS

Ahi et al., "Adenoviral Vector Immunity: Its Implications and Circumvention Strategies," *Curr. Gene Therapy*, 11(4): 307-320, Author Manuscript (Aug. 2011).
Alonso-Padilla et al., "Development of Novel Adenoviral Vectors to Overcome Challenges Observed With HAdV-5-based Constructs," *Molecular Therapy*, 24(1): 6-16 (Nov. 2015).
Altschul et al., "Basic Local Alignment Search Tool," *J. Molecular Biol.*, 215(3): 403-410 (1990).
Altschul et al., "Gapped BLAST and PSI-BLAST: a new generation of protein database search programs," *Nucleic Acids Res.*, 25(17): 3389-3402 (1997).
Aubert et al., "Accumulation of Herpes Simplex Virus Type 1 Early and Leaky-Late Proteins Correlates with Apoptosis Prevention in infected Human Hep-2 Cells," *J. Virol.*, 75(2): 1013-1030 (2001).
Bai et al., "Mutations that alter an Arg-Gly-Asp (RGD) sequence in the adenovirus type 2 penton base protein abolish its cell-rounding activity and delay virus reproduction in flat cells," *J. Virol.*, 67(9): 5198-5205 (1993).
Biegert et al., "Sequence context-specific profiles for homology searching," *Proc. Natl. Acad. Sci. USA*, 106(10): 3770-3775 (2009).
Boulanger et al., "Characterization of adenovirus protein IX," *J. Gen. Virol.*, 44(3): 783-800 (1979).
Brough et al., "Activation of transgene expression by early region 4 is responsible for a high level of persistent transgene expression from adenovirus vectors in vivo," *J. Virol.*, 71(12): 9206-9213 (1997).
Cartier et al., "Hematopoietic stem cell gene therapy with a lentiviral vector in X-linked adrenoleukodystrophy," *Science*, 326(5954): 818-823 (2009).
Cavazzana-Calvo et al., "Gene therapy of human severe combined immunodeficiency (SCID)-X1 disease," *Science*, 288(5466): 669-672 (2000).
Chen et al., "Persistence in muscle of an adenoviral vector that lacks all viral genes," *Proc. Natl. Acad. Sci. USA*, 94(5): 1645-1650 (1997).
Chroboczek et al., "The sequence of the genome of adenovirus type 5 and its comparison with the genome of adenovirus type 2," *Virology*, 186(1): 280-285 (1992).
Crawford-Miksza et al., "Analysis of 15 adenovirus hexon proteins reveals the location and structure of seven hypervariable regions containing serotype-specific residues," *J. Virol.*, 70(3): 1836-1844 (1996).
Curiel et al., "High-efficiency gene transfer mediated by adenovirus coupled to DNA-polylysine complexes," *Hum. Gene Ther.*, 3(2): 147-154 (1992).
Devaux et al., "Structure of adenovirus fibre. I. Analysis of crystals of fibre from adenovirus serotypes 2 and 5 by electron microscopy and X-ray crystallography," *J. Molec. Biol.*, 215(4): 567-588 (1990).

Dey et al., "Molecular epidemiology of adenovirus infection among infants and children with acute gastroenteritis in Dhaka City, Bangladesh," *Infect. Genet. Evol.*, 9(4) 518-522 (2009).
Dolan et al., "The genome sequence of herpes simplex virus type 2," *J. Virol.* 72(3): 2010-2021 (1998).
European Patent Office, International Search Report in International Patent Application No. PCT/US/2013/041358 (dated Dec. 11, 2014).
Field et al., "Properties of the adenovirus DNA polymerase," *J. Biol. Chem.*, 259(15): 9487-9495 (1984).
Fu et al., "A prime-boost vaccination strategy using attenuated *Salmonella typhimurium* and a replication-deficient recombinant adenovirus vector elicits protective immunity against human respiratory syncytial virus," *Biochem. and Biophys. Res. Comm.*, 395: 87-92 (2010).
Gall et al., "Construction and characterization of hexon-chimeric adenoviruses: specification of adenovirus serotype," *J. Virol.*, 72(12): 10260-10264 (1998).
Genbank Accession No. ABU95388.1, "hexon, partial [Human adenovirus 9]," (Jun. 2009).
Genbank Accession No. ABX79578, "UL47 [Human herpesvirus 2]" (Apr. 14, 2009).
Genbank Accession No. CAB06743.1, "major capsid protein [Human herpesvirus 2]" (Nov. 14, 2006).
Genbank Accession No. EDA88859.1, "hypothetical protein GOS_1918841, partial [marine metagenome]," (Apr. 2007).
Genbank Accession No. EDL20708.1, "mCG1048340," (Jun. 2007).
Genbank Accession No. FJ025900, "Simian adenovirus 43, complete genome," (Jul. 2009).
Genbank Accession No. FJ025900.1, "Simian adenovirus 43, complete genome," (Mar. 2012).
Genbank Accession No. FJ025901, "Simian adenovirus 45, complete genome," (Jul. 2009).
Genbank Accession No. FJ025901.1, "Simian adenovirus 45, complete genome," (Mar. 2012).
Genbank Accession No. JN163990.1, "Gorilla gorilla beringei adenovirus 6 hexon gene, partial cds," (Dec. 2011).
Genbank Accession No. KC702813.1 ,"Gorilla beringei beringei adenovirus 7 isolate GC44 hexon gene, complete cds" (Sep. 2013).
Genbank Accession No. KC702815.1, "Gorilla beringei graueri adenovirus 9 isolate GC46 hexon gene, complete cds," (Sep. 2013).
Genbank Accession No. KC702816, "Gorilla beringei beringei adenovirus 7 isolate GC44 DNA polymerase gene, complete cds," (Sep. 2013).
Genbank Accession No. P89442.1, "Major capsid protein" (Nov. 2005).
Genbank Accession No. P89467, "Tegument protien and transactivator of immediate early genes," (Oct. 2006).
Ghosh-Choudhury et al., "Protein IX, a minor component of the human adenovirus capsid, is essential for the packaging of full length genomes," *EMBO J.*, 6(6): 1733-1739 (1987).
Ginsberg et al., "A proposed terminology for the adenovirus antigens and virion morphological subunits," *Virology*, 28(4): 782-783 (1966).
Goins et al., "Herpes simplex virus vector-mediated gene delivery for the treatment of lower urinary tract pain," *Gene Ther.*, 16(4): 558-569 (2009).
Graham et al., "Characteristics of a human cell line transformed by DNA from human adenovirus type 5," *J. Gen. Virol.*, 36(1): 59-72 (1977).
Green et al., "Evidence for a repeating cross-beta sheet structure in the adenovirus fibre," *EMBO J.*, 2(8): 1357-1365 (1983).
Hacein-Bey-Abina et al., "A serious adverse event after successful gene therapy for X-linked severe combined immunodeficiency," *N. Engl. J. Med.*, 348(3): 255-256 (2003).
Henry et al., "Characterization of the knob domain of the adenovirus type 5 fiber protein expressed in *Escherichia coli*," *J. Virol.*, 68(8): 5239-5246 (1994).
Horvath et al., "Nonpermissivity of human peripheral blood lymphocytes to adenovirus type 2 infection," *J. Virology*, 62(1): 341-345 (1988).
Jornvall et al., "The adenovirus hexon protein. The primary structure of the polypeptide and its correlation with the hexon gene," *J. Biol. Chem.*, 256(12): 6181-6186 (1981).

(56) References Cited

OTHER PUBLICATIONS

Kannan et al., "Structural and functional diversity of the microbial kinome," *PLoS Biol.*, 5(3) E17 (2007).
Kay et al., "Viral vectors for gene therapy: the art of turning infectious agents into vehicles of therapeutics," *Nature Medicine*, 7(1): 33-40 (2001).
Kochanek et al., "High-capacity adenoviral vectors for gene transfer and somatic gene therapy," *Hum. Gene Ther.*, 10(15): 2451-2459 (1999).
Koelle et al., "CD4 T-cell responses to herpes simplex virus type 2 major capsid protein VP5: Comparison with responses to tegument and envelope glycoproteins", *J. Virol.*, 74(23):11422-11425 (2000).
Kohlmann et al., "Protective efficacy and immunogenictiy of an adenoviral vector vaccine encoding the codon-optimized F protein of respiratory syncytial virus," *J Virol.* 83(23): 12601-12610 (2009).
Lasaro et al., "New insights on adenovirus as vaccine vectors," *Molecular Therapy*, 17(8): 1333-1339 (2009).
Lutz et al., "The product of the adenovirus intermediate gene IX is a transcriptional activator," *J. Virol.*, 71(7): 5102-5109 (1997).
Mayrhofer et al., "Nonreplicating vaccinia virus vectors expressing the H5 influenza virus hemagglutinin produced in modified Vero cells induce robust protection," *J. Virol.*, 83(10): 5192-5203 (2009).
Mcvey et al., "Adenoviruses isolated from wild gorillas are closely related to human species C viruses," *Virology*, 444: 119-123 (2013).
Mease et al., "Safety, tolerability, and clinical outcomes after intraarticular injection of a recombinant adeno-associated vector containing a tumor necrosis factor antagonist gene: results of a phase 1/2 Study," *Journal of Rheumatology*, 37(4): 692-703 (2010).
Morsy et al., An adenoviral vector deleted for all viral coding sequences results in enhanced safety and extended expression of a leptin transgene, *Proc. Natl. Acad. Sci. USA*, 95: 7866-7871 (1998).
Muller et al., "Herpes simplex virus type 2 tegument proteins contain subdominant T-cell epitopes detectable in BALB/c mice after DNA immunization and infection", *J. Virol.*, 90 (5): 1153-1163 (2009).
Narum et al., "Codon Optimization of Gene Fragments Encoding Plasmodium falciparum Merzoite Proteins Enhances DNA Vaccine Protein Expression and Immunogenicity in Mice," *Infect Immun*, 69(12): 7250-7253 (2001).
NCBI reference sequence AP_000218, "E3 12.5K [Human adenovirus 5]," (Dec. 2008).
NCBI reference sequence AP_000224.1, "*Homo sapiens* genomic DNA, chromosome 21q21.2, LL56-APP region, clone:B2017A3, complete sequence," (Nov. 1991).
Neumann et al., "Determination of the nucleotide sequence for the penton-base gene of human adenovirus type 5," *Gene*, 69(1) 153-157 (1988).
Novelli et al., "Deletion analysis of functional domains in baculovirus-expressed adenovirus type 2 fiber," *Virology*, 185(1): 365-376 (1991).
Roberts et al., "Three-dimensional structure of the adenovirus major coat protein hexon," *Science*, 232(4754): 1148-1151 (1986).
Roy et al., "Generation of an adenoviral vaccine vector based on simian adenovirus 21," *Journal of General Virology* 87: 2477-2485 (2006).
Roy et al., "Isolation and Characterization of Adenoviruses Persistently Shed from the Gastrointestinal Tract of Non-Human Primates," *PLOS Pathogens*, 5(7): E1000503, 1-9, (2009).
Rusch et al., "The Sorcerer II Global Ocean Sampling expedition: northwest Atlantic through eastern tropical Pacific," *PLoS Biol.*, 5(3) E77 (2007).
Rux et al., "Structural and phylogenetic analysis of adenovirus hexons by use of high-resolution x-ray crystallographic, molecular modeling, and sequence-based methods," *J. Virol.*, 77(17): 9553-9566 (2003).
Seregin et al., "Overcoming pre-existing adenovirus immunity by genetic engineering of adenovirus-based vectors," *Expert Opinion on Biological Therapy*, 9(12): 1521-1531 (2009).
Signas et al., Adenovirus 3 Fiber Polypeptide Gene: Implications for the Structure of the Fiber Protein, *J. Virol.*, 53(2): 672-678 (1985).
Silver et al., "Interaction of human adenovirus serotype 2 with human lymphoid cells," *Virology*, 165(2): 377-387 (1988).
Soding, "Protein homology detection by HMM-HMM comparison," *Bioinformatics*, 21(7): 951-960 (2005).
Stewart et al., "Difference imaging of adenovirus: bridging the resolution gap between X-ray crystallography and electron microscopy," *EMBO J.*, 12(7): 2589-99 (1993).
Stewart et al., "Image reconstruction reveals the complex molecular organization of adenovirus," *Cell*, 67(1): 145-154 (1991).
Subak-Sharpe et al., "HSV Molecular Biology: General Aspects of Herpes Simplex Virus Molecular Biology"; *Virus Genes*, 16(3): 239-251 (1998).
Thomas et al., "Progress and problems with the use of viral vectors for gene therapy," *Nature Review Genetics*, 4(5): 346-358 (2003).
Van Oostrum et al, "Molecular composition of the adenovirus type 2 virion," *J. Virol.*, 56(2): 439-448 (1985).
Wevers et al., "A novel adenovirus of Western lowland gorillas (Gorilla gorilla gorilla)," *J. Virology*, 7(1): 1-8 (2010).
Wevers et al., "Novel Adenoviruses in Wild Primates: a High Level of Genetic Diversity and Evidence of Zoonotic Transmissions," *J. Virology*, 85(20): 10774-10784, (2011).
Yeh et al.; "Human adenovirus type 41 contains two fibers," *Virus Res.*, 33(2): 179-198 (1994).
Yooseph et al., "The Sorcerer II Global Ocean Sampling expedition: expanding the universe of protein families," *PLoS Biol.*, 5(3) E16, (2007).
U.S. Appl. No. 14/403,397, filed May 16, 2013.
U.S. Appl. No. 14/349,735, filed Sep. 18, 2014.
U.S. Appl. No. 14/373,574, filed Jun. 11, 2015.
U.S. Appl. No. 14/349,421, filed Apr. 3, 2014.
U.S. Appl. No. 14/349,426, filed Apr. 3, 2014.
U.S. Appl. No. 14/349,470, filed Apr. 3, 2014.
U.S. Appl. No. 14/992,152, filed Jan. 11, 2016.
U.S. Appl. No. 15/482,991, filed Apr. 10, 2017.
U.S. Appl. No. 15/492,016, filed Apr. 20, 2017.
U.S. Appl. No. 15/650,289, filed Jul. 14, 2017.
U.S. Appl. No. 15/618,740, filed Jun. 9, 2017.
U.S. Appl. No. 16/043,501, filed Jul. 24, 2018.
U.S. Appl. No. 16/156,520, filed Oct. 10, 2018.
U.S. Appl. No. 16/352,459, filed Mar. 13, 2019.
U.S. Appl. No. 17/002,064, filed Aug. 25, 2020.
Hong et al., "Identification of Adenovirus (Ad) Penton Base Neutralizing Epitopes by Use of Sera from Patients Who Had Received Conditionally Replicative Ad (Add/1520) for Treatment of Liver Tumors," *Journal of Virology*, 77(19): 10366-10375 (2003).
Johnson et al., "Genetic Vaccine for Respiratory Syncytial Virus Provides Protection Without Disease Potentiation," *Molecular Therapy*, 22(1): 196-205 (2014).
Limbach et al., "New gorilla adenovirus vaccine vectors induce potent immune response and protection in a mouse malaria model," *Malaria Journal*, 16: 263 (2017).
Roy et al., "Creation of a panel of vectors based on ape adenovirus isolates," *Journal of Gene Medicine*, 13: 17-25 (2011).

\* cited by examiner

SEQUENCE LISTING

<160> NUMBER OF SEQ ID NOS: 25

<210> SEQ ID NO 1
<211> LENGTH: 30
<212> TYPE: DNA
<213> ORGANISM: Gorilla beringei beringei

<400> SEQUENCE: 1
agctctttgg tggcgagcgg cgcggcctct          30

<210> SEQ ID NO 2
<211> LENGTH: 439
<212> TYPE: DNA
<213> ORGANISM: Gorilla beringei beringei

<400> SEQUENCE: 2

```
aacatcaata cctcaaagtc atggtcaggg acactttcgc cctcacccac acctccctcc      60
gcaaggcggc gcaggcctac gcgctgcccg tggagaaggg ctgttgcccc taccaggccg     120
tcaaccagtt ctacatgcta ggctcttacc gttcggacac ggacgggttt ccctccaag     180
agtactggaa agaccgcgaa gagttcgtcc tcaaccgcga gctgtggaaa aagaaggggg     240
aggataagta tgacatcatc cgcgagaccc tcgactactg cgcgctcgac gtccaggtca     300
ccgccgagct ggtgcacaag ctgcgcgagt cctacgcctc cttcgtcagg gactcggtgg     360
gcttgcaaga agcaagcttc aacgtcttcc agcggcccac catctcctcc aactcccatg     420
ccatcttcag gcagatcgc                                                  439
```

<210> SEQ ID NO 3
<211> LENGTH: 34
<212> TYPE: DNA
<213> ORGANISM: Gorilla beringei beringei

<400> SEQUENCE: 3

```
actgaggctg cggctaaggc tgaggtcgaa gcca                                   34
```

<210> SEQ ID NO 4
<211> LENGTH: 45
<212> TYPE: DNA
<213> ORGANISM: Gorilla beringei beringei

<400> SEQUENCE: 4

```
ataggtgtgg atgccacaca ggcgggagat aaccctatat atgct                       45
```

<210> SEQ ID NO 5
<211> LENGTH: 30
<212> TYPE: DNA
<213> ORGANISM: Gorilla beringei beringei

<400> SEQUENCE: 5

```
gtagcaggcc ccctagctgt ggccaatggc                                        30
```

<210> SEQ ID NO 6
<211> LENGTH: 399
<212> TYPE: DNA
<213> ORGANISM: Gorilla beringei beringei

<400> SEQUENCE: 6

```
atgagcgaca ccggcaacag ctttgatgga agcatcttta gccctatct gacagtgcgc       60
atgcctcact gggctggagt gcgtcagaat gtgatgggtt ccaacgtgga tgacgcccc      120
gttctgcctt caaattcgtc tacaatggcc tacgcgaccg tgggaggaac tccgctggac     180
gccgcgacct ccgccgccgc ctccgccgcc gccgcgaccg cgcgcagcat ggctacggac     240
ctttacagct ctttggtggc gagcggcgcg gcctctcgcg cgtctgctcg ggatgagaaa     300
ctgaccgctc tgctgcttaa actggaagac ttgacccggg agctgggtca actgacccag     360
caggtctcca gcttgcgtga gagcagcctt gcctccccc                            399
```

<210> SEQ ID NO 7

<211> LENGTH: 3168
<212> TYPE: DNA
<213> ORGANISM: Gorilla beringei beringei

<400> SEQUENCE: 7

| | |
|---|---|
| atggacagct ccaatgtgcg cgatgtcgtc atcaaactcc gcccgccgag cgccgagatc | 60 |
| tggacctgcg gctctcgcgg cgtggtggtc tgctccacca tcgccctcca ggagacagat | 120 |
| gctggcggcc agacaaccaa agtagaagac caccagccac acgggacccc aggcggggga | 180 |
| cttagattcc cgctgcgctt cctcgtcaga ggtcgccagg ttcacctcgt gcaagatata | 240 |
| caacccgtgc agcgctgcca gtactgcggt cgcttttaca aaagccagca cgagtgctcg | 300 |
| gcccgcagac gggacttcta ctttcaccac atcaacagcc aatcctccaa ctggtggcgg | 360 |
| gagatccagt tcttcccgat cggctctcat cctcgcacgg agcgcctctt tgtcacctac | 420 |
| gatgtagaga cctacacttg gatgggagcc tttggcaagc agctcgtgcc cttcatgctg | 480 |
| gtcatgaaac tggggggcga cgaggctctg tcgccgccg cgcgcgacct cgcccgagag | 540 |
| ctcagatggg acccctggga gaaagacccc ctcaccttct actgcatcac ccccgaaaag | 600 |
| atggccgtgg ggcgacagtt cagaaccttc cgcgaccgcc tgcagaccct catggcccgc | 660 |
| gacctctggc gatccttcct ggcggccaac cctcacttgc aagactgggc cctggaggag | 720 |
| cacggcctgg aatcgcccga ggagctcacc tacgaggaac tcaaaaagct cccctccatc | 780 |
| aagggccagc cccgcttttt ggagctctac atcgtgggcc acaacataaa cggctttgac | 840 |
| gagatcgtcc tggccgccca ggtcatcaac aaccgctcct cggtcccagg gccctttcgc | 900 |
| atcaccagaa acttcatgcc tcgagcgggg aagatcctct tcaatgacct caccttctcc | 960 |
| ctgcccaacc cgcgctccaa aaagcgcacg gactacaccc tgtgggaaca gggcggctgc | 1020 |
| gatgacacag acttcaaaca tcaataccte aaagtcatgg tcaggacac tttcgccctc | 1080 |
| acccacacct ccctccgcaa ggcggcgcag gcctacgcgc tgcccgtgga agggctgt | 1140 |
| tgccccctacc aggccgtcaa ccagttctac atgctaggct cttaccgttc ggacacggac | 1200 |
| gggtttcccc tccaagagta ctggaaagac cgcgaagagt tcgtcctcaa ccgcgagctg | 1260 |
| tggaaaaaga agggggagga taagtatgac atcatccgcg agaccctcga ctactgcgcg | 1320 |
| ctcgacgtcc aggtcaccgc cgagctggtg cacaagctgc gcgagtccta cgcctccttc | 1380 |
| gtcagggact cggtgggctt gcaagaagca agcttcaacg tcttccagcg cccaccatc | 1440 |
| tcctccaact cccatgccat cttcaggcag atcgccttcc gcgccgagcg ccccagcgc | 1500 |
| accaacctcg ggcccaacat gctggccccc tcccacgagc tctatgacta cgtgcgcgcc | 1560 |
| agcatccgcg gggggcgctg ctaccccacc tacctcggca tcctcaggga cccctgtac | 1620 |
| gtgtatgaca tctgcggcat gtacgcctcc gcgctcaccc accccatgcc ctggggcccg | 1680 |
| cccctcaacc cctacgagcg cgcgctcgcc gcccgcgaat ggcagcgggc tctggacatg | 1740 |
| caagcttgca agatcgacta ctttgacccg cgcttgctcc ccggggtctt caccatcgac | 1800 |
| gcggacccc caaacgagga ccagctggac cccctacccc ccttctgctc gcgcaagggc | 1860 |
| ggccgcctct gctggaccaa cgagcgcctg cgcggcgagg tcgccaccag cgtcgacatg | 1920 |
| gtcaccctgc acaaccgagg ctggagggtg cgcctaatcc cagacgagcg caccaccgtc | 1980 |
| ttccccgagt ggaagtgcgt ggcccgcgag tacgtgcaac tcaacatcgc ggccaaggag | 2040 |
| cgagccgacc gcgacaaaaa ccagaccctg cgctccatcg ccaagctgct ctccaacgcc | 2100 |
| ctctacgggt cgttcgccac caagcttgac aacaaaaaaa tagtgttttc tgaccagatg | 2160 |
| gacccaggta ccctcaaagg tatcacctcc ggacaggtga acatcaaatc ctcctcattt | 2220 |

```
ttagaaactg acaacctgag cgctgaggtc atgcccgcct tcgagaggga atacttaccc    2280
cagcagctgg ccctcgcaga cagcgatgcg gaagagagtg aagatgaaag ggcgcccacc    2340
cccttttata ccccccgtc gggaaccccc ggtcacgtgt cctacaccta caagccaatc    2400
acttttctgg acgcggagga gggggacatg tgcctgcaca ccctggagaa ggtggacccg    2460
ctagtggaca acgaccgcta cccctcccac gtggcctcct tcgtcctggc ctggacgcgg    2520
gccttcgtct cagagtggtc agagtttctc tacgaggagg acagaggcac tccgctggaa    2580
gacaggcccc tgaagtcggt ctacgggac acggacagcc tcttcgtcac cgagaaggga    2640
caccgcctca tggagagccg aggtaagaaa cgcatcaaaa agcatggggg caacctggtt    2700
tttgaccctg accgccgga gctcacttgg ctggtggaat gcgagacggt ctgcgcttcc    2760
tgcggcgcgg acgcctactc cccagagtcc gtgtttctcg ctcccaagct ctacgccctg    2820
aagagcctgc agtgccctc gtgcggcgcc acctccaagg gaaagctccg cgccaagggg    2880
cacgccgccg agggtctcga ctacgagacc atggtcaaat gctacctggc cgacgcgcag    2940
ggcgaagagc ggcagcgatt cagcaccagc agaaccagcc tcaagcgcac cctggccagc    3000
gcccaacccg gagcgcaccc cttcaccgtg acccagacca ccctgacgag gaccctgcgc    3060
ccatggaagg acatgactct ggccccgctg gacgcccatc ggctggtgcc ctacagcgaa    3120
agccgcccca acccgcgaaa cgaggagatc tgctggatcg agatgccg                3168

<210> SEQ ID NO 8
<211> LENGTH: 1974
<212> TYPE: DNA
<213> ORGANISM: Gorilla beringei beringei

<400> SEQUENCE: 8
atgcggcgcg cggcgatgtt cgaggagggg cctccccct cttacgagag cgcgatgggg    60
atttctcctg cggcgcccct gcagcctccc tacgtgcctc ctcggtacct gcaacctaca    120 gggggagaa atagcatctg ttactctgag ctgcagcccc tgtacgatac caccagactg    180
tacctggtgg acaacaagtc cgcggacgtg gcctccctga actaccagaa cgaccacagc    240 gatttttga ccacggtgat ccaaaacaac gacttcaccc caaccgaggc cagcacccag    300 accataaaacc tggataacag gtcgaactgg ggcggcgacc tgaagaccat cttgcacacc    360
aacatgccca acgtgaacga gttcatgttc accaactctt ttaaggcgcg ggtgatggtg    420
gcgcgcgagc aggggggaggc gaagtacgag tgggtggact tcacgctgcc cgagggcaac    480
tactcagaga ccatgactct cgacctgatg aacaatgcga tcgtgaaaca ctatctgaaa    540
gtgggcaggc agaacggggt gaaggaaagc gatatcgggg tcaagtttga caccagaaac    600
ttccgtctgg gctgggaccc cgtgaccggg ctggtcatgc cggggtcta caccaacgag    660 gcctttcatc ccgacatagt gcttctgccc ggctgtgggg tggacttcac ccagagccgg    720
ctgagcaacc tgctgggcat cgcaagcgg cagcctttcc aggagggttt caagatcacc    780
tatgaggatc tgaaggggg caacattccc gcgctccttg atctggacgc ctacgaggag    840
agcttgaaac ccgaggagag cgctggcgac agcggcgaga gtggcgagga gcaagccggc    900
ggcggtggcg gcgcgtcgt agaaaacgaa agtacgcccg cagtggcggc ggacgctgcg    960
gaggtcgagc cggaggccat gcagcaggac gcagaggagg gcgcacagga gggcgcgcag    1020
aaggacatga cgatgggga gatcagggga gacacattcg ccaccgggg cgaagaaaaa    1080 gaggcagagg cggcggcggc ggcgacggcg gaggccgaaa ccgaggttga ggcagaggca    1140
```

```
gagcccgaga ccgaagttat ggaagacatg aatgatggag aacgtagggg cgacacgttc    1200
gccacccggg gcgaagagaa ggcggcggag gcagaagccg cggctgagga ggcggctgcg    1260
gctgcggcca agactgaggc tgcggctaag gctgaggtcg aagccaatgt tgcggttgag    1320
gctcaggctg aggaggaggc ggcggctgaa gcagttaagg aaaaggccca ggcagagcag    1380
gaagagaaaa aacctgtcat tcaacctcta aaagaagata gcaaaaagcg cagttacaac    1440
gtcatcgagg gcagcacctt tacccagtac cgcagctggt acctggcgta caactacggc    1500
gacccggtca agggggtgcg ctcgtggacc ctgctctgca cgccggacgt cacctgcggc    1560
tccgagcaga tgtactggtc gctgccgaac atgatgcaag acccggtgac cttccgctcc    1620
acgcggcagg ttagcaactt cccggtggtg ggcgccgaac tgctgcccgt gcactccaag    1680 agttttttaca cgagcaggc cgtctactcc cagctgatcc gccaggccac ctctctgacc    1740
cacgtgttca atcgctttcc cgagaaccag attttggcgc cccgccggc ccccaccatc    1800 accaccgtga gtgaaaacgt tcctgcccte acagatcacg ggacgctacc gctgcgcaac    1860
agcatctcag gagtccagcg agtgaccatt actgacgcca gacgccggac ctgcccctac    1920
gtttacaagg ccttgggcat agtctcgccg cgcgtcctct ccagtcgcac tttt         1974

<210> SEQ ID NO 9
<211> LENGTH: 2877
<212> TYPE: DNA
<213> ORGANISM: Gorilla beringei beringei

<400> SEQUENCE: 9
atggcgaccc catcgatgat gcctcagtgg tcgtacatgc acatctcggg ccaggacgct      60
tcggagtacc tgagccccgg gctggtgcag ttcgcccgcg ccacagacac ctacttcaac     120
atgagtaaca agttcaggaa ccccactgtg gcgcccaccc acgatgtgac cacggaccgg     180
tcgcagcgcc tgacgctgcg gttcatcccc gtggatcggg aggacaccgc ctactcttac     240
aaggcgcggt tcacgctggc cgtgggcgac aaccgcgtgc tggacatggc ctccacttac     300
tttgacatca ggggggtgct ggacaggggc cccaccttca gccctactc gggtactgcc     360 tacaactccc tggcccccaa gggcgctccc aattcttgcg agtgggaaca agatgaacca     420
gctcaggcag caatagctga agatgaagaa gaacttgaag aagaacaagc tcaggacgaa     480
caggcgccca ctaagaaaac ccatgtatac gcccaggcac ctctttctgg tgaaaaaatt     540
actaaggatg gtttgcaaat aggtgtggat gccacacagg cgggagataa ccctatatat     600
gctgataaaa cattccaacc cgaacctcag ataggtgagt ctcagtggaa cgaggctgat     660
gccacagtag caggaggcag agtcttaaaa aagaccaccc ctatgagacc ttgctatgga     720
tcctatgcca aacctactaa tgccaatggc ggtcaaggga tcatggtggc caatgatcag     780
ggagcgcttg aatctaaagt tgagatgcaa tttttctcca ccacaacgtc tcttaatgta     840
agggaaggtg aaaacaatct tcagccaaaa gtagtgctat acagcgaaga tgttaacttg     900
gaatcccctg acactcattt gtcttacaaa cctaaaaagg atgacaccaa ctctaaaatc     960 atgtttgggtc agcaagccat gcccaacaga cccaacctca ttgcttttag ggacaacttt    1020
attggactta tgtactacaa cagcacaggc aacatgggag tgctggcagg acaggcctcc    1080
cagctaaacg ctgtggtaga cttgcaagac agaaacacag agctgtcata ccaactgatg    1140
cttgattcca ttggagacag atcaagatac ttttccatgt ggaaccaggc agtggacagc    1200
tatgacccag atgtcagaat cattgaaaac catgggggttg aagatgagct gcccaactat    1260 tgcttttcccc tgggcggtat tggaattaca gacacatacc agtgcataaa accaaccgca    1320
```

-continued

```
gctgctaata acactacatg gtctaaggat gaagaattta gtgatcgcaa tgaaataggg      1380
gtgggaaaca acttcgccat ggagatcaac atccaggcca acctctggag gaacttcctc      1440
tatgcgaacg tggggctcta cctgccagac aagctcaagt acaaccccac caacgtggac      1500
atctctgaca accccaacac ctatgactac atgaacaagc gtgtggtggc tcccggcctg      1560
gtggactgct ttgtcaatgt gggagccagg tggtccctgg actacatgga caacgtcaac      1620
cccttcaacc accaccgcaa tgcgggtctg cgctaccgct ccatgatcct gggcaacggg      1680
cgctacgtgc ccttccacat tcaggtgccc cagaagttct tgccatcaa gaacctcctc       1740 ctcctgccgg gctcctacac ttacgagtgg aacttcagga aggatgtcaa catggtcctg      1800
cagagctctc tgggcaatga ccttagggtg acggggcca gcatcaagtt tgacagcgtc       1860
accctctatg ctaccttctt ccccatggct cacaacaccg cctccacgct cgaggccatg      1920
ctgaggaacg acaccaacga ccagtccttc aatgactacc tctctggggc caacatgctc      1980 tacccccatcc ccgccaaggc caccaacgtg cccatctcca ttccctctcg caactgggcc     2040
gccttcagag gctgggcctt tacccgcctt aagaccaagg aaacccctc cctgggctcg       2100 ggttttgacc cctactttgt ctactcggga tccatcccct acctggatgg caccttctac      2160
ctcaaccaca cttttaagaa gatatccatc atgtatgact cctccgtcag ctggccgggc      2220
aatgaccgcc tgctcacccc caatgagttc gaggtcaagc gcgccgtgga cggcgagggc      2280
tacaacgtgg cccagtgcaa catgaccaag gactggttcc tggtgcagat gctggccaac     2340
tacaacatag gctaccaggg cttctacatc ccagagagct acaaggacag gatgtactcc      2400
ttcttcagaa atttccaacc catgagcagg caggtggtgg acgagaccaa atacaaggac      2460
tatcaggcca ttggcatcac tcaccagcac aacaactcgg gattcgtggg ctacctggct      2520
cccaccatgc gcgaggggca ggcctacccc gccaacttcc cctacccgtt gataggcaaa     2580
accgcggtcg acagcgtcac ccagaaaaag ttcctctgcg accgcaccct ctggcgcatc      2640
cccttctcta gcaacttcat gtccatgggt gcgctcacgg acctgggcca gaacctgctc      2700
tatgccaact ccgcccatgc gctggacatg acttttgagg tggacccat ggacgagccc       2760 acccttctct atattgtgtt tgaagtgttc gacgtggtca gagtgcacca gccgcaccgc      2820
ggtgtcatcg agaccgtgta cctgcgcacg cccttctcgg ccggcaacgc caccacc       2877
```

<210> SEQ ID NO 10
<211> LENGTH: 1749
<212> TYPE: DNA
<213> ORGANISM: Gorilla beringei beringei

<400> SEQUENCE: 10

```
atgaaacgcg cgagatcgtc tgacgagacc ttcaaccccg tgtaccccta cgataccgag        60
atcgctccga cttctgtccc tttccttacc cctcccttttg tgtcatccgc aggaatgcaa      120
gaaaatccag ctgggtgtgct gtccctgcac ttgtcagagc cccttaccac ccacaatggg      180
gccctgactc taaaaatggg gggcggcctg accctggaca aggaagggaa tctcacttcc      240
caaaacatca ccagtgtcga tcccctctc aaaaaaagca agaacaacat cagccttcag       300
accgccgcac ccctcgccgt cagctccggg gccctaacac ttttgccac tccccccta       360 gcggtcagtg gtgacaacct tactgtgcag tctcaggccc ctctcacttt ggaagactca      420
aaactaactc tggccaccaa aggaccccta actgtgtccg aaggcaaact tgtcctagaa      480
acagaggctc ccctgcatgc aagtgacagc agcagcctgg gccttagcgt tacggcccca      540
```

```
cttagcatta acaatgacag cctaggacta gatctgcagg cacccattgt ctctcaaaat    600
ggaaaactgg ctctaaatgt agcaggcccc ctagctgtgg ccaatggcat taatgctttg    660
acagtaggca caggcaaagg tattggtcta aatgaaacca gcactcactt gcaagcaaag    720
ttggtcgccc ccctaggctt tgataccaat ggcaacatta agctaagcgt tgcaggaggc    780
atgagactaa ataatgacac acttatacta gatgtaaact acccatttga agctcaaggc    840
caactaagtc taagagtggg ccagggtccg ctgtatgtag attctagcag ccataacctg    900
accattagat gccttagagg attatacata acatcgtcta ataaccaaac cggtctagag    960
gccaacataa aactaacaaa aggccttgtc tatgatggaa atgccatagc agtcaatgtt   1020
ggtcaaggat tgcaatacag cactactgcc acatcggaag gtgtgtatcc tatacagtct   1080
aagataggtt tgggaatgga atatgatacc aacggagcca tgatgacaaa actaggctct   1140
ggactaagct ttgacaattc aggagccatt gtagtgggaa acaaaaatga tgacaggctt   1200
actctgtgga ctacaccaga cccatctcct aactgtagaa tttattctga aaaagatact   1260
aaactaacct tggtgctgac taagtgtggc agccaaatcc taggcacagt atctgccctt   1320
gctgtcagag gcagccttgc gcccatcact aatgcatcca gcatagtcca aatatttcta   1380
agatttgatg aaaatggact attgatgagc aactcatcgc tagacggtga ttactggaat   1440
tacagaaatg gggactccac taatagcaca ccatatacaa atgcagtagg ctttatgcct   1500
aatctagcag cctatcctaa aggtcaggct acagctgcaa aaagcagtat tgtaagccag   1560
gtatacatgg atggtgacac tactaaacct ataacactaa aaataaactt caatggcatt   1620
gatgaaacaa cagaaaatac ccctgttagt aaatattcca tgacattctc atggagctgg   1680
cccaccgcaa gctacatagg ccacactttt gcaacaaact cttttacttt ctcctacatc   1740
gcccaagaa                                                            1749
```

<210> SEQ ID NO 11
<211> LENGTH: 10
<212> TYPE: PRT
<213> ORGANISM: Gorilla beringei beringei

<400> SEQUENCE: 11

Ser Ser Leu Val Ala Ser Gly Ala Ala Ser
1               5                   10

<210> SEQ ID NO 12
<211> LENGTH: 147
<212> TYPE: PRT
<213> ORGANISM: Gorilla beringei beringei

<400> SEQUENCE: 12

Lys His Gln Tyr Leu Lys Val Met Val Arg Asp Thr Phe Ala Leu Thr
1               5                   10                  15

His Thr Ser Leu Arg Lys Ala Ala Gln Ala Tyr Ala Leu Pro Val Glu
            20                  25                  30

Lys Gly Cys Cys Pro Tyr Gln Ala Val Asn Gln Phe Tyr Met Leu Gly
        35                  40                  45

Ser Tyr Arg Ser Asp Thr Asp Gly Phe Pro Leu Gln Glu Tyr Trp Lys
    50                  55                  60

Asp Arg Glu Glu Phe Val Leu Asn Arg Glu Leu Trp Lys Lys Lys Gly
65                  70                  75                  80

Glu Asp Lys Tyr Asp Ile Ile Arg Glu Thr Leu Asp Tyr Cys Ala Leu
                85                  90                  95

```
Asp Val Gln Val Thr Ala Glu Leu Val His Lys Leu Arg Glu Ser Tyr
            100                 105                 110

Ala Ser Phe Val Arg Asp Ser Val Gly Leu Gln Glu Ala Ser Phe Asn
        115                 120                 125

Val Phe Gln Arg Pro Thr Ile Ser Ser Asn Ser His Ala Ile Phe Arg
130                 135                 140

Gln Ile Ala
145

<210> SEQ ID NO 13
<211> LENGTH: 15
<212> TYPE: PRT
<213> ORGANISM: Gorilla beringei beringei

<400> SEQUENCE: 13

Lys Thr Glu Ala Ala Lys Ala Glu Val Glu Ala Asn Val Ala
1               5                   10                  15

<210> SEQ ID NO 14
<211> LENGTH: 15
<212> TYPE: PRT
<213> ORGANISM: Gorilla beringei beringei

<400> SEQUENCE: 14

Ile Gly Val Asp Ala Thr Gln Ala Gly Asp Asn Pro Ile Tyr Ala
1               5                   10                  15

<210> SEQ ID NO 15
<211> LENGTH: 15
<212> TYPE: PRT
<213> ORGANISM: Gorilla beringei beringei

<400> SEQUENCE: 15

Leu Asn Val Ala Gly Pro Leu Ala Val Ala Asn Gly Ile Asn Ala
1               5                   10                  15

<210> SEQ ID NO 16
<211> LENGTH: 133
<212> TYPE: PRT
<213> ORGANISM: Gorilla beringei beringei

<400> SEQUENCE: 16

Met Ser Asp Thr Gly Asn Ser Phe Asp Gly Ser Ile Phe Ser Pro Tyr
1               5                   10                  15

Leu Thr Val Arg Met Pro His Trp Ala Gly Val Arg Gln Asn Val Met
            20                  25                  30

Gly Ser Asn Val Asp Gly Arg Pro Val Leu Pro Ser Asn Ser Ser Thr
        35                  40                  45

Met Ala Tyr Ala Thr Val Gly Gly Thr Pro Leu Asp Ala Ala Thr Ser
    50                  55                  60

Ala Ala Ala Ser Ala Ala Ala Thr Ala Arg Ser Met Ala Thr Asp
65                  70                  75                  80

Leu Tyr Ser Ser Leu Val Ala Ser Gly Ala Ala Ser Arg Ala Ser Ala
            85                  90                  95

Arg Asp Glu Lys Leu Thr Ala Leu Leu Leu Lys Leu Glu Asp Leu Thr
        100                 105                 110

Arg Glu Leu Gly Gln Leu Thr Gln Gln Val Ser Ser Leu Arg Glu Ser
    115                 120                 125

Ser Leu Ala Ser Pro
        130
```

<210> SEQ ID NO 17
<211> LENGTH: 1056
<212> TYPE: PRT
<213> ORGANISM: Gorilla beringei beringei

<400> SEQUENCE: 17

| | | | | | | | | | | | | | | | |
|---|---|---|---|---|---|---|---|---|---|---|---|---|---|---|---|
| Met | Asp | Ser | Ser | Asn | Val | Arg | Asp | Val | Val | Ile | Lys | Leu | Arg | Pro | Pro |
| 1 | | | | 5 | | | | | 10 | | | | | 15 | |
| Ser | Ala | Glu | Ile | Trp | Thr | Cys | Gly | Ser | Arg | Gly | Val | Val | Cys | Ser | |
| | | | 20 | | | | | 25 | | | | | 30 | | |
| Thr | Ile | Ala | Leu | Gln | Glu | Thr | Asp | Ala | Gly | Gly | Gln | Thr | Thr | Lys | Val |
| | | 35 | | | | | 40 | | | | | 45 | | | |
| Glu | Asp | His | Gln | Pro | His | Gly | Thr | Pro | Gly | Gly | Gly | Leu | Arg | Phe | Pro |
| | 50 | | | | | 55 | | | | | 60 | | | | |
| Leu | Arg | Phe | Leu | Val | Arg | Gly | Arg | Gln | Val | His | Leu | Val | Gln | Asp | Ile |
| 65 | | | | | 70 | | | | | 75 | | | | | 80 |
| Gln | Pro | Val | Gln | Arg | Cys | Gln | Tyr | Cys | Gly | Arg | Phe | Tyr | Lys | Ser | Gln |
| | | | | 85 | | | | | 90 | | | | | 95 | |
| His | Glu | Cys | Ser | Ala | Arg | Arg | Asp | Phe | Tyr | Phe | His | His | Ile | Asn | |
| | | | 100 | | | | | 105 | | | | | 110 | | |
| Ser | Gln | Ser | Ser | Asn | Trp | Trp | Arg | Glu | Ile | Gln | Phe | Phe | Pro | Ile | Gly |
| | | | 115 | | | | | 120 | | | | | 125 | | |
| Ser | His | Pro | Arg | Thr | Glu | Arg | Leu | Phe | Val | Thr | Tyr | Asp | Val | Glu | Thr |
| | 130 | | | | | 135 | | | | | 140 | | | | |
| Tyr | Thr | Trp | Met | Gly | Ala | Phe | Gly | Lys | Gln | Leu | Val | Pro | Phe | Met | Leu |
| 145 | | | | | 150 | | | | | 155 | | | | | 160 |
| Val | Met | Lys | Leu | Gly | Gly | Asp | Glu | Ala | Leu | Val | Ala | Ala | Ala | Arg | Asp |
| | | | | 165 | | | | | 170 | | | | | 175 | |
| Leu | Ala | Arg | Glu | Leu | Arg | Trp | Asp | Pro | Trp | Glu | Lys | Asp | Pro | Leu | Thr |
| | | | 180 | | | | | 185 | | | | | 190 | | |
| Phe | Tyr | Cys | Ile | Thr | Pro | Glu | Lys | Met | Ala | Val | Gly | Arg | Gln | Phe | Arg |
| | | | 195 | | | | | 200 | | | | | 205 | | |
| Thr | Phe | Arg | Asp | Arg | Leu | Gln | Thr | Leu | Met | Ala | Arg | Asp | Leu | Trp | Arg |
| | 210 | | | | | 215 | | | | | 220 | | | | |
| Ser | Phe | Leu | Ala | Ala | Asn | Pro | His | Leu | Gln | Asp | Trp | Ala | Leu | Glu | Glu |
| 225 | | | | | 230 | | | | | 235 | | | | | 240 |
| His | Gly | Leu | Glu | Ser | Pro | Glu | Glu | Leu | Thr | Tyr | Glu | Glu | Leu | Lys | Lys |
| | | | | 245 | | | | | 250 | | | | | 255 | |
| Leu | Pro | Ser | Ile | Lys | Gly | Gln | Pro | Arg | Phe | Leu | Glu | Leu | Tyr | Ile | Val |
| | | | 260 | | | | | 265 | | | | | 270 | | |
| Gly | His | Asn | Ile | Asn | Gly | Phe | Asp | Glu | Ile | Val | Leu | Ala | Ala | Gln | Val |
| | | 275 | | | | | 280 | | | | | 285 | | | |
| Ile | Asn | Asn | Arg | Ser | Ser | Val | Pro | Gly | Pro | Phe | Arg | Ile | Thr | Arg | Asn |
| | 290 | | | | | 295 | | | | | 300 | | | | |
| Phe | Met | Pro | Arg | Ala | Gly | Lys | Ile | Leu | Phe | Asn | Asp | Leu | Thr | Phe | Ser |
| 305 | | | | | 310 | | | | | 315 | | | | | 320 |
| Leu | Pro | Asn | Pro | Arg | Ser | Lys | Lys | Arg | Thr | Asp | Tyr | Thr | Leu | Trp | Glu |
| | | | | 325 | | | | | 330 | | | | | 335 | |
| Gln | Gly | Gly | Cys | Asp | Asp | Thr | Asp | Phe | Lys | His | Gln | Tyr | Leu | Lys | Val |
| | | | 340 | | | | | 345 | | | | | 350 | | |
| Met | Val | Arg | Asp | Thr | Phe | Ala | Leu | Thr | His | Thr | Ser | Leu | Arg | Lys | Ala |
| | | 355 | | | | | 360 | | | | | 365 | | | |
| Ala | Gln | Ala | Tyr | Ala | Leu | Pro | Val | Glu | Lys | Gly | Cys | Cys | Pro | Tyr | Gln |

```
                370              375              380
        Ala Val Asn Gln Phe Tyr Met Leu Gly Ser Tyr Arg Ser Asp Thr Asp
        385              390              395              400

Gly Phe Pro Leu Gln Glu Tyr Trp Lys Asp Arg Glu Phe Val Leu
                         405              410              415

Asn Arg Glu Leu Trp Lys Lys Gly Glu Asp Lys Tyr Asp Ile Ile
                         420              425              430

Arg Glu Thr Leu Asp Tyr Cys Ala Leu Asp Val Gln Val Thr Ala Glu
                         435              440              445

Leu Val His Lys Leu Arg Glu Ser Tyr Ala Ser Phe Val Arg Asp Ser
                         450              455              460

Val Gly Leu Gln Glu Ala Ser Phe Asn Val Phe Gln Arg Pro Thr Ile
        465              470              475              480

Ser Ser Asn Ser His Ala Ile Phe Arg Gln Ile Ala Phe Arg Ala Glu
                         485              490              495

Arg Pro Gln Arg Thr Asn Leu Gly Pro Asn Met Leu Ala Pro Ser His
                         500              505              510

Glu Leu Tyr Asp Tyr Val Arg Ala Ser Ile Arg Gly Gly Arg Cys Tyr
                         515              520              525

Pro Thr Tyr Leu Gly Ile Leu Arg Glu Pro Leu Tyr Val Tyr Asp Ile
                         530              535              540

Cys Gly Met Tyr Ala Ser Ala Leu Thr His Pro Met Pro Trp Gly Pro
        545              550              555              560

Pro Leu Asn Pro Tyr Glu Arg Ala Leu Ala Ala Arg Glu Trp Gln Arg
                         565              570              575

Ala Leu Asp Met Gln Ala Cys Lys Ile Asp Tyr Phe Asp Pro Arg Leu
                         580              585              590

Leu Pro Gly Val Phe Thr Ile Asp Ala Asp Pro Pro Asn Glu Asp Gln
                         595              600              605

Leu Asp Pro Leu Pro Pro Phe Cys Ser Arg Lys Gly Gly Arg Leu Cys
                         610              615              620

Trp Thr Asn Glu Arg Leu Arg Gly Glu Val Ala Thr Ser Val Asp Met
        625              630              635              640

Val Thr Leu His Asn Arg Gly Trp Arg Val Arg Leu Ile Pro Asp Glu
                         645              650              655

Arg Thr Thr Val Phe Pro Glu Trp Lys Cys Val Ala Arg Glu Tyr Val
                         660              665              670

Gln Leu Asn Ile Ala Ala Lys Glu Arg Ala Asp Arg Asp Lys Asn Gln
                         675              680              685

Thr Leu Arg Ser Ile Ala Lys Leu Leu Ser Asn Ala Leu Tyr Gly Ser
        690              695              700

Phe Ala Thr Lys Leu Asp Asn Lys Lys Ile Val Phe Ser Asp Gln Met
        705              710              715              720

Asp Pro Gly Thr Leu Lys Gly Ile Thr Ser Gly Gln Val Asn Ile Lys
                         725              730              735

Ser Ser Ser Phe Leu Glu Thr Asp Asn Leu Ser Ala Glu Val Met Pro
                         740              745              750

Ala Phe Glu Arg Glu Tyr Leu Pro Gln Gln Leu Ala Leu Ala Asp Ser
                         755              760              765

Asp Ala Glu Glu Ser Glu Asp Glu Arg Ala Pro Thr Pro Phe Tyr Thr
                         770              775              780

Pro Pro Ser Gly Thr Pro Gly His Val Ser Tyr Thr Tyr Lys Pro Ile
        785              790              795              800
```

```
Thr Phe Leu Asp Ala Glu Glu Gly Asp Met Cys Leu His Thr Leu Glu
            805                 810                 815

Lys Val Asp Pro Leu Val Asp Asn Asp Arg Tyr Pro Ser His Val Ala
        820                 825                 830

Ser Phe Val Leu Ala Trp Thr Arg Ala Phe Val Ser Glu Trp Ser Glu
        835                 840                 845

Phe Leu Tyr Glu Glu Asp Arg Gly Thr Pro Leu Glu Asp Arg Pro Leu
    850                 855                 860

Lys Ser Val Tyr Gly Asp Thr Asp Ser Leu Phe Val Thr Glu Lys Gly
865                 870                 875                 880

His Arg Leu Met Glu Ser Arg Gly Lys Lys Arg Ile Lys Lys His Gly
                885                 890                 895

Gly Asn Leu Val Phe Asp Pro Asp Arg Pro Glu Leu Thr Trp Leu Val
                900                 905                 910

Glu Cys Glu Thr Val Cys Ala Ser Cys Gly Ala Asp Ala Tyr Ser Pro
            915                 920                 925

Glu Ser Val Phe Leu Ala Pro Lys Leu Tyr Ala Leu Lys Ser Leu Gln
    930                 935                 940

Cys Pro Ser Cys Gly Ala Thr Ser Lys Gly Lys Leu Arg Ala Lys Gly
945                 950                 955                 960

His Ala Ala Glu Gly Leu Asp Tyr Glu Thr Met Val Lys Cys Tyr Leu
                965                 970                 975

Ala Asp Ala Gln Gly Glu Glu Arg Gln Arg Phe Ser Thr Ser Arg Thr
            980                 985                 990

Ser Leu Lys Arg Thr Leu Ala Ser Ala Gln Pro Gly Ala His Pro Phe
    995                 1000                1005

Thr Val Thr Gln Thr Thr Leu Thr Arg Thr Leu Arg Pro Trp Lys
    1010                1015                1020

Asp Met Thr Leu Ala Pro Leu Asp Ala His Arg Leu Val Pro Tyr
    1025                1030                1035

Ser Glu Ser Arg Pro Asn Pro Arg Asn Glu Glu Ile Cys Trp Ile
    1040                1045                1050

Glu Met Pro
    1055

<210> SEQ ID NO 18
<211> LENGTH: 658
<212> TYPE: PRT
<213> ORGANISM: Gorilla beringei beringei

<400> SEQUENCE: 18

Met Arg Arg Ala Ala Met Phe Glu Glu Gly Pro Pro Ser Tyr Glu
1               5                   10                  15

Ser Ala Met Gly Ile Ser Pro Ala Ala Pro Leu Gln Pro Pro Tyr Val
            20                  25                  30

Pro Pro Arg Tyr Leu Gln Pro Thr Gly Gly Arg Asn Ser Ile Cys Tyr
        35                  40                  45

Ser Glu Leu Gln Pro Leu Tyr Asp Thr Thr Arg Leu Tyr Leu Val Asp
    50                  55                  60

Asn Lys Ser Ala Asp Val Ala Ser Leu Asn Tyr Gln Asn Asp His Ser
65                  70                  75                  80

Asp Phe Leu Thr Thr Val Ile Gln Asn Asn Asp Phe Thr Pro Thr Glu
                85                  90                  95

Ala Ser Thr Gln Thr Ile Asn Leu Asp Asn Arg Ser Asn Trp Gly Gly
```

```
              100                 105                 110
Asp Leu Lys Thr Ile Leu His Thr Asn Met Pro Asn Val Asn Glu Phe
        115                 120                 125
Met Phe Thr Asn Ser Phe Lys Ala Arg Val Met Val Ala Arg Glu Gln
        130                 135                 140
Gly Glu Ala Lys Tyr Glu Trp Val Asp Phe Thr Leu Pro Glu Gly Asn
145                 150                 155                 160
Tyr Ser Glu Thr Met Thr Leu Asp Leu Met Asn Asn Ala Ile Val Glu
                165                 170                 175
His Tyr Leu Lys Val Gly Arg Gln Asn Gly Val Lys Glu Ser Asp Ile
        180                 185                 190
Gly Val Lys Phe Asp Thr Arg Asn Phe Arg Leu Gly Trp Asp Pro Val
        195                 200                 205
Thr Gly Leu Val Met Pro Gly Val Tyr Thr Asn Glu Ala Phe His Pro
        210                 215                 220
Asp Ile Val Leu Leu Pro Gly Cys Gly Val Asp Phe Thr Gln Ser Arg
225                 230                 235                 240
Leu Ser Asn Leu Leu Gly Ile Arg Lys Arg Gln Pro Phe Gln Glu Gly
                245                 250                 255
Phe Lys Ile Thr Tyr Glu Asp Leu Lys Gly Gly Asn Ile Pro Ala Leu
        260                 265                 270
Leu Asp Leu Asp Ala Tyr Glu Glu Ser Leu Lys Pro Glu Glu Ser Ala
        275                 280                 285
Gly Asp Ser Gly Glu Ser Gly Glu Glu Gln Ala Gly Gly Gly Gly Gly
        290                 295                 300
Ala Ser Val Glu Asn Glu Ser Thr Pro Ala Val Ala Ala Asp Ala Ala
305                 310                 315                 320
Glu Val Glu Pro Glu Ala Met Gln Gln Asp Ala Glu Gly Ala Gly Gln
                325                 330                 335
Glu Gly Ala Gln Lys Asp Met Asn Asp Gly Glu Ile Arg Gly Asp Thr
        340                 345                 350
Phe Ala Thr Arg Gly Glu Glu Lys Glu Ala Glu Ala Ala Ala Ala Ala
        355                 360                 365
Thr Ala Glu Ala Glu Thr Glu Val Glu Ala Glu Ala Glu Pro Glu Thr
        370                 375                 380
Glu Val Met Glu Asp Met Asn Asp Gly Glu Arg Arg Gly Asp Thr Phe
385                 390                 395                 400
Ala Thr Arg Gly Glu Glu Lys Ala Ala Glu Ala Glu Ala Ala Ala Glu
                405                 410                 415
Glu Ala Ala Ala Ala Ala Ala Lys Thr Glu Ala Ala Lys Ala Glu
        420                 425                 430
Val Glu Ala Asn Val Ala Val Glu Ala Gln Ala Glu Glu Glu Ala Ala
        435                 440                 445
Ala Glu Ala Val Lys Glu Lys Ala Gln Ala Glu Gln Glu Glu Lys Lys
        450                 455                 460
Pro Val Ile Gln Pro Leu Lys Glu Asp Ser Lys Lys Arg Ser Tyr Asn
465                 470                 475                 480
Val Ile Glu Gly Ser Thr Phe Thr Gln Tyr Arg Ser Trp Tyr Leu Ala
                485                 490                 495
Tyr Asn Tyr Gly Asp Pro Val Lys Gly Val Arg Ser Trp Thr Leu Leu
        500                 505                 510
Cys Thr Pro Asp Val Thr Cys Gly Ser Glu Gln Met Tyr Trp Ser Leu
        515                 520                 525
```

```
Pro Asn Met Met Gln Asp Pro Val Thr Phe Arg Ser Thr Arg Gln Val
    530                 535                 540

Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
            580                 585                 590

Ala Arg Pro Pro Ala Pro Thr Ile Thr Thr Val Ser Glu Asn Val Pro
        595                 600                 605

Ala Leu Thr Asp His Gly Thr Leu Pro Leu Arg Asn Ser Ile Ser Gly
    610                 615                 620

Val Gln Arg Val Thr Ile Thr Asp Ala Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe

<210> SEQ ID NO 19
<211> LENGTH: 959
<212> TYPE: PRT
<213> ORGANISM: Gorilla beringei beringei

<400> SEQUENCE: 19

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Asn Met Ser Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
                100                 105                 110

Phe Lys Pro Tyr Ser Gly Thr Ala Tyr Asn Ser Leu Ala Pro Lys Gly
            115                 120                 125

Ala Pro Asn Ser Cys Glu Trp Glu Gln Asp Glu Pro Ala Gln Ala Ala
        130                 135                 140

Ile Ala Glu Asp Glu Glu Leu Glu Glu Gln Ala Gln Asp Glu
145                 150                 155                 160

Gln Ala Pro Thr Lys Lys Thr His Val Tyr Ala Gln Ala Pro Leu Ser
                165                 170                 175

Gly Glu Lys Ile Thr Lys Asp Gly Leu Gln Ile Gly Val Asp Ala Thr
                180                 185                 190

Gln Ala Gly Asp Asn Pro Ile Tyr Ala Asp Lys Thr Phe Gln Pro Glu
            195                 200                 205

Pro Gln Ile Gly Glu Ser Gln Trp Asn Glu Ala Asp Ala Thr Val Ala
        210                 215                 220

Gly Gly Arg Val Leu Lys Lys Thr Thr Pro Met Arg Pro Cys Tyr Gly
225                 230                 235                 240
```

```
Ser Tyr Ala Lys Pro Thr Asn Ala Asn Gly Gly Gln Gly Ile Met Val
            245                 250                 255

Ala Asn Asp Gln Gly Ala Leu Glu Ser Lys Val Glu Met Gln Phe Phe
        260                 265                 270

Ser Thr Thr Thr Ser Leu Asn Val Arg Glu Gly Glu Asn Asn Leu Gln
        275                 280                 285

Pro Lys Val Val Leu Tyr Ser Glu Asp Val Asn Leu Glu Ser Pro Asp
    290                 295                 300

Thr His Leu Ser Tyr Lys Pro Lys Lys Asp Asp Thr Asn Ser Lys Ile
305                 310                 315                 320

Met Leu Gly Gln Gln Ala Met Pro Asn Arg Pro Asn Leu Ile Ala Phe
                325                 330                 335

Arg Asp Asn Phe Ile Gly Leu Met Tyr Tyr Asn Ser Thr Gly Asn Met
                340                 345                 350

Gly Val Leu Ala Gly Gln Ala Ser Gln Leu Asn Ala Val Val Asp Leu
                355                 360                 365

Gln Asp Arg Asn Thr Glu Leu Ser Tyr Gln Leu Met Leu Asp Ser Ile
    370                 375                 380

Gly Asp Arg Ser Arg Tyr Phe Ser Met Trp Asn Gln Ala Val Asp Ser
385                 390                 395                 400

Tyr Asp Pro Asp Val Arg Ile Ile Glu Asn His Gly Val Glu Asp Glu
                405                 410                 415

Leu Pro Asn Tyr Cys Phe Pro Leu Gly Gly Ile Gly Ile Thr Asp Thr
                420                 425                 430

Tyr Gln Cys Ile Lys Pro Thr Ala Ala Asn Asn Thr Thr Trp Ser
                435                 440                 445

Lys Asp Glu Glu Phe Ser Asp Arg Asn Glu Ile Gly Val Gly Asn Asn
    450                 455                 460

Phe Ala Met Glu Ile Asn Ile Gln Ala Asn Leu Trp Arg Asn Phe Leu
465                 470                 475                 480

Tyr Ala Asn Val Gly Leu Tyr Leu Pro Asp Lys Leu Lys Tyr Asn Pro
                485                 490                 495

Thr Asn Val Asp Ile Ser Asp Asn Pro Asn Thr Tyr Tyr Met Asn
                500                 505                 510

Lys Arg Val Val Ala Pro Gly Leu Val Asp Cys Phe Val Asn Val Gly
    515                 520                 525

Ala Arg Trp Ser Leu Asp Tyr Met Asp Asn Val Asn Pro Phe Asn His
530                 535                 540

His Arg Asn Ala Gly Leu Arg Tyr Arg Ser Met Ile Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
                580                 585                 590

Arg Lys Asp Val Asn Met Val Leu Gln Ser Ser Leu Gly Asn Asp Leu
    595                 600                 605

Arg Val Asp Gly Ala Ser Ile Lys Phe Asp Ser Val Thr Leu Tyr Ala
    610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Gly
                645                 650                 655
```

Ala Asn Met Leu Tyr Pro Ile Pro Ala Lys Ala Thr Asn Val Pro Ile
            660                 665                 670

Ser Ile Pro Ser Arg Asn Trp Ala Ala Phe Arg Gly Trp Ala Phe Thr
        675                 680                 685

Arg Leu Lys Thr Lys Glu Thr Pro Ser Leu Gly Ser Gly Phe Asp Pro
    690                 695                 700

Tyr Phe Val Tyr Ser Gly Ser Ile Pro Tyr Leu Asp Gly Thr Phe Tyr
705                 710                 715                 720

Leu Asn His Thr Phe Lys Lys Ile Ser Ile Met Tyr Asp Ser Ser Val
                725                 730                 735

Ser Trp Pro Gly Asn Asp Arg Leu Leu Thr Pro Asn Glu Phe Glu Val
            740                 745                 750

Lys Arg Ala Val Asp Gly Glu Gly Tyr Asn Val Ala Gln Cys Asn Met
        755                 760                 765

Thr Lys Asp Trp Phe Leu Val Gln Met Leu Ala Asn Tyr Asn Ile Gly
    770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Glu Thr
                805                 810                 815

Lys Tyr Lys Asp Tyr Gln Ala Ile Gly Ile Thr His Gln His Asn Asn
            820                 825                 830

Ser Gly Phe Val Gly Tyr Leu Ala Pro Thr Met Arg Glu Gly Gln Ala
        835                 840                 845

Tyr Pro Ala Asn Phe Pro Tyr Pro Leu Ile Gly Lys Thr Ala Val Asp
    850                 855                 860

Ser Val Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Ile Val Phe Glu
        915                 920                 925

Val Phe Asp Val Val Arg Val His Gln Pro Arg Gly Val Ile Glu
    930                 935                 940

Thr Val Tyr Leu Arg Thr Pro Phe Ser Ala Gly Asn Ala Thr Thr
945                 950                 955

<210> SEQ ID NO 20
<211> LENGTH: 583
<212> TYPE: PRT
<213> ORGANISM: Gorilla beringei beringei

<400> SEQUENCE: 20

Met Lys Arg Ala Arg Ser Ser Asp Glu Thr Phe Asn Pro Val Tyr Pro
1               5                   10                  15

Tyr Asp Thr Glu Ile Ala Pro Thr Ser Val Pro Phe Leu Thr Pro Pro
            20                  25                  30

Phe Val Ser Ser Ala Gly Met Gln Glu Asn Pro Ala Gly Val Leu Ser
        35                  40                  45

Leu His Leu Ser Glu Pro Leu Thr Thr His Asn Gly Ala Leu Thr Leu
    50                  55                  60

Lys Met Gly Gly Gly Leu Thr Leu Asp Lys Glu Gly Asn Leu Thr Ser
65                  70                  75                  80

```
Gln Asn Ile Thr Ser Val Asp Pro Pro Leu Lys Lys Ser Lys Asn Asn
                85                  90                  95

Ile Ser Leu Gln Thr Ala Ala Pro Leu Ala Val Ser Ser Gly Ala Leu
            100                 105                 110

Thr Leu Phe Ala Thr Pro Pro Leu Ala Val Ser Gly Asp Asn Leu Thr
        115                 120                 125

Val Gln Ser Gln Ala Pro Leu Thr Leu Glu Asp Ser Lys Leu Thr Leu
130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Leu Gly Leu Ser
                165                 170                 175

Val Thr Ala Pro Leu Ser Ile Asn Asn Asp Ser Leu Gly Leu Asp Leu
            180                 185                 190

Gln Ala Pro Ile Val Ser Gln Asn Gly Lys Leu Ala Leu Asn Val Ala
        195                 200                 205

Gly Pro Leu Ala Val Ala Asn Gly Ile Asn Ala Leu Thr Val Gly Thr
210                 215                 220

Gly Lys Gly Ile Gly Leu Asn Glu Thr Ser Thr His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asp Thr Leu Ile Leu Asp Val
            260                 265                 270

Asn Tyr Pro Phe Glu Ala Gln Gly Gln Leu Ser Leu Arg Val Gly Gln
        275                 280                 285

Gly Pro Leu Tyr Val Asp Ser Ser Ser His Asn Leu Thr Ile Arg Cys
290                 295                 300

Leu Arg Gly Leu Tyr Ile Thr Ser Ser Asn Asn Gln Thr Gly Leu Glu
305                 310                 315                 320

Ala Asn Ile Lys Leu Thr Lys Gly Leu Val Tyr Asp Gly Asn Ala Ile
                325                 330                 335

Ala Val Asn Val Gly Gln Gly Leu Gln Tyr Ser Thr Thr Ala Thr Ser
            340                 345                 350

Glu Gly Val Tyr Pro Ile Gln Ser Lys Ile Gly Leu Gly Met Glu Tyr
        355                 360                 365

Asp Thr Asn Gly Ala Met Met Thr Lys Leu Gly Ser Gly Leu Ser Phe
370                 375                 380

Asp Asn Ser Gly Ala Ile Val Val Gly Asn Lys Asn Asp Asp Arg Leu
385                 390                 395                 400

Thr Leu Trp Thr Thr Pro Asp Pro Ser Pro Asn Cys Arg Ile Tyr Ser
                405                 410                 415

Glu Lys Asp Thr Lys Leu Thr Leu Val Leu Thr Lys Cys Gly Ser Gln
            420                 425                 430

Ile Leu Gly Thr Val Ser Ala Leu Ala Val Arg Gly Ser Leu Ala Pro
        435                 440                 445

Ile Thr Asn Ala Ser Ser Ile Val Gln Ile Phe Leu Arg Phe Asp Glu
450                 455                 460

Asn Gly Leu Leu Met Ser Asn Ser Ser Leu Asp Gly Asp Tyr Trp Asn
465                 470                 475                 480

Tyr Arg Asn Gly Asp Ser Thr Asn Ser Thr Pro Tyr Thr Asn Ala Val
                485                 490                 495
```

```
Gly Phe Met Pro Asn Leu Ala Ala Tyr Pro Lys Gly Gln Ala Thr Ala
            500                 505                 510
Ala Lys Ser Ser Ile Val Ser Gln Val Tyr Met Asp Gly Asp Thr Thr
        515                 520                 525
Lys Pro Ile Thr Leu Lys Ile Asn Phe Asn Gly Ile Asp Glu Thr Thr
    530                 535                 540
Glu Asn Thr Pro Val Ser Lys Tyr Ser Met Thr Phe Ser Trp Ser Trp
545                 550                 555                 560
Pro Thr Ala Ser Tyr Ile Gly His Thr Phe Ala Thr Asn Ser Phe Thr
                565                 570                 575
Phe Ser Tyr Ile Ala Gln Glu
            580

<210> SEQ ID NO 21
<211> LENGTH: 37229
<212> TYPE: DNA
<213> ORGANISM: Gorilla beringei beringei

<400> SEQUENCE: 21
```

| | | | | | | |
|---|---|---|---|---|---|---|
| catcatcaat | aatatacctt | attttggatt | gtggccaata | tgataatgag | gtgggcgggg | 60 |
| agaggcgggg | cgggtgacgt | aggacgcgcg | agtagggttg | ggaggtgtgg | cggaagtgtg | 120 |
| gcatttgcaa | gtgggaggag | ctcacatgca | agcttccgtc | gcggaaaatg | tgacgttttt | 180 |
| gatgagcgcc | gcctacctcc | ggaagtgcca | attttcgcgc | gcttttcacc | ggatatcgta | 240 |
| gtaattttgg | gcgggaccat | gtaagatttg | gccattttcg | cgcgaaaagt | gaaacgggga | 300 |
| agtgaaaact | gaataatagg | gcgttagtca | tagcgcgtaa | tatttaccga | gggccgaggg | 360 |
| actttgaccg | attacgtgga | ggactcgccc | aggtgttttt | tacgtgaatt | tccgcgttcc | 420 |
| gggtcaaagt | ctccgttttt | attgtcaccg | tcatttgacg | cggagggtat | ttaaacccgc | 480 |
| tgcgctcctc | aagaggccac | tcttgagtgc | cagcgagaag | agttttctcc | tctgctccgc | 540 |
| ttcggtgatc | gaaaaatgag | acacatagcc | tgcactccgg | gtcttttgtc | cggtcgggcg | 600 |
| gcggccgagc | ttttggacgc | tttgatcaat | gatgtcctaa | gcgatgattt | tccgtctact | 660 |
| acccacttta | gcccacctac | tcttcacgaa | ctgtacgatc | tggatgtact | ggtggatgtg | 720 |
| aacgatccca | acgaggaggc | ggtttctgcg | ttttttcccg | agtctgcgct | gttggccgct | 780 |
| caggagggat | tgacctaca | cactccgccg | cctattttag | agtctccgct | gccggagccc | 840 |
| agtggtatac | cttatatgcc | tgaactgctt | cccgaagtgg | tagacctgac | ctgccacgag | 900 |
| cctggctttc | cgcccagcga | cgatgagggt | gagccttttg | ttttagactt | tgctgagata | 960 |
| cctgggcacg | gttgcaggtc | ttgtgcatat | catcagaggg | ttaccggaga | ccccgaggtt | 1020 |
| aagtgttcgc | tgtgctatat | gaggatgacc | tcttccttta | tctacagtaa | gttttttgtct | 1080 |
| aggtgggctt | ttgggtaggt | gggttttgtg | tcagaacagg | tgtaaacgtt | gcttgtgttt | 1140 |
| tttgtacctg | taggtccggt | gtccgagcca | gacccggagc | ccgaccgcga | tcccgagccg | 1200 |
| gatcccgagc | ctcctcgcag | gacaaggaaa | ctaccttcca | ttctgtgcaa | gtctcagaca | 1260 |
| cctgtaagga | ccagcgaggc | agacagcacc | gactctggca | cttctacctc | tcccccctgaa | 1320 |
| attcacccag | tggttcctct | gggtatacat | aaacctgttg | ctgttaaagt | ttgcgggcga | 1380 |
| cgccctgcag | tacagtgcat | tgaggacttg | cttcacgatc | ccgaggaacc | tttggacttg | 1440 |
| agccttaaac | gccctaggca | ataaaacccca | cctaagtaat | aaaccccacc | taagtaataa | 1500 |
| accctgccgc | ccttggttat | tgagatgacg | cccaatgttt | gcttttgaat | gacttcatgt | 1560 |
| gtgtaataaa | agtgagtgtg | atcataggtc | tcttgtttgt | ctgggcgggg | cttaagggta | 1620 |

```
tataagtctc ttggggctaa acttggttac acttgacccc aatggaggcg tgggggtgct    1680
tggaggagtt tgcggacgtg cgccgtttgc tggacgagag ctctagcaat acctatacta    1740
tttggaggta tctgtggggc tctactcagg ccaagttggt ttccagaatt aagcaggatt    1800
acaagtgcga ttttgaagag cttttagtt cctgcggtga gcttttgcaa tccttgaatc    1860
tgggccatca ggctattttc caggaaaagg ttctctcgac tttggatttt tccactcccg    1920
ggcgcaccgc cgcttgtgtg gcttttgtgt cttttgtgca agataaatgg agcgaggaga    1980
cccacctgag tcacggctac gtactggatt tcatggcgat ggctctttgg agggctcaca    2040
acaaatggaa gattcagaag gaactgtacg gttccgccct acgtcgtcca cttctgtcgc    2100
gacaggggct gaggtttccc gaccatcggc agcatcagaa tctggaagac gagtcggagg    2160
agcgagcgga ggagaagatc agcttgagag ccggcctgga ccctcctcag gaggaatgaa    2220
tctcccgcag gtggttgacc tgtttccaga actgagacgg gtcctgacta tcagggagga    2280
tggtcagttt gtgaagaagt ttaagaggga tcggggtgag ggagatgatg aggcggctag    2340
caatttagct tttagtctga tgactcgcca ccgaccggaa tgtattacct atcagcagat    2400
taaggagagt tgtgccaacg agctggatct tttgggtcag aagtatagca tagaacagct    2460
taccacttac tggcttcagc ctggggatga ttgggaagag gcgatcaggg tgtatgcaaa    2520
ggtggccctg cggcccgatt gcaagtataa gattactaag ttggttaata ttagaaactg    2580
ctgctatatt tctgggaacg gggccgaagt ggagatagat actcaggaca gggtggcttt    2640
taggtgttgc atgataaaca tgtggcccgg gatactgggg atggatgggg tggtattcat    2700
gaatgtgagg tttacgggcc ccaactttaa tggcacggtg ttcatgggca acaccaactt    2760
gctcctgcat ggtgcgagtt tctatggggt taataacacc tgtatagagg cctggaccga    2820
tgtaaaggtt cgaggttgtt cctttttatag ctgttggaag gcggtggtgt gtcgccctaa    2880
aagcaggggt tctgtgaaaa aatgcttgtt tgaaaggtgc accttaggca tcctctctga    2940
gggcaactcc agggtgcgcc ataatgtggc ttcgaactgc ggttgcttca tgcaagtgaa    3000
gggggtgagc gttatcaagc ataactcggt gtgtggaaac tgcgaggatc gcgcctccca    3060
gatgctgacc tgctttgatg caactgtca cctgttgaag accattcata taagcagcca    3120
ccccagaaag gcctggcccg tgtttgagca taacatcttg acccgctgct ccttgcatct    3180
gggggtcagg aggggtatgt tcctgcctta ccagtgtaac tttagccaca ctaaaatcct    3240
gctggaaccc gagtgcatga ccaaggtcag cctgaatggt gtgtttgatg tgactctgaa    3300
aatctgaaag gtgctgaggt atgatgagac caggaccagg tgccgaccct gcgagtgcgg    3360
cggcaagcac atgagaaatc agcctgtgat gttggatgtg accgaggagc ttaggcctga    3420
ccatctggtg ctgcctgca ccagggccga gtttgggtct agcgatgagg ataccgattg    3480
aggtgggtaa ggtgggcgtg gctagaaggg tggggcgtgt ataaattggg ggtctaaggg    3540
tctctctgtt ttgtcttgca acagccgccg ccatgagcga caccggcaac agctttgatg    3600
gaagcatctt tagcccctat ctgacagtgc gcatgcctca ctgggctgga gtgcgtcaga    3660
atgtgatggg ttccaacgtg gatggacgcc ccgttctgcc ttcaaattcg tctacaatgg    3720
cctacgcgac cgtgggagga actccgctgg acgccgcgac ctccgccgcc gcctccgccg    3780
ccgccgcgac cgcgcgcagc atggctacgg acctttacag ctctttggtg gcgagcggcg    3840
cggcctctcg cgcgtctgct cgggatgaga aactgaccgc tctgctgctt aaactggaag    3900
acttgacccg ggagctgggt caactgaccc agcaggtctc cagcttgcgt gagagcagcc    3960
```

```
ttgcctcccc ctaatggccc ataatataaa taaaagccag tctgtttgga ttaagcaagt    4020
gtatgttctt tatttaactc tccgcgcgcg gtaagcccgg gaccagcggt ctcggtcgtt    4080
tagggtgcgg tggattcttt ccaacacgtg gtacaggtgg ctctggatgt ttagatacat    4140
gggcatgagt ccatccctgg ggtggaggta gcaccactgc agagcttcgt gctcggggt     4200
ggtgttgtat atgatccagt cgtagcagga gcgctgggcg tggtgctgaa aaatgtcctt    4260
aagcaagagg cttatagcta gggggaggcc cttggtgtaa gtgtttacaa atctgctcag    4320
ttgggagggg tgcatccggg gggatataat gtgcatcttg gactggatttt ttaggttggc   4380
tatgttccca cccagatccc ttctgggatt catgttgtgc aggaccacca gcacggtata    4440
tccagtgcac ttgggaaatt tatcgtggag cttagacggg aatgcatgga agaacttgga    4500
gacgcccttg tggcctccca gattttccat acattcgtcc atgatgatgg caatgggccc    4560
gtgggaagct gcctgagcaa aaatgtttct gggatcgctc acatcgtagt tatgttccag    4620
ggtgaggtca tcataggaca tctttacgaa tcggggcgg agggtcccgg actgggggat     4680
gatggtaccc tcgggccccg gggcgtagtt cccctcacag atctgcatct cccaggcttt    4740
catttcagag ggagggatca tatccacctg cggagcgatg aaaaacacag tttctggcgc    4800
aggggagatt aactgggatg agagcaggtt tctgagcagc tgtgactttc cacagccggt    4860
gggcccatat atcacgccta tcaccggctg cagctggtag ttaagagagc tgcagctgcc    4920
gtcctcccgg agcaggggg ccacctcgtt cagcatatcc ctgacgtgga tgttctccct     4980
gaccaattcc gccagaaggc gctcgccgcc cagcgaaagc agctcttgca aggaagcaaa    5040
attttcagc ggttttaggc cgtcggccgt gggcatgttt ttcagcgtct gggtcagcag     5100
ttccagcctg tcccacagct cggtgatgtg ctctacggca tctcgatcca gcagatctcc    5160
tcgtttcgcg ggttggggcg gctttcgctg tagggcacca gccgatgggc gtccagcggg    5220
gccagagtca tgtccttcca tgggcgcagg gtcctcgtca gggtggtctg ggtcacggtg    5280
aaggggtgcg ctccggggttg ggcgctggcc agggtgcgct tgaggctggt tctgctggtg   5340
ctgaatcgct gccgctcttc gccctgcgcg tcggccaggt agcatttgac catggtctcg    5400
tagtcgagac cctcggcggc gtgccccttg gcgcggagct ttcccttgga ggtggcgccg    5460
cacgaggggc actgcaggct cttcagggcg tagagcttgg gagcgagaaa cacggactct    5520
ggggagtagg cgtccgcgcc gcaggaagcg cagaccgtct cgcattccac cagccaagtg    5580
agctccgggc ggtcagggtc aaaaaccagg ttgcccccat gcttttgat gcgtttctta     5640
cctcggctct ccatgaggcg gtgtcccttc tcggtgacga agaggctgtc cgtgtccccg    5700
tagaccgact tcagggcct gtcttccagc ggagtgcctc tgtcctcctc gtagagaaac     5760
tctgaccact ctgagacgaa ggcccgcgtc caggccagga cgaaggaggc cacgtgggag    5820
gggtagcggt cgttgtccac tagcgggtcc accttctcca gggtgtgcag gcacatgtcc    5880
ccctcctccg cgtccagaaa agtgattggc ttgtaggtgt aggacacgtg accgggggtt    5940
cccgacgggg gggtataaaa gggggtgggc gccctttcat cttcactctc ttccgcatcg    6000
ctgtctgcga gggccagctg ctggggtaag tattccctct cgaaggcggg catgacctca    6060
gcgctcaggt tgtcagtttc taaaaatgag gaggatttga tgttcacctg tccggaggtg    6120
ataccttga gggtacctgg gtccatctgg tcagaaaaca ctattttttt gttgtcaagc     6180
ttggtggcga acgacccgta gagggcgttg gagagcagct tggcgatgga gcgcagggtc    6240
tggttttgt cgcggtcggc tcgctccttg gccgcgatgt tgagttgcac gtactcgcgg     6300
gccacgcact tccactcggg gaagacggtg gtgcgctcgt ctgggattag gcgcaccctc    6360
```

```
cagcctcggt tgtgcagggt gaccatgtcg acgctggtgg cgacctcgcc gcgcaggcgc    6420
tcgttggtcc agcagaggcg gccgcccttg cgcgagcaga agggggggtag ggggtccagc    6480 tggtcctcgt ttgggggggtc cgcgtcgatg gtgaagaccc cggggagcaa gcgcgggtca    6540
aagtagtcga tcttgcaagc ttgcatgtcc agagcccgct gccattcgcg ggcggcgagc    6600
gcgcgctcgt aggggttgag gggcgggccc cagggcatgg ggtgggtgag cgcggaggcg    6660
tacatgccgc agatgtcata cacgtacagg ggttccctga ggatgccgag gtaggtgggg    6720
tagcagcgcc ccccgcggat gctggcgcgc acgtagtcat agagctcgtg ggaggggggcc   6780 agcatgttgg gcccgaggtt ggtgcgctgg gggcgctcgg cgcggaaggc gatctgcctg    6840
aagatggcat gggagttgga ggagatggtg ggccgctgga agacgttgaa gcttgcttct    6900
tgcaagccca ccgagtccct gacgaaggag gcgtaggact cgcgcagctt gtgcaccagc    6960
tcggcggtga cctggacgtc gagcgcgcag tagtcgaggg tctcgcggat gatgtcatac    7020
ttatcctccc ccttctttt ccacagctcg cggttgagga cgaactcttc gcggtctttc    7080
cagtactctt ggaggggaaa cccgtccgtg tccgaacggt aagagcctag catgtagaac    7140
tggttgacgg cctggtaggg gcaacagccc ttctccacgg gcagcgcgta ggcctgcgcc    7200
gccttgcgga gggaggtgtg ggtgagggcg aaagtgtccc tgaccatgac tttgaggtat    7260
tgatgtttga agtctgtgtc atcgcagccg ccctgttccc acagggtgta gtccgtgcgc    7320
tttttggagc gcgggttggg cagggagaag gtgaggtcat tgaagaggat cttccccgct    7380
cgaggcatga agtttctggt gatgcgaaag ggccctggga ccgaggagcg gttgttgatg    7440
acctgggcgg ccaggacgat ctcgtcaaag ccgtttatgt tgtggcccac gatgtagagc    7500
tccaaaaagc ggggctggcc cttgatggag gggagcttt tgagttcctc gtaggtgagc     7560
tcctcgggcg attccaggcc gtgctcctcc agggcccagt cttgcaagtg agggttggcc    7620
gccaggaagg atcgccagag gtcgcgggcc atgagggtct gcaggcggtc gcggaaggtt    7680
ctgaactgtc gccccacggc catcttttcg ggggtgatgc agtagaaggt gaggggggtct   7740 ttctcccagg ggtcccatct gagctctcgg gcgaggtcgc gcgcggcggc gaccagagcc    7800
tcgtcgcccc ccagtttcat gaccagcatg aagggcacga gctgcttgcc aaaggctccc    7860
atccaagtgt aggtctctac atcgtaggtg acaaagaggc gctccgtgcg aggatgagag    7920
ccgatcggga agaactggat ctcccgccac cagttggagg attggctgtt gatgtggtga    7980
aagtagaagt cccgtctgcg ggccgagcac tcgtgctggc ttttgtaaaa gcgaccgcag    8040
tactggcagc gctgcacggg ttgtatatct tgcacgaggt gaacctggcg acctctgacg    8100
aggaagcgca gcgggaatct aagtcccccg cctggggtcc cgtgtggctg gtggtcttct    8160
actttggttg tctggccgcc agcatctgtc tcctggaggg cgatggtgga gcagaccacc    8220
acgccgcgag agccgcaggt ccagatctcg gcgctcggcg ggcggagttt gatgacgaca    8280
tcgcgcacat tggagctgtc catggtctcc agctcccgcg gcgcaggtc agctgggagt     8340 tcctggaggt tcacctcgca gagacgggtc aaggcgcggg cagtgttgag atggtatctg    8400
atttcaaggg gcgtgttggc ggcggagtcg atggcttgca ggaggccgca gccccggggg    8460
gccacgatgg ttccccgcgg ggcgcgaggg gaggcggaag ctgggggtgt gttcagaagc    8520
ggtgacgcgg gcgggccccc ggaggtaggg ggggttccgg ccccacaggc atgggcggca    8580
ggggcacgtc ttcgccgcgc gcgggcaggg gctggtgctg gctccgaaga gcgcttgcgt    8640
gcgcgacgac gcgacggttg gtgtcctgta tctgacgcct ctgagtgaag accacgggtc    8700
```

-continued

```
ccgtgacctt gaacctgaaa gagagttcga cagaatcaat ctcggcatcg ttgacagcgg    8760
cctggcgcag gatctcctgc acgtcgcccg agttgtcctg gtaggcgatc tctgccatga    8820
actgctcgat ctcttcttcc tggagatctc ctcgtccggc gcgctccacg gtggccgcca    8880
ggtcgttgga gatgcgaccc atgagctgtg agaaggcgtt gagcccgccc tcgttccaga    8940
cccggctgta gaccacgccc ccctcggcgt cgcgagcgcg catgaccacc tgggccaggt    9000
tgagctccac gtgtcgcgtg aagacggcgt agttgcgcag gcgctggaaa aggtagttca    9060
gggtggtggc ggtgtgctcg gcgacgaaga agtacatgac ccagcgccgc aacgtggatt    9120
cattgatgtc ccccaaggcc tccaggcgct ccatggcctc gtagaagtcc acggcgaagt    9180
tgaaaaactg ggagttgcga gcggacacgg tcaactcctc ctccagaaga cggatgagct    9240
cggcgacagt gttgcgcacc tcgcgctcga aggccacggg gggcgcttct tcctcttcca    9300
cctcttcttc catgatcgct tcttcttctt cctcagccgg gacgggaggg ggcggcggcg    9360
gcggggagg ggcgcggcgg cggcggcggc gcaccgggag gcggtcgatg aagcgctcga    9420
tcatctcccc ccgcatgcgg cgcatggtct cggtgacggc gcggccgttc tcccgggggc    9480
gcagctcgaa gacgccgcct ctcatctcgc cgcggggcga gcggccgtga ggtagcgaga    9540
cggcgctgac tatgcatctt aacaattgct gtgtaggtac accgccgagg gacctgattg    9600
agtccagatc caccggatcc gaaaaccttt ggaggaaagc gtctatccag tcgcagtcgc    9660
aaggtaggct gagcaccgtg gcgggcgggg gcgggtctgg agagttcctg gcggagatgc    9720
tgctgatgat gtaattaaag taggcggtct tgagaaggcg gatggtggac aggagcacca    9780
tgtctttggg tccggcctgt tggatgcgga ggcggtcggc catgccccag gcctcgttct    9840
gacaccggcg caggtctttg tagtagtctt gcatgagtct ttccaccggc acctcttctc    9900
cttcctcttc tccatctcgc cggtggtttc tcgcgccgcc catgcgcgtg accccaaagc    9960
ccctgagcgg ctgcagcagg gccaggtcgg cgaccacgcg ctcggccaag atggcctgct   10020
gcacctgagt gagggtcctc tcgaagtcat ccatgtccac gaagcggtgg taggcgcccg   10080
tgttgatggt gtaggtgcag ttggccatga cggaccagtt gacggtctgg tgtcccggct   10140
gcgagagctc cgtgtaccgc aggcgcgaga aggcgcggga atcgaacacg tagtcgttgc   10200
aagtccgcac cagatactgg tagcccacca ggaagtgcgg cggaggttgg cgatagaggg   10260
gccagcgctg ggtggcgggg gcgccgggcg ccaggtcttc cagcatgagg cggtggtatc   10320
cgtagatgta cctggacatc caggtgatgc cggcggcggt ggtggtggcg cgcgcgtagt   10380
cgcggacccg gttccagatg tttcgcaggg gcgagaagtg ttccatggtc ggcacgctct   10440
ggccggtgag gcgcgcgcag tcgttgacgc tctatacaca cacaaaaacg aaagcgttta   10500
cagggctttc gttctgtagc ctggaggaaa gtaaatgggt tgggttgcgg tgtgcccgg    10560
ttcgagacca agctgagctc ggccggctga agccgcagct aacgtggtat tggcagtccc   10620
gtctcgaccc aggccctgta tcctccagga tacggtcgag agcccttttg ctttcttggc   10680
caagcgcccg tggcgcgatc tgggatagat ggtcgcgatg agaggacaaa agcggctcgc   10740
ttccgtagtc tggagaaaca atcgccaggg ttgcgttgcg gcgtaccccg gttcgagccc   10800
ctatggcggc ttgaatcggc cggaaccgcg gctaacgagg gccgtggcag ccccgtcctc   10860
aggaccccgc cagccgactt ctccagttac gggagcgagc ccctttttgtt ttttattttt   10920
tagatgcatc ccgtgctgcg gcagatgcgc ccctcgcccc ggcccgatca gcagcagcaa   10980
cagcaggcat gcagacccc ctctcccctt tccgccccgg tcaccacggc cgcggcggcc   11040
gtgtcgggcg cggggggcgc gctggagtca gatgagccac cgcggcggcg acctaggcag   11100
```

```
tatctggact tggaagaggg cgagggactg gcgcggctgg gggcgaactc tccagagcgc   11160
cacccgcggg tgcagttgaa aagggacgcg cgcgaggcgt acctgccgcg gcagaacctg   11220
tttcgcgacc gcggggggcga ggagcccgag gagatgcgag actgcaggtt ccaagcgggg   11280
cgcgagctgc ggcgcgggct ggacagacag cgcctgctgc gcgaggagga ctttgagccc   11340
gacacgcaga cgggcatcag ccccgcgcgc gcgcacgtag ccgcggccga cctggtgacc   11400
gcctacgagc agacggtaaa ccaggagcgc aacttccaaa agagcttcaa caaccacgtg   11460
cgcacgctgg tggcgcgcga ggaggtgacc ctgggtctca tgcatctgtg ggacctggtg   11520
gaggcgatcg tgcagaaccc cagcagcaag cccctgaccg cgcagctgtt cctggtggtg   11580
cagcacagca gggacaacga ggccttcagg gaggcgctgc tgaacatcac cgagccggag   11640
gggcgctggt cctggacct gataaacatc ctgcagagca tagtggtgca ggagcgcagc   11700
ctgagcctgg ccgagaaggt ggcggccatc aactactcta tgctgagcct gggcaagttc   11760
tacgcccgca agatctacaa gaccccctac gtgcccatag acaaggaggt gaagatagac   11820
agcttctaca tgcgcatggc gctgaaggtg ctgaccctga gcgacgacct gggagtgtac   11880
cgcaacgagc gcatccacaa ggccgtgagc gccagccggc ggcgcgagct gagcgaccgc   11940
gagctgatgc acagtctgca gcgcgcgctg accggcgcgg gcgagggcga cagggaggtc   12000
gagtcctact tcgacatggg ggccgacctg cactggcagc cgagccgccg cgccctggag   12060
gcggcggggg cgtacggcgg cccccctggcg gccgatgacc aggaagagga ggactatgag   12120
ctagaggagg cgagtacct ggaggactga cctggctggt ggtgttttgg tatagatgca   12180
agatccgaac gtggcggacc cggcggtccg ggcggcgctg caaagccagc cgtccggcat   12240
taactcctct gacgactggg ccgcggccat gggtcgcatc atgggccctga ccgcgcgcaa   12300 ccccgaggct ttcaggcagc agcctcaggc caaccggctg gcggccatct tggaagcggt   12360
agtgcccgcg cgctccaacc ccacccacga gaaggtgctg gccatagtca acgcgctggc   12420
ggagagcagg gccatccgcg cggacgaggc cggactggtg tacgatgcgc tgctgcagcg   12480
ggtggcgcgg tacaacagcg gcaacgtgca gaccaacctg gaccgcctgg tgacggacgt   12540
gcgcgaggcc gtggcgcagc gcgagcgctt gcatcaggac ggtaacctgg gctcgctggt   12600
ggcgctaaac gccttcctca gcacccagcc ggccaacgta ccgcgggggc aggaggacta   12660
caccaacttt ttgagcgcgc tgcggctgat ggtgaccgag gtccctcaga gcgaggtgta   12720
ccagtcgggg cccgactact tcttccagac cagcagacag ggcttgcaaa ccgtgaacct   12780
gagccaggct ttcaagaacc tgcgggggct gtggggagtg aaggcgccca ccggcgaccg   12840
ggctacggtg tccagcctgc taacccccaa ctcgcgcctg ctgctgctgc tgatcgcgcc   12900
cttcacggac agcgggagcg tctcgcggga gacctatctg ggccacctgc tgacgctgta   12960
ccgcgaggcc atcgggcagg cgcaggtgga cgagcacacc ttccaagaga tcaccagcgt   13020
gagccacgcg ctggggcagg aggacacggg cagcctgcag gcgaccctga actacctgct   13080
gaccaacagg cggcagaaga ttcccacgct gcacagcctg acccaggagg aggagcgcat   13140
cttgcgctac gtgcagcaga gcgtgagcct gaacctgatg cgcgacggcg tgacgcccag   13200
cgtggcgctg gacatgaccg cgcgcaacat ggaaccgggc atgtacgcct cccaccggcc   13260
gtttatcaac cgcctgatgg actacttgca tcgggcggcg gccgtgaacc ccgagtactt   13320
cactaatgcc attctgaatc cccactggat gccccctccg ggtttctaca acggggactt   13380
tgaggtgccc gaggtcaacg acgggttcct ctgggatgac atggatgaca gtgtgttctc   13440
```

```
acccaacccg ctgcgcgccg cgtctctgcg attgaaggag ggctctgaca gggaaggacc   13500
gaggagtctg gcctcctccc tggctctggg agcggtgggc gccacgggcg cggcggcgcg   13560
gggcagtagc cccttcccca gcctggcaga ctctctgaac agcgggcggg tgagcaggcc   13620
ccgcttgcta ggcgaggagg agtatctgaa caactccctg ctgcagcccg cgagggacaa   13680
gaacgctcag cggcagcagt ttcccaacaa tgggatagag agcctggtgg acaagatgtc   13740
cagatggaag acgtatgcgc aggagtacaa ggagtgggag gaccgccagc cgcggccctt   13800
gccgcccccT aggcagcgct ggcagcggcg cgcgtccaac cgccgctgga ggcaggggcc   13860
cgaggacgat gatgactctg cagatgacag cagcgtgttg gacctgggcg ggagcgggaa   13920
ccccttttcg cacctgcgcc cacgcctggg caagatgttt taaaagaaaa aaaaaataaa   13980
actcaccaag gccatggcga cgagcgttgg ttttttgttc ccttccttag tatgcggcgc   14040
gcggcgatgt tcgaggaggg gcctcccccc tcttacgaga gcgcgatggg gatttctcct   14100
gcggcgcccc tgcagcctcc ctacgtgcct cctcggtacc tgcaacctac agggggggaga   14160 aatagcatct gttactctga gctgcagccc ctgtacgata ccaccagact gtacctggtg   14220
gacaacaagt ccgcggacgt ggcctccctg aactaccaga acgaccacag cgattttttg   14280
accacggtga tccaaaacaa cgacttcacc ccaaccgagg ccagcaccca gaccataaac   14340
ctggataaca ggtcgaactg gggcggcgac ctgaagacca tcttgcacac caacatgccc   14400
aacgtgaacg agttcatgtt caccaactct tttaaggcgc gggtgatggt ggcgcgcgag   14460 caggggggagg cgaagtacga gtgggtggac ttcacgctgc ccgagggcaa ctactcagag   14520
accatgactc tcgacctgat gaacaatgcg atcgtggaac actatctgaa agtgggcagg   14580
cagaacgggg tgaaggaaag cgatatcggg gtcaagtttg acaccagaaa cttccgtctg   14640
ggctgggacc ccgtgaccgg gctggtcatg ccggggggtct acaccaacga ggccttTcaT   14700
cccgacatag tgcttctgcc cggctgtggg gtggacttca cccagagccg gctgagcaac   14760
ctgctgggca ttcgcaagcg gcagccttTc caggagggtt tcaagatcac ctatgaggat   14820
ctgaaggggg gcaacattcc cgcgctcctt gatctggacg cctacgagga gagcttgaaa   14880
cccgaggaga gcgctggcga cagcggcgag agtggcgagg agcaagccgg cggcggtggc   14940
ggcgcgtcgg tagaaaacga aagtacgccc gcagtggcgg cggacgctgc ggaggtcgag   15000
ccggaggcca tgcagcagga cgcagaggag ggcgcacagg agggcgcgca gaaggacatg   15060
aacgatgggg agatcagggg agacacattc gccacccggg gcgaagaaaa agaggcagag   15120
gcggcggcgc cggcgacggc ggaggccgaa accgaggttg aggcagaggc agagcccgag   15180
accgaagtta tggaagacat gaatgatgga gaacgtaggg gcgacacgtt cgccacccgg   15240
ggcgaagaga aggcggcgga ggcagaagcc gcggctgagg aggcggctgc ggctgcggcc   15300
aagactgagg ctgcggctaa ggctgaggtc gaagccaatg ttgcggttga ggctcaggct   15360
gaggaggagg cggcggctga agcagttaag gaaaaggccc aggcagagca ggaagagaaa   15420
aaacctgtca ttcaacctct aaaagaagat agcaaaaagc gcagttacaa cgtcatcgag   15480
ggcagcacct ttacccagta ccgcagctgg taCctggcgt acaactacgg cgacccggtc   15540
aagggggtgc gctcgtggac cctgctctgc acgccgacg tcacctgcgg ctccgagcag   15600
atgtactggt cgctgccgaa catgatgcaa gacccggtga ccttccgctc cacgcggcag   15660
gttagcaact tcccggtggt gggcgccgaa ctgctgcccg tgcactccaa gagttTtTac   15720
aacgagcagg ccgtctactc ccagctgatc cgccaggcca cctctctgac ccacgtgttc   15780
aatcgctttc ccgagaacca gatttTggcg cgcccgccgg ccccaccaT caccaccgtg   15840
```

```
agtgaaaacg ttcctgccct cacagatcac gggacgctac cgctgcgcaa cagcatctca   15900
ggagtccagc gagtgaccat tactgacgcc agacgccgga cctgcccta cgtttacaag    15960 gccttgggca tagtctcgcc gcgcgtcctc tccagtcgca cttttaaaa cacatctacc    16020 cacacgttcc aaaatcatgt ccgtactcat ctcacccagc aacaacaccg gctgggggct   16080
gcgcgcgccc agcaagatgt ttggagggc gaggaagcgc tccgaccagc accctgtgcg    16140
cgtgcgcggc cactaccgcg cgccctgggg agcgcacaag cgcgggcgca cagggcgcac   16200
cactgtggac gacgtcattg actccgtagt ggagcaagcg cgccactaca cacccggcgc   16260
gccgaccgcc cccgccgtgt ccaccgtgga ccaggcgatc gaaagcgtgg tacagggcgc   16320
gcggcactat gccaaccta aaagtcgccg ccgccgcgtg gcccgccgcc atcgccggag    16380
accccgggcc accgccgccg cgcgccttac taaggctctg ctcaggcgcg ccaggcgaac   16440
tggccaccgg gccgccatga gggccgcacg gcgggctgcc gctgccgcaa gcgtcgtggc   16500
cccgcgggca cgaaggcgcg cggccgctgc cgccgccgcc gccatttcca gcttggcctc   16560
gacgcggcgc ggtaacatat actgggtgcg cgactcggta accggcacgc gggtacccgt   16620
gcgctttcgc ccccgcgga attagcacaa gacaacatac acactgagtc tcctgctgtt    16680
gtgtatccca gcggcgaccg tcagcagcgg cgacatgtcc aagcgcaaaa ttaaagaaga   16740
gatgctccag gtcatcgcgc cggagatcta tgggcccccg aagaaggagg aggatgatta   16800
caagccccgc aagctaaagc gggtcaaaaa gaaaagaaa gatgatgatg acgaggcggt    16860
ggagtttgtc cgccgcatgg cacccaggcg ccccgtgcag tggaagggcc ggcgcgtgca   16920
gcgcgttttg cgccccggca ccgcggtggt cttcacgccc ggcgagcgct ccacgcgcac   16980
tttcaagcgg gtgtacgatg aggtgtacgg cgacgaggac ctgttggagc aggccaacca   17040
gcgctttggg gagtttgcat atgggaaacg gccccgcgag agtctaaaag aggacctgct   17100
ggcgctaccg ctggacgagg gcaatcccac cccgagtctg aagccggtaa ccctgcaaca   17160
ggtgctgcct ttgagcgcgc ccagcgagca taagcgaggg ttgaagcgcg aaggcggga    17220 cctggcgccc accgtgcagt tgatggtgcc caagcggcag aagctggagg acgtgctgga   17280
gaaaatgaaa gtagagcccg ggatccagcc cgagatcaag gtccgcccca tcaagcaggt   17340
ggcgcccggc gtgggagtcc agaccgtgga cgttaggatt cccacggagg agatggaaac   17400
ccaaaccgcc actccctctt cggcggccag cgccaccacc ggcaccgctt cggtagaggt   17460
gcagacggac ccctggctac ccgccaccgc tgttgccgcc gccgccccc gttcgcgcgg    17520 gcgcaagaga aattatccag cggccagcgc gctcatgccc cagtacgcac tgcatccatc   17580
catcgtgccc acccccggct accgcgggta ctcgtaccgc ccgcgcagat cagccggcac   17640
tcgcggccgc cgccgccgtg cgaccacaac cagccgccgc cgtcgccgcc gccgccagcc   17700
agtgctgacc cccgtgtctg taaggaaggt ggctcgctcg gggagcacgc tggtggtgcc   17760
cagagcgcgc taccaccccca gcatcgttta aagccggtct ctgtatggtt cttgcagata   17820
tggccctcac ttgtcgcctc cgcttccgg tgccgggata ccgaggaaga actcaccgcc    17880
gcagaggcat ggcgggcagc ggtctccgcg gcggccgtcg ccatcgccgg cgcgcaaaaa   17940
gcaggcgcat gcgcggcggt gtgctgcctc tgctaatccc gctaatcgcc gcggcgatcg   18000
gtgccgtacc cgggatcgcc tccgtggccc tgcaggcgtc ccagaaacgt tgactcttgc   18060
aaccttgcaa gcttgcattt tttgaggaa aaataaaaaa aagtctagac tctcacgctc    18120
gcttggtcct gtgactattt tgtagaaaaa aagatggaag acatcaactt tgcgtcgctg   18180
```

```
gccccgcgtc acggctcgcg cccgttcatg ggagactgga cagatatcgg caccagcaat    18240
atgagcggtg gcgccttcag ctggggcagt ctgtggagcg gccttaaaaa ttttggttcc    18300
accattaaga actatggcaa caaagcgtgg aacagcagca cgggccagat gctgagagac    18360
aagttgaaag agcagaactt ccaggagaag gtggcgcagg gcctggcctc tggcatcagc    18420
ggggtggtgg acatagctaa ccaggccgtg cagaaaaaga taaacagtca tctggacccc    18480
cgtcctcagg tggaggaaat gcctccagcg atggagacgg tgtctcccga gggcaaaggc    18540
gaaaagcgcc cgcggcccga cagagaagag accctggtgt cacacaccga ggagccgccc    18600
tcttacgagg aggcagtcaa ggccggcctg cccaccactc gccccatagc ccccatggcc    18660
accggtgtgg tgggccacag gcaacacact cccgcaacac tagatctgcc cccgccgtcc    18720
gagccgccgc gccagccaaa ggcggcgacg gtgcccgctc cctccacttc cgccgccaac    18780
agagtgcccc tgcgccgcgc cgcgagcggc ccccgggcct cgcgagttag cggcaactgg    18840
cagagcacac tgaacagcat cgtgggcctg ggagtgagga gtgtgaagcg ccgccgttgc    18900
tactgaatga gcaagctagc taacgtgttg tatgtgtgta tgcgtcctat gtcgccgcca    18960
gaggagctgt tgagccgccg gcgccgtctg cactccagcg aatttcaaga tggcgacccc    19020
atcgatgatg cctcagtggt cgtacatgca catctcgggc caggacgctt cggagtacct    19080
gagccccggg ctggtgcagt tcgcccgcgc cacagacacc tacttcaaca tgagtaacaa    19140
gttcaggaac cccactgtgg cgcccaccca cgatgtgacc acggaccggt cgcagcgcct    19200
gacgctgcgg ttcatccccg tggatcggga ggacaccgcc tactcttaca aggcgcggtt    19260
cacgctggcc gtgggcgaca accgcgtgct ggacatggcc tccacttact ttgacatcag    19320
gggggtgctg gacaggggcc ccaccttcaa gccctactcg ggtactgcct acaactccct    19380 ggccccccaag ggcgctccca attcttgcga gtgggaacaa gatgaaccag ctcaggcagc    19440
aatagctgaa gatgaagaag aacttgaaga agaacaagct caggacgaac aggcgcccac    19500
taagaaaacc catgtatacg cccaggcacc tctttctggt gaaaaaatta ctaaggatgg    19560
tttgcaaata ggtgtggatg ccacacaggc gggagataac cctatatatg ctgataaaac    19620
attccaaccc gaacctcaga taggtgagtc tcagtggaac gaggctgatg ccacagtagc    19680
aggaggcaga gtcttaaaaa agaccacccc tatgagacct tgctatggat cctatgccaa    19740
acctactaat gccaatggcg gtcaagggat catggtggcc aatgatcagg gagcgcttga    19800
atctaaagtt gagatgcaat ttttctccac cacaacgtct cttaatgtaa gggaaggtga    19860
aaacaatctt cagccaaaag tagtgctata cagcgaagat gttaacttgg aatcccctga    19920
cactcatttg tcttacaaac taaaaagga tgacaccaac tctaaaatca tgttgggtca    19980
gcaagccatg cccaacagac ccaacctcat tgcttttagg gacaacttta ttggacttat    20040
gtactacaac agcacaggca acatgggagt gctggcagga caggcctccc agctaaacgc    20100
tgtggtagac ttgcaagaca gaaacacaga gctgtcatac caactgatgc ttgattccat    20160
tggagacaga tcaagatact tttccatgtg aaccaggca gtggacagct atgacccaga    20220
tgtcagaatc attgaaaacc atggggttga agatgagctg cccaactatt gctttccct    20280 gggcggtatt ggaattacag acacatacca gtgcataaaa ccaaccgcag ctgctaataa    20340
cactacatgg tctaaggatg aagaatttag tgatcgcaat gaaataggg tgggaaacaa    20400 cttcgccatg gagatcaaca tccaggccaa cctctggagg aacttcctct atgcgaacgt    20460
ggggctctac ctgccagaca agctcaagta caacccccacc aacgtggaca tctctgacaa    20520
ccccaacacc tatgactaca tgaacaagcg tgtggtggct cccggcctgg tggactgctt    20580
```

```
tgtcaatgtg ggagccaggt ggtccctgga ctacatggac aacgtcaacc ccttcaacca   20640
ccaccgcaat gcgggtctgc gctaccgctc catgatcctg ggcaacgggc gctacgtgcc   20700
cttccacatt caggtgcccc agaagttctt tgccatcaag aacctcctcc tcctgccggg   20760
ctcctacact tacgagtgga acttcaggaa ggatgtcaac atggtcctgc agagctctct   20820
gggcaatgac cttagggtgg acggggccag catcaagttt gacagcgtca ccctctatgc   20880
taccttcttc cccatggctc acaacaccgc ctccacgctc gaggccatgc tgaggaacga   20940
caccaacgac cagtccttca atgactacct ctctggggcc aacatgctct accccatccc   21000
cgccaaggcc accaacgtgc ccatctccat tccctctcgc aactgggccg ccttcagagg   21060
ctgggccttt acccgcctta agaccaagga aacccctcc ctgggctcgg gttttgaccc   21120
ctactttgtc tactcgggat ccatccccta cctggatggc accttctacc tcaaccacac   21180
ttttaagaag atatccatca tgtatgactc ctccgtcagc tggccgggca atgaccgcct   21240
gctcaccccc aatgagttcg aggtcaagcg cgccgtggac ggcgagggct acaacgtggc   21300
ccagtgcaac atgaccaagg actggttcct ggtgcagatg ctggccaact acaacatagg   21360
ctaccagggc ttctacatcc cagagagcta caaggacagg atgtactcct tcttcagaaa   21420
tttccaaccc atgagcaggc aggtggtgga cgagaccaaa tacaaggact atcaggccat   21480
tggcatcact caccagcaca caactcggg attcgtgggc tacctggctc ccaccatgcg   21540
cgaggggcag gcctaccccg ccaacttccc ctacccgttg ataggcaaaa ccgcggtcga   21600
cagcgtcacc cagaaaaagt tcctctgcga ccgcaccctc tggcgcatcc ccttctctag   21660
caacttcatg tccatgggtg cgctcacgga cctgggccag aacctgctct atgccaactc   21720
cgcccatgcg ctggacatga cttttgaggt ggaccccatg gacgagccca cccttctcta   21780
tattgtgttt gaagtgttcg acgtggtcag agtgcaccag ccgcaccgcg tgtcatcga   21840 gaccgtgtac ctgcgcacgc ccttctcggc cggcaacgcc accacctaag gagacagcgc   21900
cgccgcctgc atgacgggtt ccaccgagca agagctcagg gccatcgcca gagacctggg   21960
atgcggaccc tatttttgg gcacctatga caaacgcttc ccgggcttca tctcccgaga   22020
caagctcgcc tgcgccatcg tcaacacggc cgcgcgcgag accggggcg tgcactggct   22080 ggcctttggc tgggacccgc gctccaaaac ctgctacctc ttcgacccct ttggcttctc   22140
cgatcagcgc ctcagacaga tctatagagtt tgagtacgag gggctgctgc cccgcagcgc   22200
gcttgcctcc tcgcccgacc gctgcatcac ccttgagaag tccaccgaga ccgtgcaggg   22260
gccccactcg gccgcctgcg gtctcttctg ctgcatgttt ttgcacgcct ttgtgcgctg   22320
gccccagagt cccatggatc gcaaccccac catgaacttg ctcaagggag tgcccaacgc   22380
catgctccag agcccccagg tccagcccac cctgcgccac aaccaggaac agctctaccg   22440
cttcctggag cgccactccc cctacttccg cagtcacagc gcgcacatcc gggggccac   22500 ctctttctgc cacttgcaag aaaacatgca agacggaaaa tgatgtacag ctcgcttttt   22560
aataaatgta aagactgtgc actttattta tacacgggct ctttctggtt atttattcaa   22620
caccgccgtc gccatctaga aatcgaaagg gttctgccgc gcgtcgccgt gcgccacggg   22680
cagagacacg ttgcgatact ggaagcggct cgccccactta aactcgggca ccaccatgcg   22740
gggcagtggt tcctcgggga agttctcgcc ccacagggtg cgggtcagct gcagcgcgct   22800
caggaggtcg ggagccgaga tcttgaagtc gcagttgggg ccggaaccct gcgcgcgcga   22860
gttgcggtac acggggttgc agcactggaa caccagcagg gccggattat gcacgctggc   22920
```

```
cagcaggctc tcgtcgctga tcatgtcgct gtccagatcc tccgcgttgc tcagggcgaa   22980
cggggtcatc ttgcagacct gcctgcccag gaaaggcggc agcccgggct tgccgttgca   23040
gtcgcagcgc agggcatca gcaggtgccc gcggcccgac tgcgcctgcg ggtacagcgc    23100
gcgcatgaag gcttcgatct gcctgaaagc cacctgcgtc ttggctccct ccgaaaagaa   23160
catcccacag gacttgctgg agaactggtt cgcgggacag ctggcatcgt gcaggcagca   23220
gcgcgcgtcg gtgttggcga tctgcaccac gttgcgaccc caccggttct tcactatctt   23280
ggccttggaa gcctgctcct tcagcgcgcg ctggccgttc tcgctggtca catccatctc   23340
tatcacctgc tccttgttga tcatgtttgt accgtgcaga cacttcaggt cgccctccgt   23400
ctgggtgcag cggtgctccc acagcgcgca accggtgggc tcccaatttt tgtgggtcac   23460
ccccgcgtag gcctgcaggt aggcctgcaa gaagcgcccc atcatggcca caaaggtctt   23520
ctggctcgta aaggtcagct gcaggccgcg atgctcttcg ttcagccagg tcttgcagat   23580
ggcggccagc gcctcggtct gctcgggcag catcctaaaa tttgtcttca ggtcgttatc   23640
cacgtggtac ttgtccatca tggcgcgcgc cgcctccatg cccttctccc aggcggacac   23700
catgggcagg cttagggggt ttatcacttc caccggcgag gacaccgtac tttcgatttc   23760
ttcttcctcc ccctcttccc ggcgcgcgcc cacgctgctg cgcgctctca ccgcctgcac   23820
caaggggtcg tcttcaggca agcgccgcac cgagcgcttg ccgcccttga cctgcttaat   23880
cagcaccggc gggttgctga agcccaccat ggtcagcgcc gctgctctt cttcgtcttc     23940 gctgtctacc actatctctg gggaagggct tctccgctct gcggcggcgc gcttctttt     24000 tttcttggga gcggccgtga tggagtccgc cacggcgacg gaggtcgagg gcgtggggct   24060
gggggtgcgc ggtaccaggg cctcgtcgcc ctcggactct tcctctgact ccaggcggcg   24120
gcggagtcgc ttctttgggg gcgcgcgcgt cagcggcggc ggagacgggg acggggacgg   24180
ggacgggacg ccctccacag ggggtggtct tcgcgcagac ccgcggccgc gctcggggt     24240 cttctcgagc tggtcttggt cccgactggc cattgtatcc tcctcctcct aggcagagag   24300
acataaggag tctatcatgc aagtcgagaa ggaggagagc ttaaccaccc cctctgagac   24360
cgccgatgcg cccgccgtcg ccgtcgcccc gctgccgcc gacgcgcccg ccacaccgag    24420 cgacacccc gcggacccc ccgccgacgc accctgttc gaggaagcgg ccgtggagca      24480
ggacccgggc tttgtctcgg cagaggagga tttgcgagag gaggaggata aggagaagaa   24540
gccctcagtg ccaaaagatg ataaagagca agacgagcac gacgcagatg cacaccaggg   24600
tgaagtcggg cgggggacg gagggcatga cggcgccgac tacctagacg aagggaacga    24660
cgtgctcttg aagcacctgc atcgtcagtg cgccattgtt tgcgacgctc tgcaggagcg   24720
cagcgaagtg cccctcagcg tggcggaggt cagccacgcc tacgagctca gcctcttctc   24780
cccccgggtg ccccccgcc gccgcgaaaa cggcacatgc gagcccaacc cgcgcctcaa     24840
cttctacccc gcctttgtgg tacccgaggt cctggccacc tatcacatct tctttcaaaa   24900
ttgcaagatc ccctctcgt gccgcgccaa ccgtagccgc gccgataaga tgctggccct     24960
gcgccagggc gaccacatac ctgatatcgc cgctttggaa gatgtaccaa agatcttcga   25020
gggtctgggt cgcaacgaga agcgggcagc aaactctctg caacaggaaa acagcgaaaa   25080
tgagagtcac accggggtac tggtggagct cgagggcgac aacgcccgcc tggcggtggt   25140
caagcgcagc atcgaggtca cccactttgc ctaccccgcg ctaaacctgc cccccaaagt   25200
catgaacgcg gccatggacg ggctgatcat gcgccgcggc cggcccctcg ctccagatgc   25260
aaacttgcat gaggagaccg aggacggcca gcccgtggtc agcgacgagc agctggcgcg   25320
```

```
ctggctggag accgcggacc ccgccgaact ggaggagcgg cgcaagatga tgatggccgt     25380
ggtgctggtc accgtagagc tggagtgtct gcagcgcttc ttcggcgacc ccagagatgca    25440 gagaaaggtc gaggagaccc tgcactacac cttccgccag ggctacgtgc gccaggcttg    25500
caagatctcc aacgtggagc tcagcaacct ggtgtcctac ctgggcatct tgcatgagaa    25560
ccgcctcggg cagagcgtgc tgcactccac cctgcgcggg gaggcgcgcc gcgactacgt    25620
gcgcgactgc gtttacctct tcctctgcta cacctggcag acggccatgg gggtctggca    25680
gcagtgcctg gaggagcgca acctcaagga gctggagaag ctcctgcagc gcgcgctcaa    25740
agatctctgg acgggctaca acgagcgctc ggtggccgcc gcgctggccg acctcatctt    25800
ccccgagcgc ctgctcaaaa ccctccagca ggggctgccc gacttcacca gccaaagcat    25860
gttgcaaaac ttcaggaact ttatcctgga gcgttctggc atcctacccg ccacctgctg    25920
cgccctgccc agcgactttg tccccctcgt gtaccgcgag tgcccccgc cgctgtgggg    25980 tcactgctac ctgttccaac tggccaacta cctgtcctac cacgcggacc tcatggagga    26040
ctccagcggc gaggggctca tggagtgcca ctgccgctgc aacctctgca cgccccaccg    26100
ctccctggtc tgcaacaccc aactgctcag cgagagtcag attatcggta ccttcgagct    26160
acagggtccg tcctcctcag acgagaagtc cgcggctccg gggctaaaac tcactccggg    26220
gctgtggact tccgcctacc tgcgcaaatt tgtacctgaa gactaccacg cccacgagat    26280
caggttttac gaagaccaat cccgcccgcc caaggcggag ctgaccgcct gcgtcatcac    26340
ccagggcgag atcctaggcc aattgcaagc catccaaaaa gcccgccaag acttttttgct    26400 gaagaagggt cgggggtgt atctggaccc ccagtcgggt gaggagctca cccggttcc     26460 cccgctgccg ccgccgcggg accttgcttc ccaggataag catcgccatg gctcccagaa    26520
agaagcagca gcggccgcca ctgccgccac cccacatgct ggaggaagag gaggaatact    26580
gggacagtca ggcagaggag gtttcggacg aggaggagcc ggagacggag atggaagagt    26640
gggaggagga cagcttagac gaggaggctt ccgaagccga agaggcagac gcaacaccgt    26700 cacccctcggc cgcagccccc tcgcaggcgc cccgaagtc cgctcccagc atcagcagca    26760
acagcagcgc tataacctcc gctcctccac cgccgcgacc cacggccgac cgcagaccca    26820
accgtagatg ggacaccacc ggaaccgggg ccggtaagtc ctccgggaga ggcaagcaag    26880
cgcagcgcca aggctaccgc tcgtggcgcg ctcacaagaa cgccatagtc gcttgcttgc    26940
aagactgcgg ggggaacatc tccttcgccc gccgcttcct gctcttccac cacggtgtgg    27000 ccttccccg taacgtcctg cattactacc gtcatctcta cagcccctac tgcggcggca    27060
gtgagccaga cacggtcggc ggcggcggcg gcgcccgttt cggcgcctag gaagacccag    27120
ggcaagactt cagccaagaa actcgcgcg ccgcggcga acgcggtcgc ggggccctg     27180 cgcctgacgg tgaacgaacc cctgtcgacc cgcgaactga ggaaccgaat cttccccact    27240
ctctatgcca tcttccagca gagcagaggg caggatcagg aactgaaagt aaaaaacagg    27300
tctctgcgct ccctcacccg cagctgtctg tatcacaaga gcgaagacca gcttcggcgc    27360
acgctggagg acgctgaggc actcttcagc aaatactgcg cgctcactct taaggactag    27420
ctccgcgccc ttctcgaatt taggcgggaa cgcctacgtc atcgcagcgc cgccgtcatg    27480
agcaaggaca ttcccacgcc atacatgtgg agctatcagc cgcagatggg actcgcggcg    27540
ggcgcctccc aagactactc caccccgcatg aactggctca gtgccggccc acacatgatc    27600
tcacaggtta atgatatccg cacccatcga aaccaaatat tggtggagca ggcggcaatt    27660
```

```
accaccacgc cccgcaataa tcccaacccc agggagtggc ccgcgtccct ggtgtatcag    27720
gaaattcccg gccccaccac cgtactactt ccgcgtgatt cccaggccga agtccaaatg    27780
actaactcag gggcacagct cgcgggcggc tgtcgtcaca gggtgcggcc tcctcgccag    27840
ggtataactc acctggagat ccgaggcaga ggtattcagc tcaacgacga gtcggtgagc    27900
tcctcgctcg gtctcagacc tgacgggacc ttccagatag ccggagccgg ccgatcttcc    27960
ttcacgcccc gccaggcgta cctgactctg caaagctcgt cctcggcgcc gcgctcgggc    28020
ggcatcggga ctctccagtt cgtgcaggag tttgtgccct cggtctactt caaccccttc    28080
tcgggctctc ccggtcgcta cccggaccag ttcatctcga actttgacgc cgcgagggac    28140
tcggtggacg gctacgactg aatgtcgggt ggacccggtg cagagcaact tcgcctgaag    28200
cacctcgacc actgccgccg ccctcagtgc tttgcccgct gtcagaccgg tgagttccag    28260 tactttccc tgcccgactc gcacccggac ggcccggcgc acggggtgcg cttttttcatc    28320 ccgagtcagg tgcgctctac cctaatcagg gagtttaccg cccgtcccct actggcggag    28380
ttggaaaagg ggccttctat cctaaccatt gcctgcatct gctctaaccc tggattgcac    28440
caagatcttt gctgtcattt gtgtgctgag tataataaag gctgagatca gaatctactc    28500
gggctcctgt cgccatcctg tcaacgccac cgtccaagcc cggcccgatc agcccgaggt    28560
gaacctcacc tgcggtctgc accggcgcct gaggaaatac ctagcttggt actacaacag    28620
cactcccttt gtggtttaca acagctttga ccaggacggg gtctcactga gggataacct    28680
ctcgaacctg agctactcca tcaggaagaa cagcacccct gagctacttc ctccttacct    28740
gcccgggact taccagtgtg tcaccggtcc ctgcacccac acccacctgt tgatcgtaaa    28800
cgactctctt ccgagaacag acctcaataa ctcctcttcg cagttcccca gaacaggagg    28860
tgagctcagg aaaccccggg taagaagggg tggacgagag ttaacacttg tggggttttct   28920 ggtgtatgtg acgctggtgg tggctctttt gattaaggct tttccttcca tgtctgaact    28980
ctccctcttc ttttatgaac aactcgacta gtgctaacgg gacccaccc aacgaatcgg     29040 gattgaatat cggtaaccag gttgcagttt cactttgat taccttcata gtcctcttcc     29100
tgctagtgct gtcgcttctg tgcctgcgga tcggggctg ctgcatccac gtttatatct     29160
ggtgctggct gtttagaagg ttcggagacc atcgcaggta gaataaacat gctgctgctt    29220
accctctttg tcctggcgct ggccgccagc tgccaagcct tttccgaggc tgactttata    29280
gagccccagt gtaatgtgac ttttaaagcc catgcacagc gttgtcatac tataatcaaa    29340
tgtgccaccg aacacgatga ataccttatc cagtataaag ataaatcaca caaagtggca    29400
cttgttgaca tctggaaacc cgaagaccct ttggaataca atgtgaccgt tttccagggt    29460
gacctcttca aaatttacaa ttacactttc ccatttgacc agatgtgtga ctttgtcatg    29520
tacatggaaa agcagcacaa gctgtggcct ccgactcccc agggctgtgt ggaaaatcca    29580 ggctcttttct gcatgatctc tctctgtgta actgtgctgg cactaatact cacgcttttg    29640
tatatcagat ttaaatcaag gcaaagcttc attgatgaaa agaaaatgcc ttaatcgctt    29700
tcacgcttga ttgctaacac cgggtttta tccgcagaat gattggaatc accctactaa    29760
tcacctccct ccttgcgatt gcccatgggt tggaacgaat cgaagtccct gtgggggcca    29820
atgttaccct ggtggggcct gtcggcaatg ctacattaat gtgggaaaaa tatactaaaa    29880
atcaatgggt ctcttactgc actaacaaaa atagccacaa gcccagagcc atctgcgatg    29940
ggcaaaatct aaccttgatt gatgttcaat tgctggatgc gggctactat tatgggcagc    30000
tgggtacaat gattaattac tggagacccc acagagatta catgctccac gtagtaaagg    30060
```

```
gtccccttag cagcccaccc actaccacct ctactacccc cactaccacc actactccca   30120
ccaccagcac tgccgcccag cctcctcata gcagaacaac cacttttatc aattccaagt   30180
cccactcccc ccacattgcc ggcgggccct ccgcctcaga ctccgaaacc accgagatct   30240
gcttctgcaa atgctctgac gccattgccc aggatttgga agatcacgag gaagatgagc   30300
atgacttcgc agatgcatgc caggcatcag agccagaagc gctgccggtg gccctcaaac   30360
agtatgcaga ccccacacc acccccgacc ttcctccacc ttcccagaag ccaagtttcc   30420
tgggggaaaa tgaaactctg cctctctcca tactcgctct gacatctgtt gctatgttga   30480
ccgctctgct ggtgcttcta tgctctatat gctacctgat ctgctgcaga aagaaaaaat   30540
ctcacggcca tgctcaccag cccctcatgc acttcccttaa ccctccagag ctgggcgacc   30600
acaaacttta agtctgcagt aactatctgc ccatcccttg tcagtcgaca gcgatgagcc   30660
ccactaatct aacggcctct ggacttacaa catcgtctct taatgagacc accgctcctc   30720
aagacctgta cgatggtgtc tccgcgctgg ttaaccagtg ggatcacctg ggcatatggt   30780
ggctcctcat aggagcagtg accctgtgcc taatcctggt ctggatcatc tgctgcatca   30840
aaagcagaag acccaggcgg cggcccatct acaggccctt tgtcatcaca cctgaagatg   30900
atgatgacac cacttccagg ctgcagaggc taaagcagct actcttctct tttacagcat   30960
ggtaaattga atcatgcctc gcattttcat ctacttgtct ctccttccac tttttctggg   31020
ctcttctaca ttggccgctg tgtcccacat cgaggtagac tgcctcacgc ccttcacagt   31080
ctacctgctt ttcggcttg tcatctgcac ctttgtctgc agcgttatca ctgtagtgat   31140
ctgcttcata cagtgcatcg actacgtctg cgtgcgggtg gcttacttta gacaccaccc   31200
ccagtatcgc aacagggaca tagcggctct cctaagactt gtttaaaatc atggccaaat   31260
taactgtgat tggtcttctg atcatctgct gcgtcctagc cgcgattggg actcaagctc   31320
ctaccaccac cagcgctccc agaaagagac atgtatcctg cagcttcaag cgtccctgga   31380
atatacccca atgctttact gatgaacctg aaatctcttt ggcttggtac ttcagcgtca   31440
ccgcccttct tatcttctgc agtacggtta ttgcccttgc catctaccct tcccttgacc   31500
tgggctggaa tgctgtcaac tctatggaat atcccacctt cccagaacca gacctgccag   31560
acctggttgt tctaaacgcg tttcctcctc ctgctcccgt tcaaaatcag tttcgccctc   31620 cgtccccac gcccactgag gtcagctact ttaatctaac aggcggagat gactgaaaac   31680
ctagacctag aaatggacgg tctctgcagc gagcaacgca cactagagag gcgccggcaa   31740
aaagagctcg agcgtcttaa acaagagctc caagacgcgg tggccataca ccagtgcaaa   31800 aaggtgtct tctgtctggt aaaacaggcc acgctcacct atgaaaaaac aggtgacacc   31860
caccgcctag gatacaagct gcccacacag cgccaaaagt tcgccctcat gataggcgaa   31920
caacccatca ccgtgaccca gcactccgtg gagacagaag gctgcataca tgctccctgt   31980
aggggcgctg actgcctcta cacttgatc aaaacccctct gcggtctcag agaccttatc   32040
cctttcaatt aatcataact gtaatcaata aaaatcact tacttgaaat ctgatagcaa   32100
gcctctgtcc aattttttca gcaacacttc cttcccctcc tcccaactct ggtactctag   32160
gcgcctccta gctgcaaact tcctccacag tctgaaggga atgtcagatt cctcctcctg   32220
tccctccgca cccacgatct tcatgttgtt gcagatgaaa cgcgcgagat cgtctgacga   32280
gaccttcaac cccgtgtacc cctacgatac cgagatcgct ccgacttctg tccctttcct   32340
taccctcccc tttgtgtcat ccgcaggaat gcaagaaaat ccagctgggg tgctgtccct   32400
```

```
gcacttgtca gagccccttg ccacccacaa tgggcccctg actctaaaaa tgggggcgg     32460 cctgaccctg gacaaggaag ggaatctcac ttcccaaaac atcaccagtg tcgatccccc     32520
tctcaaaaaa agcaagaaca acatcagcct tcagaccgcc gcaccctcg ccgtcagctc      32580 cggggcccta acacttttg ccactccccc cctagcggtc agtggtgaca accttactgt      32640
gcagtctcag gccctctca ctttggaaga ctcaaaacta actctggcca ccaaaggacc      32700
cctaactgtg tccgaaggca aacttgtcct agaaacagag gctcccctgc atgcaagtga      32760
cagcagcagc ctgggcctta gcgttacggc cccacttagc attaacaatg acagcctagg      32820
actagatctg caggcaccca ttgtctctca aaatggaaaa ctggctctaa atgtagcagg      32880 cccctagct gtggccaatg gcattaatgc tttgacagta ggcacaggca aaggtattgg       32940
tctaaatgaa accagcactc acttgcaagc aaagttggtc gccccctag gctttgatac       33000 caatggcaac attaagctaa gcgttgcagg aggcatgaga ctaaataatg acacacttat      33060
actagatgta aactacccat ttgaagctca aggccaacta agtctaagag tgggccaggg      33120
tccgctgtat gtagattcta gcagccataa cctgaccatt agatgcctta gaggattata     33180
cataacatcg tctaataacc aaaccggtct agaggccaac ataaaactaa caaaaggcct     33240
tgtctatgat ggaaatgcca tagcagtcaa tgttggtcaa ggattgcaat acagcactac     33300
tgccacatcg gaaggtgtgt atcctataca gtctaagata ggtttgggaa tggaatatga    33360
taccaacgga gccatgatga caaaactagg ctctggacta agctttgaca attcaggagc     33420
cattgtagtg ggaaacaaaa atgatgacag gcttactctg tggactacac cagacccatc     33480
tcctaactgt agaattttatt ctgaaaaaga tactaaacta accttggtgc tgactaagtg     33540
tggcagccaa atcctaggca cagtatctgc ccttgctgtc agaggcagcc ttgcgcccat     33600
cactaatgca tccagcatag tccaaatatt tctaagattt gatgaaaatg gactattgat     33660
gagcaactca tcgctagacg gtgattactg gaattacaga aatggggact ccactaatag     33720
cacaccatat acaaatgcag taggcttttat gcctaatcta gcagcctatc ctaaaggtca     33780
ggctacagct gcaaaaagca gtattgtaag ccaggtatac atggatggtg acactactaa     33840
acctataaca ctaaaaataa acttcaatgg cattgatgaa acaacagaaa ataccccctgt    33900 tagtaaatat tccatgacat tctcatggag ctggcccacc gcaagctaca taggccacac    33960
ttttgcaaca aactcttta ctttctccta catcgcccaa gaataaagaa agcacagaga       34020
tgcttgtttt gatttcaaaa ttgtgtgctt ttatttattt tcagcttaca gtatttccag    34080
tagtcattcg aataaagctt aatcaaactg catgagaacc cttccacata gcttaaatta    34140
gcaccagtgc aaatggagaa aattcaacat accttttta tccagatatc agagaactct     34200
agtggtcagt tttccccccac cctcccagct cacagaatac acagtccttt cccccggct     34260 ggctttaaac aacactatct cattggtaac agacatattc ttaggtgtaa taatccacac    34320
ggtctcttgg cgggccaagc gctggtcggt gatgttaata aactccccag gcagctcttt    34380
caagttcacg tcgctgtcca actgctgaag cgctcgcggc tccgactgcg cctctagcgg   34440
aggcaacggc aacacccgat ccttgatcta taaggagta gagtcataat cccccataag   34500
aatagggcgg tgatgcagca acaaggcgcg cagcaactcc tgccgccgcc tctccgtacg    34560
acaggaatgc aacggcgtgg tggtctcctc cgcgataatc cgcaccgctc gcagcatcag    34620
catcctcgtc ctccgggcac agcagcgcat cctgatctca ctgagatcgg cgcagtaagt    34680
gcagcacaaa accaagatgt tatttaagat cccacagtgc aaagcactgt acccaaagct    34740
catggcggga aggacagccc ccacgtgacc atcataccag atccttaggt aaatcaaatg    34800
```

```
acgacctctc ataaacacgc tggacatgta catcacctcc ttgggcatgc gctgattcac  34860
cacctctcga taccacaagc atcgctgatt aattaaagac ccctcaagca ccatcctgaa  34920
ccaggaagcc agcacctgac cccccgccag gcactgcagg gaccccggtg aattgcagtg  34980
gcagtgaaga ctccagcgct cgtagccgtg aaccatagac ccggtcatta tatccacatt  35040
ggcacaacac aaacacactt tcatacactt tttcatgatt agcagctcct ctctagtcag  35100
gaccatatcc caaggaatca cccactcttg aatcaaggta aatcccacac agcagggcag  35160
gcctctcaca taactcacgt tatgcatagt gagcgtgtcg caatctggaa ataccggatg  35220
atcttccatc accgaagctc gcgtctccgt ctcaaaggga ggtaaacggt ccctcgtgta  35280
gggacagtgg cgggataatc gagatcgtgt tgaacgtaga gtcatgccaa agggaacagc  35340
ggacgtactc atatttcctc cagcagaacc aagtgcgcgc gtggcagcta tccctgcgtc  35400
ttctgtctcg ccgcctgccc cgctcggtgt agtagttgta atacagccac tccctcagac  35460
cgtcaaggcg ctccctggcg tccggatcta taacaacacc gtcctgcagc gccgccctga  35520
tgacatccac caccgtagag tatgccaagc ccagccagga aatgcattca ctttgacagc  35580
gagagatagg aggagcggga agagatggaa gaaccatgat agtaaaagac ttttattcca  35640
atcgatcctc tacaatgtca aagtgtagat ctataagatg acactggtct cctccgctga  35700
gtcgatcaaa ataacagct aaaccacaaa caacacgatt ggtcaaatgc tccacaaggg  35760
cttgcagcat aaaatcgcct cgaaagtcca ccgcaagcat aacatcaaag ccaccgcccc  35820
tatcatgatc tataataaaa accccacagc tatccaccag acccataaag ttttcatctc  35880
tccatcgtga aaaaatattt acaagctcct cctttaaatc acctccaacc aattgaaaaa  35940
gttgagccaa accgccctcc accttcattt tcagcaagcg catcatgatt gcaaaaattc  36000
aggctcctga gacacctgta taagattgag aagcggaacg ttaacgtcaa tgtttcgctc  36060
gcgaagatcg cgcctcagtg caagcatgat ataatcccac aggtcggagc ggatcagcga  36120
ggacatctcc ccgccaggaa ccaactcaac ggagcctatg ctgattataa tacgcatatt  36180
cggggctatg ctgaccagca cggccccccaa ataggcgtac tgcataggcg gcgacaaaaa  36240
gtgaacagtt tgggttaaaa aatcaggcaa acagtcgcgc aaaaaagcaa gaacatcata  36300
accatgctca tgcaaataga tgcaagtaag ctcaggaacg accacagaaa aatgcacaat  36360
ttttctctca aacatgactg cgagccctgc aaaaaataaa aaagaaacat tacacaagag  36420
tagcctgtct tacgatggga tagactactc taaccaacat aagacgggcc acaacatcgc  36480
ccgcgtggcc ataaaaaaaa ttgtccgtgt gattaaaaag aagcacagat agctggccag  36540
tcatatccgg agtcatcacg tgtgaacccg tgtagacccc cggggttgga catcggcca  36600 aacaaagaaa gcggccaatg tacccaggag gaatcataac actaagacga agatacaaca  36660
gaataacccc atgaggggga ataacaaagt tagtaggtga ataaaaacga taaacacccg  36720
aaactccctc ctgcgtaggc aaaatagcac cctccccttc caaaacaaca tatagcgctt  36780
ccacagcagc catgacaaaa gactcaaaac actcaaaaga ctcagtctta ccaggaaaat  36840
aaaagcactc tcacagcacc agcactaatc agagtgtgaa gagggccaag tgccgaacga  36900
gtatatatag gaataaaaaa tgacgtaaat gtgtaaaggt cagaaaacgc ccagaaaaat  36960
acacagacca acgcccgaaa cgaaaacccg cgaaaaaata cccagaactt cctcaacaac  37020
cgccacttcc ggtttctcac ggtacgtcac ttccgcaaga aaagcaaaac tacatttccc  37080
acatgtgtaa aaacgaaacc ccgccccttg taactgccca caacttacat catcaaaaca  37140
```

```
taaactccta cgtcacccgc cccgcctctc cccgcccacc tcattatcat attggccaca    37200
atccaaaata aggtatatta ttgatgatg                                     37229

<210> SEQ ID NO 22
<211> LENGTH: 37232
<212> TYPE: DNA
<213> ORGANISM: Gorilla beringei beringei

<400> SEQUENCE: 22
catcatcaat aatataccct attttggatt gtggccaata tgataatgag gtgggcgggg      60
agaggcgggg cgggtgacgt aggacgcgcg agtagggttg ggaggtgtgg cggaagtgtg     120
gcatttgcaa gtgggaggag ctcacatgca agcttccgtc gcggaaaatg tgacgttttt     180
gatgagcgcc gcctacctcc ggaagtgcca atttcgcgc gcttttcacc ggatatcgta      240
gtaattttgg gcgggaccat gtaagatttg gccatttcg cgcgaaaagt gaaacgggga      300
agtgaaaact gaataatagg gcgttagtca tagcgcgtaa tatttaccga gggccgaggg     360
actttgaccg attacgtgga ggactcgccc aggtgttttt tacgtgaatt ccgcgttcc      420 gggtcaaagt ctccgttttt attgtcaccg tcatttgacg cggagggtat ttaaacccgc     480
tgcgctcctc aagaggccac tcttgagtgc cagcgagaag agtttctcc tctgctccgc     540 ttcggtgatc gaaaaatgag acacatagcc tgcactccgg gtcttttgtc cggtcgggcg     600
gcggccgagc ttttgacgc tttgatcaat gatgtcctaa gcgatgattt tccgtctact      660 acccactta gcccacctac tcttcacgaa ctgtacgatc tggatgtact ggtggatgtg      720
aacgatccca acgaggaggc ggtttctgcg tttttttccg agtctgcgct gttggccgct     780
caggagggat ttgacctaca cactccgccg cctattttag agtctccgct gccggagccc     840
agtggtatac cttatatgcc tgaactgctt cccgaagtgg tagacctgac ctgccacgag     900
cctggctttc cgcccagcga cgatgagggt gagccttttg ttttagactt tgctgagata     960
cctgggcacg gttgcaggtc ttgtgcatat catcagaggg ttaccggaga ccccgaggtt    1020
aagtgttcgc tgtgctatat gaggatgacc tcttcctta tctacagtaa gttttttgtct    1080 aggtgggctt tgggtaggt gggttttgtg tcagaacagg tgtaaacgtt gcttgtgttt     1140
tttgtacctg taggtccggt gtccgagcca gacccggagc ccgaccgcga tcccgagccg    1200
gatcccgagc ctcctcgcag gacaaggaaa ctaccttcca ttctgtgcaa gtctcagaca    1260
cctgtaagga ccagcgaggc agacagcacc gactctggca cttctacctc tcccccctgaa   1320 attcacccag tggttcctct gggtatacat aaacctgttg ctgttaaagt ttgcgggcga    1380
cgccctgcag tacagtgcat tgaggacttg cttcacgatc ccgaggaacc tttggacttg    1440
agccttaaac gccctaggca ataaaccca cctaagtaat aaaccccacc taagtaataa     1500
accctgccgc ccttggttat tgagatgacg cccaatgttt gcttttgaat gacttcatgt    1560
gtgtaataaa agtgagtgtg atcataggtc tcttgtttgt ctgggcgggg cttaagggta    1620
tataagtctc ttggggctaa acttggttac acttgaccc aatggaggcg tgggggtgct     1680
tggaggagtt tgcggacgtg cgccgttttgc tggacgagag ctctagcaat acctatacta   1740
tttggaggta tctgtgggc tctactcagg ccaagtggt ttccagaatt aagcaggatt      1800
acaagtgcga ttttgaagag cttttagtt cctgcggtga gcttttgcaa tccttgaatc     1860
tgggccatca ggctattttc caggaaaagg ttctctcgac tttggatttt tccactcccg    1920
ggcgcaccgc cgcttgtgtg gcttttgtgt cttttgtgca agataaatgg agcgaggaga    1980
cccacctgag tcacggctac gtactggatt tcatggcgat ggctcttggg agggctcaca    2040
```

```
acaaatggaa gattcagaag gaactgtacg gttccgccct acgtcgtcca cttctgtcgc   2100
gacaggggct gaggtttccc gaccatcggc agcatcagaa tctggaagac gagtcggagg   2160
agcgagcgga ggagaagatc agcttgagag ccggcctgga ccctcctcag gaggaatgaa   2220
tctcccgcag gtggttgacc tgtttccaga actgagacgg gtcctgacta tcagggagga   2280
tggtcagttt gtgaagaagt ttaagaggga tcggggtgag ggagatgatg aggcggctag   2340
caatttagct tttagtctga tgactcgcca ccgaccggaa tgtattacct atcagcagat   2400
taaggagagt tgtgccaacg agctggatct tttgggtcag aagtatagca tagaacagct   2460
taccacttac tggcttcagc ctggggatga ttgggaagag gcgatcaggg tgtatgcaaa   2520
ggtggccctg cggcccgatt gcaagtataa gattactaag ttggttaata ttagaaactg   2580
ctgctatatt tctgggaacg gggccgaagt ggagatagat actcaggaca gggtggcttt   2640
taggtgttgc atgataaaca tgtggcccgg gatactgggg atggatgggg tggtattcat   2700
gaatgtgagg tttacgggcc ccaactttaa tggcacggtg ttcatgggca acaccaactt   2760
gctcctgcat ggtgcgagtt tctatgggtt taataacacc tgtatagagg cctggaccga   2820
tgtaaaggtt cgaggttgtt ccttttatag ctgttggaag gcggtggtgt gtcgccctaa   2880 aagcagggt tctgtgaaaa aatgcttgtt tgaaggtgc accttaggca tcctctctga    2940
```

-continued

```
tatgttccca cccagatccc ttctgggatt catgttgtgc aggaccacca gcacggtata    4440
tccagtgcac ttgggaaatt tatcgtggag cttagacggg aatgcatgga agaacttgga    4500
gacgcccttg tggcctccca gattttccat acattcgtcc atgatgatgg caatgggccc    4560
gtgggaagct gcctgagcaa aaatgttttct gggatcgctc acatcgtagt tatgttccag   4620
ggtgaggtca tcataggaca tctttacgaa tcggggcgg agggtcccgg actgggggat     4680
gatggtaccc tcgggcccg gggcgtagtt cccctcacag atctgcatct cccaggcttt     4740
catttcagag ggagggatca tatccacctg cggagcgatg aaaaacacag tttctggcgc    4800
aggggagatt aactgggatg agagcaggtt tctgagcagc tgtgactttc cacagccggt    4860
gggcccatat atcacgccta tcaccggctg cagctggtag ttaagagagc tgcagctgcc    4920
gtcctcccgg agcagggggg ccacctcgtt cagcatatcc ctgacgtgga tgttctccct    4980
gaccaattcc gccagaaggc gctcgccgcc cagcgaaagc agctcttgca aggaagcaaa    5040
attttcagc ggttttaggc cgtcggccgt gggcatgttt ttcagcgtct gggtcagcag     5100
ttccagcctg tcccacagct cggtgatgtg ctctacggca tctcgatcca gcagatctcc    5160
tcgtttcgcg ggttgggcg ctttcgctg tagggcacca gccgatgggc gtccagcggg      5220
gccagagtca tgtccttcca tgggcgcagg gtcctcgtca gggtggtctg ggtcacggtg    5280
aaggggtgcg ctccggggttg ggcgctggcc agggtgcgct tgaggctggt tctgctggtg   5340
ctgaatcgct gccgctcttc gccctgcgcg tcggccaggt agcatttgac catggtctcg   5400
tagtcgagac cctcggcggc gtgccccttg gcgcggagct ttcccttgga ggtggcgccg   5460
cacgaggggc actgcaggct cttcagggcg tagagcttgg gagcgagaaa cacggactct   5520
ggggagtagg cgtccgcgcc gcaggaagcg cagaccgtct cgcattccac cagccaagtg    5580
agctccgggc ggtcagggtc aaaaaccagg ttgcccccat gcttttttgat gcgtttctta  5640
cctcggctct ccatgaggcg gtgtcccttc tcggtgacga agaggctgtc cgtgtccccg    5700
tagaccgact tcagggggcct gtcttccagc ggagtgcctc tgtcctcctc gtagagaaac   5760
tctgaccact ctgagacgaa ggcccgcgtc caggccagga cgaaggaggc cacgtgggag    5820
gggtagcggt cgttgtccac tagcgggtcc accttctcca gggtgtgcag gcacatgtcc   5880
ccctcctccg cgtccagaaa agtgattggc ttgtaggtgt aggacacgtg accgggggtt   5940
cccgacgggg gggtataaaa gggggtgggc gcccttcat cttcactctc ttccgcatcg     6000
ctgtctgcga gggccagctg ctggggtaag tattccctct cgaaggcggg catgacctca    6060
gcgctcaggt tgtcagtttc taaaaatgag gaggatttga tgttcacctg tccggaggtg    6120
atacctttga gggtacctgg gtccatctgg tcagaaaaca ctattttttt gttgtcaagc    6180
ttggtggcga acgacccgta gagggcgttg gagagcagct tggcgatgga gcgcagggtc    6240
tggttttgt cgcggtcggc tcgctccttg gccgcgatgt tgagttgcac gtactcgcgg     6300
gccacgcact tccactcggg gaagacggtg gtgcgctcgt ctgggattag gcgcaccctc    6360
cagcctcggt tgtgcagggt gaccatgtcg acgctggtgg cgacctcgcc gcgcaggcgc    6420
tcgttggtcc agcagaggcg gccgcccttg cgcgagcaga aggggggtag ggggtccagc    6480
tggtcctcgt ttgggggtc cgcgtcgatg gtgaagaccc cggggagcaa gcgcgggtca    6540
aagtagtcga tcttgcaagc ttgcatgtcc agagcccgct gccattcgcg ggcggcgagc    6600
gcgcgctcgt aggggttgag gggcgggccc cagggcatgg ggtgggtgag cgcggaggcg    6660
tacatgccgc agatgtcata cacgtacagg ggttccctga ggatgccgag gtaggtgggg   6720
tagcagcgcc ccccgcggat gctggcgcgc acgtagtcat agagctcgtg ggagggggcc    6780
```

```
agcatgttgg gcccgaggtt ggtgcgctgg gggcgctcgg cgcggaaggc gatctgcctg    6840
aagatggcat gggagttgga ggagatggtg ggccgctgga agacgttgaa gcttgcttct    6900
tgcaagccca ccgagtccct gacgaaggag gcgtaggact cgcgcagctt gtgcaccagc    6960
tcggcggtga cctggacgtc gagcgcgcag tagtcgaggg tctcgcggat gatgtcatac    7020
ttatcctccc ccttcttttt ccacagctcg cggttgagga cgaactcttc gcggtctttc    7080
cagtactctt ggaggggaaa cccgtccgtg tccgaacggt aagagcctag catgtagaac    7140
tggttgacgg cctggtaggg gcaacagccc ttctccacgg gcagcgcgta ggcctgcgcc    7200
gccttgcgga gggaggtgtg ggtgagggcg aaagtgtccc tgaccatgac tttgaggtat    7260
tgatgtttga agtctgtgtc atcgcagccg ccctgttccc acagggtgta gtccgtgcgc    7320
tttttggagc gcgggttggg cagggagaag gtgaggtcat tgaagaggat cttccccgct    7380
cgaggcatga agtttctggt gatgcgaaag ggccctggga ccgaggagcg gttgttgatg    7440
acctgggcgg ccaggacgat ctcgtcaaag ccgtttatgt tgtggcccac gatgtagagc    7500
tccaaaaagc ggggctggcc cttgatggag gggagctttt tgagttcctc gtaggtgagc    7560
tcctcgggcg attccaggcc gtgctcctcc agggcccagt cttgcaagtg agggttggcc    7620
gccaggaagg atcgccagag gtcgcgggcc atgagggtct gcaggcggtc gcggaaggtt    7680
ctgaactgtc gccccacggc catctttttcg ggggtgatgc agtagaaggt gaggggg tct    7740 ttctcccagg ggtcccatct gagctctcgg gcgaggtcgc gcgcggcggc gaccagagcc    7800
tcgtcgcccc ccagtttcat gaccagcatg aagggcacga gctgcttgcc aaaggctccc    7860
atccaagtgt aggtctctac atcgtaggtg acaaagaggc gctccgtgcg aggatgagag    7920
ccgatcggga agaactggat ctcccgccac cagttggagg attggctgtt gatgtggtga    7980
aagtagaagt cccgtctgcg ggccgagcac tcgtgctggc ttttgtaaaa gcgaccgcag    8040
tactggcagc gctgcacggg ttgtatatct tgcacgaggt gaacctggcg acctctgacg    8100
aggaagcgca gcgggaatct aagtcccccg cctggggtcc cgtgtggctg gtggtcttct    8160
actttggttg tctggccgcc agcatctgtc tcctggaggg cgatggtgga gcagaccacc    8220
acgccgcgag agccgcaggt ccagatctcg gcgctcggcg ggcggagttt gatgacgaca    8280
tcgcgcacat tggagctgtc catggtctcc agctcccgcg gcggcaggtc agctgggagt    8340
tcctggaggt tcacctcgca gagacgggtc aaggcgcggg cagtgttgag atggtatctg    8400
atttcaaggg gcgtgttggc ggcggagtcg atggcttgca ggaggccgca gccccggggg    8460
gccacgatgg ttccccgcgg ggcgcgaggg gaggcggaag ctgggggtgt gttcagaagc    8520
ggtgacgcgg gcgggccccc ggaggtaggg ggggttccgg ccccacaggc atgggcggca    8580
ggggcacgtc ttcgccgcgc gcgggcaggg gctggtgctg gctccgaaga gcgcttgcgt    8640
gcgcgacgac gcgacggttg gtgtcctgta tctgacgcct ctgagtgaag accacgggtc    8700
ccgtgacctt gaacctgaaa gagagttcga cagaatcaat ctcggcatcg ttgacagcgg    8760
cctggcgcag gatctcctgc acgtcgcccg agttgtcctg gtaggcgatc tctgccatga    8820
actgctcgat ctcttcttcc tggagatctc ctcgtccggc gcgctccacg gtggccgcca    8880
ggtcgttgga gatgcgaccc atgagctgtg agaaggcgtt gagcccgccc tcgttccaga    8940
cccggctgta gaccacgccc ccctcggcgt cgcgagcgcg catgaccacc tgggccaggt    9000
tgagctccac gtgtcgcgtg aagacggcgt agttgcgcag gcgctggaaa aggtagttca    9060
gggtggtggc ggtgtgctcg gcgacgaaga agtacatgac ccagcgccgc aacgtggatt    9120
```

```
cattgatgtc ccccaaggcc tccaggcgct ccatggcctc gtagaagtcc acggcgaagt    9180
tgaaaaactg ggagttgcga gcggacacgg tcaactcctc ctccagaaga cggatgagct    9240
cggcgacagt gttgcgcacc tcgcgctcga aggccacggg gggcgcttct tcctcttcca    9300
cctcttcttc catgatcgct tcttcttctt cctcagccgg gacgggaggg ggcggcggcg    9360 gcggggagg ggcgcggcgg cggcggcggc gcaccgggag gcggtcgatg aagcgctcga    9420
tcatctcccc ccgcatgcgg cgcatggtct cggtgacggc gcggccgttc tcccgggggc    9480
gcagctcgaa gacgccgcct ctcatctcgc cgcggggcga gcggccgtga ggtagcgaga    9540
cggcgctgac tatgcatctt aacaattgct gtgtaggtac accgccgagg acctgattg     9600 agtccagatc caccggatcc gaaaaccttt ggaggaaagc gtctatccag tcgcagtcgc    9660
aaggtaggct gagcaccgtg gcgggcgggg gcgggtctgg agagttcctg gcggagatgc    9720
tgctgatgat gtaattaaag taggcggtct tgagaaggcg gatggtggac aggagcacca    9780
tgtctttggg tccggcctgt tggatgcgga ggcggtcggc catgcccag gcctcgttct     9840 gacaccggcg caggtctttg tagtagtctt gcatgagtct ttccaccggc acctcttctc    9900
cttcctcttc tccatctcgc cggtggtttc tcgcgccgcc catgcgcgtg accccaaagc    9960
ccctgagcgg ctgcagcagg gccaggtcgg cgaccacgcg ctcggccaag atggcctgct    10020
gcacctgagt gagggtcctc tcgaagtcat ccatgtccac gaagcggtgg taggcgcccg    10080
tgttgatggt gtaggtgcag ttggccatga cggaccagtt gacggtctgg tgtcccggct    10140
gcgagagctc cgtgtaccgc aggcgcgaga aggcgcggga atcgaacacg tagtcgttgc    10200
aagtccgcac cagatactgg tagcccacca ggaagtgcgg cggaggttgg cgatagaggg    10260
gccagcgctg ggtggcgggg gcgccgggcg ccaggtcttc cagcatgagg cggtggtatc    10320
cgtagatgta cctggacatc caggtgatgc cggcggcggt ggtggtggcg cgcgcgtagt    10380
cgcggacccg gttccagatg tttcgcaggg gcgagaagtg ttccatggtc ggcacgctct    10440
ggccggtgag gcgcgcgcag tcgttgacgc tctatacaca cacaaaaacg aaagcgttta    10500
cagggctttc gttctgtagc ctggaggaaa gtaaatgggt tgggttgcgg tgtgccccgg    10560
ttcgagacca agctgagctc ggccggctga agccgcagct aacgtggtat tggcagtccc    10620
gtctcgaccc aggccctgta tcctccagga tacggtcgag agcccttttg ctttcttggc    10680
caagcgcccg tggcgcgatc tgggatagat ggtcgcgatg agaggacaaa agcggctcgc    10740
ttccgtagtc tggagaaaca atcgccaggg ttgcgttgcg gcgtaccccg gttcgagccc    10800
ctatggcggt ttgaatcggc cggaaccgcg gctaacgagg gccgtggcag ccccgtcctc    10860
aggaccccgc cagccgactt ctccagttac gggagcgagc ccctttgtt ttttattttt     10920 tagatgcatc ccgtgctgcg gcagatgcgc ccctcgcccc ggcccgatca gcagcagcaa    10980
cagcaggcat gcagaccccc ctctcccctt tccgccccgg tcaccacggc cgcggcggcc    11040
gtgtcgggcg cgggggggcgc gctggagtca gatgagccac cgcggcggcg acctaggcag    11100
tatctggact tggaagaggg cgagggactg gcgcggctgg gggcgaactc tccagagcgc    11160 caccccgcggg tgcagttgaa aagggacgcg cgcgaggcgt acctgccgcg gcagaacctg    11220
tttcgcgacc gcgggggcga ggagcccgag gagatgcgag actgcaggtt ccaagcgggg    11280
cgcgagctgc ggcgcgggct ggacagacag cgcctgctgc gcgaggagga ctttgagccc    11340
gacacgcaga cgggcatcag ccccgcgcgc gcgcacgtag ccgcggccga cctggtgacc    11400
gcctacgagc agacggtaaa ccaggagcgc aacttccaaa agagcttcaa caaccacgtg    11460
cgcacgctgg tggcgcgcga ggaggtgacc ctgggtctca tgcatctgtg ggacctggtg    11520
```

```
gaggcgatcg tgcagaaccc cagcagcaag ccoctgaccg cgcagctgtt cctggtggtg    11580
cagcacagca gggacaacga ggccttcagg gaggcgctgc tgaacatcac cgagccgag    11640 gggcgctggc tcctggacct gataaacatc ctgcagagca tagtggtgca ggagcgcagc    11700
ctgagcctgg ccgagaaggt ggcggccatc aactactcta tgctgagcct gggcaagttc    11760
tacgcccgca agatctacaa gaccccctac gtgcccatag acaaggaggt gaagatagac    11820
agcttctaca tgcgcatggc gctgaaggtg ctgaccctga cgacgacct gggagtgtac    11880 cgcaacgagc gcatccacaa ggccgtgagc gccagccggc ggcgcgagct gagcgaccgc    11940
gagctgatgc acagtctgca gcgcgcgctg accggcgcgg gcgagggcga cagggaggtc    12000
gagtcctact tcgacatggg ggccgacctg cactggcagc cgagccgccg cgcctggag    12060 gcggcggggg cgtacggcgg ccccctggcg gccgatgacc aggaagagga ggactatgag    12120
ctagaggagg gcgagtacct ggaggactga cctggctggt ggtgttttgg tatagatgca    12180
agatccgaac gtggcggacc cggcggtccg ggcggcgctg caaagccagc cgtccggcat    12240
taactcctct gacgactggg ccgcggccat gggtcgcatc atgggccctga ccgcgcgcaa    12300 ccccgaggct ttcaggcagc agcctcaggc caaccggctg gcggccatct tggaagcggt    12360
agtgcccgcg cgctccaacc ccacccacga aaggtgctg gccatagtca acgcgctggc    12420
ggagagcagg gccatccgcg cggacgaggc cggactggtg tacgatgcgc tgctgcagcg    12480
ggtggcgcgg tacaacagcg gcaacgtgca gaccaacctg gaccgcctgg tgacggacgt    12540
gcgcgaggcc gtggcgcagc gcgagcgctt gcatcaggac ggtaacctgg gctcgctggt    12600
ggcgctaaac gccttcctca gcacccagcc ggccaacgta ccgcggggggc aggaggacta    12660 caccaacttt ttgagcgcgc tgcggctgat ggtgaccgag gtccctcaga gcagggtgta    12720
ccagtcgggg cccgactact tcttccagac cagcagacag ggcttgcaaa ccgtgaacct    12780
gagccaggct ttcaagaacc tgcgggggct gtgggagtg aaggcgccca ccggcgaccg    12840
ggctacggtg tccagcctgc taaccccaa ctcgcgcctg ctgctgctgc tgatcgcgcc    12900
cttcacggac agcgggagcg tctcgcggga gacctatctg ggccacctgc tgacgctgta    12960 cccgcgaggcc atcgggcagg cgcaggtgga cgagcacacc ttccaagaga tcaccagcgt    13020
gagccacgcg ctggggcagg aggacacggg cagcctgcag gcgaccctga actacctgct    13080
gaccaacagg cggcagaaga ttcccacgct gcacagcctg acccaggagg aggagcgcat    13140
cttgcgctac gtgcagcaga gcgtgagcct gaacctgatg cgcgacggcg tgacgcccag    13200
cgtggcgctg gacatgaccg cgcgcaacat ggaaccgggc atgtacgcct cccaccggcc    13260
gtttatcaac cgcctgatgg actacttgca tcgggcggcg ccgtgaaccc ccgagtactt    13320
cactaatgcc attctgaatc cccactgat gcccctccg ggtttctaca acggggactt    13380
tgaggtgccc gaggtcaacg acgggttct ctgggatgac atggatgaca gtgtgttctc    13440
acccaacccg ctgcgcgccg cgtctctgcg attgaaggag ggctctgaca gggaaggacc    13500
gaggagtctg gcctcctccc tggctctggg agcggtgggc gccacgggcg cggcggcgcg    13560
gggcagtagc ccccttcccca gcctggcaga ctctctgaac agcgggcggg tgagcaggcc    13620
ccgcttgcta ggcgaggagg agtatctgaa caactccctg ctgcagcccg cgaggacaa    13680 gaacgctcag cggcagcagt ttcccaacaa tgggatagag agcctggtgg acaagatgtc    13740
cagatggaag acgtatgcgc aggagtacaa ggagtgggag gaccgccagc gcggggccttt    13800 gccgcccct aggcagcgct ggcagcggcg cgcgtccaac cgccgctgga ggcagggggcc    13860
```

```
cgaggacgat gatgactctg cagatgacag cagcgtgttg gacctgggcg ggagcgggaa    13920
ccccttttcg cacctgcgcc cacgcctggg caagatgttt taaaagaaaa aaaaaaataa    13980
aactcaccaa ggccatggcg acgagcgttg gttttttgtt cccttcctta gtatgcggcg    14040
cgcggcgatg ttcgaggagg ggcctccccc ctcttacgag agcgcgatgg ggatttctcc    14100
tgcggcgccc ctgcagcctc cctacgtgcc tcctcggtac ctgcaaccta caggggggag    14160
aaatagcatc tgttactctg agctgcagcc cctgtacgat accaccagac tgtacctggt    14220
ggacaacaag tccgcggacg tggcctccct gaactaccag aacgaccaca gcgatttttt    14280
gaccacggtg atccaaaaca acgacttcac cccaaccgag gccagcaccc agaccataaa    14340
cctggataac aggtcgaact ggggcggcga cctgaagacc atcttgcaca ccaacatgcc    14400
caacgtgaac gagttcatgt tcaccaactc ttttaaggcg cgggtgatgg tggcgcgcga    14460 gcaggggag gcgaagtacg agtgggtgga cttcacgctg cccgagggca actactcaga    14520
gaccatgact ctcgacctga tgaacaatgc gatcgtggaa cactatctga agtgggcag    14580 gcagaacggg gtgaaggaaa gcgatatcgg ggtcaagttt gacaccagaa acttccgtct    14640
gggctgggac cccgtgaccg ggctggtcat gccggggtc tacaccaacg aggcctttca    14700
tcccgacata gtgcttctgc ccggctgtgg ggtggacttc acccagagcc ggctgagcaa    14760
cctgctgggc attcgcaagc ggcagccttt ccaggagggt ttcaagatca cctatgagga    14820
tctgaagggg ggcaacattc ccgcgctcct tgatctggac gcctacgagg agagcttgaa    14880
acccgaggag agcgctggcg acagcggcga gagtggcgag gagcaagccg gcggcggtgg    14940
cggcgcgtcg gtagaaaacg aaagtacgcc cgcagtggcg gcggacgctg cggaggtcga    15000
gccggaggcc atgcagcagg acgcagagga gggcgcacag gagggcgcgc agaaggacat    15060
gaacgatggg gagatcaggg gagacacatt cgccacccgg ggcgaagaaa aagaggcaga    15120
ggcggcggcg gcggcgacgg cggaggccga aaccgaggtt gaggcagagg cagagcccga    15180
gaccgaagtt atgaagaca tgaatgatgg agaacgtagg ggcgacacgt tcgccacccg    15240
gggcgaagag aaggcggcgg aggcagaagc cgcggctgag gaggcggctg cggctgcggc    15300
caagactgag gctgcggcta aggctgaggt cgaagccaat gttgcggttg aggctcaggc    15360
tgaggaggag gcggcggctg aagcagttaa ggaaaaggcc caggcagagc aggaagagaa    15420
aaaacctgtc attcaacctc taaaagaaga tagcaaaaag cgcagttaca acgtcatcga    15480
gggcagcacc tttacccagt accgcagctg gtacctggcg tacaactacg cgacccggt    15540 caaggggtg cgctcgtgga ccctgctctg cacgccggac gtcacctgcg gctccgagca    15600
gatgtactgg tcgctgccga acatgatgca agacccggtg accttccgct ccacgcggca    15660
ggttagcaac ttcccggtgg tgggcgccga actgctgccc gtgcactcca agagttttta    15720
caacgagcag gccgtctact cccagctgat ccgccaggcc acctctctga cccacgtgtt    15780
caatcgcttt cccgagaacc agattttggc gcgcccgccg gcccccacca tcaccaccgt    15840
gagtgaaaac gttcctgccc tcacagatca cgggacgcta ccgctgcgca acagcatctc    15900
aggagtccag cgagtgacca ttactgacgc cagacgccgg acctgcccct acgtttacaa    15960
ggccttgggc atagtctcgc cgcgcgtcct ctccagtcgc acttttttaaa acacatctac    16020 ccacacgttc caaaatcatg tccgtactca tctcacccag caacaacacc ggctgggggc    16080
tgcgcgcgcc cagcaagatg tttgagggg cgaggaagcg ctccgaccag caccctgtgc    16140
gcgtgcgcgg ccactaccgc gcgccctggg gagcgcacaa gcgcgggcgc acagggcgca    16200
ccactgtgga cgacgtcatt gactccgtag tggagcaagc gcgccactac acacccggcg    16260
```

```
cgccgaccgc ccccgccgtg tccaccgtgg accaggcgat cgaaagcgtg gtacagggcg    16320
cgcggcacta tgccaacctt aaaagtcgcc gccgccgcgt ggcccgccgc catcgccgga    16380
gaccccgggc caccgccgcc gcgcgcctta ctaaggctct gctcaggcgc gccaggcgaa    16440
ctggccaccg ggccgccatg agggccgcac ggcgggctgc cgctgccgca agcgtcgtgg    16500
ccccgcgggc acgaaggcgc gcggccgctg ccgccgccgc cgccatttcc agcttggcct    16560
cgacgcggcg cggtaacata tactgggtgc gcgactcggt aaccggcacg cgggtacccg    16620
tgcgctttcg ccccccgcgg aattagcaca agacaacata cacactgagt ctcctgctgt    16680
tgtgtatccc agcggcgacc gtcagcagcg gcgacatgtc caagcgcaaa attaaagaag    16740
agatgctcca ggtcatcgcg ccggagatct atgggccccc gaagaaggag gaggatgatt    16800
acaagccccg caagctaaag cgggtcaaaa agaaaaagaa agatgatgat gacgaggcgg    16860
tggagtttgt ccgccgcatg gcacccaggc gccccgtgca gtggaagggc cggcgcgtgc    16920
agcgcgtttt gcgccccggc accgcggtgg tcttcacgcc cggcgagcgc tccacgcgca    16980 cttttcaagcg ggtgtacgat gaggtgtacg gcgacgagga cctgttggag caggccaacc    17040
agcgctttgg ggagtttgca tatgggaaac ggccccgcga gagtctaaaa gaggacctgc    17100
tggcgctacc gctggacgag ggcaatccca ccccgagtct gaagccggta accctgcaac    17160
aggtgctgcc tttgagcgcg cccagcgagc ataagcgagg gttgaagcgc gaaggcgggg    17220
acctggcgcc caccgtgcag ttgatggtgc ccaagcggca gaagctggag gacgtgctgg    17280
agaaaatgaa agtagagccc gggatccagc ccgagatcaa ggtccgcccc atcaagcagg    17340
tggcgcccgg cgtgggagtc cagaccgtgg acgttaggat tcccacggag gagatggaaa    17400
cccaaaccgc cactccctct tcggcggcca gcgccaccac cggcaccgct tcggtagagg    17460
tgcagacgga cccctggcta cccgccaccg ctgttgccgc cgccgccccc cgttcgcgcg    17520
ggcgcaagag aaattatcca gcggccagcg cgctcatgcc ccagtacgca ctgcatccat    17580
ccatcgtgcc cacccccggc taccgcgggt actcgtaccg cccgcgcaga tcagccggca    17640
ctcgcggccg ccgccgccgt gcgaccacaa ccagccgccg ccgtcgccgc cgccgccagc    17700
cagtgctgac ccccgtgtct gtaaggaagg tggctcgctc ggggagcacg ctggtggtgc    17760
ccagagcgcg ctaccacccc agcatcgttt aaagccggtc tctgtatggt tcttgcagat    17820
atggccctca cttgtcgcct ccgcttcccg gtgccgggat accgaggaag aactcaccgc    17880
cgcagaggca tggcgggcag cggtctccgc ggcggccgtc gccatcgccg gcgcgcaaaa    17940
agcaggcgca tgcgcggcgg tgtgctgcct ctgctaatcc cgctaatcgc gcggcgatc    18000 ggtgccgtac ccgggatcgc ctccgtggcc ctgcaggcgt cccagaaacg ttgactcttg    18060
caaccttgca agcttgcatt ttttggagga aaaataaaa aaaagtcta gactctcacg    18120 ctcgcttggt cctgtgacta ttttgtagaa aaaagatgg aagacatcaa ctttgcgtcg    18180
ctggccccgc gtcacggctc gcgccgttc atggagact ggacagatat cggcaccagc    18240
aatatgagcg gtggcgcctt cagctgggc agtctgtgga gcggccttaa aaatttggt    18300 tccaccatta agaactatgg caacaaagcg tggaacagca gcacgggcca gatgctgaga    18360
gacaagttga aagagcagaa cttccaggag aaggtggcgc agggcctggc ctctggcatc    18420
agcggggtgg tggacatagc taaccaggcc gtgcagaaaa agataaacag tcatctggac    18480
ccccgtcctc aggtgaggga aatgcctcca gcgatggaga cggtgtctcc cgagggcaaa    18540
ggcgaaaagc gcccgcggcc cgacagagaa gagaccctgg tgtcacacac cgaggagccg    18600
```

```
ccctcttacg aggaggcagt caaggccggc ctgcccacca ctcgcccat  agccccatg   18660 gccaccggtg tggtgggcca caggcaacac actcccgcaa cactagatct gccccgccg   18720 tccgagccgc cgcgccagcc aaaggcggcg acggtgcccg ctccctccac ttccgccgcc  18780
aacagagtgc ccctgcgccg cgccgcgagc ggccccgggg cctcgcgagt tagcggcaac  18840
tggcagagca cactgaacag catcgtgggc ctgggagtga ggagtgtgaa gcgccgccgt  18900
tgctactgaa tgagcaagct agctaacgtg ttgtatgtgt gtatgcgtcc tatgtcgccg  18960
ccagaggagc tgttgagccg ccggcgccgt ctgcactcca gcgaatttca agatggcgac  19020
cccatcgatg atgcctcagt ggtcgtacat gcacatctcg ggccaggacg cttcggagta  19080
cctgagcccc gggctggtgc agttcgcccg cgccacagac acctacttca acatgagtaa  19140
caagttcagg aaccccactg tggcgcccac ccacgatgtg accacggacc ggtcgcagcg  19200
cctgacgctg cggttcatcc ccgtggatcg ggaggacacc gcctactctt acaaggcgcg  19260
gttcacgctg gccgtgggcg acaaccgcgt gctggacatg gcctccactt actttgacat  19320
caggggggtg ctggacaggg gccccacctt caagccctac tcgggtactg cctacaactc  19380
cctggccccc aagggcgctc ccaattcttg cgagtgggaa caagatgaac cagctcaggc  19440
agcaatagct gaagatgaag aagaacttga agaagaacaa gctcaggacg aacaggcgcc  19500
cactaagaaa acccatgtat acgcccaggc acctctttct ggtgaaaaaa ttactaagga  19560
tggtttgcaa ataggtgtgg atgccacaca ggcgggagat aaccctatat atgctgataa  19620
aacattccaa cccgaacctc agataggtga gtctcagtgg aacgaggctg atgccacagt  19680
agcaggaggc agagtcttaa aaaagaccac ccctatgaga ccttgctatg atcctatgc   19740 caaacctact aatgccaatg gcggtcaagg gatcatggtg gccaatgatc agggagcgct  19800
tgaatctaaa gttgagatgc aattttctc  caccacaacg tctcttaatg taagggaagg  19860
tgaaaacaat cttcagccaa aagtagtgct atacagcgaa gatgttaact tggaatcccc  19920
tgacactcat ttgtcttaca aacctaaaaa ggatgacacc aactctaaaa tcatgttggg  19980
tcagcaagcc atgcccaaca gacccaacct cattgctttt agggacaact ttattggact  20040
tatgtactac aacagcacag gcaacatggg agtgctggca ggacaggcct cccagctaaa  20100
cgctgtggta gacttgcaag acagaaacac agagctgtca taccaactga tgcttgattc  20160
cattggagac agatcaagat acttttccat gtggaaccag gcagtggaca gctatgaccc  20220
agatgtcaga atcattgaaa accatggggt tgaagatgag ctgcccaact attgctttcc  20280
cctgggcggt attggaatta cagacacata ccagtgcata aaaccaaccg cagctgctaa  20340
taacactaca tggtctaagg atgaagaatt tagtgatcgc aatgaaatag gggtgggaaa  20400
caacttcgcc atggagatca acatccaggc caacctctgg aggaacttcc tctatgcgaa  20460 cgtgggctc  tacctgccag acaagctcaa gtacaacccc accaacgtgg acatctctga  20520 caacccccaac acctatgact acatgaacaa gcgtgtggtg gctcccggcc tggtggactg  20580
ctttgtcaat gtgggagcca ggtggtccct ggactacatg acaacgtca  accccttcaa  20640 ccaccaccgc aatgcgggtc tgcgctaccg ctccatgatc ctgggcaacg ggcgctacgt  20700
gcccttccac attcaggtgc cccagaagtt ctttgccatc aagaacctcc tcctcctgcc  20760
gggctcctac acttacgagt ggaacttcag gaaggatgtc aacatggtcc tgcagagctc  20820
tctgggcaat gaccttaggg tggacggggc cagcatcaag tttgacagcg tcaccctcta  20880
tgctaccttc ttccccatgg ctcacaacac cgcctcacg  ctcgaggcca tgctgaggaa  20940
cgacaccaac gaccagtcct tcaatgacta cctctctggg gccaacatgc tctaccccat  21000
```

```
ccccgccaag gccaccaacg tgcccatctc cattccctct cgcaactggg ccgccttcag   21060
aggctgggcc tttacccgcc ttaagaccaa ggaaaccccc tccctgggct cgggttttga   21120
cccctacttt gtctactcgg gatccatccc ctacctggat ggcaccttct acctcaacca   21180
cacttttaag aagatatcca tcatgtatga ctcctccgtc agctggccgg gcaatgaccg   21240
cctgctcacc cccaatgagt tcgaggtcaa gcgcgccgtg gacggcgagg gctacaacgt   21300
ggcccagtgc aacatgacca aggactggtt cctggtgcag atgctggcca actacaacat   21360
aggctaccag ggcttctaca tcccagagag ctacaaggac aggatgtact ccttcttcag   21420
aaatttccaa cccatgagca ggcaggtggt ggacgagacc aaatacaagg actatcaggc   21480
cattggcatc actcaccagc acaacaactc gggattcgtg ggctacctgg ctcccaccat   21540
gcgcgagggg caggcctacc ccgccaactt cccctacccg ttgataggca aaaccgcggt   21600
cgacagcgtc acccagaaaa agttcctctg cgaccgcacc ctctggcgca tccccttctc   21660
tagcaacttc atgtccatgg gtgcgctcac ggacctgggc cagaacctgc tctatgccaa   21720
ctccgcccat gcgctggaca tgacttttga ggtggacccc atggacgagc ccacccttct   21780
ctatattgtg tttgaagtgt tcgacgtggt cagagtgcac cagccgcacc gcggtgtcat   21840
cgagaccgtg tacctgcgca cgcccttctc ggccggcaac gccaccacct aaggagacag   21900
cgccgccgcc tgcatgacgg gttccaccga gcaagagctc agggcatcg ccagagacct   21960
gggatgcgga ccctattttt tgggcaccta tgacaaacgc ttcccgggct tcatctcccg   22020
agacaagctc gcctgcgcca tcgtcaacac ggccgcgcgc gagaccgggg gcgtgcactg   22080
gctggccttt ggctgggacc cgcgctccaa aacctgctac ctcttcgacc cctttggctt   22140
ctccgatcag cgcctcagac agatctatga gtttgagtac gaggggctgc tgcgccgcag   22200
cgcgcttgcc tcctcgcccg accgctgcat cacccttgag aagtccaccg agaccgtgca   22260
ggggccccac tcggccgcct gcggtctctt ctgctgcatg tttttgcacg cctttgtgcg   22320
ctggccccag agtcccatgg atcgcaaccc caccatgaac ttgctcaagg gagtgccaa    22380
cgccatgctc cagagccccc aggtccagcc caccctgcgc cacaaccagg aacagctcta   22440
ccgcttcctg gagcgccact cccctactt ccgcagtcac agcgcgcaca tccgggggc    22500
cacctctttc tgccacttgc aagaaaacat gcaagacgga aaatgatgta cagctcgctt   22560
tttaataaat gtaaagactg tgcactttat ttatacacgg gctctttctg gttatttatt   22620
caacaccgcc gtcgccatct agaaatcgaa agggttctgc cgcgcgtcgc cgtgcgccac   22680
gggcagagac acgttgcgat actggaagcg gctcgcccac ttaaactcgg gcaccaccat   22740
gcggggcagt ggttcctcgg ggaagttctc gccccacagg gtgcgggtca gctgcagcgc   22800
gctcaggagg tcgggagccg agatcttgaa gtcgcagttg gggccggaac cctgcgcgcg   22860
cgagttgcgg tacacggggt gcagcactg gaacaccagc agggccggat tatgcacgct   22920
ggccagcagg ctctcgtcgc tgatcatgtc gctgtccaga tcctccgcgt tgctcagggc   22980
gaacggggtc atcttgcaga cctgcctgcc caggaaaggc ggcagcccgg gcttgccgtt   23040
gcagtcgcag cgcaggggca tcagcaggtg cccgcggccc gactgcgcct gcgggtacag   23100
cgcgcgcatg aaggcttcga tctgcctgaa agccacctgc gtcttggctc cctccgaaaa   23160
gaacatccca caggacttgc tggagaactg gttcgcggga cagctggcat cgtgcaggca   23220
gcagcgcgcg tcggtgttgg cgatctgcac cacgttgcga ccccaccggt tcttcactat   23280
cttggccttg gaagcctgct ccttcagcgc gcgctggccg ttctcgctgg tcacatccat   23340
```

```
ctctatcacc tgctccttgt tgatcatgtt tgtaccgtgc agacacttca ggtcgccctc   23400
cgtctgggtg cagcggtgct cccacagcgc gcaaccggtg ggctcccaat ttttgtgggt   23460
cacccccgcg taggcctgca ggtaggcctg caagaagcgc cccatcatgg ccacaaaggt   23520
cttctggctc gtaaaggtca gctgcaggcc gcgatgctct tcgttcagcc aggtcttgca   23580
gatggcggcc agcgcctcgg tctgctcggg cagcatccta aaatttgtct tcaggtcgtt   23640
atccacgtgg tacttgtcca tcatggcgcg cgccgcctcc atgcccttct cccaggcgga   23700
caccatgggc aggcttaggg ggtttatcac ttccaccggc gaggacaccg tactttcgat   23760
ttcttcttcc tccccctctt cccggcgcgc gcccacgctg ctgcgcgctc tcaccgcctg   23820
caccaagggg tcgtcttcag gcaagcgccg caccgagcgc ttgccgccct tgacctgctt   23880
aatcagcacc ggcgggttgc tgaagcccac catggtcagc gccgcctgct cttcttcgtc   23940
ttcgctgtct accactatct ctgggaagg  gcttctccgc tctgcggcgg cgcgcttctt   24000 tttttcttg  ggagcggccg tgatggagtc cgccacggcg acggaggtcg agggcgtggg   24060
gctgggggtg cgcggtacca gggcctcgtc gccctcggac tcttcctctg actccaggcg   24120
gcggcggagt cgcttctttg ggggcgcgcg cgtcagcggc ggcggagacg gggacgggga   24180
cggggacggg acgccctcca caggggtgg  tcttcgcgca gacccgcggc cgcgctcggg   24240
ggtcttctcg agctggtctt ggtcccgact ggccattgta tcctcctcct cctaggcaga   24300
gagacataag gagtctatca tgcaagtcga aaggaggag  agcttaacca ccccctctga   24360
gaccgccgat gcgcccgccg tcgccgtcgc cccgctgcc  gccgacgcgc cgccacacc   24420 gagcgacacc cccgcggacc cccccgccga cgcacccctg ttcgaggaag cggccgtgga   24480
gcaggacccg ggctttgtct cggcagagga ggatttgcga gaggaggagg ataaggagaa   24540
gaagccctca gtgccaaaag atgataaaga gcaagacgag cacgacgcag atgcacacca   24600
gggtgaagtc gggcgggggg acggagggca tgacggcgcc gactacctag acgaagggaa   24660
cgacgtgctc ttgaagcacc tgcatcgtca gtgcgccatt gtttgcgacg ctctgcagga   24720
gcgcagcgaa gtgcccctca cgtggcgga  ggtcagccac gcctacgagc tcagcctctt   24780 ctcccccgg  gtgccccccc gccgccgcga aaacggcaca tgcgagccca cccgcgcct   24840 caacttctac cccgcctttg tggtacccga ggtcctggcc acctatcaca tcttctttca   24900
aaattgcaag atccccctct cgtgccgcgc caaccgtagc cgcgccgata agatgctggc   24960
cctgcgccag ggcgaccaca tacctgatat cgccgctttg gaagatgtac caaagatctt   25020
cgagggtctg ggtcgcaacg agaagcgggc agcaaactct ctgcaacagg aaaacagcga   25080
aaatgagagt cacaccgggg tactggtgga gctcgagggc gacaacgccc gcctggcggt   25140
ggtcaagcgc agcatcgagg tcacccactt tgcctacccc gcgctaaacc tgccccccaa   25200
agtcatgaac gcggccatgg acgggctgat catgcgccgc ggccggcccc tcgctccaga   25260
tgcaaacttg catgaggaga ccgaggacgg ccagcccgtg gtcagcgacg agcagctggc   25320
gcgctggctg gagaccgcgg accccgccga actggaggag cggcgcaaga tgatgatggc   25380
cgtggtgctg gtcaccgtag agctggagtg tctgcagcgc ttcttcggcg accccgagat   25440
gcagagaaag gtcgaggaga ccctgcacta caccttccgc cagggctacg tgcgccaggc   25500
ttgcaagatc tccaacgtgg agctcagcaa cctggtgtcc tacctgggca tcttgcatga   25560
gaaccgcctc gggcagagcg tgctgcactc caccctgcgc ggggaggcgc gccgcgacta   25620
cgtgcgcgac tgcgtttacc tcttcctctg ctacacctgg cagacggcca tggggtctg   25680 gcagcagtgc ctggaggagc gcaacctcaa ggagctggag aagctcctgc agcgcgcgct   25740
```

```
caaagatctc tggacgggct acaacgagcg ctcggtggcc gccgcgctgg ccgacctcat    25800
cttccccgag cgcctgctca aaaccctcca gcagggctg cccgacttca ccagccaaag    25860
catgttgcaa aacttcagga actttatcct ggagcgttct ggcatcctac ccgccacctg    25920
ctgcgccctg cccagcgact ttgtcccct cgtgtaccgc gagtgccccc cgccgctgtg    25980
gggtcactgc tacctgttcc aactggccaa ctacctgtcc taccacgcgg acctcatgga    26040
ggactccagc ggcgagggc tcatggagtg ccactgccgc tgcaacctct gcacgcccca    26100
ccgctccctg gtctgcaaca cccaactgct cagcgagagt cagattatcg gtaccttcga    26160
gctacagggt ccgtcctcct cagacgagaa gtccgcggct ccggggctaa aactcactcc    26220
ggggctgtgg acttccgcct acctgcgcaa atttgtacct gaagactacc acgcccacga    26280
gatcaggttt tacgaagacc aatcccgccc gccaaggcg gagctgaccg cctgcgtcat    26340
cacccagggc gagatcctag gccaattgca agccatccaa aaagcccgcc aagactttt    26400 gctgaagaag gtcgggggg tgtatctgga ccccagtcg ggtgaggagc tcaacccggt    26460
tcccccgctg ccgccgccgc gggaccttgc ttcccaggat aagcatcgcc atggctccca    26520
gaaagaagca gcagcggccg ccactgccgc caccccacat gctggaggaa gaggaggaat    26580
actgggacag tcaggcagag gaggtttcgg acgaggagga gccggagacg gagatggaag    26640
agtgggagga ggacagctta gacgaggagg cttccgaagc cgaagaggca gacgcaacac    26700 cgtcacccte ggccgcagcc ccctcgcagg cgccccgaa gtccgctccc agcatcagca    26760
gcaacagcag cgctataacc tccgctcctc caccgccgcg acccacgcc gaccgcagac    26820 ccaaccgtag atgggacacc accggaaccg gggccggtaa gtcctccggg agaggcaagc    26880
aagcgcagcg ccaaggctac cgctcgtggc gcgctcacaa gaacgccata gtcgcttgct    26940
tgcaagactg cggggggaac atctccttcg cccgccgctt cctgctcttc caccacggtg    27000
tggccttccc ccgtaacgtc ctgcattact accgtcatct ctacagcccc tactgcggcg    27060
gcagtgagcc agagacggtc ggcggcggcg gcggcgcccg tttcggcgcc taggaagacc    27120
cagggcaaga cttcagccaa gaaactcgcg gcggccgcgg cgaacgcggt cgcggggcc    27180 ctgcgcctga cggtgaacga accctgtcg acccgcgaac tgaggaaccg aatcttcccc    27240
actctctatg ccatcttcca gcagagcaga gggcaggatc aggaactgaa agtaaaaaac    27300
aggtctctgc gctccctcac ccgcagctgt ctgtatcaca agagcgaaga ccagcttcgg    27360
cgcacgctgg aggacgctga ggcactcttc agcaaatact gcgcgctcac tcttaaggac    27420
tagctccgcg cccttctcga atttaggcgg gaacgcctac gtcatcgcag cgccgccgtc    27480
atgagcaagg acattcccac gccatacatg tggagctatc agccgcagat gggactcgcg    27540
gcgggcgcct cccaagacta ctccaccgcg atgaactggc tcagtgccgg cccacacatg    27600
atctcacagg ttaatgatat ccgcacccat cgaaaccaaa tattggtgga gcaggcggca    27660
attaccacca cgccccgcaa taatcccaac cccagggagt ggcccgcgtc cctggtgtat    27720
caggaaattc ccggccccac caccgtacta cttccgcgtg attcccaggc cgaagtccaa    27780
atgactaact caggggcaca gctcgcgggc ggctgtcgtc acagggtgcg gcctcctcgc    27840
cagggtataa ctcacctgga gatccgaggc agaggtattc agctcaacga cgagtcggtg    27900
agctcctcgc tcggtctcag acctgacggg accttccaga tagccggagc cggccgatct    27960
tccttcacgc cccgccaggc gtacctgact ctgcaaagct cgtcctcggc gccgcgctcg    28020
ggcggcatcg ggactctcca gttcgtgcag gagtttgtgc cctcggtcta cttcaacccc    28080
```

```
ttctcgggct ctcccggtcg ctacccggac cagttcatct cgaactttga cgccgcgagg    28140
gactcggtgg acggctacga ctgaatgtcg ggtggacccg gtgcagagca acttcgcctg    28200
aagcacctcg accactgccg ccgccctcag tgctttgccc gctgtcagac cggtgagttc    28260
cagtactttt ccctgcccga ctcgcacccg gacggcccgg cgcacggggt gcgcttttc    28320 atcccgagtc aggtgcgctc taccctaatc agggagttta ccgcccgtcc cctactggcg    28380
gagttggaaa aggggccttc tatcctaacc attgcctgca tctgctctaa ccctggattg    28440
caccaagatc tttgctgtca tttgtgtgct gagtataata aaggctgaga tcagaatcta    28500
ctcgggctcc tgtcgccatc ctgtcaacgc caccgtccaa gcccggcccg atcagcccga    28560
ggtgaacctc acctgcggtc tgcaccggcg cctgaggaaa tacctagctt ggtactacaa    28620
cagcactccc tttgtggttt acaacagctt tgaccaggac ggggtctcac tgagggataa    28680
cctctcgaac ctgagctact ccatcaggaa gaacagcacc ctcgagctac ttcctcctta    28740
cctgcccggg acttaccagt gtgtcaccgg tccctgcacc cacacccacc tgttgatcgt    28800
aaacgactct cttccgagaa cagacctcaa taactcctct tcgcagttcc ccagaacagg    28860
aggtgagctc aggaaacccc gggtaaagaa gggtggacga gagttaacac ttgtggggtt    28920
tctggtgtat gtgacgctgg tggtggctct tttgattaag gcttttcctt ccatgtctga    28980
actctccctc ttcttttatg aacaactcga ctagtgctaa cgggacccta cccaacgaat    29040
cgggattgaa tatcggtaac caggttgcag tttcactttt gattaccttc atagtcctct    29100
tcctgctagt gctgtcgctt ctgtgcctgc ggatcggggg ctgctgcatc cacgtttata    29160
tctggtgctg gctgtttaga aggttcggag accatcgcag gtagaataaa catgctgctg    29220
cttaccctct ttgtcctggc gctggccgcc agctgccaag ccttttccga ggctgacttt    29280
atagagcccc agtgtaatgt gacttttaaa gcccatgcac agcgttgtca tactataatc    29340
aaatgtgcca ccgaacacga tgaataccttatccagtata aagataaatc acacaaagtg    29400
gcacttgttg acatctggaa acccgaagac cctttggaat acaatgtgac cgttttccag    29460
ggtgacctct tcaaaattta caattacact ttcccatttg accagatgtg tgactttgtc    29520
atgtacatgg aaaagcagca caagctgtgg cctccgactc cccagggctg tgtggaaaat    29580
ccaggctctt tctgcatgat ctctctctgt gtaactgtgc tggcactaat actcacgctt    29640
ttgtatatca gatttaaatc aaggcaaagc ttcattgatg aaaagaaaat gccttaatcg    29700 cttttcacgct tgattgctaa caccgggttt ttatccgcag aatgattgga atcaccctac    29760
taatcacctc cctccttgcg attgcccatg ggttggaacg aatcgaagtc cctgtggggg    29820
ccaatgttac cctggtgggg cctgtcggca atgctacatt aatgtgggaa aaatatacta    29880
aaaatcaatg ggtctcttac tgcactaaca aaaatagcca caagcccaga gccatctgcg    29940
atgggcaaaa tctaaccttg attgatgttc aattgctgga tgcgggctac tattatgggc    30000
agctgggtac aatgattaat tactggagac cccacagaga ttacatgctc cacgtagtaa    30060
agggtcccct tagcagccca cccactacca cctctactac ccccactacc accactctc    30120 ccaccaccag cactgccgcc cagcctcctc atagcagaac aaccacttttt atcaattcca    30180 agtcccactc ccccccacatt gccggcgggc cctccgcctc agactccgaa accaccgaga    30240
tctgcttctg caaatgctct gacgccattg cccaggattt ggaagatcac gaggaagatg    30300
agcatgactt cgcagatgca tgccaggcat cagagccaga agcgctgccg gtggccctca    30360
aacagtatgc agaccccac accaccccg accttcctcc accttcccag aagccaagtt    30420
tcctggggga aaatgaaact ctgcctctct ccatactcgc tctgacatct gttgctatgt    30480
```

```
tgaccgctct gctggtgctt ctatgctcta tatgctacct gatctgctgc agaaagaaaa    30540
aatctcacgg ccatgctcac cagcccctca tgcacttccc ttaccctcca gagctgggcg    30600
accacaaact ttaagtctgc agtaactatc tgcccatccc ttgtcagtcg acagcgatga    30660
gccccactaa tctaacggcc tctggactta caacatcgtc tcttaatgag accaccgctc    30720
ctcaagacct gtacgatggt gtctccgcgc tggttaacca gtgggatcac ctgggcatat    30780
ggtggctcct cataggagca gtgaccccgt gcctaatcct ggtctggatc atctgctgca    30840
tcaaaagcag aagacccagg cggcggccca tctacaggcc ctttgtcatc acacctgaag    30900
atgatgatga caccacttcc aggctgcaga ggctaaagca gctactcttc tcttttacag    30960
catggtaaat tgaatcatgc ctcgcatttt catctacttg tctctccttc cacttttttct   31020 gggctcttct acattggccg ctgtgtccca catcgaggta gactgcctca cgcccttcac    31080
agtctacctg cttttcggct ttgtcatctg caccctttgtc tgcagcgtta tcactgtagt    31140
gatctgcttc atacagtgca tcgactacgt ctgcgtgcgg gtggcttact ttagacacca    31200
cccccagtat cgcaacaggg acatagcggc tctcctaaga cttgtttaaa atcatggcca    31260
aattaactgt gattggtctt ctgatcatct gctgcgtcct agccgcgatt gggactcaag    31320
ctcctaccac caccagcgct cccagaaaga gacatgtatc ctgcagcttc aagcgtccct    31380
ggaatatacc ccaatgcttt actgatgaac ctgaaatctc tttggcttgg tacttcagcg    31440
tcaccgccct tcttatcttc tgcagtacgg ttattgccct tgccatctac ccttcccttg    31500
acctgggctg gaatgctgtc aactctatgg aatatcccac cttcccagaa ccagacctgc    31560
cagacctggt tgttctaaac gcgtttcctc ctcctgctcc cgttcaaaat cagtttcgcc    31620
ctccgtcccc cacgcccact gaggtcagct actttaatct aacaggcgga gatgactgaa    31680
aacctagacc tagaaatgga cggtctctgc agcgagcaac gcacactaga gaggcgccgg    31740 caaaagagc tcgagcgtct taaacaagag ctccaagacg cggtggccat acaccagtgc    31800
aaaaaaggtg tcttctgtct ggtaaaacag gccacgctca cctatgaaaa aacaggtgac    31860
acccaccgcc taggatacaa gctgcccaca cagcgccaaa agttcgccct catgataggc    31920
gaacaaccca tcaccgtgac ccagcactcc gtggagacaa aaggctgcat acatgctccc    31980
tgtaggggcg ctgactgcct ctacaccttg atcaaaaccc tctgcggtct cagagacctt    32040
atccctttca attaatcata actgtaatca ataaaaaatc acttacttga aatctgatag    32100
caagcctctg tccaattttt tcagcaacac ttccttcccc tcctcccaac tctggtactc    32160
taggcgcctc ctagctgcaa acttcctcca cagtctgaag ggaatgtcag attcctcctc    32220
ctgtccctcc gcacccacga tcttcatgtt gttgcagatg aaacgcgcga tcgtctga     32280 cgagaccttc aaccccgtgt accctacga taccgagatc gctccgactt ctgtcccttt    32340
ccttacccct ccctttgtgt catccgcagg aatgcaagaa atccagctg gggtgctgtc     32400 cctgcacttg tcagagcccc ttaccaccca caatgggggcc ctgactctaa aaatggggg    32460 cggcctgacc ctggacaagg aagggaatct cacttcccaa aacatcacca gtgtcgatcc    32520
ccctctcaaa aaaagcaaga acaacatcag ccttcagacc gccgcacccc tcgccgtcag    32580
ctccggggcc ctaacacttt ttgccactcc cccctagcg gtcagtggtg acaaccttac     32640
tgtgcagtct caggcccctc tcactttgga agactcaaaa ctaactctgg ccaccaaagg    32700 accccctaact gtgtccgaag gcaaaacttgt cctagaaaca gaggctcccc tgcatgcaag    32760
tgacagcagc agcctgggcc ttagcgttac ggccccactt agcattaaca atgacagcct    32820
```

```
aggactagat ctgcaggcac ccattgtctc tcaaaatgga aaactggctc taaatgtagc   32880
aggcccccta gctgtggcca atggcattaa tgctttgaca gtaggcacag gcaaaggtat   32940
tggtctaaat gaaaccagca ctcacttgca agcaaagttg gtcgccccc  taggctttga   33000 taccaatggc aacattaagc taagcgttgc aggaggcatg agactaaata atgacacact   33060
tatactagat gtaaactacc catttgaagc tcaaggccaa ctaagtctaa gagtgggcca   33120
gggtccgctg tatgtagatt ctagcagcca taacctgacc attagatgcc ttagaggatt   33180
atacataaca tcgtctaata accaaaccgg tctagaggcc aacataaaac taacaaaagg   33240
ccttgtctat gatggaaatg ccatagcagt caatgttggt caaggattgc aatacagcac   33300
tactgccaca tcggaaggtg tgtatcctat acagtctaag ataggtttgg gaatggaata   33360
tgataccaac ggagccatga tgacaaaact aggctctgga ctaagctttg acaattcagg   33420
agccattgta gtgggaaaca aaatgatga  caggcttact ctgtggacta caccagaccc   33480
atctcctaac tgtagaattt attctgaaaa agatactaaa ctaaccttgg tgctgactaa   33540
gtgtggcagc caaatcctag gcacagtatc tgcccttgct gtcagaggca gccttgcgcc   33600
catcactaat gcatccagca tagtccaaat atttctaaga tttgatgaaa atggactatt   33660
gatgagcaac tcatcgctag acggtgatta ctggaattac agaaatgggg actccactaa   33720
tagcacacca tatacaaatg cagtaggctt tatgcctaat ctagcagcct atcctaaagg   33780
tcaggctaca gctgcaaaaa gcagtattgt aagccaggta tacatggatg gtgacactac   33840
taaacctata acactaaaaa taaacttcaa tggcattgat gaaacaacag aaaataccc c   33900 tgttagtaaa tattccatga cattctcatg gagctggccc accgcaagct acataggcca   33960
cacttttgca acaaactctt ttactttctc ctacatcgcc caagaataaa gaaagcacag   34020
agatgcttgt tttgatttca aaattgtgtg cttttattta ttttcagctt acagtatttc   34080
cagtagtcat tcgaataaag cttaatcaaa ctgcatgaga accttccac  atagcttaaa   34140 ttagcaccag tgcaaatgga gaaaattcaa catacctttt ttatccagat atcagagaac   34200
tctagtggtc agttttcccc caccctccca gctcacagaa tacacagtcc tttcccccg    34260 gctggcttta aacaacacta tctcattggt aacagacata ttcttaggtg taataatcca   34320
cacggtctct tggcgggcca agcgctggtc ggtgatgtta ataaactccc caggcagctc   34380
tttcaagttc acgtcgctgt ccaactgctg aagcgctcgc ggctccgact gcgcctctag   34440
cggaggcaac ggcaacaccc gatccttgat ctataaagga gtagagtcat aatcccccat   34500
aagaataggg cggtgatgca gcaacaaggc gcgcagcaac tcctgccgcc gcctctccgt   34560
acgacaggaa tgcaacggcg tggtggtctc ctccgcgata atccgcaccg ctcgcagcat   34620
cagcatcctc gtcctccggg cacagcagcg catcctgatc tcactgagat cggcgcagta   34680
agtgcagcac aaaaccaaga tgttatttaa gatcccacag tgcaaagcac tgtacccaaa   34740
gctcatggcg ggaaggacag cccccacgtg accatcatac cagatcctta ggtaaatcaa   34800
atgacgacct ctcataaaca cgctggacat gtacatcacc tccttgggca tgcgctgatt   34860
caccacctct cgataccaca agcatcgctg attaattaaa gaccccctcaa gcaccatcct   34920 gaaccaggaa gccagcacct gacccccgc  caggcactgc agggaccccg gtgaattgca   34980
gtggcagtga agactccagc gctcgtagcc gtgaaccata gagccggtca ttatatccac   35040
attggcacaa cacaaacaca ctttcataca cttttcatg  attagcagct cctctctagt   35100
caggaccata tcccaaggaa tcacccactc ttgaatcaag gtaaatccca cacagcaggg   35160
caggcctctc acataactca cgttatgcat agtgagcgtg tcgcaatctg gaaataccgg   35220
```

```
atgatcttcc atcaccgaag ctcgcgtctc cgtctcaaag ggaggtaaac ggtccctcgt    35280
gtagggacag tggcgggata tcgagatcg tgttgaacgt agagtcatgc caaagggaac    35340
agcggacgta ctcatatttc ctccagcaga accaagtgcg cgcgtggcag ctatccctgc    35400
gtcttctgtc tcgccgcctg ccccgctcgg tgtagtagtt gtaatacagc cactccctca    35460
gaccgtcaag gcgctccctg gcgtccggat ctataacaac accgtcctgc agcgccgccc    35520
tgatgacatc caccaccgta gagtatgcca agcccagcca ggaaatgcat tcactttgac    35580
agcgagagat aggaggagcg ggaagagatg gaagaaccat gatagtaaaa gacttttatt    35640
ccaatcgatc ctctacaatg tcaaagtgta gatctataag atgacactgg tctcctccgc    35700
tgagtcgatc aaaaataaca gctaaaccac aaacaacacg attggtcaaa tgctccacaa    35760
gggcttgcag cataaaatcg cctcgaaagt ccaccgcaag cataacatca aagccaccgc    35820
ccctatcatg atctataata aaaccccac agctatccac cagacccata agttttcat    35880 ctctccatcg tgaaaaaata tttacaagct cctcctttaa atcacctcca accaattgaa    35940
aaagttgagc caaaccgccc tccaccttca ttttcagcaa gcgcatcatg attgcaaaaa    36000
ttcaggctcc tgagacacct gtataagatt gagaagcgga acgttaacgt caatgtttcg    36060
ctcgcgaaga tcgcgcctca gtgcaagcat gatataatcc cacaggtcgg agcggatcag    36120
cgaggacatc tccccgccag gaaccaactc aacggagcct atgctgatta taatacgcat    36180
attcggggct atgctgacca gcacggcccc caaataggcg tactgcatag gcggcgacaa    36240
aaagtgaaca gtttgggtta aaaaatcagg caaacagtcg cgcaaaaaag caagaacatc    36300
ataaccatgc tcatgcaaat agatgcaagt aagctcagga acgaccacag aaaaatgcac    36360
aatttttctc tcaaacatga ctgcgagccc tgcaaaaaat aaaaaagaaa cattacacaa    36420
gagtagcctg tcttacgatg ggatagacta ctctaaccaa cataagacgg ccacaacat    36480 cgcccgcgtg gccataaaaa aaattgtccg tgtgattaaa aagaagcaca gatagctggc    36540
cagtcatatc cggagtcatc acgtgtgaac ccgtgtagac ccccgggttg gacacatcgg    36600
ccaaacaaag aaagcggcca atgtacccag gaggaatcat aacactaaga cgaagataca    36660
acagaataac cccatgaggg ggaataacaa agttagtagg tgaataaaaa cgataaacac    36720
ccgaaactcc ctcctgcgta ggcaaaaatag cacctccc ttccaaaaca acatatagcg    36780
cttccacagc agccatgaca aaagactcaa aacactcaaa agactcagtc ttaccaggaa    36840
aataaaagca ctctcacagc accagcacta atcagagtgt gaagagggcc aagtgccgaa    36900
cgagtatata taggaataaa aaatgacgta aatgtgtaaa ggtcagaaaa cgcccagaaa    36960
aatacacaga ccaacgcccg aaacgaaaac ccgcgaaaaa atacccagaa cttcctcaac    37020
aaccgccact tccggtttct cacggtacgt cacttccgca agaaaagcaa aactacattt    37080
cccacatgtg taaaaacgaa accccgcccc ttgtaactgc ccacaactta catcatcaaa    37140
acataaactc ctacgtcacc cgccccgcct ctccccgccc acctcattat catattggcc    37200
acaatccaaa ataaggtata ttattgatga tg    37232
```

<210> SEQ ID NO 23
<211> LENGTH: 37213
<212> TYPE: DNA
<213> ORGANISM: Gorilla beringei beringei

<400> SEQUENCE: 23

```
ataatatacc ttattttgga ttgtggccaa tatgataatg aggtgggcgg ggagaggcgg       60
```

-continued

```
ggcgggtgac gtaggacgcg cgagtagggt tgggaggtgt ggcggaagtg tggcatttgc    120
aagtgggagg agctcacatg caagcttccg tcgcggaaaa tgtgacgttt ttgatgagcg    180
ccgcctacct ccggaagtgc aattttcgc gcgcttttca ccggatatcg tagtaatttt     240
gggcgggacc atgtaagatt tggccatttt cgcgcgaaaa gtgaaacggg gaagtgaaaa    300
ctgaataata gggcgttagt catagcgcgt aatatttacc gagggccgag ggactttgac    360
cgattacgtg gaggactcgc ccaggtgttt tttacgtgaa tttccgcgtt ccgggtcaaa    420
gtctccgttt ttattgtcac cgtcatttga cgcggagggt atttaaaccc gctgcgctcc    480
tcaagaggcc actcttgagt gccagcgaga agagttttct cctctgctcc gcttcggtga    540
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagttttgt ctaggtgggc    1080 ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
gaccagcgag gcagacagca ccgactctgg cacttctacc tctccccctg aaattcaccc   1320
agtggttcct ctgggtatac ataaacctgt tgctgttaaa gtttgcgggc gacgccctgc   1380
agtacagtgc attgaggact tgcttcacga tcccgaggaa cctttggact tgagccttaa   1440
acgccctagg caataaaccc cacctaagta ataaaccca cctaagtaat aaaccctgcc    1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca ataccctatac tatttggagg   1740 tatctgtggg gctctactca ggccaagttg gtttccagaa ttaagcagga ttacaagtgc   1800
gattttgaag agctttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca aacaaatgg    2040 aagattcaga aggaactgta cggttccgcc ctacgtcgtc cacttctgtc gcacagggg    2100 ctgaggtttc ccgaccatcg gcagcatcag aatctggaag acgagtcgga ggagcgagcg    2160
gaggagaaga tcagcttgag agccggcctg gaccctcctc aggaggaatg aatctcccgc    2220
aggtggttga cctgtttcca gaactgagac gggtcctgac tatcagggag gatggtcagt    2280
ttgtgaagaa gtttaagagg gatcggggtg agggagatga tgaggcggct agcaatttag    2340
cttttagtct gatgactcgc caccgaccgg aatgtattac ctatcagcag attaaggaga    2400
gttgtgccaa cgagctggat cttttgggtc agaagtatag catagaacag cttaccactt    2460
```

```
actggcttca gcctggggat gattgggaag aggcgatcag ggtgtatgca aaggtggccc    2520
tgcggcccga ttgcaagtat aagattacta agttggttaa tattagaaac tgctgctata    2580
tttctgggaa cggggccgaa gtggagatag atactcagga caggatggct tttaggtgtt    2640
gcatgataaa catgtggccc gggatactgg ggatggatgg ggtggtattc atgaatgtga    2700
ggtttacggg ccccaacttt aatggcacgg tgttcatggg caacaccaac ttgctcctgc    2760
atggtgcgag tttctatggg tttaataaca cctgtataga ggcctggacc gatgtaaagg    2820
ttcgaggttg ttccttttat agctgttgga aggcggtggt gtgtcgccct aaaagcaggg    2880
gttctgtgaa aaaatgcttg tttgaaaggt gcaccttagg catcctctct gagggcaact    2940
ccagggtgcg ccataatgtg gcttcgaact gcggttgctt catgcaagtg aaggggtga    3000
gcgttatcaa gcataactcg gtgtgtggaa actgcgagga tcgcgcctcc cagatgctga    3060
cctgctttga tggcaactgt cacctgttga agaccattca tataagcagc cacccagaa    3120
aggcctggcc cgtgtttgag cataacatct tgacccgctg ctccttgcat ctggggtca    3180
ggagggtat gttcctgcct taccagtgta actttagcca cactaaaatc ctgctggaac    3240
ccgagtgcat gaccaaggtc agcctgaatg gtgtgtttga tgtgactctg aaaatctgga    3300
aggtgctgag gtatgatgag accaggacca ggtgccgacc ctgcgagtgc ggcggcaagc    3360
acatgagaaa tcagcctgtg atgttggatg tgaccgagga gcttaggcct gaccatctgg    3420
tgctggcctg caccagggcc gagtttgggt ctagcgatga ggataccgat tgaggtgggt    3480
aaggtgggcg tggctagaag ggtggggcgt gtataaattg ggggtctaag ggtctctctg    3540
ttttgtcttg caacagccgc cgccatgagc gacaccggca acagctttga tggaagcatc    3600
tttagcccct atctgacagt gcgcatgcct cactgggctg gagtgcgtca gaatgtgatg    3660
ggttccaacg tggatggacg ccccgttctg ccttcaaatt cgtctacaat ggcctacgcg    3720
accgtgggag gaactccgct ggacgccgcg acctccgccg ccgcctccgc cgccgccgcg    3780
accgcgcgca gcatggctac ggacctttac agctcttttgg tggcgagcgg cgcggcctct    3840
cgcgcgtctg ctcgggatga gaaactgacc gctctgctgc ttaaactgga agacttgacc    3900
cgggagctgg gtcaactgac ccagcaggtc tccagcttgc gtgagagcag ccttgcctcc    3960
ccctaatggc ccataatata aataaaagcc agtctgtttg gattaagcaa gtgtatgttc    4020
tttatttaac tctccgcgcg cggtaagccc gggaccagcg gtctcggtcg tttagggtgc    4080
ggtggattct ttccaacacg tggtacaggt ggctctggat gtttagatac atgggcatga    4140
gtccatccct gggatggagg tagcaccact gcagagcttc gtgctcgggg gtggtgttgt    4200
atatgatcca gtcgtagcag gagcgctggg cgtggtgctg aaaaatgtcc ttaagcaaga    4260
ggcttatagc taggggaggg cccttggtgt aagtgtttac aaatctgctc agttgggagg    4320
ggtgcatccg ggggatata atgtgcatct tggactggat tttaggttg gctatgttcc      4380
cacccagatc ccttctggga ttcatgttgt gcaggaccac cagcacggta tatccagtgc    4440
acttgggaaa tttatcgtgg agcttagacg ggaatgcatg gaagaacttg gagacgccct    4500
tgtggcctcc cagatttttcc atacattcgt ccatgatgat ggcaatgggc ccgtgggaag    4560
ctgcctgagc aaaaatgttt ctgggatcgc tcacatcgta gttatgttcc agggtgaggt    4620
catcatagga catctttacg aatcgggggc ggagggtccc ggactggggg atgatggtac    4680
cctcgggccc cggggcgtag ttcccctcac agatctgcat ctcccaggct ttcatttcag    4740
agggagggat catatccacc tgcggagcga tgaaaaacac agtttctggc gcaggggaga    4800
```

-continued

| | |
|---|---|
| ttaactggga tgagagcagg tttctgagca gctgtgactt tccacagccg gtgggcccat | 4860 |
| atatcacgcc tatcaccggc tgcagctggt agttaagaga gctgcagctg ccgtcctccc | 4920 |
| ggagcagggg ggccacctcg ttcagcatat ccctgacgtg gatgttctcc ctgaccaatt | 4980 |
| ccgccagaag cgctcgccg cccagcgaaa gcagctcttg caaggaagca aaatttttca | 5040 |
| gcggttttag gccgtcggcc gtgggcatgt ttttcagcgt ctgggtcagc agttccagcc | 5100 |
| tgtcccacag ctcggtgatg tgctctacgg catctcgatc cagcagatct cctcgtttcg | 5160 |
| cgggttgggg cggctttcgc tgtagggcac cagccgatgg gcgtccagcg gggccagagt | 5220 |
| catgtccttc catgggcgca gggtcctcgt caggtggtc tgggtcacgg tgaaggggtg | 5280 |
| cgctccgggt tgggcgctgg ccagggtgcg cttgaggctg gttctgctgg tgctgaatcg | 5340 |
| ctgccgctct tcgccctgcg cgtcggccag gtagcatttg accatggtct cgtagtcgag | 5400 |
| accctcggcg gcgtgcccct tggcgcggag cttccccttg gaggtggcgc cgcacgaggg | 5460 |
| gcactgcagg ctcttcaggg cgtagagctt gggagcgaga acacggact ctggggagta | 5520 |
| ggcgtccgcg ccgcaggaag cgcagaccgt ctcgcattcc accagccaag tgagctccgg | 5580 |
| gcggtcaggg tcaaaaacca ggttgccccc atgctttttg atgcgtttct tacctcggct | 5640 |
| ctccatgagg cggtgtccct tctcggtgac gaagaggctg tccgtgtccc cgtagaccga | 5700 |
| cttcaggggc ctgtcttcca gcggagtgcc tctgtcctcc tcgtagagaa actctgacca | 5760 |
| ctctgagacg aaggcccgcg tccaggccag gacgaaggag gccacgtggg aggggtagcg | 5820 |
| gtcgttgtcc actagcgggt ccaccttctc cagggtgtgc aggcacatgt ccccctcctc | 5880 |
| cgcgtccaga aaagtgattg gcttgtaggt gtaggacacg tgaccggggg ttcccgacgg | 5940 |
| gggggtataa aaggggtgg gcgcccttc atcttcactc tcttccgcat cgctgtctgc | 6000 |
| gagggccagc tgctggggta agtattccct ctcgaaggcg ggcatgacct cagcgctcag | 6060 |
| gttgtcagtt tctaaaaatg aggaggattt gatgttcacc tgtccggagg tgatacccttt | 6120 |
| gagggtacct gggtccatct ggtcagaaaa cactattttt ttgttgtcaa gcttggtggc | 6180 |
| gaacgacccg tagagggcgt tggagagcag cttggcgatg gagcgcaggg tctggttttt | 6240 |
| gtcgcggtcg gctcgctcct tggccgcgat gttgagttgc acgtactcgc gggccacgca | 6300 |
| cttccactcg gggaagacgg tggtgcgctc gtctgggatt aggcgcaccc tccagcctcg | 6360 |
| gttgtgcagg gtgaccatgt cgacgctggt ggcgacctcg ccgcgcaggc gctcgttggt | 6420 |
| ccagcagagg cggccgccct tgcgcgagca gaagggggt aggggtcca gctggtcctc | 6480 |
| gtttgggggg tccgcgtcga tggtgaagac cccggggagc aagcgcgggt caaagtagtc | 6540 |
| gatcttgcaa gcttgcatgt ccagagcccg ctgccattcg cgggcggcga gcgcgcgctc | 6600 |
| gtaggggttg aggggcgggc cccagggcat ggggtgggtg agcgcggagg cgtacatgcc | 6660 |
| gcagatgtca tacacgtaca ggggttccct gaggatgccg aggtaggtgg ggtagcagcg | 6720 |
| ccccccgcgg atgctggcgc gcacgtagtc atagagctcg tgggaggggg ccagcatgtt | 6780 |
| gggcccgagg ttggtgcgct gggggcgctc ggcgcggaag gcgatctgcc tgaagatggc | 6840 |
| atgggagttg gaggagatgg tgggccgctg gaagacgttg aagcttgctt cttgcaagcc | 6900 |
| caccgagtcc ctgacgaagg aggcgtagga ctcgcgcagc ttgtgcacca gctcggcggt | 6960 |
| gacctggacg tcgagcgcgc agtagtcgag ggtctcgcgg atgatgtcat acttatcctc | 7020 |
| cccttcttt ttccacagct cgcggttgag gacgaactct tcgcggtctt tccagtactc | 7080 |
| ttggagggga aacccgtccg tgtccgaacg gtaagagcct agcatgtaga actggttgac | 7140 |
| ggcctggtag gggcaacagc ccttctccac gggcagcgcg taggcctgcg ccgccttgcg | 7200 |

```
gagggaggtg tgggtgaggg cgaaagtgtc cctgaccatg actttgaggt attgatgttt    7260
gaagtctgtg tcatcgcagc cgccctgttc ccacagggtg tagtccgtgc gcttttttgga   7320 gcgcgggttg ggcagggaga aggtgaggtc attgaagagg atcttcccg ctcgaggcat    7380 gaagtttctg gtgatgcgaa agggccctgg gaccgaggag cggttgttga tgacctgggc    7440
ggccaggacg atctcgtcaa agccgtttat gttgtggccc acgatgtaga gctccaaaaa    7500
gcggggctgg cccttgatgg aggggagctt tttgagttcc tcgtaggtga gctcctcggg    7560
cgattccagg ccgtgctcct ccagggccca gtcttgcaag tgagggttgg ccgccaggaa    7620
ggatcgccag aggtcgcggg ccatgagggt ctgcaggcgg tcgcggaagg ttctgaactg    7680
tcgccccacg gccatctttt cgggggtgat gcagtagaag gtgaggggt ctttctccca    7740 ggggtcccat ctgagctctc gggcgaggtc gcgcgcggcg gcgaccagag cctcgtcgcc    7800
ccccagtttc atgaccagca tgaagggcac gagctgcttg ccaaaggctc ccatccaagt    7860
gtaggtctct acatcgtagg tgacaaagag gcgctccgtg cgaggatgag agccgatcgg    7920
gaagaactgg atctcccgcc accagttgga ggattggctg ttgatgtggt gaaagtagaa    7980
gtcccgtctg cgggccgagc actcgtgctg gcttttgtaa aagcgaccgc agtactggca    8040
gcgctgcacg ggttgtatat cttgcacgag gtgaacctgg cgacctctga cgaggaagcg    8100
cagcgggaat ctaagtcccc cgcctggggt cccgtgtggc tggtggtctt ctactttggt    8160
tgtctggccg ccagcatctg tctcctggag ggcgatggtg gagcagacca ccacgccgcg    8220
agagccgcag gtccagatct cggcgctcgg cgggcgagt ttgatgacga catcgcgcac    8280
attggagctg tccatggtct ccagctcccg cggcggcagg tcagctggga gttcctggag    8340
gttcacctcg cagagacggg tcaaggcgcg ggcagtgttg agatggtatc tgatttcaag    8400
gggcgtgttg gcggcggagt cgatggcttg caggaggccg cagccccggg gggccacgat    8460
ggttccccgc ggggcgcgag gggaggcgga agctggggt gtgttcagaa gcggtgacgc    8520
gggcgggccc ccggaggtag gggggggttcc ggccccacag gcatgggcgg caggggcacg    8580
tcttcgccgc gcgcgggcag gggctggtgc tggctccgaa gagcgcttgc gtgcgcgacg    8640
acgcgacggt tggtgtcctg tatctgacgc ctctgagtga agaccacggg tcccgtgacc    8700
ttgaacctga aagagagttc gacagaatca atctcggcat cgttgacagc ggcctggcgc    8760
aggatctcct gcacgtcgcc cgagttgtcc tggtaggcga tctctgccat gaactgctcg    8820
atctcttctt cctggagatc tcctcgtccg gcgcgctcca cggtggccgc caggtcgttg    8880
gagatgcgac ccatgagctg tgagaaggcg ttgagcccgc cctcgttcca gacccggctg    8940
tagaccacgc ccccctcggc gtcgcgagcg cgcatgacca cctgggccag gttgagctcc    9000
acgtgtcgcg tgaagacggc gtagttcgcg aggcgctgga aaaggtagtt cagggtggtg    9060
gcggtgtgct cggcgacgaa gaagtacatg acccagcgcc gcaacgtgga ttcattgatg    9120
tcccccaagg cctccaggcg ctccatggcc tcgtagaagt ccacggcgaa gttgaaaaac    9180
tgggagttgc gagcggacac ggtcaactcc tcctccagaa gacggatgag ctcggcgaca    9240
gtgttgcgca cctcgcgctc gaaggccacg gggggcgctt cttcctcttc cacctcttct    9300
tccatgatcg cttcttcttc ttcctcagcc gggacggga gggcggcgg cggcggggga    9360 ggggcgcggc ggcggcggcg gcgcaccggg aggcggtcga tgaagcgctc gatcatctcc    9420
ccccgcatgc ggcgcatggt ctcggtgacg gcgcggccgt tctcccgggg gcgcagctcg    9480
aagacgccgc ctctcatctc gccgcggggc gagcggccgt gaggtagcga gacggcgctg    9540
```

```
actatgcatc ttaacaattg ctgtgtaggt acaccgccga gggacctgat tgagtccaga    9600
tccaccggat ccgaaaacct ttggaggaaa gcgtctatcc agtcgcagtc gcaaggtagg    9660
ctgagcaccg tggcgggcgg gggcgggtct ggagagttcc tggcggagat gctgctgatg    9720
atgtaattaa agtaggcggt cttgagaagg cggatggtgg acaggagcac catgtctttg    9780
ggtccggcct gttggatgcg gaggcggtcg gccatgcccc aggcctcgtt ctgacaccgg    9840
cgcaggtctt tgtagtagtc ttgcatgagt ctttccaccg gcacctcttc tccttcctct    9900
tctccatctc gccggtggtt tctcgcgccg cccatgcgcg tgaccccaaa gcccctgagc    9960
ggctgcagca gggccaggtc ggcgaccacg cgctcggcca agatggcctg ctgcacctga   10020
gtgagggtcc tctcgaagtc atccatgtcc acgaagcggt ggtaggcgcc cgtgttgatg   10080
gtgtaggtgc agttggccat gacggaccag ttgacggtct ggtgtcccgg ctgcgagagc   10140
tccgtgtacc gcaggcgcga aaggcgcgg gaatcgaaca cgtagtcgtt gcaagtccgc   10200
accagatact ggtagcccac caggaagtgc ggcggaggtt ggcgatagag gggccagcgc   10260
tgggtggcgg gggcgccggg cgccaggtct tccagcatga ggcggtggta tccgtagatg   10320
tacctggaca tccaggtgat gccggcggcg gtggtggtgg cgcgcgcgta gtcgcggacc   10380
cggttccaga tgtttcgcag gggcgagaag tgttccatgg tcggcacgct ctggccggtg   10440
aggcgcgcgc agtcgttgac gctctataca cacacaaaaa cgaaagcgtt tacagggctt   10500
tcgttctgta gcctggagga aagtaaatgg gttgggttgc ggtgtgcccc ggttcgagac   10560
caagctgagc tcggccggct gaagccgcag ctaacgtggt attggcagtc ccgtctcgac   10620
ccaggccctg tatcctccag gatacggtcg agagcccttt tgctttcttg gccaagcgcc   10680
cgtggcgcga tctgggatag atggtcgcga tgagaggaca aaagcggctc gcttccgtag   10740
tctggagaaa caatcgccag ggttgcgttg cggcgtaccc cggttcgagc ccctatggcg   10800
gcttgaatcg gccggaaccg cggctaacga gggccgtggc agcccgtcc tcaggacccc   10860
gccagccgac ttctccagtt acgggagcga gccccttttg tttttatttt tttagatgca   10920
tcccgtgctg cggcagatgc gcccctcgcc ccggcccgat cagcagcagc aacagcaggc   10980
atgcagaccc ccctctcccc tttccgcccc ggtcaccacg gccgcggcgg ccgtgtcggg   11040
cgcgggggc gcgctggagt cagatgagcc accgcggcgg cgacctaggc agtatctgga   11100
cttggaagag ggcgagggac tggcgcggct ggggcgaac tctccagagc gccaccgcg   11160
ggtgcagttg aaaagggacg cgcgcgaggc gtacctgccg cggcagaacc tgtttcgcga   11220
ccgcgggggc gaggagcccg aggagatgcg agactgcagg ttccaagcgg ggcgcgagct   11280
gcggcgcggg ctgacagac agcgcctgct gcgcgaggag gactttgagc ccgacacgca   11340
gacgggcatc agccccgcgc gcgcgcacgt agccgcggcc gacctggtga ccgcctacga   11400
gcagacggta aaccaggagc gcaacttcca aaagagcttc aacaaccacg tgcgcacgct   11460
ggtggcgcgc gaggaggtga ccctgggtct catgcatctg tgggacctgg tggaggcgat   11520
cgtgcagaac cccagcagca gcccctgac cgcgcagctg ttcctggtgg tgcagcacag   11580
cagggacaac gaggccttca gggaggcgct gctgaacatc accgagccgg aggggcgctg   11640
gctcctggac ctgataaaca tcctgcagag catagtggtg caggagcgca gcctgagcct   11700
ggccgagaag gtggcggcca tcaactactc tatgctgagc ctgggcaagt tctacgcccg   11760
caagatctac aagaccccct acgtgcccat agacaaggag gtgaagatag acagcttcta   11820
catgcgcatg gcgctgaagg tgctgaccct gagcgacgac ctgggagtgt accgcaacga   11880
gcgcatccac aaggccgtga gcgccagccg gcggcgcgag ctgagcgacc gcgagctgat   11940
```

```
gcacagtctg cagcgcgcgc tgaccggcgc gggcgagggc gacagggagg tcgagtccta    12000
cttcgacatg ggggccgacc tgcactggca gccgagccgc cgcgccctgg aggcggcggg    12060
ggcgtacggc ggccccctgg cggccgatga ccaggaagag gaggactatg agctagagga    12120
gggcgagtac ctggaggact gacctggctg gtggtgtttt ggtatagatg caagatccga    12180
acgtggcgga cccggcggtc cgggcggcgc tgcaaagcca gccgtccggc attaactcct    12240
ctgacgactg ggccgcggcc atgggtcgca tcatggccct gaccgcgcgc aaccccgagg    12300 cttttcaggca gcagcctcag gccaaccggc tggcggccat cttggaagcg gtagtgcccg    12360
cgcgctccaa ccccacccac gagaaggtgc tggccatagt caacgcgctg gcggagagca    12420
gggccatccg cgcggacgag gccggactgg tgtacgatgc gctgctgcag cgggtggcgc    12480
ggtacaacag cggcaacgtg cagaccaacc tggaccgcct ggtgacggac gtgcgcgagg    12540
ccgtggcgca gcgcgagcgc ttgcatcagg acggtaacct gggctcgctg gtggcgctaa    12600
acgccttcct cagcacccag ccggccaacg taccgcgggg gcaggaggac tacaccaact    12660
ttttgagcgc gctgcggctg atggtgaccg aggtccctca gagcgaggtg taccagtcgg    12720
ggcccgacta cttcttccag accagcagac agggcttgca aaccgtgaac ctgagccagg    12780 cttttcaagaa cctgcggggg ctgtggggag tgaaggcgcc caccggcgac cgggctacgg    12840
tgtccagcct gctaaccccc aactcgcgcc tgctgctgct gctgatcgcg cccttcacgg    12900
acagcgggag cgtctcgcgg gagacctatc tgggccacct gctgacgctg taccgcgagg    12960
ccatcgggca ggcgcaggtg gacgagcaca ccttccaaga gatcaccagc gtgagccacg    13020
cgctggggca ggaggacacg ggcagcctgc aggcgaccct gaactacctg ctgaccaaca    13080
ggcggcagaa gattcccacg ctgcacagcc tgacccagga ggaggagcgc atcttgcgct    13140
acgtgcagca gagcgtgagc ctgaacctga tgcgcgacgg cgtgacgccc agcgtggcgc    13200
tggacatgac cgcgcgcaac atggaaccgg gcatgtacgc ctcccaccgg ccgtttatca    13260
accgcctgat ggactacttg catcgggcgg cggccgtgaa ccccgagtac ttcactaatg    13320
ccattctgaa tccccactgg atgccccctc cgggtttcta caacggggac tttgaggtgc    13380
ccgaggtcaa cgacgggttc ctctgggatg acatggatga cagtgtgttc tcacccaacc    13440
cgctgcgcgc cgcgtctctg cgattgaagg agggctctga cagggaagga ccgaggagtc    13500
tggcctcctc cctggctctg ggagcggtgg gcgccacggg cgcggcggcg cggggcagta    13560
gccccttccc cagcctggca gactctctga acagcgggcg ggtgagcagg ccccgcttgc    13620
taggcgagga ggagtatctg aacaactccc tgctgcagcc cgcgagggac aagaacgctc    13680
agcggcagca gtttcccaac aatgggatag agagcctggt ggacaagatg tccagatgga    13740
agacgtatgc gcaggagtac aaggagtggg aggaccgcca gccgcggccc ttgccgcccc    13800
ctaggcagcg ctggcagcgg cgcgcgtcca accgccgctg gaggcagggg cccgaggacg    13860
atgatgactc tgcagatgac agcagcgtgt ggacctggg cgggagcggg aacccctttt    13920
cgcacctgcg cccacgcctg ggcaagatgt tttaaaagaa aaaaaaaata aaactcacca    13980
aggccatggc gacgagcgtt ggtttttttgt tcccttcctt agtatgcggc gcgcggcgat    14040
gttcgaggag gggcctcccc cctcttacga gagcgcgatg gggatttctc ctgcggcgcc    14100
cctgcagcct ccctacgtgc ctcctcggta cctgcaacct acaggggga gaaatagcat    14160 ctgttactct gagctgcagc ccctgtacga taccaccaga ctgtacctgg tggacaacaa    14220
gtccgcggac gtggcctccc tgaactacca gaacgaccac agcgattttt tgaccacggt    14280
```

```
gatccaaaac aacgacttca ccccaaccga ggccagcacc cagaccataa acctggataa    14340
caggtcgaac tggggcggcg acctgaagac catcttgcac accaacatgc ccaacgtgaa    14400
cgagttcatg ttcaccaact cttttaaggc gcgggtgatg gtggcgcgcg agcaggggga    14460
ggcgaagtac gagtgggtgg acttcacgct gcccgagggc aactactcag agaccatgac    14520
tctcgacctg atgaacaatg cgatcgtgga acactatctg aaagtgggca ggcagaacgg    14580
ggtgaaggaa agcgatatcg gggtcaagtt tgacaccaga aacttccgtc tgggctggga    14640
ccccgtgacc gggctggtca tgccgggggt ctacaccaac gaggcctttc atcccgacat    14700
agtgcttctg cccggctgtg gggtggactt cacccagagc cggctgagca acctgctggg    14760
cattcgcaag cggcagcctt ccaggagggg tttcaagatc acctatgagg atctgaaggg    14820
gggcaacatt cccgcgctcc ttgatctgga cgcctacgag gagagcttga acccgagga    14880 gagcgctggc gacagcggcg agagtggcga ggagcaagcc ggcggcggtg gcggcgcgtc    14940
ggtagaaaac gaaagtacgc ccgcagtggc ggcggacgct gcggaggtcg agccggaggc    15000
catgcagcag gacgcagagg agggcgcaca ggagggcgcg cagaaggaca tgaacgatgg    15060
ggagatcagg ggagacacat tcgccacccg gggcgaagaa aaagaggcag aggcggcggc    15120
ggcggcgacg gcggaggccg aaaccgaggt tgaggcagag gcagagcccg agaccgaagt    15180
tatggaagac atgaatgatg agaacgtag gggcgacacg ttcgccaccc ggggcgaaga    15240
gaaggcggcg gaggcagaag ccgcggctga ggaggcggct gcggctgcgg ccaagactga    15300
ggctgcggct aaggctgagg tcgaagccaa tgttgcggtt gaggctcagg ctgaggagga    15360
ggcggcggct gaagcagtta aggaaaaggc ccaggcagag caggaagaga aaaaacctgt    15420
cattcaacct ctaaaagaag atagcaaaaa gcgcagttac aacgtcatcg agggcagcac    15480
ctttacccag taccgcagct ggtacctggc gtacaactac ggcgaccggg tcaagggggt    15540
gcgctcgtgg accctgctct gcacgccgga cgtcacctgc ggctccgagc agatgtactg    15600
gtcgctgccg aacatgatgc aagacccggt gaccttccgc tccacgcggc aggttagcaa    15660
cttcccggtg gtgggcgccg aactgctgcc cgtgcactcc aagagttttt acaacgagca    15720
ggccgtctac tccagctga tccgccaggc caccctctctg acccacgtgt caatcgctt    15780 tcccgagaac cagattttgg cgcgcccgcc ggcccccacc atcaccaccg tgagtgaaaa    15840
cgttcctgcc ctcacagatc acgggacgct accgctgcgc aacagcatct caggagtcca    15900
gcgagtgacc attactgacg ccagacgccg gacctgcccc tacgtttaca aggccttggg    15960
catagtctcg ccgcgcgtcc tctccagtcg cacttttaa aacacatcta cccacacgtt    16020
ccaaaatcat gtccgtactc atctcaccca gcaacaacac cggctggggg ctgcgcgcgc    16080
ccagcaagat gtttggaggg gcgaggaagc gctccgacca gcaccctgtg cgcgtgcgcg    16140
gccactaccg cgcgccctgg ggagcgcaca agcgcgggcg cacagggcgc accactgtgg    16200
acgacgtcat tgactccgta gtggagcaag cgcgccacta cacacccggc gcgccgaccg    16260
cccccgccgt gtccaccgtg gaccaggcga tcgaaagcgt ggtacagggc gcgcggcact    16320
atgccaacct taaaagtcgc cgccgccgcg tggcccgccg ccatcgccgg agaccccggg    16380
ccaccgccgc cgcgcgcctt actaaggctc tgctcaggcg cgccaggcga actgccacc    16440 gggccgccat gagggccgca cggcgggctg ccgctgccgc aagcgtcgtg gccccgcggg    16500
cacgaaggcg cgcggccgct gccgccgccg ccgccatttc cagcttggcc tcgacgcggc    16560
gcggtaacat atactgggtg cgcgactcgg taaccggcac gcgggtaccc gtgcgctttc    16620 gcccccgcg gaattagcac aagacaacat acacactgag tctcctgctg ttgtgtatcc    16680
```

```
cagcggcgac cgtcagcagc ggcgacatgt ccaagcgcaa aattaaagaa gagatgctcc    16740
aggtcatcgc gccggagatc tatgggcccc cgaagaagga ggaggatgat tacaagcccc    16800
gcaagctaaa gcgggtcaaa aagaaaaaga aagatgatga tgacgaggcg gtggagtttg    16860
tccgccgcat ggcacccagg cgcccgtgc agtggaaggg ccggcgcgtg cagcgcgttt     16920
tgcgccccgg caccgcggtg gtcttcacgc ccggcgagcg ctccacgcgc actttcaagc    16980
gggtgtacga tgaggtgtac ggcgacgagg acctgttgga gcaggccaac cagcgctttg    17040
gggagtttgc atatgggaaa cggccccgcg agagtctaaa agaggacctg ctggcgctac    17100
cgctggacga gggcaatccc accccgagtc tgaagccggt aaccctgcaa caggtgctgc    17160
ctttgagcgc gcccagcgag cataagcgag ggttgaagcg cgaaggcggg gacctggcgc    17220
ccaccgtgca gttgatggtg cccaagcggc agaagctgga ggacgtgctg gagaaaatga    17280
aagtagagcc cgggatccag cccgagatca aggtccgccc catcaagcag gtggcgcccg    17340
gcgtgggagt ccagaccgtg gacgttagga ttcccacgga ggagatggaa acccaaaccg    17400
ccactccctc ttcggcggcc agcgccacca ccggcaccgc ttcggtagag gtgcagacgg    17460
acccctggct acccgccacc gctgttgccg ccgccgcccc ccgttcgcgc gggcgcaaga    17520
gaaattatcc agcggccagc gcgctcatgc cccagtacgc actgcatcca tccatcgtgc    17580
ccaccccggg ctaccgcggg tactcgtacc gccgcgcag atcagccggc actcgcggcc     17640
gccgccgccg tgcgaccaca accagccgcc gccgtcgccg ccgccgccag ccagtgctga    17700
cccccgtgtc tgtaaggaag gtggctcgct cggggagcac gctggtggtg cccagagcgc    17760
gctaccaccc cagcatcgtt taaagccggt ctctgtatgg ttcttgcaga tatggccctc    17820
acttgtcgcc tccgcttccc ggtgccggga taccgaggaa gaactcaccg ccgcagaggc    17880
atggcgggca gcggtctccg cggcggccgt cgccatcgcc ggcgcgcaaa aagcaggcgc    17940
atgcgcggcg gtgtgctgcc tctgctaatc ccgctaatcg ccgcggcgat cggtgccgta    18000
cccgggatcg cctccgtggc cctgcaggcg tcccagaaac gttgactctt gcaaccttgc    18060
aagcttgcat tttttggagg aaaaataaaa aaagtctag actctcacgc tcgcttggtc     18120
ctgtgactat tttgtagaaa aaagatgga agacatcaac tttgcgtcgc tggccccgcg    18180
tcacggctcg cgcccgttca tgggagactg gacagatatc ggcaccagca atatgagcgg    18240
tggcgccttc agctggggca gtctgtggag cggccttaaa aattttggtt ccaccattaa    18300
gaactatggc aacaaagcgt ggaacagcag cacgggccag atgctgagag acaagttgaa    18360
agagcagaac ttccaggaga aggtggcgca gggcctggcc tctggcatca gcggggtggt    18420
ggacatagct aaccaggccg tgcagaaaaa gataaacagt catctggacc cccgtcctca    18480
ggtggaggaa atgcctccag cgatggggac ggtgtctccc gagggcaaag gcgaaaagcg    18540
cccgcggccc gacagagaag agaccctggt gtcacacacc gaggagccgc cctcttacga    18600
ggaggcagtc aaggccggcc tgcccaccac tcgccccata gccccatgg ccaccggtgt     18660 ggtgggccac aggcaacaca ctcccgcaac actagatctg ccccgccgt ccgagccgcc     18720 gcgccagcca aaggcggcga cggtgccgc tccctccact tccgccgcca acagagtgcc     18780
cctgcgccgc gccgcgagcg gccccgggc ctcgcgagtt agcggcaact ggcagagcac     18840
actgaacagc atcgtgggcc tgggagtgag gagtgtgaag cgccgccgtt gctactgaat    18900
gagcaagcta gctaacgtgt tgtatgtgtg tatgcgtcct atgtcgccgc cagaggagct    18960
gttgagccgc cggcgccgtc tgcactccag cgaatttcaa gatggcgacc ccatcgatga    19020
```

```
tgcctcagtg gtcgtacatg cacatctcgg gccaggacgc ttcggagtac ctgagccccg   19080
ggctggtgca gttcgcccgc gccacagaca cctacttcaa catgagtaac aagttcagga   19140
accccactgt ggcgcccacc cacgatgtga ccacggaccg gtcgcagcgc ctgacgctgc   19200
ggttcatccc cgtggatcgg gaggacaccg cctactctta caaggcgcgg ttcacgctgg   19260
ccgtgggcga caaccgcgtg ctggacatgg cctccactta ctttgacatc aggggggtgc   19320
tggacagggg ccccaccttc aagcccact cgggtactgc ctacaactcc ctggccccca    19380
agggcgctcc caattcttgc gagtgggaac aagatgaacc agctcaggca gcaatagctg   19440
aagatgaaga agaacttgaa gaagaacaag ctcaggacga acaggcgccc actaagaaaa   19500
cccatgtata cgcccaggca cctctttctg gtgaaaaaat tactaaggat ggtttgcaaa   19560
taggtgtgga tgccacacag gcgggagata accctatata tgctgataaa acattccaac   19620
ccgaacctca gataggtgag tctcagtgga acgaggctga tgccacagta gcaggaggca   19680
gagtcttaaa aaagaccacc cctatgagac cttgctatgg atcctatgcc aaacctacta   19740
atgccaatgg cggtcaaggg atcatggtgg ccaatgatca gggagcgctt gaatctaaag   19800
ttgagatgca attttctcc accacaacgt ctcttaatgt aagggaaggt gaaaacaatc     19860
ttcagccaaa agtagtgcta tacagcgaag atgttaactt ggaatcccct gacactcatt   19920
tgtcttacaa acctaaaaag gatgacacca actctaaaat catgttgggt cagcaagcca   19980
tgcccaacag acccaacctc attgctttta gggacaactt tattggactt atgtactaca   20040
acagcacagg caacatggga gtgctggcag acaggcctc ccagctaaac gctgtggtag    20100
acttgcaaga cagaaacaca gagctgtcat accaactgat gcttgattcc attggagaca   20160
gatcaagata cttttccatg tggaaccagg cagtggacag ctatgaccca gatgtcagaa   20220
tcattgaaaa ccatggggtt gaagatgagc tgcccaacta ttgcttccc ctgggcggta    20280 ttggaattac agacacatac cagtgcataa aaccaaccgc agctgctaat aacactacat   20340
ggtctaagga tgaagaattt agtgatcgca atgaaatagg ggtgggaaac aacttcgcca   20400
tggagatcaa catccaggcc aacctctgga ggaacttcct ctatgcgaac gtggggctct   20460
acctgccaga caagctcaag tacaaccca ccaacgtgga catctctgac aaccccaaca    20520
cctatgacta catgaacaag cgtgtggtgg ctcccggcct ggtggactgc tttgtcaatg   20580
tgggagccag gtggtccctg gactacatgg acaacgtcaa ccccttcaac caccaccgca   20640
atgcgggtct gcgctaccgc tccatgatcc tgggcaacgg gcgctacgtg cccttccaca   20700
ttcaggtgcc ccagaagttc tttgccatca gaacctcct cctcctgccg ggctcctaca   20760
cttacgagtg gaacttcagg aaggatgtca acatggtcct gcagagctct ctgggcaatg   20820
accttagggt ggacgggcc agcatcaagt ttgacagcgt caccctctat gctaccttct   20880
tccccatggc tcacaacacc gcctccacgc tcgaggccat gctgaggaac acaccaacg    20940 accagtcctt caatgactac ctctctgggg ccaacatgct ctaccccatc ccgccaagg    21000 ccaccaacgt gcccatctcc attccctctc gcaactgggc cgccttcaga ggctgggcct   21060
ttacccgcct taagaccaag gaaaccccct ccctgggctc gggttttgac ccctactttg   21120
tctactcggg atccatcccc tacctggatg gcaccttcta cctcaaccac acttttaaga   21180
agatatccat catgtatgac tcctccgtca gctggcgggg caatgaccgc tgctcaccc    21240 ccaatgagtt cgaggtcaag cgcgccgtgg acggcgaggg ctacaacgtg gcccagtgca   21300
acatgaccaa ggactggttc ctggtgcaga tgctggccaa ctacaacata ggctaccagg   21360
gcttctacat cccagagagc tacaaggaca ggatgtactc cttcttcaga aatttccaac   21420
```

```
ccatgagcag gcaggtggtg gacgagacca aatacaagga ctatcaggcc attggcatca    21480
ctcaccagca caacaactcg ggattcgtgg gctacctggc tcccaccatg cgcgaggggc    21540
aggcctaccc cgccaacttc ccctacccgt tgataggcaa aaccgcggtc gacagcgtca    21600
cccagaaaaa gttcctctgc gaccgcaccc tctggcgcat cccttctct agcaacttca    21660 tgtccatggg tgcgctcacg gacctgggcc agaacctgct ctatgccaac tccgcccatg    21720
cgctggacat gacttttgag gtggacccca tggacgagcc caccttctc tatattgtgt     21780 ttgaagtgtt cgacgtggtc agagtgcacc agccgcaccg cggtgtcatc gagaccgtgt    21840
acctgcgcac gcccttctcg gccggcaacg ccaccaccta aggagacagc gccgccgcct    21900
gcatgacggg ttccaccgag caagagctca gggccatcgc cagagacctg ggatgcggac    21960
cctatttttt gggcacctat gacaaacgct tcccgggctt catctcccga gacaagctcg    22020
cctgcgccat cgtcaacacg gccgcgcgcg agaccggggg cgtgcactgg ctggcctttg    22080
gctgggaccc cgcgctccaaa acctgctacc tcttcgaccc cttggcttc tccgatcagc    22140 gcctcagaca gatctatgag tttgagtacg aggggctgct gcgccgcagc gcgcttgcct    22200
cctcgcccga ccgctgcatc acccttgaga agtccaccga gaccgtgcag gggcccact    22260 cggccgcctg cggtctcttc tgctgcatgt ttttgcacgc ctttgtgcgc tggccccaga    22320
gtcccatgga tcgcaacccc accatgaact tgctcaaggg agtgcccaac gccatgctcc    22380
agagccccca ggtccagccc accctgcgcc acaaccagga acagctctac cgcttcctgg    22440
agcgccactc cccctacttc cgcagtcaca gcgcgcacat ccgggggggcc acctctttct    22500 gccacttgca agaaaacatg caagacggaa aatgatgtac agctcgcttt ttaataaatg    22560
taaagactgt gcactttatt tatacacggg ctctttctgg ttatttattc aacaccgccg    22620
tcgccatcta gaaatcgaaa gggttctgcc gcgcgtcgcc gtgcgccacg ggcagagaca    22680
cgttgcgata ctggaagcgg ctcgcccact taaactcggg caccaccatg cggggcagtg    22740
gttcctcggg gaagttctcg ccccacaggg tgcgggtcag ctgcagcgcg ctcaggaggt    22800
cgggagccga gatcttgaag tcgcagttgg ggccggaacc ctgcgcgcgc gagttgcggt    22860
acacggggtt gcagcactgg aacaccagca gggccggatt atgcacgctg gccagcaggc    22920
tctcgtcgct gatcatgtcg ctgtccagat cctccgcgtt gctcagggcg aacggggtca    22980
tcttgcagac ctgcctgccc aggaaaggcg gcagcccggg cttgccgttg cagtcgcagc    23040 gcagggcat cagcaggtgc ccgcggcccg actgcgcctg cgggtacagc gcgcgcatga     23100
aggcttcgat ctgcctgaaa gccacctgcg tcttggctcc ctccgaaaag aacatcccac    23160
aggacttgct ggagaactgg ttcgcgggac agctggcatc gtgcaggcag cagcgcgcgt    23220
cggtgttggc gatctgcacc acgttgcgac cccaccggtt cttcactatc ttggccttgg    23280
aagcctgctc cttcagcgcg cgctggccgt tctcgctggt cacatccatc tctatcacct    23340
gctccttgtt gatcatgttt gtaccgtgca gacacttcag gtcgccctcc gtctgggtgc    23400
agcggtgctc ccacagcgcg caaccggtgg gctcccaatt tttgtgggtc accccgcgt    23460 aggcctgcag gtaggcctgc aagaagcgcc ccatcatggc cacaaaggtc ttctggctcg    23520
taaaggtcag ctgcaggccg cgatgctctt cgttcagcca ggtcttgcag atggcggcca    23580
gcgcctcggt ctgctcgggc agcatcctaa aatttgtctt caggtcgtta ccacgtggt     23640 acttgtccat catggcgcgc gccgcctcca tgcccttctc ccaggcggac accatgggca    23700
ggcttagggg gtttatcact tccaccggcg aggacaccgt actttcgatt tcttcttcct    23760
```

```
cccctcttc ccggcgcgcg cccacgctgc tgcgcgctct caccgcctgc accaagggt    23820 cgtcttcagg caagcgccgc accgagcgct tgccgcccct tgacctgctta atcagcaccg    23880 gcgggttgct gaagcccacc atggtcagcg ccgcctgctc ttcttcgtct tcgctgtcta    23940
ccactatctc tggggaaggg cttctccgct ctgcggcggc gcgcttcttt tttttcttgg    24000
gagcggccgt gatggagtcc gccacggcga cggaggtcga gggcgtgggg ctggggtgc    24060 gcggtaccag ggcctcgtcg ccctcggact cttcctctga ctccaggcgg cggcggagtc    24120
gcttctttgg gggcgcgcgc gtcagcggcg gcggagacgg ggacggggac ggggacggga    24180
cgccctccac aggggtggt cttcgcgcag acccgcggcc gcgtcggggg gtcttctcga    24240
gctggtcttg gtcccgactg gccattgtat cctcctcctc ctaggcagag agacataagg    24300
agtctatcat gcaagtcgag aaggaggaga gcttaaccac cccctctgag accgccgatg    24360
cgcccgccgt cgccgtcgcc cccgctgccg ccgacgcgcc cgccacaccg agcgacaccc    24420
ccgcggaccc ccccgccgac gcaccccttgt cgaggaagc ggccgtggag caggacccgg    24480
gctttgtctc ggcagaggag gatttgcgag aggaggagga taaggagaag aagccctcag    24540
tgccaaaaga tgataaagag caagacgagc acgacgcaga tgcacaccag ggtgaagtcg    24600
ggcgggggga cggagggcat gacggcgccg actacctaga cgaagggaac gacgtgctct    24660
tgaagcacct gcatcgtcag tgcgccattg tttgcgacgc tctgcaggag cgcagcgaag    24720
tgcccctcag cgtggcggag gtcagccacg cctacgagct cagcctcttc tccccccggg    24780
tgcccccccg ccgccgcgaa aacggcacat gcgagcccaa cccgcgcctc aacttctacc    24840
ccgcctttgt ggtacccgag gtcctggcca cctatcacat cttctttcaa aattgcaaga    24900
tccccctctc gtgccgcgcc aaccgtagcc gcgccgataa gatgctggcc ctgcgccagg    24960
gcgaccacat acctgatatc gccgctttgg aagatgtacc aaagatcttc gagggtctgg    25020
gtcgcaacga gaagcgggca gcaaactctc tgcaacagga aaacagcgaa aatgagagtc    25080
acaccggggt actggtggag ctcgaggcg acaacgcccg cctggcggtg gtcaagcgca    25140
gcatcgaggt cacccacttt gcctaccccg cgctaaacct gccccccaaa gtcatgaacg    25200
cggccatgga cgggctgatc atgcgccgcg gccggcccct cgctccagat gcaaacttgc    25260
atgaggagac cgaggacggc cagcccgtgg tcagcgacga gcagctggcg cgctggctgg    25320
agaccgcgga ccccgccgaa ctggaggagc ggcgcaagat gatgatgcc gtggtgctgg    25380 tcaccgtaga gctggagtgt ctgcagcgct tcttcggcga ccccgagatg cagagaaagg    25440
tcgaggagac cctgcactac accttccgcc agggctacgt gcgccaggct tgcaagatct    25500
ccaacgtgga gctcagcaac ctggtgtcct acctgggcat cttgcatgag aaccgcctcg    25560
ggcagagcgt gctgcactcc accctgcgcg gggaggcgcg ccgcgactac gtgcgcgact    25620
gcgtttacct cttcctctgc tacacctggc agacggccat gggggtctgg cagcagtgcc    25680
tggaggagcg caacctcaag gagctggaga agctcctgca gcgcgcgctc aaagatctct    25740
ggacgggcta caacgagcgc tcggtggccg ccgcgctggc cgacctcatc ttccccgagc    25800
gcctgctcaa aaccctccag caggggctgc ccgacttcac cagccaaagc atgttgcaaa    25860
acttcaggaa ctttatcctg gagcgttctg gcatcctacc cgccacctgc tgcgccctgc    25920
ccagcgactt tgtccccctc gtgtaccgcg agtgcccccc gccgctgtgg ggtcactgct    25980
acctgttcca actggccaac tacctgtcct accacgcgga cctcatggag gactccagcg    26040
gcgaggggct catggagtgc cactgccgct gcaacctctg cacgcccac cgctccctgg    26100 tctgcaacac ccaactgctc agcgagagtc agattatcgg taccttcgag ctacagggtc    26160
```

```
cgtcctcctc agacgagaag tccgcggctc cggggctaaa actcactccg gggctgtgga   26220
cttccgccta cctgcgcaaa tttgtacctg aagactacca cgcccacgag atcaggtttt   26280
acgaagacca atcccgcccg cccaaggcgg agctgaccgc ctgcgtcatc acccagggcg   26340
agatcctagg ccaattgcaa gccatccaaa aagcccgcca agacttttg ctgaagaagg   26400 gtcgggggt gtatctggac ccccagtcgg gtgaggagct caacccggtt ccccgctgc    26460 cgccgccgcg ggaccttgct tcccaggata agcatcgcca tggctcccag aaagaagcag   26520
cagcggccgc cactgccgcc accccacatg ctggaggaag aggaggaata ctgggacagt   26580
caggcagagg aggtttcgga cgaggaggag ccggagacgg agatggaaga gtgggaggag   26640
gacagcttag acgaggaggc ttccgaagcc gaagaggcag acgcaacacc gtcaccctcg   26700
gccgcagccc cctcgcaggc gccccgaag tccgctccca gcatcagcag caacagcagc    26760
gctataacct ccgctcctcc accgccgcga cccacggccg accgcagacc caaccgtaga   26820
tgggacacca ccggaaccgg ggccggtaag tcctccggga gaggcaagca agcgcagcgc   26880
caaggctacc gctcgtggcg cgctcacaag aacgccatag tcgcttgctt gcaagactgc   26940 gggggaaca tctccttcgc ccgccgcttc ctgctcttcc accacggtgt ggccttcccc    27000
cgtaacgtcc tgcattacta ccgtcatctc tacagcccct actgcggcgg cagtgagcca   27060
gagacggtcg gcgcggcgg cggcgcccgt ttcggcgcct aggaagaccc agggcaagac    27120
ttcagccaag aaactcgcgg cggccgcggc gaacgcggtc gcggggcccc tgcgcctgac   27180
ggtgaacgaa ccctgtcga cccgcgaact gaggaaccga atcttcccca ctctctatgc    27240
catcttccag cagagcagag ggcaggatca ggaactgaaa gtaaaaaaca ggtctctgcg   27300
ctccctcacc cgcagctgtc tgtatcacaa gagcgaagac cagcttcggc gcacgctgga   27360
ggacgctgag gcactcttca gcaaatactg cgcgctcact cttaaggact agctccgcgc   27420
ccttctcgaa tttaggcggg aacgcctacg tcatcgcagc gccgccgtca tgagcaagga   27480
cattcccacg ccatacatgt ggagctatca gccgcagatg ggactcgcgg cgggcgcctc   27540
ccaagactac tccacccgca tgaactggct cagtgccggc ccacacatga tctcacaggt   27600
taatgatatc cgcacccatc gaaaccaaat attggtggag caggcggcaa ttaccaccac   27660
gccccgcaat aatcccaacc ccagggagtg gcccgcgtcc ctggtgtatc aggaaattcc   27720 cggcccacc accgtactac ttccgcgtga ttcccaggcc gaagtccaaa tgactaactc    27780
aggggcacag ctcgcgggcg gctgtcgtca cagggtgcgg cctcctcgcc agggtataac   27840
tcacctggag atccgaggca gaggtattca gctcaacgac gagtcggtga gctcctcgct   27900
cggtctcaga cctgacggga ccttccagat agccggagcc ggccgatctt ccttcacgcc   27960
ccgccaggcg tacctgactc tgcaaagctc gtccctcggc gccgcgctcgg gcggcatcgg   28020 gactctccag ttcgtgcagg agtttgtgcc ctcggtctac ttcaacccct ctcgggctc    28080 tcccggtcgc tacccggacc agttcatctc gaactttgac gccgcgaggg actcggtgga   28140
cggctacgac tgaatgtcgg gtggacccgg tgcagagcaa cttcgcctga agcacctcga   28200
ccactgccgc cgcccctcagt gctttgcccg ctgtcagacc ggtgagttcc agtactttc    28260 cctgcccgac tcgcacccgg acggcccggc gcacggggtg cgcttttca tcccgagtca    28320 ggtgcgctct accctaatca gggagtttac cgcccgtccc ctactggcgg agttggaaaa   28380
ggggccttct atcctaacca ttgcctgcat ctgctctaac cctggattgc accaagatct   28440
ttgctgtcat ttgtgtgctg agtataataa aggctgagat cagaatctac tcgggctcct   28500
```

```
gtcgccatcc tgtcaacgcc accgtccaag cccggcccga tcagcccgag gtgaacctca    28560
cctgcggtct gcaccggcgc ctgaggaaat acctagcttg gtactacaac agcactccct    28620
ttgtggttta caacagcttt gaccaggacg gggtctcact gagggataac ctctcgaacc    28680
tgagctactc catcaggaag aacagcaccc tcgagctact tcctccttac ctgcccggga    28740
cttaccagtg tgtcaccggt ccctgcaccc acacccacct gttgatcgta aacgactctc    28800
ttccgagaac agacctcaat aactcctctt cgcagttccc cagaacagga ggtgagctca    28860
ggaaaccccg ggtaaagaag ggtggacgag agttaacact tgtggggttt ctggtgtatg    28920
tgacgctggt ggtggctctt ttgattaagg cttttccttc catgtctgaa ctctccctct    28980
tcttttatga acaactcgac tagtgctaac gggaccctac ccaacgaatc gggattgaat    29040
atcggtaacc aggttgcagt ttcacttttg attaccttca tagtcctctt cctgctagtg    29100
ctgtcgcttc tgtgcctgcg gatcgggggc tgctgcatcc acgtttatat ctggtgctgg    29160
ctgtttagaa ggttcggaga ccatcgcagg tagaataaac atgctgctgc ttaccctctt    29220
tgtcctggcg ctggccgcca gctgccaagc cttttccgag gctgacttta tagagcccca    29280
gtgtaatgtg acttttaaag cccatgcaca gcgttgtcat actataatca aatgtgccac    29340
cgaacacgat gaatacctta tccagtataa agataaatca cacaaagtgg cacttgttga    29400
catctggaaa cccgaagacc ctttggaata caatgtgacc gttttccagg gtgacctctt    29460
caaaatttac aattacactt tcccatttga ccagatgtgt gactttgtca tgtacatgga    29520
aaagcagcac aagctgtggc tccgactccc caggctgt gtggaaaatc caggctcttt    29580
ctgcatgatc tctctctgtg taactgtgct ggcactaata tcacgcttt tgtatatcag    29640
atttaaatca aggcaaagct tcattgatga aagaaaatg ccttaatcgc tttcacgctt    29700
gattgctaac accgggtttt tatccgcaga atgattggaa tcaccctact aatcacctcc    29760
ctccttgcga ttgcccatgg gttggaacga atcgaagtcc ctgtgggggc caatgttacc    29820
ctggtggggc ctgtcggcaa tgctacatta atgtgggaaa aatatactaa aaatcaatgg    29880
gtctcttact gcactaacaa aaatagccac aagcccagag ccatctgcga tgggcaaaat    29940
ctaaccttga ttgatgttca attgctggat gcgggctact attatgggca gctgggtaca    30000
atgattaatt actggagacc ccacagagat tacatgctcc acgtagtaaa gggtcccctt    30060
agcagcccac ccactaccac ctctactacc cccactacca ccactactcc caccaccagc    30120
actgccgccc agcctcctca tagcagaaca accactttta tcaattccaa gtcccactcc    30180
ccccacattg ccggcgggcc ctcgcctca gactccgaaa ccaccgagat ctgcttctgc    30240
aaatgctctg acgccattgc ccaggatttg gaagatcacg aggaagatga gcatgacttc    30300
gcagatgcat gccaggcatc agagccgaa gcgctgccgg tggccctcaa acagtatgca    30360
gacccccaca ccacccccga ccttcctcca ccttcccaga agccaagttt cctggggaa    30420
aatgaaactc tgcctctctc catactcgct ctgacatctg ttgctatgtt gaccgctctg    30480
ctggtgcttc tatgctctat atgctacctg atctgctgca gaaagaaaaa atctcacggc    30540
catgctcacc agcccctcat gcacttccct taccctccag agctgggcga ccacaaactt    30600
taagtctgca gtaactatct gcccatccct tgtcagtcga cagcgatgag ccccactaat    30660
ctaacggcct ctggacttac aacatcgtct cttaatgaga ccaccgctcc tcaagacctg    30720
tacgatggtg tctccgcgct ggttaaccag tgggatcacc tgggcatatg gtggctcctc    30780
ataggagcag tgacctgtgt cctaatcctg gtctggatca tctgctgcat caaaagcaga    30840
agacccaggc ggcggcccat ctacaggccc tttgtcatca cacctgaaga tgatgatgac    30900
```

```
accacttcca ggctgcagag gctaaagcag ctactcttct cttttacagc atggtaaatt   30960
gaatcatgcc tcgcattttc atctacttgt ctctccttcc acttttctg ggctcttcta    31020
cattggccgc tgtgtcccac atcgaggtag actgcctcac gcccttcaca gtctacctgc   31080
ttttcggctt tgtcatctgc acctttgtct gcagcgttat cactgtagtg atctgcttca   31140
tacagtgcat cgactacgtc tgcgtgcggg tggcttactt tagacaccac ccccagtatc   31200
gcaacaggga catagcggct ctcctaagac ttgtttaaaa tcatggccaa attaactgtg   31260
attggtcttc tgatcatctg ctgcgtccta gccgcgattg ggactcaagc tcctaccacc   31320
accagcgctc ccagaaagag acatgtatcc tgcagcttca agcgtccctg gaatataccc   31380
caatgcttta ctgatgaacc tgaaatctct ttggcttggt acttcagcgt caccgccctt   31440
cttatcttct gcagtacggt tattgcccct gccatctacc cttcccttga cctgggctgg   31500
aatgctgtca actctatgga atatcccacc ttcccagaac cagacctgcc agacctggtt   31560
gttctaaacg cgtttcctcc tcctgctccc gttcaaaatc agtttcgccc tccgtccccc   31620
acgcccactg aggtcagcta ctttaatcta acaggcggag atgactgaaa acctagacct   31680
agaaatggac ggtctctgca gcgagcaacg cacactagag aggcgccggc aaaaagagct   31740
cgagcgtctt aaacaagagc tccaagacgc ggtggccata caccagtgca aaaaaggtgt   31800
cttctgtctg gtaaaacagg ccacgctcac ctatgaaaaa acaggtgaca cccaccgcct   31860
aggatacaag ctgcccacac agcgccaaaa gttcgccctc atgataggcg aacaacccat   31920
caccgtgacc cagcactccg tggagacaga aggctgcata catgctccct gtaggggcgc   31980
tgactgcctc tacaccttga tcaaaaccct ctgcggtctc agagaccttac tcccttttcaa   32040
ttaatcataa ctgtaatcaa taaaaaatca cttacttgaa atctgatagc aagcctctgt   32100
ccaattttt cagcaacact tccttcccct cctcccaact ctggtactct aggcgcctcc     32160
tagctgcaaa cttcctccac agtctgaagg gaatgtcaga ttcctcctcc tgtccctccg   32220
cacccacgat cttcatgttg ttgcagatga aacgcgcgag atcgtctgac gagaccttca   32280
accccgtgta cccctacgat accgagatcg ctccgacttc tgtcccttc cttacccctc    32340
cctttgtgtc atccgcagga atgcaagaaa atccagctgg ggtgctgtcc ctgcacttgt   32400
cagagcccct taccacccac aatgggggcc tgactctaaa aatgggggc ggcctgaccc    32460
tggacaagga agggaatctc acttcccaaa acatcaccag tgtcgatccc cctctcaaaa   32520
aaagcaagaa caacatcagc cttcagaccg ccgcaccccct cgccgtcagc tcggggccc   32580
taacactttt tgccactccc ccctagcgg tcagtggtga caaccttact gtgcagtctc    32640
aggcccctct cactttggaa gactcaaaac taactctggc caccaaagga cccctaactg   32700
tgtccgaagg caaacttgtc ctagaaacag aggctcccct gcatgcaagt gacagcagca   32760
gcctgggcct tagcgttacg gccccactta gcattaacaa tgacagccta ggactagatc   32820
tgcaggcacc cattgtctct caaaatggaa aactggctct aaatgtagca ggcccctag    32880
ctgtggccaa tggcattaat gctttgacag taggcacagg caaggtatt ggtctaaatg     32940
aaaccagcac tcacttgcaa gcaaagttgg tcgcccccct aggctttgat accaatggca   33000
acattaagct aagcgttgca ggaggcatga gactaaataa tgcacactt atactagatg    33060
taaactaccc atttgaagct caaggccaac taagtctaag agtgggccag gtccgctgt    33120
atgtagattc tagcagccat aacctgacca ttagatgcct tagaggatta tacataacat   33180
cgtctaataa ccaaaccggt ctagaggcca acataaaact aacaaaaggc cttgtctatg   33240
```

-continued

```
atggaaatgc catagcagtc aatgttggtc aaggattgca atacagcact actgccacat    33300
cggaaggtgt gtatcctata cagtctaaga taggtttggg aatggaatat gataccaacg    33360
gagccatgat gacaaaacta ggctctggac taagctttga caattcagga gccattgtag    33420
tgggaaacaa aaatgatgac aggcttactc tgtggactac accagaccca tctcctaact    33480
gtagaattta ttctgaaaaa gatactaaac taaccttggt gctgactaag tgtggcagcc    33540
aaatcctagg cacagtatct gcccttgctg tcagaggcag ccttgcgccc atcactaatg    33600
catccagcat agtccaaata tttctaagat tgatgaaaa tggactattg atgagcaact     33660
catcgctaga cggtgattac tggaattaca gaaatgggga ctccactaat agcacaccat    33720
atacaaatgc agtaggcttt atgcctaatc tagcagccta tcctaaaggt caggctacag    33780
ctgcaaaaag cagtattgta agccaggtat acatggatgg tgacactact aaacctataa    33840
cactaaaaat aaacttcaat ggcattgatg aaacaacaga aataccccct gttagtaaat    33900
attccatgac attctcatgg agctggccca ccgcaagcta cataggccac acttttgcaa    33960
caaactcttt tactttctcc tacatcgccc aagaataaag aaagcacaga gatgcttgtt    34020
ttgatttcaa aattgtgtgc ttttatttat tttcagctta cagtatttcc agtagtcatt    34080
cgaataaagc ttaatcaaac tgcatgagaa cccttccaca tagcttaaat tagcaccagt    34140
gcaaatggag aaaattcaac ataccttttt tatccagata tcagagaact ctagtggtca    34200
gttttccccc accctcccag ctcacagaat acacagtcct ttccccccgg ctggcttttaa   34260
acaaacactat ctcattggta acagacatat tcttaggtgt aataatccac acggtctctt   34320
ggcgggccaa gcgctggtcg gtgatgttaa taaactcccc aggcagctct ttcaagttca    34380
cgtcgctgtc caactgctga agcgctcgcg gctccgactg cgcctctagc ggaggcaacg    34440
gcaacacccg atccttgatc tataaaggag tagagtcata atcccccata agaatagggc    34500
ggtgatgcag caacaaggcg cgcagcaact cctgccgccg cctctccgta cgacaggaat    34560
gcaacggcgt ggtggtctcc tccgcgataa tccgcaccgc tcgcagcatc agcatcctcg    34620
tcctccgggc acagcagcgc atcctgatct cactgagatc ggcgcagtaa gtgcagcaca    34680
aaaccaagat gttatttaag atcccacagt gcaaagcact gtacccaaag ctcatggcgg    34740
gaaggacagc ccccacgtga ccatcatacc agatccttag gtaaatcaaa tgacgacctc    34800
tcataaacac gctggacatg tacatcacct ccttgggcat gcgctgattc accacctctc    34860
gataccacaa gcatcgctga ttaattaaag accccctcaag caccatcctg aaccaggaag    34920
ccagcacctg acccccgcc aggcactgca gggaccccgg tgaattgcag tggcagtgaa     34980
gactccagcg ctcgtagccg tgaaccatag agccggtcat tatatccaca ttggcacaac    35040
acaaacacac tttcatacac tttttcatga ttagcagctc ctctctagtc aggaccatat    35100
cccaaggaat cacccactct tgaatcaagg taaatcccac acagcagggc aggcctctca    35160
cataactcac gttatgcata gtgagcgtgt cgcaatctgg aaataccgga tgatcttcca    35220
tcaccgaagc tcgcgtctcc gtctcaaagg gaggtaaacg gtccctcgtg tagggacagt    35280
ggcgggataa tcgagatcgt gttgaacgta gagtcatgcc aaagggaaca gcggacgtac    35340
tcatatttcc tccagcagaa ccaagtgcgc gcgtggcagc tatccctgcg tcttctgtct    35400
cgccgcctgc cccgctcggt gtagtagttg taatacagcc actccctcag accgtcaagg    35460
cgctccctgg cgtccggatc tataacaaca ccgtcctgca gcgccgccct gatgacatcc    35520
accaccgtag agtatgccaa gcccagccag gaaatgcatt cactttgaca gcgagagata    35580
ggaggagcgg gaagagatgg aagaaccatg atagtaaaag acttttattc caatcgatcc    35640
```

```
tctacaatgt caaagtgtag atctataaga tgacactggt ctcctccgct gagtcgatca   35700
aaaataacag ctaaaccaca aacaacacga ttggtcaaat gctccacaag ggcttgcagc   35760
ataaaatcgc ctcgaaagtc caccgcaagc ataacatcaa agccaccgcc cctatcatga   35820
tctataataa aaaccccaca gctatccacc agacccataa agttttcatc tctccatcgt   35880
gaaaaaatat ttacaagctc ctcctttaaa tcacctccaa ccaattgaaa aagttgagcc   35940
aaaccgccct ccaccttcat tttcagcaag cgcatcatga ttgcaaaaat tcaggctcct   36000
gagacacctg tataagattg agaagcggaa cgttaacgtc aatgtttcgc tcgcgaagat   36060
cgcgcctcag tgcaagcatg atataatccc acaggtcgga gcggatcagc gaggacatct   36120
ccccgccagg aaccaactca acggagccta tgctgattat aatacgcata ttcggggcta   36180
tgctgaccag cacggccccc aaataggcgt actgcatagg cggcgacaaa aagtgaacag   36240
tttgggttaa aaaatcaggc aaacagtcgc gcaaaaaagc aagaacatca taaccatgct   36300
catgcaaata gatgcaagta agctcaggaa cgaccacaga aaaatgcaca attttttctct  36360
caaacatgac tgcgagccct gcaaaaaata aaaagaaac attacacaag agtagcctgt    36420
cttacgatgg gatagactac tctaaccaac ataagacggg ccacaacatc gcccgcgtgg   36480
ccataaaaaa aattgtccgt gtgattaaaa agaagcacag atagctggcc agtcatatcc   36540
ggagtcatca cgtgtgaacc cgtgtagacc cccgggttgg acacatcggc caaacaaaga   36600
aagcggccaa tgtacccagg aggaatcata acactaagac gaagatacaa cagaataacc   36660
ccatgagggg gaataacaaa gttagtaggt gaataaaaac gataaacacc cgaaactccc   36720
tcctgcgtag gcaaaatagc accctcccct tccaaaacaa catatagcgc ttccacagca   36780
gccatgacaa aagactcaaa acactcaaaa gactcagtct taccaggaaa ataaaagcac   36840
tctcacagca ccagcactaa tcagagtgtg aagagggcca agtgccgaac gagtatatat   36900
aggaataaaa aatgacgtaa atgtgtaaag gtcagaaaac gcccagaaaa atacacagac   36960
caacgcccga aacgaaaacc cgcgaaaaaa tacccagaac ttcctcaaca accgccactt   37020
ccggtttctc acggtacgtc acttccgcaa gaaaagcaaa actacatttc ccacatgtgt   37080
aaaaacgaaa ccccgcccct tgtaactgcc cacaacttac atcatcaaaa cataaactcc   37140
tacgtcaccc gccccgcctc tccccgccca cctcattatc atattggcca caatccaaaa   37200
taaggtatat tat                                                     37213
```

<210> SEQ ID NO 24
<211> LENGTH: 37216
<212> TYPE: DNA
<213> ORGANISM: Gorilla beringei beringei

<400> SEQUENCE: 24

```
ataatatacc ttattttgga ttgtggccaa tatgataatg aggtgggcgg ggagaggcgg     60
ggcgggtgac gtaggacgcg cgagtagggt tgggaggtgt ggcggaagtg tggcatttgc    120
aagtgggagg agctcacatg caagcttccg tcgcggaaaa tgtgacgttt ttgatgagcg    180
ccgcctacct ccggaagtgc caattttcgc gcgcttttca ccggatatcg tagtaatttt    240
gggcgggacc atgtaagatt tggccatttt cgcgcgaaaa gtgaacggg gaagtgaaaa     300
ctgaataata gggcgttagt catagcgcgt aatatttacc gagggccgag ggactttgac    360
cgattacgtg gaggactcgc ccaggtgttt tttacgtgaa tttccgcgtt ccgggtcaaa    420
gtctccgttt ttattgtcac cgtcatttga cgcggagggt atttaaaccc gctgcgctcc    480
```

```
tcaagaggcc actcttgagt gccagcgaga agagttttct cctctgctcc gcttcggtga    540
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagttttttgt ctaggtgggc   1080
ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
gaccagcgag gcagacagca ccgactctgg cacttctacc tctcccctg aaattcaccc    1320
agtggttcct ctgggtatac ataaacctgt tgctgttaaa gtttgcgggc gacgccctgc   1380
agtacagtgc attgaggact tgcttcacga tcccgaggaa cctttggact tgagccttaa   1440
acgccctagg caataaaccc cacctaagta ataaacccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca atacctatac tatttggagg   1740
tatctgtggg gctctactca ggccaagttg gttttccagaa ttaagcagga ttacaagtgc   1800
gattttgaag agcttttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca aacaaatgg    2040
aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
```

```
gttctgtgaa aaaatgcttg tttgaaaggt gcaccttagg catcctctct gagggcaact    2940
ccagggtgcg ccataatgtg gcttcgaact gcggttgctt catgcaagtg aaggggggtga   3000
gcgttatcaa gcataactcg gtgtgtggaa actgcgagga tcgcgcctcc cagatgctga    3060
cctgctttga tggcaactgt cacctgttga agaccattca tataagcagc caccccagaa    3120
aggcctggcc cgtgtttgag cataacatct tgacccgctg ctccttgcat ctgggggtca    3180
ggaggggtat gttcctgcct taccagtgta actttagcca cactaaaatc ctgctggaac    3240
ccgagtgcat gaccaaggtc agcctgaatg gtgtgtttga tgtgactctg aaaatctgga    3300
aggtgctgag gtatgatgag accaggacca ggtgccgacc ctgcgagtgc ggcggcaagc    3360
acatgagaaa tcagcctgtg atgttggatg tgaccgagga gcttaggcct gaccatctgg    3420
tgctggcctg caccagggcc gagtttgggt ctagcgatga ggataccgat tgaggtgggt    3480
aaggtgggcg tggctagaag ggtggggcgt gtataaattg ggggtctaag ggtctctctg    3540
ttttgtcttg caacagccgc cgccatgagc gacaccggca acagctttga tggaagcatc    3600
tttagcccct atctgacagt gcgcatgcct cactgggctg gagtgcgtca gaatgtgatg    3660
ggttccaacg tggatggacg ccccgttctg ccttcaaatt cgtctacaat ggcctacgcg    3720
accgtgggag gaactccgct ggacgccgcg acctccgccg ccgcctccgc cgccgccgcg    3780
accgcgcgca gcatggctac ggacctttac agctctttgg tggcgagcgg cgcggcctct    3840
cgcgcgtctg ctcgggatga gaaactgacc gctctgctgc ttaaactgga agacttgacc    3900
cgggagctgg gtcaactgac ccagcaggtc tccagcttgc gtgagagcag ccttgcctcc    3960
ccctaatggc ccataatata aataaaagcc agtctgtttg gattaagcaa gtgtatgttc    4020
tttatttaac tctccgcgcg cggtaagccc gggaccagcg gtctcggtcg tttagggtgc    4080
ggtggattct ttccaacacg tggtacaggt ggctctggat gtttagatac atgggcatga    4140
gtccatccct ggggtggagg tagcaccact gcagagcttc gtgctcgggg gtggtgttgt    4200
atatgatcca gtcgtagcag gagcgctggg cgtggtgctg aaaaatgtcc ttaagcaaga    4260
ggcttatagc taggggagg cccttggtgt aagtgtttac aaatctgctc agttgggagg    4320
ggtgcatccg gggggatata atgtgcatct tggactggat ttttaggttg gctatgttcc    4380
cacccagatc ccttctggga ttcatgttgt gcaggaccac cagcacggta tatccagtgc    4440
acttgggaaa tttatcgtgg agcttagacg ggaatgcatg gaagaacttg gagacgccct    4500
tgtggcctcc cagattttcc atacattcgt ccatgatgat ggcaatgggc ccgtgggaag    4560
ctgcctgagc aaaaatgttt ctgggatcgc tcacatcgta gttatgttcc agggtgaggt    4620
catcatagga catctttacg aatcgggggc ggagggtccc ggactggggg atgatggtac    4680
cctcgggccc cggggcgtag ttcccctcac agatctgcat ctcccaggct ttcatttcag    4740
agggagggat catatccacc tgcggagcga tgaaaaacac agtttctggc gcaggggaga    4800
ttaactggga tgagagcagg tttctgagca gctgtgactt tccacagccg gtgggcccat    4860
atatcacgcc tatcaccggc tgcagctggt agttaagaga gctgcagctg ccgtcctccc    4920
ggagcagggg ggccacctcg ttcagcatat ccctgacgtg gatgttctcc ctgaccaatt    4980
ccgccagaag gcgctcgccg cccagcgaaa gcagctcttg caaggaagca aaattttca    5040
gcggttttag gccgtcggcc gtgggcatgt ttttcagcgt ctgggtcagc agttccagcc    5100
tgtcccacag ctcggtgatg tgctctacgg catctcgatc cagcagatct cctcgtttcg    5160
cgggttgggg cggctttcgc tgtagggcac cagccgatgg gcgtccagcg gggccagagt    5220
```

```
catgtccttc catgggcgca gggtcctcgt cagggtggtc tgggtcacgg tgaagggtg     5280
cgctccgggt tgggcgctgg ccagggtgcg cttgaggctg ttctgctgg tgctgaatcg     5340
ctgccgctct tcgccctgcg cgtcggccag gtagcatttg accatggtct cgtagtcgag    5400
accctcggcg gcgtgcccct tggcgcgag cttccccttg gaggtggcgc cgcacgaggg     5460
gcactgcagg ctcttcaggg cgtagagctt gggagcgaga aacacggact ctggggagta    5520
ggcgtccgcg ccgcaggaag cgcagaccgt ctcgcattcc accagccaag tgagctccgg    5580
gcggtcaggg tcaaaaacca ggttgccccc atgcttttg atgcgtttct tacctcggct     5640
ctccatgagg cggtgtccct tctcggtgac gaagaggctg tccgtgtccc cgtagaccga    5700
cttcaggggc ctgtcttcca gcggagtgcc tctgtcctcc tcgtagagaa actctgacca    5760
ctctgagacg aaggccccgcg tccaggccag gacgaaggag gccacgtggg agggtagcg    5820
gtcgttgtcc actagcgggt ccaccttctc cagggtgtgc aggcacatgt ccccctcctc    5880
cgcgtccaga aaagtgattg gcttgtaggt gtaggacacg tgaccggggg ttcccgacgg    5940
gggggtataa aaggggtgg gcgccctttc atcttcactc tcttccgcat cgctgtctgc    6000
gagggccagc tgctgggta agtattccct ctcgaaggcg ggcatgacct cagcgctcag    6060
gttgtcagtt tctaaaaatg aggaggattt gatgttcacc tgtccggagg tgataccttt   6120
gagggtacct gggtccatct ggtcagaaaa cactattttt ttgttgtcaa gcttggtggc   6180
gaacgacccg tagagggcgt tggagagcag cttggcgatg gagcgcaggg tctggttttt   6240
gtcgcggtcg gctcgctcct tggccgcgat gttgagttgc acgtactcgc gggccacgca   6300
cttccactcg gggaagacgg tggtgcgctc gtctgggatt aggcgcaccc tccagcctcg   6360
gttgtgcagg gtgaccatgt cgacgctggt ggcgacctcg ccgcgcaggc gctcgttggt   6420
ccagcagagg cggccgccct tgcgcgagca aagggggggt agggggtcca gctggtcctc   6480
gtttgggggg tccgcgtcga tggtgaagac cccggggagc aagcgcgggt caaagtagtc   6540
gatcttgcaa gcttgcatgt ccagagcccg ctgccattcg cgggcggcga gcgcgcgctc   6600
gtaggggttg agggggcgggc cccagggcat ggggtgggtg agcgcggagg cgtacatgcc   6660
gcagatgtca tacacgtaca gggttccct gaggatgccg aggtaggtgg ggtagcagcg   6720
cccccgcgg atgctggcgc gcacgtagtc atagagctcg tgggagggg ccagcatgtt   6780
gggcccgagg ttggtgcgct gggggcgctc ggcgcggaag gcgatctgcc tgaagatggc   6840
atgggagttg gaggagatgg tgggccgctg gaagacgttg aagcttgctt cttgcaagcc   6900
caccgagtcc ctgacgaagg aggcgtagga ctcgcgcagc ttgtgcacca gctcggcggt   6960
gacctggacg tcgagcgcgc agtagtcgag ggtctcgcgg atgatgtcat acttatcctc   7020
cccctcttt ttccacagct cgcggttgag gacgaactct tcgcggtctt tccagtactc    7080
ttggaggga aacccgtccg tgtccgaacg gtaagagcct agcatgtaga actggttgac    7140
ggcctggtag gggcaacagc ccttctccac gggcagcgcg taggcctgcg ccgccttgcg   7200
gagggaggtg tgggtgaggg cgaaagtgtc cctgaccatg actttgaggt attgatgttt   7260
gaagtctgtg tcatcgcagc cgccctgttc ccacagggtg tagtccgtgc gcttttttgga  7320
gcgcgggttg ggcagggaga aggtgaggtc attgaagagg atcttccccg ctcgaggcat   7380
gaagtttctg gtgatgcgaa agggccctgg gaccgaggag cggttgttga tgacctgggc   7440
ggccaggacg atctcgtcaa agccgtttat gttgtggccc acgatgtaga gctccaaaaa   7500
gcggggctgg cccttgatgg aggggagctt tttgagttcc tcgtaggtga gctcctcggg   7560
cgattccagg ccgtgctcct ccagggccca gtcttgcaag tgagggttgg ccgccaggaa   7620
```

```
ggatcgccag aggtcgcggg ccatgagggt ctgcaggcgg tcgcggaagg ttctgaactg   7680
tcgccccacg gccatctttt cggggggtgat gcagtagaag gtgagggggt ctttctccca   7740
ggggtcccat ctgagctctc gggcgaggtc gcgcgcggcg gcgaccagag cctcgtcgcc   7800
ccccagtttc atgaccagca tgaagggcac gagctgcttg ccaaaggctc ccatccaagt   7860
gtaggtctct acatcgtagg tgacaaagag gcgctccgtg cgaggatgag agccgatcgg   7920
gaagaactgg atctcccgcc accagttgga ggattggctg ttgatgtggt gaaagtagaa   7980
gtcccgtctg cgggccgagc actcgtgctg gcttttgtaa aagcgaccgc agtactggca   8040
gcgctgcacg ggttgtatat cttgcacgag gtgaacctgg cgacctctga cgaggaagcg   8100
cagcgggaat ctaagtcccc cgcctggggt cccgtgtggc tggtggtctt ctactttggt   8160
tgtctggccg ccagcatctg tctcctggag ggcgatggtg gagcagacca ccacgccgcg   8220
agagccgcag gtccagatct cggcgctcgg cgggcggagt ttgatgacga catcgcgcac   8280
attggagctg tccatggtct ccagctcccg cggcggcagg tcagctggga gttcctggag   8340
gttcacctcg cagagacggg tcaaggcgcg ggcagtgttg agatggtatc tgatttcaag   8400
gggcgtgttg gcgcggagt cgatggcttg caggaggccg cagccccggg gggccacgat   8460
ggttccccgc ggggcgcgag gggaggcgga agctgggggt gtgttcagaa gcggtgacgc   8520
gggcgggccc ccggaggtag ggggggttcc ggccccacag gcatgggcgg caggggcacg   8580
tcttcgccgc gcgcgggcag gggctggtgc tggctccgaa gagcgcttgc gtgcgcgacg   8640
acgcgacggt tggtgtcctg tatctgacgc ctctgagtga agaccacggg tcccgtgacc   8700
ttgaacctga aagagagttc gacagaatca atctcggcat cgttgacagc ggcctggcgc   8760
aggatctcct gcacgtcgcc cgagttgtcc tggtaggcga tctctgccat gaactgctcg   8820
atctcttctt cctggagatc tcctcgtccg gcgcgctcca cggtggccgc caggtcgttg   8880
gagatgcgac ccatgagctg tgagaaggcg ttgagcccgc cctcgttcca gacccggctg   8940
tagaccacgc ccccctcggc gtcgcgagcg cgcatgacca cctgggccag gttgagctcc   9000
acgtgtcgcg tgaagacggc gtagttcgcg aggcgctgga aaaggtagtt cagggtggtg   9060
gcggtgtgct cggcgacgaa gaagtacatg acccagcgcc gcaacgtgga ttcattgatg   9120
tcccccaagg cctccaggcg ctccatggcc tcgtagaagt ccacggcgaa gttgaaaaac   9180
tgggagttgc gagcggacac ggtcaactcc tcctccagaa gacggatgag ctcggcgaca   9240
gtgttgcgca cctcgcgctc gaaggccacg gggggcgctt cttcctcttc cacctcttct   9300
tccatgatcg cttcttcttc ttcctcagcc gggacgggag ggggcggcgg cggcggggga   9360
ggggcgcggc ggcggcggcg gcgcaccggg aggcggtcga tgaagcgctc gatcatctcc   9420
ccccgcatgc ggcgcatggt ctcggtgacg gcgcggccgt tctcccgggg gcgcagctcg   9480
aagacgccgc ctctcatctc gccgcggggc gagcggccgt gaggtagcga gacggcgctg   9540
actatgcatc ttaacaattg ctgtgtaggt acaccgccga gggacctgat tgagtccaga   9600
tccaccggat ccgaaaacct ttggaggaaa gcgtctatcc agtcgcagtc gcaaggtagg   9660
ctgagcaccg tggcgggcgg gggcgggtct ggagagttcc tggcggagat gctgctgatg   9720
atgtaattaa agtaggcggt cttgagaagg cggatggtgg acaggagcac catgtctttg   9780
ggtccggcct gttggatgcg gaggcggtcg gccatgcccc aggcctcgtt ctgacaccgg   9840
cgcaggtctt tgtagtagtc ttgcatgagt ctttccaccg gcacctcttc tccttcctct   9900
tctccatctc gccggtggtt tctcgcgccg cccatgcgcg tgaccccaaa gccctgagc   9960
```

```
ggctgcagca gggccaggtc ggcgaccacg cgctcggcca agatggcctg ctgcacctga    10020
gtgagggtcc tctcgaagtc atccatgtcc acgaagcggt ggtaggcgcc cgtgttgatg    10080
gtgtaggtgc agttggccat gacggaccag ttgacggtct ggtgtcccgg ctgcgagagc    10140
tccgtgtacc gcaggcgcga gaaggcgcgg gaatcgaaca cgtagtcgtt gcaagtccgc    10200
accagatact ggtagcccac caggaagtgc ggcggaggtt ggcgatagag gggccagcgc    10260
tgggtggcgg gggcgccggg cgccaggtct tccagcatga ggcggtggta tccgtagatg    10320
tacctggaca tccaggtgat gccggcggcg gtggtggtgg cgcgcgcgta gtcgcggacc    10380
cggttccaga tgtttcgcag gggcgagaag tgttccatgg tcggcacgct ctggccggtg    10440
aggcgcgcgc agtcgttgac gctctataca cacacaaaaa cgaaagcgtt tacagggctt    10500
tcgttctgta gcctggagga aagtaaatgg gttgggttgc ggtgtgcccc ggttcgagac    10560
caagctgagc tcggccggct gaagccgcag ctaacgtggt attggcagtc ccgtctcgac    10620
ccaggccctg tatcctccag gatacggtcg agagcccttt tgctttcttg gccaagcgcc    10680
cgtgcgcgca tctgggatag atggtcgcga tgagaggaca aaagcggctc gcttccgtag    10740
tctggagaaa caatcgccag ggttgcgttg cggcgtaccc cggttcgagc ccctatggcg    10800
gcttgaatcg gccggaaccg cggctaacga gggccgtggc agccccgtcc tcaggacccc    10860
gccagccgac ttctccagtt acgggagcga gccccttttg ttttttattt tttagatgca    10920
tcccgtgctg cggcagatgc gcccctcgcc ccggcccgat cagcagcagc aacagcaggc    10980
atgcagaccc ccctctcccc tttccgcccc ggtcaccacg gccgcggcgg ccgtgtcggg    11040 cgcgggggggc gcgctggagt cagatgagcc accgcggcgg cgacctaggc agtatctgga    11100
cttggaagag ggcgagggac tggcgcggct gggggcgaac tctccagagc gccacccgcg    11160
ggtgcagttg aaaagggacg cgcgcgaggc gtacctgccg cggcagaacc tgtttcgcga    11220 ccgcggggggc gaggagcccg aggagatgcg agactgcagg ttccaagcgg ggcgcgagct    11280
gcggcgcggg ctggacagac agcgcctgct gcgcgaggag gactttgagc ccgacacgca    11340
gacgggcatc agccccgcgc gcgcgcacgt agccgcggcc gacctggtga ccgcctacga    11400
gcagacggta aaccaggagc gcaacttcca aaagagcttc aacaaccacg tgcgcacgct    11460
ggtggcgcgc gaggaggtga ccctgggtct catgcatctg tgggacctgg tggaggcgat    11520
cgtgcagaac cccagcagca agccctgac cgcgcagctg ttcctggtgg tgcagcacag    11580
cagggacaac gaggccttca gggaggcgct gctgaacatc accgagccgg aggggcgctg    11640
gctcctggac ctgataaaca tcctgcagag catagtggtg caggagcgca gcctgagcct    11700
ggccgagaag gtggcggcca tcaactactc tatgctgagc ctgggcaagt tctacgcccg    11760
caagatctac aagacccccct acgtgcccat agacaaggag gtgaagatag acagcttcta    11820
catgcgcatg gcgctgaagg tgctgaccct gagcgacgac ctgggagtgt accgcaacga    11880
gcgcatccac aaggccgtga gcgccagccg gcggcgcgag ctgagcgacc gcagctgat    11940 gcacagtctg cagcgcgcgc tgaccggcgc gggcgagggc acagggagg tcgagtccta    12000 cttcgacatg ggggccgacc tgcactggca gccgagccgc cgcgccctgg aggcggcggg    12060
ggcgtacggc ggcccctgg cggccgatga ccaggaagag gaggactatg agctagagga    12120
gggcgagtac ctggaggact gacctggctg gtggtgtttt ggtatagatg caagatccga    12180
acgtggcgga cccggcggtc cgggcggcgc tgcaaagcca gccgtccggc attaactcct    12240
ctgacgactg ggccgcggcc atgggtcgca tcatggccct gaccgcgcgc aaccccgagg    12300
ctttcaggca gcagcctcag gccaaccggc tggcggccat cttggaagcg gtagtgcccg    12360
```

```
cgcgctccaa ccccacccac gagaaggtgc tggccatagt caacgcgctg gcggagagca   12420
gggccatccg cgcggacgag gccggactgg tgtacgatgc gctgctgcag cgggtggcgc   12480
ggtacaacag cggcaacgtg cagaccaacc tggaccgcct ggtgacggac gtgcgcgagg   12540
ccgtggcgca gcgcgagcgc ttgcatcagg acggtaacct gggctcgctg gtggcgctaa   12600
acgccttcct cagcacccag ccggccaacg taccgcgggg gcaggaggac tacaccaact   12660
ttttgagcgc gctgcggctg atggtgaccg aggtccctca gagcgaggtg taccagtcgg   12720
ggcccgacta cttcttccag accagcagac agggcttgca aaccgtgaac ctgagccagg   12780 cttttcaagaa cctgcggggg ctgtggggag tgaaggcgcc caccggcgac cgggctacgg   12840
tgtccagcct gctaaccccc aactcgcgcc tgctgctgct gctgatcgcg cccttcacgg   12900
acagcgggag cgtctcgcgg gagacctatc tgggccacct gctgacgctg taccgcgagg   12960
ccatcgggca ggcgcaggtg gacgagcaca ccttccaaga gatcaccagc gtgagccacg   13020
cgctggggca ggaggacacg ggcagcctgc aggcgaccct gaactacctg ctgaccaaca   13080
ggcggcagaa gattcccacg ctgcacagcc tgacccagga ggaggagcgc atcttgcgct   13140
acgtgcagca gagcgtgagc ctgaacctga tgcgcgacgg cgtgacgccc agcgtggcgc   13200
tggacatgac cgcgcgcaac atggaaccgg gcatgtacgc ctcccaccgg ccgtttatca   13260
accgcctgat ggactacttg catcgggcgg cggccgtgaa ccccgagtac ttcactaatg   13320
ccattctgaa tccccactgg atgccccctc cgggtttcta caacggggac tttgaggtgc   13380
ccgaggtcaa cgacgggttc ctctgggatg acatggatga cagtgtgttc tcacccaacc   13440
cgctgcgcgc cgcgtctctg cgattgaagg agggctctga cagggaagga ccgaggagtc   13500
tggcctcctc cctggctctg ggagcggtgg gcgccacggg cgcggcgcg cggggcagta   13560 gccccttccc cagcctggca gactctctga cagcgggcg ggtgagcagg ccccgcttgc   13620
taggcgagga ggagtatctg aacaactccc tgctgcagcc cgcgagggac aagaacgctc   13680
agcggcagca gtttcccaac aatgggatag agagcctggt ggacaagatg tccagatgga   13740
agacgtatgc gcaggagtac aaggagtggg aggaccgcca gccgcggccc ttgccgcccc   13800
ctaggcagcg ctggcagcgg cgcgcgtcca accgccgctg gaggcagggg cccgaggacg   13860
atgatgactc tgcagatgac agcagcgtgt tggacctggg cgggagcggg aacccctttt   13920
cgcacctgcg cccacgcctg ggcaagatgt tttaaaagaa aaaaaaaaat aaaactcacc   13980
aaggccatgg cgacgagcgt tggttttttg ttcccttcct tagtatgcgg cgcgcggcga   14040
tgttcgagga ggggcctccc ccctcttacg agagcgcgat ggggatttct cctgcggcgc   14100
ccctgcagcc tccctacgtg cctcctcggt acctgcaacc tacaggggga agaaatagca   14160
tctgttactc tgagctgcag cccctgtacg ataccaccag actgtacctg gtggacaaca   14220
agtccgcgga cgtggcctcc ctgaactacc agaacgacca cagcgatttt ttgaccacgg   14280
tgatccaaaa caacgacttc accccaaccg aggccagcac ccagaccata aacctggata   14340
acaggtcgaa ctggggcggc gacctgaaga ccatcttgca caccaacatg cccaacgtga   14400
acgagttcat gttcaccaac tcttttaagg cgcgggtgat ggtggcgcgc gagcagggga   14460
aggcgaagta cgagtgggtg gacttcacgc tgcccgaggg caactactca gagaccatga   14520
ctctcgacct gatgaacaat gcgatcgtgg aacactatct gaaagtgggc aggcagaacg   14580
gggtgaagga aagcgatatc ggggtcaagt ttgacaccag aaacttccgt ctgggctggg   14640
accccgtgac cgggctggtc atgccggggg tctacaccaa cgaggccttt catcccgaca   14700
```

```
tagtgcttct gcccggctgt ggggtggact tcacccagag ccggctgagc aacctgctgg    14760
gcattcgcaa gcggcagcct ttccaggagg gtttcaagat cacctatgag gatctgaagg    14820
ggggcaacat tcccgcgctc cttgatctgg acgcctacga ggagagcttg aaacccgagg    14880
agagcgctgg cgacagcggc gagagtggcg aggagcaagc cggcggcggt ggcggcgcgt    14940
cggtagaaaa cgaaagtacg cccgcagtgg cggcggacgc tgcggaggtc gagccggagg    15000
ccatgcagca ggacgcagag gagggcgcac aggagggcgc gcagaaggac atgaacgatg    15060
gggagatcag gggagacaca ttcgccaccc ggggcgaaga aaaagaggca gaggcggcgg    15120
cggcggcgac ggcggaggcc gaaaccgagg ttgaggcaga ggcagagccc gagaccgaag    15180
ttatggaaga catgaatgat ggagaacgta ggggcgacac gttcgccacc cggggcgaag    15240
agaaggcggc ggaggcagaa gccgcggctg aggaggcggc tgcggctgcg gccaagactg    15300
aggctgcggc taaggctgag gtcgaagcca atgttgcggt tgaggctcag gctgaggagg    15360
aggcggcggc tgaagcagtt aaggaaaagg cccaggcaga gcaggaagag aaaaaacctg    15420
tcattcaacc tctaaaagaa gatagcaaaa agcgcagtta caacgtcatc gagggcagca    15480
cctttaccca gtaccgcagc tggtacctgg cgtacaacta cggcgacccg gtcaaggggg    15540
tgcgctcgtg gacgctgctc tgcacgccgg acgtcacctg cggctccgag cagatgtact    15600
ggtcgctgcc gaacatgatg caagacccgg tgaccttccg ctccacgcgg caggttagca    15660
acttcccggt ggtgggcgcc gaactgctgc ccgtgcactc caagagtttt tacaacgagc    15720
aggccgtcta ctcccagctg atccgccagg ccacctctct gacccacgtg ttcaatcgct    15780
ttcccgagaa ccagattttg gcgcgcccgc cggcccccac catcaccacc gtgagtgaaa    15840
acgttcctgc cctcacagat cacgggacgc taccgctgcg caacagcatc tcaggagtcc    15900
agcgagtgac cattactgac gccagacgcc ggacctgccc ctacgtttac aaggccttgg    15960
gcatagtctc gccgcgcgtc ctctccagtc gcactttttta aaacacatct acccacacgt    16020
tccaaaatca tgtccgtact catctcaccc agcaacaaca ccggctgggg gctgcgcgcg    16080
cccagcaaga tgtttggagg ggcgaggaag cgctccgacc agcaccctgt gcgcgtgcgc    16140
ggccactacc gcgcgccctg gggagcgcac aagcgcgggc gcacagggcg caccactgtg    16200
gacgacgtca ttgactccgt agtggagcaa gcgcgccact acacacccgg cgcgccgacc    16260 gccccgccg tgtccaccgt ggaccaggcg atcgaaagcg tggtacaggg cgcgcggcac    16320
tatgccaacc ttaaaagtcg ccgccgccgc gtggcccgcc gccatcgccg gagacccgg    16380 gccaccgccg ccgcgcgcct tactaaggct ctgctcaggc gcgccaggcg aactggccac    16440
cgggccgcca tgagggccgc acggcgggct gccgctgccg caagcgtcgt ggccccgcgg    16500
gcacgaaggc gcgcggccgc tgccgccgcc gccgccattt ccagcttggc ctcgacgcgg    16560
cgcggtaaca tatactgggt gcgcgactcg gtaaccggca cgcgggtacc cgtgcgcttt    16620
cgccccccgc ggaattagca caagacaaca tacacactga gtctcctgct gttgtgtatc    16680
ccagcggcga ccgtcagcag cggcgacatg tccaagcgca aaattaaaga agagatgctc    16740
caggtcatcg cgccggagat ctatgggccc ccgaagaagg aggaggatga ttacaagccc    16800
cgcaagctaa agcgggtcaa aaagaaaaag aaagatgatg atgacgaggc ggtggagttt    16860
gtccgccgca tggcacccag gcgccccgtg cagtggaagg gccggcgcgt gcagcgcgtt    16920
ttgcgccccg gcaccgcggt ggtcttcacg cccggcgagc gctccacgcg cacttttcaag    16980 cgggtgtacg atgaggtgta cggcgacgag gacctgttgg agcaggccaa ccagcgcttt    17040
ggggagtttg catatgggaa acggccccgc gagagtctaa aagaggacct gctggcgcta    17100
```

```
ccgctggacg agggcaatcc caccccgagt ctgaagccgg taaccctgca acaggtgctg   17160
cctttgagcg cgcccagcga gcataagcga gggttgaagc gcgaaggcgg ggacctggcg   17220
cccaccgtgc agttgatggt gcccaagcgg cagaagctgg aggacgtgct ggagaaaatg   17280
aaagtagagc ccgggatcca gcccgagatc aaggtccgcc ccatcaagca ggtggcgccc   17340
ggcgtgggag tccagaccgt ggacgttagg attcccacgg aggagatgga aacccaaacc   17400
gccactccct cttcggcggc cagcgccacc accggcaccg cttcggtaga ggtgcagacg   17460
gaccccctggc tacccgccac cgctgttgcc gccgccgccc ccgttcgcg cgggcgcaag   17520
agaaattatc cagcggccag cgcgctcatg ccccagtacg cactgcatcc atccatcgtg   17580
cccaccccg gctaccgcgg gtactcgtac cgcccgcgca gatcagccgg cactcgcggc   17640
cgccgccgcc gtgcgaccac aaccagccgc cgccgtcgcc gccgccgcca gccagtgctg   17700
accccgtgt ctgtaaggaa ggtggctcgc tcggggagca cgctggtggt gcccagagcg   17760
cgctaccacc ccagcatcgt ttaaagccgg tctctgtatg gttcttgcag atatggccct   17820
cacttgtcgc ctccgcttcc cggtgccggg ataccgagga agaactcacc gccgcagagg   17880
catggcgggc agcggtctcc gcggcggccg tcgccatcgc cggcgcgcaa aaagcaggcg   17940
catgcgcggc ggtgtgctgc ctctgctaat cccgctaatc gccgcggcga tcggtgccgt   18000
acccgggatc gcctccgtgg ccctgcaggc gtcccagaaa cgttgactct tgcaaccttg   18060
caagcttgca ttttttggag gaaaaaataa aaaaaagtc tagactctca cgctcgcttg   18120
gtcctgtgac tattttgtag aaaaaaagat ggaagacatc aactttgcgt cgctggcccc   18180
gcgtcacggc tcgcgcccgt tcatgggaga ctggacagat atcggcacca gcaatatgag   18240
cggtggcgcc ttcagctggg gcagtctgtg gagcggcctt aaaaattttg gttccaccat   18300
taagaactat ggcaacaaag cgtggaacag cagcacgggc cagatgctga gagacaagtt   18360
gaaagagcag aacttccagg agaaggtggc gcagggcctg gcctctggca tcagcggggt   18420
ggtggacata gctaaccagg ccgtgcagaa aaagataaac agtcatctgg accccgtcc   18480
tcaggtggag gaaatgcctc cagcgatgga gacggtgtct cccgagggca aggcgaaaa   18540
gcgcccgcgg cccgacagag aagagaccct ggtgtcacac accgaggagc cgccctctta   18600
cgaggaggca gtcaaggccg gcctgccccac cactcgcccc atagccccca tggccaccgg   18660
tgtggtgggc cacaggcaac acactccgc aacactagat ctgcccccgc cgtccgagcc   18720
gccgcgccag ccaaaggcgg cgacggtgcc cgctccctcc acttccgccg ccaacagagt   18780
gccccctgcgc cgcgccgcga gcggccccg ggcctcgcga gttagcggca actggcgagg   18840
cacactgaac agcatcgtgg gcctgggagt gaggagtgtg aagcgccgcc gttgctactg   18900
aatgagcaag ctagctaacg tgttgtatgt gtgtatgcgt cctatgtcgc cgccagagga   18960
gctgttgagc cgccggcgcc gtctgcactc cagcgaattt caagatggcg accccatcga   19020
tgatgcctca gtggtcgtac atgcacatct cgggccagga cgcttcggag tacctgagcc   19080
ccgggctggt gcagttcgcc cgcgccacag acacctactt caacatgagt aacaagttca   19140
ggaaccccac tgtggcgccc acccacgatg tgaccacgga ccgtcgcag cgcctgacgc   19200
tgcggttcat ccccgtggat cgggaggaca ccgcctactc ttacaaggcg cggttcacgc   19260
tggccgtggg cgacaaccgc gtgctggaca tggcctccac ttactttgac atcagggggg   19320
tgctggacag gggccccacc ttcaagccct actcgggtac tgcctacaac tccctggccc   19380
ccaagggcgc tcccaattct tgcgagtggg aacaagatga accagctcag gcagcaatag   19440
```

```
ctgaagatga agaagaactt gaagaagaac aagctcagga cgaacaggcg cccactaaga    19500
aaacccatgt atacgcccag gcacctcttt ctggtgaaaa aattactaag gatggtttgc    19560
aaataggtgt ggatgccaca caggcgggag ataaccctat atatgctgat aaaacattcc    19620
aacccgaacc tcagataggt gagtctcagt ggaacgaggc tgatgccaca gtagcaggag    19680
gcagagtctt aaaaaagacc accccctatga gaccttgcta tggatcctat gccaaaccta    19740
ctaatgccaa tggcggtcaa gggatcatgg tggccaatga tcaggagcg cttgaatcta    19800 aagttgagat gcaattttc tccaccacaa cgtctcttaa tgtaagggaa ggtgaaaaca    19860
atcttcagcc aaaagtagtg ctatacagcg aagatgttaa cttggaatcc cctgacactc    19920
atttgtctta caaacctaaa aaggatgaca ccaactctaa aatcatgttg ggtcagcaag    19980
ccatgcccaa cagacccaac ctcattgctt ttagggacaa cttttattgga cttatgtact    20040 acaacagcac aggcaacatg ggagtgctgg caggacaggc ctcccagcta aacgctgtgg    20100
tagacttgca agacagaaac acagagctgt cataccaact gatgcttgat tccattggag    20160
acagatcaag atacttttcc atgtggaacc aggcagtgga cagctatgac ccagatgtca    20220
gaatcattga aaaccatggg gttgaagatg agctgcccaa ctattgcttt ccctgggcg    20280 gtattggaat tacagacaca taccagtgca taaaaccaac cgcagctgct aataacacta    20340
catggtctaa ggatgaagaa tttagtgatc gcaatgaaat aggggtggga aacaacttcg    20400
ccatggagat caacatccag gccaacctct ggaggaactt cctctatgcg aacgtggggc    20460
tctacctgcc agacaagctc aagtacaacc ccaccaacgt ggacatctct gacaaccca    20520 acacctatga ctacatgaac aagcgtgtgg tggctcccgg cctggtggac tgctttgtca    20580
atgtgggagc caggtggtcc ctggactaca tggacaacgt caaccccttc aaccaccacc    20640
gcaatgcggg tctgcgctac cgctccatga tcctgggcaa cggggcgtac gtgcccttcc    20700
acattcaggt gccccagaag ttctttgcca tcaagaacct cctcctcctg ccgggctcct    20760
acacttacga gtggaacttc aggaaggatg tcaacatggt cctgcagagc tctctgggca    20820
atgaccttag ggtggacggg gccagcatca gttttgacag cgtcacctc tatgctacct    20880 tcttcccat ggctcacaac accgcctcca cgctcgaggc catgctgagg aacgacacca    20940
acgaccagtc cttcaatgac tacctctctg gggccaacat gctctacccc atccccgcca    21000
aggccaccaa cgtgcccatc tccattcct ctcgcaactg gccgccttc agaggctggg    21060 cctttaccg ccttaagacc aaggaaaccc cctccctggg ctcgggtttt gacccctact    21120
ttgtctactc gggatccatc ccctacctgg atggcacctt ctacctcaac cacacttta    21180 agaagatatc catcatgtat gactcctccg tcagctggcc gggcaatgac cgcctgctca    21240
cccccaatga gttcgaggtc aagcgcgccg tggacggcga gggctacaac gtggcccagt    21300
gcaacatgac caaggactgg ttcctggtgc agatgctggc caactacaac ataggctacc    21360
agggcttcta catcccagag agctacaagg acaggatgta ctccttcttc agaaattcc    21420 aacccatgag caggcaggtg gtggacgaga ccaaatacaa ggactatcag gccattggca    21480
tcactcacca gcacaacaac tcgggattcg tgggctacct ggctcccacc atgcgcgagg    21540
ggcaggccta ccccgccaac ttccccctacc cgttgatagg caaaaccgcg gtcgacagcg    21600
tcacccagaa aaagttcctc tgcgaccgca cctctggcg catcccttc tctagcaact    21660 tcatgtccat gggtgcgctc acggacctgg ccagaacct gctctatgcc aactccgccc    21720
atgcgctgga catgactttt gaggtggacc ccatggacga gccaccctt ctctatattg    21780 tgtttgaagt gttcgacgtg gtcagagtgc accagccgca ccgcggtgtc atcgagaccg    21840
```

```
tgtacctgcg cacgcccttc tcggccggca acgccaccac ctaaggagac agcgccgccg  21900
cctgcatgac gggttccacc gagcaagagc tcagggccat cgccagagac ctgggatgcg  21960
gaccctattt tttgggcacc tatgacaaac gcttcccggg cttcatctcc cgagacaagc  22020
tcgcctgcgc catcgtcaac acggccgcgc gcgagaccgg gggcgtgcac tggctggcct  22080
ttggctggga cccgcgctcc aaaacctgct acctcttcga ccccttggc ttctccgatc  22140
agcgcctcag acagatctat gagtttgagt acgaggggct gctgcgccgc agcgcgcttg  22200
cctcctcgcc cgaccgctgc atcacccttg agaagtccac cgagaccgtg caggggcccc  22260
actcggccgc ctgcggtctc ttctgctgca tgttttttgca cgcctttgtg cgctggcccc  22320
agagtcccat ggatcgcaac cccaccatga acttgctcaa gggagtgccc aacgccatgc  22380
tccagagccc ccaggtccag cccacccctgc gccacaacca ggaacagctc taccgcttcc  22440
tggagcgcca ctcccctac ttccgcagtc acagcgcgca catccggggg gccacctctt  22500
tctgccactt gcaagaaaac atgcaagacg gaaaatgatg tacagctcgc tttttaataa  22560
atgtaaagac tgtgcacttt atttatacac gggctctttc tggttattta ttcaacaccg  22620
ccgtcgccat ctagaaatcg aaagggttct cccgcgcgtc gccgtgcgcc acgggcagag  22680
acacgttgcg atactggaag cggctcgccc acttaaactc gggcaccacc atgcggggca  22740
gtggttcctc ggggaagttc tcgccccaca gggtgcgggt cagctgcagc gcgctcagga  22800
ggtcgggagc cgagatcttg aagtcgcagt tggggccgga accctgcgcg cgcgagttgc  22860
ggtacacggg gttgcagcac tggaacacca gcagggccgg attatgcacg ctggccagca  22920
ggctctcgtc gctgatcatg tcgctgtcca gatcctccgc gttgctcagg gcgaacgggg  22980
tcatcttgca gacctgcctg cccaggaaag gcggcagccc gggcttgccg ttgcagtcgc  23040
agcgcagggg catcagcagg tgcccgcggc ccgactgcgc ctgcgggtac agcgcgcgca  23100
tgaaggcttc gatctgcctg aaagccacct gcgtcttggc tccctccgaa aagaacatcc  23160
cacaggactt gctggagaac tggttcgcgg gacagctggc atcgtgcagg cagcagcgcg  23220
cgtcggtgtt ggcgatctgc accacgttgc gaccccaccg gttcttcact atcttggcct  23280
tggaagcctg ctccttcagc gcgcgctggc cgttctcgct ggtcacatcc atctctatca  23340
cctgctcctt gttgatcatg tttgtaccgt gcagacactt caggtcgccc tccgtctggg  23400
tgcagcggtg ctcccacagc gcgcaaccgg tgggctccca attttgtgg gtcacccccg  23460
cgtaggcctg caggtaggcc tgcaagaagc gccccatcat ggccacaaag gtcttctggc  23520
tcgtaaaggt cagctgcagg ccgcgatgct cttcgttcag ccaggtcttg cagatggcgg  23580
ccagcgcctc ggtctgctcg ggcagcatcc taaaatttgt cttcaggtcg ttatccacgt  23640
ggtacttgtc catcatggcg cgcgccgcct ccatgcccct ctcccaggcg acaccatgg  23700
gcaggcttag ggggtttatc acttccaccg gcgaggacac cgtactttcg atttcttctt  23760
cctcccctc ttcccggcgc gcgcccacgc tgctgcgcgc tctcaccgcc tgcaccaagg  23820
ggtcgtcttc aggcaagcgc cgcaccgagc gcttgccgcc cttgacctgc ttaatcagca  23880
ccggcgggtt gctgaagccc accatggtca gcgccgcctg ctcttcttcg tcttcgctgt  23940
ctaccactat ctctggggaa gggcttctcc gctctgcggg ggcgcgcttc tttttttct  24000
tgggagcggc cgtgatggag tccgccacgg cgacggaggt cgagggcgtg gggctggggg  24060
tgcgcggtac cagggcctcg tcgccctcgg actcttcctc tgactccagg cggcggcgga  24120
gtcgcttctt tggggggcgcg cgcgtcagcg gcggcggaga cggggacggg gacggggacg  24180
```

```
ggacgccctc cacagggggt ggtcttcgcg cagacccgcg gccgcgctcg ggggtcttct    24240
cgagctggtc ttggtcccga ctggccattg tatcctcctc ctcctaggca gagagacata    24300
aggagtctat catgcaagtc gagaaggagg agagcttaac cacccctct gagaccgccg    24360 atgcgcccgc cgtcgccgtc gccccgcgct ccgccgacgc gcccgccaca ccgagcgaca    24420 ccccgcgga cccccccgcc gacgcacccc tgttcgagga agcggccgtg gagcaggacc    24480
cgggctttgt ctcggcagag gaggatttgc gagaggagga ggataaggag aagaagccct    24540
cagtgccaaa agatgataaa gagcaagacg agcacgacgc agatgcacac cagggtgaag    24600
tcgggcgggg ggacggaggg catgacgcg ccgactacct agacgaaggg aacgacgtgc    24660
tcttgaagca cctgcatcgt cagtgcgcca ttgtttgcga cgctctgcag gagcgcagcg    24720
aagtgcccct cagcgtggcg gaggtcagcc acgcctacga gctcagcctc ttctcccccc    24780 gggtgcccc cgccgccgc gaaaacggca catgcgagcc caacccgcgc ctcaacttct    24840
accccgcctt tgtggtaccc gaggtcctgg ccacctatca catcttcttt caaaattgca    24900
agatccccct ctcgtgccgc gccaaccgta gccgcgccga taagatgctg gccctgcgcc    24960
agggcgacca catacctgat atcgccgctt tggaagatgt accaaagatc ttcgagggtc    25020
tgggtcgcaa cgagaagcgg gcagcaaact ctctgcaaca ggaaaacagc gaaaatgaga    25080
gtcacaccgg ggtactggtg gagctcgagg gcgacaacgc ccgcctggcg gtggtcaagc    25140
gcagcatcga ggtcacccac tttgcctacc ccgcgctaaa cctgccccc aaagtcatga    25200 acgcggccat ggacgggctg atcatgcgcc gcggccggcc cctcgctcca gatgcaaact    25260
tgcatgagga gaccgaggac ggccagcccg tggtcagcga cgagcagctg gcgcgctggc    25320
tggagaccgc ggaccccgcc gaactggagg agcggcgcaa gatgatgatg gccgtggtgc    25380
tggtcaccgt agagctggag tgtctgcagc gcttcttcgg cgaccccgag atgcagagaa    25440
aggtcgagga gaccctgcac tacaccttcc gccagggcta cgtgcgccag gcttgcaaga    25500
tctccaacgt ggagctcagc aacctggtgt cctacctggg catcttgcat gagaaccgcc    25560
tcgggcagag cgtgctgcac tccaccctgc gcggggaggc gcgccgcgac tacgtgcgcg    25620
actgcgttta cctcttcctc tgctacacct ggcagacggc catgggggtc tggcagcagt    25680
gcctggagga gcgcaacctc aaggagctgg agaagctcct gcagcgcgcg ctcaaagatc    25740
tctgacgggg ctacaacgag cgctcggtgg ccgccgcgct ggccgacctc atcttccccg    25800
agcgcctgct caaaaccctc cagcagggc tgcccgactt caccagccaa agcatgttgc    25860
aaaacttcag gaactttatc ctggagcgtt ctggcatcct acccgccacc tgctgcgccc    25920
tgcccagcga cttttgtcccc ctcgtgtacc gcgagtgccc ccgccgctg tggggtcact    25980 gctacctgtt ccaactggcc aactaccgtg cctaccacgc ggacctcatg gaggactcca    26040
gcggcgaggg gctcatggag tgccactgcc gctgcaacct ctgcacgccc caccgctccc    26100
tggtctgcaa cacccaactg ctcagcgaga gtcagattat cggtaccttc gagctacagg    26160
gtccgtcctc ctcagacgag aagtccgcgg ctccgggggct aaaactcact ccggggctgt    26220
ggacttccgc ctacctgcgc aaatttgtac ctgaagacta ccacgcccac gagatcaggt    26280
tttacgaaga ccaatcccgc ccgcccaagg cggagctgac cgcctgcgtc atcacccagg    26340
gcgagatcct aggccaattg caagccatcc aaaaagcccg ccaagacttt ttgctgaaga    26400
agggtcgggg ggtgtatctg gaccccccagt cgggtgagga gctcaacccg gttccccgc    26460 tgccgccgcc gcgggacctt gcttcccagg ataagcatcg ccatggctcc cagaaagaag    26520
cagcagcggc cgccactgcc gccaccccac atgctggagg aagaggagga atactgggac    26580
```

```
agtcaggcag aggaggtttc ggacgaggag gagccggaga cggagatgga agagtgggag  26640
gaggacagct tagacgagga ggcttccgaa gccgaagagg cagacgcaac accgtcaccc  26700
tcggccgcag ccccctcgca ggcgccccg aagtccgctc ccagcatcag cagcaacagc  26760
agcgctataa cctccgctcc tccaccgccg cgacccacgg ccgaccgcag acccaaccgt  26820
agatgggaca ccaccggaac cggggccggt aagtcctccg ggagaggcaa gcaagcgcag  26880
cgccaaggct accgctcgtg gcgcgctcac aagaacgcca tagtcgcttg cttgcaagac  26940
tgcgggggga acatctcctt cgcccgccgc ttcctgctct tccaccacgg tgtggccttc  27000
ccccgtaacg tcctgcatta ctaccgtcat ctctacagcc cctactgcgg cggcagtgag  27060
ccagagacgg tcggcggcgg cggcggcgcc cgtttcggcg cctaggaaga cccagggcaa  27120
gacttcagcc aagaaactcg cggcggccgc ggcgaacgcg gtcgcggggg ccctgcgcct  27180
gacggtgaac gaaccctgt cgacccgcga actgaggaac cgaatcttcc ccactctcta  27240
tgccatcttc cagcagagca gagggcagga tcaggaactg aaagtaaaaa acaggtctct  27300
gcgctccctc acccgcagct gtctgtatca caagagcgaa gaccagcttc ggcgcacgct  27360
ggaggacgct gaggcactct tcagcaaata ctgcgcgctc actcttaagg actagctccg  27420
cgcccttctc gaatttaggc gggaacgcct acgtcatcgc agcgccgccg tcatgagcaa  27480
ggacattccc acgccataca tgtggagcta tcagccgcag atgggactcg cggcgggcgc  27540
ctcccaagac tactccaccc gcatgaactg gctcagtgcc ggcccacaca tgatctcaca  27600
ggttaatgat atccgcaccc atcgaaacca aatattggtg gagcaggcgg caattaccac  27660
cacgccccgc aataatccca accccaggga gtggcccgcg tccctggtgt atcaggaaat  27720
tcccggcccc accaccgtac tacttccgcg tgattcccag gccgaagtcc aaatgactaa  27780 ctcagggca cagctcgcgg gcggctgtcg tcacagggtg cggcctcctc gccagggtat  27840
aactcacctg gagatccgag gcagaggtat tcagctcaac gacgagtcgg tgagctcctc  27900
gctcggtctc agacctgacg ggaccttcca gatagccgga gccggccgat cttccttcac  27960
gccccgccag gcgtacctga ctctgcaaag ctcgtcctcg gcgccgcgct cgggcggcat  28020
cgggactctc cagttcgtgc aggagtttgt gccctcggtc tacttcaacc ccttctcggg  28080
ctctcccggt cgctacccgg accagttcat ctcgaacttt gacgccgcga gggactcggt  28140
ggacggctac gactgaatgt cgggtggacc cggtgcagag caacttcgcc tgaagcacct  28200
cgaccactgc cgccgccctc agtgctttgc ccgctgtcag accggtgagt tccagtactt  28260
ttccctgccc gactcgcacc cggacggcc ggcgcacggg gtgcgctttt tcatcccgag  28320
tcaggtgcgc tctaccctaa tcagggagtt taccgcccgt cccctactgg cggagttgga  28380 aaagggggcct tctatcctaa ccattgcctg catctgctct aaccctggat tgcaccaaga  28440 tcttgtgctgt catttgtgtg ctgagtataa taaaggctga gatcagaatc tactcgggct  28500
cctgtcgcca tcctgtcaac gccaccgtcc aagcccggcc cgatcagccc gaggtgaacc  28560
tcacctgcgg tctgcaccgg cgcctgagga aataccagc ttggtactac aacagcactc  28620
cctttgtggt ttacaacagc tttgaccagg acggggtctc actgagggat aacctctcga  28680
acctgagcta ctccatcagg aagaacagca ccctcgagct acttcctcct tacctgcccg  28740
ggacttacca gtgtgtcacc ggtcctgca cccacaccca cctgttgatc gtaaacgact  28800
ctcttccgag aacagacctc aataactcct cttcgcagtt ccccagaaca ggaggtgagc  28860
tcaggaaacc ccgggtaaag aagggtggac gagagttaac acttgtgggg tttctggtgt  28920
```

```
atgtgacgct ggtggtggct cttttgatta aggcttttcc ttccatgtct gaactctccc   28980 tcttcttttta tgaacaactc gactagtgct aacgggaccc tacccaacga atcgggattg   29040
aatatcggta accaggttgc agtttcactt ttgattacct tcatagtcct cttcctgcta   29100
gtgctgtcgc ttctgtgcct gcggatcggg ggctgctgca tccacgttta tatctggtgc   29160
tggctgttta gaaggttcgg agaccatcgc aggtagaata aacatgctgc tgcttaccct   29220
ctttgtcctg gcgctggccg ccagctgcca agccttttcc gaggctgact ttatagagcc   29280
ccagtgtaat gtgacttta aagcccatgc acagcgttgt catactataa tcaaatgtgc   29340
caccgaacac gatgaatacc ttatccagta taaagataaa tcacacaaag tggcacttgt   29400
tgacatctgg aaacccgaag acctttgga atacaatgtg accgttttcc agggtgacct   29460
cttcaaaatt tacaattaca cttttcccatt tgaccagatg tgtgactttg tcatgtacat   29520
ggaaaagcag cacaagctgt ggcctccgac tccccagggc tgtgtggaaa atccaggctc   29580
tttctgcatg atctctctct gtgtaactgt gctggcacta atactcacgc ttttgtatat   29640
cagatttaaa tcaaggcaaa gcttcattga tgaaaagaaa atgccttaat cgctttcacg   29700
cttgattgct aacaccgggt ttttatccgc agaatgattg gaatcaccct actaatcacc   29760
tccctccttg cgattgccca tgggttggaa cgaatcgaag tccctgtggg ggccaatgtt   29820
accctggtgg ggcctgtcgg caatgctaca ttaatgtggg aaaaatatac taaaaatcaa   29880
tgggtctctt actgcactaa caaaaatagc cacaagccca gagccatctg cgatgggcaa   29940
aatctaacct tgattgatgt tcaattgctg gatgcgggct actattatgg gcagctgggt   30000
acaatgatta attactggag accccacaga gattacatgc tccacgtagt aaagggtccc   30060
cttagcagcc cacccactac cacctctact accccccacta ccaccactac tcccaccacc   30120
agcactgccg cccagcctcc tcatagcaga acaaccactt tatcaattc caagtcccac   30180 tcccccacc ttgccggcgg gccctccgcc tcagactccg aaaccaccga gatctgcttc   30240
tgcaaatgct ctgacgccat gcccaggat ttggaagatc acgaggaaga tgagcatgac   30300
ttcgcagatg catgccaggc atcagagcca gaagcgctgc cggtggccct caaacagtat   30360 gcagacccc acaccacccc cgaccttcct ccaccttccc agaagccaag tttcctgggg   30420
gaaaatgaaa ctctgcctct ctccatactc gctctgacat ctgttgctat gttgaccgct   30480
ctgctggtgc ttctatgctc tatatgctac ctgatctgct gcagaaagaa aaaatctcac   30540
ggccatgctc accagcccct catgcacttc ccttacccctc cagagctggg cgaccacaaa   30600
ctttaagtct gcagtaacta tctgcccatc ccttgtcagt cgacagcgat gagccccact   30660
aatctaacgg cctctggact tacaacatcg tctcttaatg agaccaccgc tcctcaagac   30720
ctgtacgatg gtgtctccgc gctggttaac cagtgggatc acctgggcat atggtggctc   30780
ctcataggag cagtgaccct gtgcctaatc ctggtctgga tcatctgctg catcaaaagc   30840
agaagaccca ggcggcggcc catctacagg cccttttgtca tcacacctga agatgatgat   30900
gacaccactt ccaggctgca gaggctaaag cagctactct tctctttttac agcatggtaa   30960 attgaatcat gcctcgcatt ttcatctact tgtctctcct tccacttttt ctgggctctt   31020
ctacattggc cgctgtgtcc cacatcgagg tagactgcct cacgcccttc acagtctacc   31080
tgcttttcgg ctttgtcatc tgcaccttttg tctgcagcgt tatcactgta gtgatctgct   31140
tcatacagtg catcgactac gtctgcgtgc gggtggctta ctttagacac cacccccagt   31200
atcgcaacag ggacatagcg gctctcctaa gacttgttta aaatcatggc caaattaact   31260
gtgattggtc ttctgatcat ctgctgcgtc ctagccgcga ttgggactca agctcctacc   31320
```

```
accaccagcg ctcccagaaa gagacatgta tcctgcagct tcaagcgtcc ctggaatata   31380 cccaatgct ttactgatga acctgaaatc tctttggctt ggtacttcag cgtcaccgcc    31440
cttcttatct tctgcagtac ggttattgcc cttgccatct acccttccct tgacctgggc   31500
tggaatgctg tcaactctat ggaatatccc accttcccag aaccagacct gccagacctg   31560
gttgttctaa acgcgtttcc tcctcctgct cccgttcaaa atcagtttcg ccctccgtcc   31620
cccacgccca ctgaggtcag ctactttaat ctaacaggcg gagatgactg aaaacctaga   31680
cctagaaatg gacggtctct gcagcgagca acgcacacta gagaggcgcc ggcaaaaaga   31740
gctcgagcgt cttaaacaag agctccaaga cgcggtggcc atacaccagt gcaaaaaagg   31800
tgtcttctgt ctggtaaaac aggccacgct cacctatgaa aaaacaggtg acacccaccg   31860
cctaggatac aagctgccca cacagcgcca aaagttcgcc ctcatgatag gcgaacaacc   31920
catcaccgtg acccagcact ccgtggagac agaaggctgc atacatgctc cctgtagggg   31980
cgctgactgc ctctacacct tgatcaaaac cctctgcggt tcagagacc ttatcccttt    32040 caattaatca taactgtaat caataaaaaa tcacttactt gaaatctgat agcaagcctc   32100
tgtccaattt tttcagcaac acttccttcc cctcctccca actctggtac tctaggcgcc   32160
tcctagctgc aaacttcctc cacagtctga agggaatgtc agattcctcc tcctgtccct   32220
ccgcacccac gatcttcatg ttgttgcaga tgaaacgcgc gagatcgtct gacgagacct   32280 tcaacccgt gtaccctac gataccgaga tcgctccgac ttctgtccct ttccttaccc     32340 ctcccctttgt gtcatccgca ggaatgcaag aaaatccagc tggggtgctg tccctgcact  32400
tgtcagagcc ccttaccacc cacaatgggg ccctgactct aaaaatgggg ggcggcctga   32460
ccctggacaa ggaagggaat ctcacttccc aaaacatcac cagtgtcgat cccctctca    32520 aaaaaagcaa gaacaacatc agccttcaga ccgccgcacc cctcgccgtc agctccgggg   32580
ccctaacact ttttgccact ccccccctag cggtcagtgg tgacaacctt actgtgcagt   32640
ctcaggcccc tctcactttg gaagactcaa aactaactct ggccaccaaa ggaccctaa    32700 ctgtgtccga aggcaaactt gtcctagaaa cagaggctcc cctgcatgca agtgacagca   32760
gcagcctggg ccttagcgtt acggcccac ttagcattaa caatgacagc ctaggactag    32820
atctgcaggc acccattgtc tctcaaaatg gaaaactggc tctaaatgta gcaggccccc   32880
tagctgtggc caatggcatt aatgctttga cagtaggcac aggcaaaggt attggtctaa   32940
atgaaaccag cactcacttg caagcaaagt tggtcgcccc cctaggcttt gataccaatg   33000
gcaacattaa gctaagcgtt gcaggaggca tgagactaaa taatgacaca cttatactag   33060
atgtaaacta cccatttgaa gctcaaggcc aactaagtct aagagtgggc cagggtccgc   33120
tgtatgtaga ttctagcagc cataacctga ccattagatg ccttagagga ttatacataa   33180
catcgtctaa taaccaaacc ggtctagagg ccaacataaa actaacaaaa ggccttgtct   33240
atgatggaaa tgccatagca gtcaatgttg gtcaaggatt gcaatacagc actactgcca   33300
catcggaagg tgtgtatcct atacagtcta agataggttt gggaatggaa tatgatacca   33360
acggagccat gatgacaaaa ctaggctctg gactaagctt tgacaattca ggagccattg   33420
tagtgggaaa caaaaatgat gacaggctta ctctgtggac tacaccagac ccatctccta   33480
actgtagaat ttattctgaa aaagatacta aactaaccct ggtgctgact aagtgtggca   33540
gccaaatcct aggcacagta tctgccttg ctgtcagagg cagccttgcg cccatcacta   33600
atgcatccag catagtccaa atatttctaa gatttgatga aaatggacta ttgatgagca   33660
```

```
actcatcgct agacggtgat tactggaatt acagaaatgg ggactccact aatagcacac  33720
catatacaaa tgcagtaggc tttatgccta atctagcagc ctatcctaaa ggtcaggcta  33780
cagctgcaaa aagcagtatt gtaagccagg tatacatgga tggtgacact actaaaccta  33840
taacactaaa aataaacttc aatggcattg atgaaacaac agaaaatacc cctgttagta  33900
aatattccat gacattctca tggagctggc ccaccgcaag ctacataggc cacacttttg  33960
caacaaactc ttttactttc tcctacatcg cccaagaata aagaaagcac agagatgctt  34020
gttttgattt caaaattgtg tgcttttatt tattttcagc ttacagtatt ccagtagtc   34080 attcgaataa agcttaatca aactgcatga gaacccttcc acatagctta aattagcacc  34140
agtgcaaatg gagaaaattc aacatacctt ttttatccag atatcagaga actctagtgg  34200
tcagttttcc cccacccctcc cagctcacag aatacacagt cctttccccc cggctggctt  34260
taaacaacac tatctcattg gtaacagaca tattcttagg tgtaataatc cacacggtct  34320
cttggcgggc caagcgctgg tcggtgatgt taataaactc cccaggcagc tctttcaagt  34380
tcacgtcgct gtccaactgc tgaagcgctc gcggctccga ctgcgcctct agcggaggca  34440
acggcaacac ccgatccttg atctataaag gagtagagtc ataatccccc ataagaatag  34500
ggcggtgatg cagcaacaag gcgcgcagca actcctgccg ccgcctctcc gtacgacagg  34560
aatgcaacgg cgtggtggtc tcctccgcga taatccgcac cgctcgcagc atcagcatcc  34620
tcgtcctccg ggcacagcag cgcatcctga tctcactgag atcggcgcag taagtgcagc  34680
acaaaaccaa gatgttattt aagatcccac agtgcaaagc actgtaccca aagctcatgg  34740
cgggaaggac agcccccacg tgaccatcat accagatcct taggtaaatc aaatgacgac  34800
ctctcataaa cacgctggac atgtacatca cctccttggg catgcgctga ttcaccacct  34860
ctcgatacca caagcatcgc tgattaatta aagaccctc aagcaccatc ctgaaccagg   34920
aagccagcac ctgaccccc gccaggcact gcagggaccc cggtgaattg cagtggcagt    34980
gaagactcca gcgctcgtag ccgtgaacca tagagccggt cattatatcc acattggcac  35040
aacacaaaca cactttcata cactttttca tgattagcag ctcctctcta gtcaggacca  35100
tatcccaagg aatcacccac tcttgaatca aggtaaatcc cacacagcag ggcaggcctc  35160
tcacataact cacgttatgc atagtgagcg tgtcgcaatc tggaaatacc ggatgatctt  35220
ccatcaccga agctcgcgtc tccgtctcaa agggaggtaa acggtccctc gtgtagggac  35280
agtggcggga taatcgagat cgtgttgaac gtagagtcat gccaaaggga acagcggacg  35340
tactcatatt tcctccagca gaaccaagtg cgcgcgtggc agctatccct gcgtcttctg  35400
tctcgccgcc tgccccgctc ggtgtagtag ttgtaataca gccactccct cagaccgtca  35460
aggcgctccc tggcgtccgg atctataaca acaccgtcct gcagcgccgc cctgatgaca  35520
tccaccaccg tagagtatgc caagcccagc caggaaatgc attcactttg acagcgagag  35580
ataggaggag cgggaagaga tggaagaacc atgatagtaa aagacttta ttccaatcga    35640 tcctctacaa tgtcaaagtg tagatctata agatgacact ggtctcctcc gctgagtcga  35700
tcaaaaataa cagctaaacc acaaacaaca cgattggtca aatgctccac aagggcttgc  35760
agcataaaat cgcctcgaaa gtccaccgca agcataacat caaagccacc gccctatca   35820 tgatctataa taaaaacccc acagctatcc accagaccca taaagttttc atctctccat  35880
cgtgaaaaaa tatttacaag ctcctccttt aaatcacctc caaccaattg aaaaagttga  35940
gccaaaccgc cctccacctt cattttcagc aagcgcatca tgattgcaaa aattcaggct  36000
cctgagacac ctgtataaga ttgagaagcg gaacgttaac gtcaatgttt cgctcgcgaa  36060
```

```
gatcgcgcct cagtgcaagc atgatataat cccacaggtc ggagcggatc agcgaggaca    36120
tctccccgcc aggaaccaac tcaacggagc ctatgctgat tataatacgc atattcgggg    36180
ctatgctgac cagcacggcc cccaaatagg cgtactgcat aggcggcgac aaaaagtgaa    36240
cagtttgggt taaaaaatca ggcaaacagt cgcgcaaaaa agcaagaaca tcataaccat    36300
gctcatgcaa atagatgcaa gtaagctcag gaacgaccac agaaaaatgc acaattttc    36360 tctcaaacat gactgcgagc cctgcaaaaa ataaaaaaga acattacac aagagtagcc    36420 tgtcttacga tgggatagac tactctaacc aacataagac gggccacaac atcgcccgcg    36480
tggccataaa aaaattgtc cgtgtgatta aaaagaagca cagatagctg gccagtcata    36540
tccggagtca tcacgtgtga acccgtgtag accccgggt tggacacatc ggccaaacaa    36600
agaaagcggc caatgtaccc aggaggaatc ataacactaa gacgaagata caacagaata    36660
accccatgag ggggaataac aaagttagta ggtgaataaa aacgataaac acccgaaact    36720
ccctcctgcg taggcaaaat agcaccctcc ccttccaaaa caacatatag cgcttccaca    36780
gcagccatga caaaagactc aaaacactca aaagactcag tcttaccagg aaaataaaag    36840
cactctcaca gcaccagcac taatcagagt gtgaagaggg ccaagtgccg aacgagtata    36900
tataggaata aaaaatgacg taaatgtgta aaggtcagaa aacgcccaga aaaatacaca    36960
gaccaacgcc cgaaacgaaa acccgcgaaa aaatacccag aacttcctca acaaccgcca    37020
cttccggttt ctcacggtac gtcacttccg caagaaaagc aaaactacat ttcccacatg    37080
tgtaaaaacg aaaccccgcc ccttgtaact gcccacaact tacatcatca aaacataaac    37140
tcctacgtca cccgccccgc ctctccccgc ccacctcatt atcatattgg ccacaatcca    37200
aaataaggta tattat                                                   37216

<210> SEQ ID NO 25
<211> LENGTH: 34029
<212> TYPE: DNA
<213> ORGANISM: Gorilla beringei beringei

<400> SEQUENCE: 25
catcatcaat aatataccct attttggatt gtggccaata tgataatgag gtgggcgggg      60
agaggcgggg cggtgacgt aggacgcgcg agtagggttg ggaggtgtgg cggaagtgtg     120
gcatttgcaa gtgggaggag ctcacatgca agcttccgtc gcggaaaatg tgacgttttt     180
gatgagcgcc gcctacctcc ggaagtgcca attttcgcgc gcttttcacc ggatatcgta     240
gtaattttgg gcgggaccat gtaagatttg gccattttcg cgcgaaaagt gaaacgggga     300
agtgaaaact gaataatagg gcgttagtca tagtgcgtaa tatttaccga gggccgaggg     360
actttgaccg attacgtgga ggactcgccc aggtgttttt tacgtgaatt ccgcgttcc     420 gggtcaaagt ctccgtttta ttgtcaccgt catttgacgc ttaggcctga ccatctggtg     480
ctggcctgca ccagggccga gtttgggtct agcgatgagg ataccgattg aggtgggtaa     540
ggtgggcgtg gctagaaggg tggggcgtgt ataaattggg ggtctaaggg tctctctgtt     600
ttgtcttgca acagccgccg ccatgagcga caccggcaac agctttgatg gaagcatctt     660
tagcccctat ctgacagtgc gcatgcctca ctgggctgga gtgcgtcaga atgtgatggg     720
ttccaacgtg gatggacgcc ccgttctgcc ttcaaattcg tctacaatgg cctacgcgac     780
cgtgggagga actccgctgg acgccgcgac ctccgccgcc gctccgccg ccgccgcgac     840 cgcgcgcagc atggctacgg acctttacag ctctttggtg gcgagcggcg cggcctctcg     900
```

```
cgcgtctgct cgggatgaga aactgaccgc tctgctgctt aaactggaag acttgacccg    960
ggagctgggt caactgaccc agcaggtctc cagcttgcgt gagagcagcc ttgcctcccc   1020
ctaatggccc ataatataaa taaaagccag tctgttttgga ttaagcaagt gtatgttctt  1080
tatttaactc tccgcgcgcg gtaagccgg gaccagcggt ctcggtcgtt tagggtgcgg    1140
tggattcttt ccaacacgtg gtacaggtgg ctctggatgt ttagatacat gggcatgagt   1200
ccatccctgg ggtggaggta gcaccactgc agagcttcgt gctcggggt ggtgttgtat    1260
atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata tccagtgcac   1500
ttgggaaatt tatcgtggag cttagacggg aatgcatgga agaacttgga gacgcccttg   1560
tggcctccca gattttccat acattcgtc atgatgatgg caatgggccc gtgggaagct    1620
gcctgagcaa aaatgtttct gggatcgctc acatcgtagt tatgttccag ggtgaggtca   1680
tcataggaca tctttacgaa tcggggcgg agggtcccgg actggggat gatggtaccc     1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa attttttcagc  2100
ggttttaggc cgtcggccgt gggcatgttt ttcagcgtct gggtcagcag ttccagcctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tgggcgcagg gtcctcgtca gggtggtctg ggtcacggtg aagggtgcg    2340
ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgccccat gcttttttgat gcgtttctta cctcggctct   2700
ccatgaggcg gtgtcccttc tcggtgacga agaggctgtc cgtgtcccg tagaccgact    2760
tcaggggcct gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accgggggtt cccgacgggg   3000
gggtataaaa gggggtgggc gccctttcat cttcactctc ttccgcatcg ctgtctgcga   3060
gggccagctg ctgggtaag tattccctct cgaaggcggg catgacctca gcgctcaggt    3120
tgtcagtttc taaaaatgag gaggatttga tgttcacctg tccggaggtg atacctttga   3180
gggtacctgg gtccatctgg tcagaaaaca ctatttttt gttgtcaagc ttggtggcga    3240
acgacccgta gagggcgttg gagagcagct tggcgatgga gcgcagggtc tggtttttgt   3300
```

```
cgcggtcggc tcgctccttg gccgcgatgt tgagttgcac gtactcgcgg gccacgcact   3360
tccactcggg gaagacggtg gtgcgctcgt ctgggattag gcgcaccctc cagcctcggt   3420
tgtgcagggt gaccatgtcg acgctggtgg cgacctcgcc gcgcaggcgc tcgttggtcc   3480
agcagaggcg gccgcccttg cgcgagcaga agggggtag gggtccagc tggtcctcgt     3540 ttgggggtc cgcgtcgatg gtgaagaccc cggggagcaa gcgcgggtca agtagtcga    3600 tcttgcaagc ttgcatgtcc agagcccgct gccattcgcg ggcggcgagc gcgcgctcgt   3660
aggggttgag gggcgggccc cagggcatgg ggtgggtgag cgcggaggcg tacatgccgc   3720
agatgtcata cacgtacagg ggttccctga ggatgccgag gtaggtgggg tagcagcgcc   3780
ccccgcggat gctggcgcgc acgtagtcat agagctcgtg ggagggggcc agcatgttgg   3840
gcccgaggtt ggtgcgctgg gggcgctcgg cgcggaaggc gatctgcctg aagatggcat   3900
gggagttgga ggagatggtg ggccgctgga agacgttgaa gcttgcttct tgcaagccca   3960
ccgagtccct gacgaaggag gcgtaggact cgcgcagctt gtgcaccagc tcggcggtga   4020
cctggacgtc gagcgcgcag tagtcgaggg tctcgcggat gatgtcatac ttatcctccc   4080 ccttctttt ccacagctcg cggttgagga cgaactcttc gcggtctttc cagtactctt    4140 ggagggaaa cccgtccgtg tccgaacggt aagagcctag catgtagaac tggttgacgg    4200
cctggtaggg gcaacagccc ttctccacgg gcagcgcgta ggcctgcgcc gccttgcgga   4260
gggaggtgtg ggtgagggcg aaagtgtccc tgaccatgac tttgaggtat tgatgtttga   4320
agtctgtgtc atcgcagccg ccctgttccc acagggtgta gtccgtgcgc ttttggagc    4380 gcgggttggg caggagaag gtgaggtcat tgaagaggat cttccccgct cgaggcatga    4440
agtttctggt gatgcgaaag ggccctggga ccgaggagcg gttgttgatg acctgggcgg   4500
ccaggacgat ctcgtcaaag ccgtttatgt tgtggcccac gatgtagagc tccaaaaagc   4560
ggggctggcc cttgatggag gggagctttt tgagttcctc gtaggtgagc tcctcgggcg   4620
attccaggcc gtgctcctcc agggcccagt cttgcaagtg agggttggcc gccaggaagg   4680
atcgccagag gtcgcgggcc atgagggtct gcaggcggtc gcggaaggtt ctgaactgtc   4740
gccccacggc catctttcg ggggtgatgc agtagaaggt gagggggtct ttctcccagg    4800
ggtcccatct gagctctcgg gcgaggtcgc gcgcggcggc gaccagagcc tcgtcgcccc   4860
ccagtttcat gaccagcatg aagggcacga gctgcttgcc aaaggctccc atccaagtgt   4920
aggtctctac atcgtaggtg acaaagaggc gctccgtgcg aggatgagag ccgatcggga   4980
agaactggat ctcccgccac cagttggagg attggctgtt gatgtggtga agtagaagt    5040 cccgtctgcg ggccgagcac tcgtgctggc ttttgtaaaa gcgaccgcag tactggcagc   5100
gctgcacggg ttgtatatct tgcacgaggt gaacctggcg acctctgacg aggaagcgca   5160
gcgggaatct aagtccccg cctggggtcc cgtgtggctg gtggtcttct actttggttg    5220
tctgccgcag cagcatctgtc tcctggaggg cgatggtgga gcagaccacc acgccgcgag   5280
agccgcaggt ccagatctcg gcgctcggcg ggcggagttt gatgacgaca tcgcgcacat   5340
tggagctgtc catggtctcc agctcccgcg gcggcaggtc agctgggagt tcctggaggt   5400
tcacctcgca gagacgggtc aaggcgcggg cagtgttgag atggtatctg atttcaaggg   5460
gcgtgttggc ggcggagtcg atggcttgca ggaggccgca gccccggggg gccacgatgg   5520
ttccccgcgg ggcgcgaggg gaggcggaag ctggggtgt gttcagaagc ggtgacgcgg    5580
gcgggccccc ggaggtaggg ggggttccgg ccccacaggc atgggcggca ggggcacgtc   5640
```

```
ttcgccgcgc gcgggcaggg gctggtgctg gctccgaaga gcgcttgcgt gcgcgacgac    5700
gcgacggttg gtgtcctgta tctgacgcct ctgagtgaag accacgggtc ccgtgacctt    5760
gaacctgaaa gagagttcga cagaatcaat ctcggcatcg ttgacagcgg cctggcgcag    5820
gatctcctgc acgtcgcccg agttgtcctg gtaggcgatc tctgccatga actgctcgat    5880
ctcttcttcc tggagatctc ctcgtccggc gcgctccacg gtggccgcca ggtcgttgga    5940
gatgcgaccc atgagctgtg agaaggcgtt gagcccgccc tcgttccaga cccggctgta    6000
gaccacgccc ccctcggcgt cgcgagcgcg catgaccacc tgggccaggt tgagctccac    6060
gtgtcgcgtg aagacggcgt agttgcgcag gcgctggaaa aggtagttca gggtggtggc    6120
ggtgtgctcg gcgacgaaga agtacatgac ccagcgccgc aacgtggatt cattgatgtc    6180
ccccaaggcc tccaggcgct ccatggcctc gtagaagtcc acggcgaagt tgaaaaactg    6240
ggagttgcga gcggacacgg tcaactcctc ctccagaaga cggatgagct cggcgacagt    6300
gttgcgcacc tcgcgctcga aggccacggg gggcgcttct tcctcttcca cctcttcttc    6360
catgatcgct tcttcttctt cctcagccgg gacgggaggg ggcggcggcg gcggggagg    6420 ggcgcggcgg cggcggcggc gcaccgggag gcggtcgatg aagcgctcga tcatctcccc    6480
ccgcatgcgg cgcatggtct cggtgacggc gcggccgttc tcccgggggc gcagctcgaa    6540
gacgccgcct ctcatctcgc gcggggcga gcggccgtga ggtagcgaga cggcgctgac    6600
tatgcatctt aacaattgct gtgtaggtac accgccgagg gacctgattg agtccagatc    6660
caccggatcc gaaaaccttt ggaggaaagc gtctatccag tcgcagtcgc aaggtaggct    6720
gagcaccgtg gcgggcgggg gcgggtctgg agagttcctg gcggagatgc tgctgatgat    6780
gtaattaaag taggcggtct tgagaaggcg gatggtggac aggagcacca tgtctttggg    6840
tccggcctgt tggatgcgga ggcggtcggc catgccccag gcctcgttct gacaccggcg    6900
caggtctttg tagtagtctt gcatgagtct ttccaccggc acctcttctc cttcctcttc    6960
tccatctcgc cggtggtttc tcgcgccgcc catgcgcgtg accccaaagc ccctgagcgg    7020
ctgcagcagg gccaggtcgg cgaccacgcg ctcggccaag atggcctgct gcacctgagt    7080
gagggtcctc tcgaagtcat ccatgtccac gaagcggtgg taggcgcccg tgttgatggt    7140
gtaggtgcag ttggccatga cggaccagtt gacggtctgg tgtcccggct gcgagagctc    7200
cgtgtaccgc aggcgcgaga aggcgcggga atcgaacacg tagtcgttgc aagtccgcac    7260
cagatactgg tagcccacca ggaagtgcgg cggaggttgg cgatagaggg gccagcgctg    7320
ggtggcgggg gcgccgggcg ccaggtcttc cagcatgagg cggtggtatc cgtagatgta    7380
cctggacatc caggtgatgc cggcggcggt ggtggtggcg cgcgcgtagt cgcggacccg    7440
gttccagatg tttcgcaggg gcgagaagtg ttccatggtc ggcacgctct ggccggtgag    7500
gcgcgcgcag tcgttgacgc tctatacaca cacaaaaacg aaagcgttta cagggctttc    7560
gttctgtagc ctggaggaaa gtaaatgggt tgggttgcgg tgtgcccgg ttcgagacca    7620 agctgagctc ggccggctga agccgcagct aacgtggtat tggcagtccc gtctcgaccc    7680
aggccctgta tcctccagga tacggtcgag agccctttg ctttcttggc caagcgcccg    7740
tggcgcgatc tgggatagat ggtcgcgatg agaggacaaa agcggctcgc ttccgtagtc    7800
tggagaaaca atcgccaggg ttgcgttgcg gcgtaccccg gttcgagccc ctatggcggc    7860
ttgaatcggc cggaaccgcg gctaacgagg gccgtggcag cccgtcctc aggacccgc    7920 cagccgactt ctccagttac gggagcgagc ccctttgtt ttttattttt tagatgcatc    7980
ccgtgctgcg gcagatgcgc ccctcgcccc ggcccgatca gcagcagcaa cagcaggcat    8040
```

```
gcagacccce ctctcccctt tccgccccgg tcaccacggc cgcggcggcc gtgtcgggcg    8100 cgggggggcgc gctggagtca gatgagccac cgcggcggcg acctaggcag tatctggact    8160
tggaagaggg cgaggactg gcgcggctgg gggcgaactc tccagagcgc cacccgcggg    8220
tgcagttgaa aagggacgcg cgcgaggcgt acctgccgcg gcagaacctg tttcgcgacc    8280 gcggggggcga ggagcccgag gagatgcgag actgcaggtt ccaagcgggg cgcgagctgc    8340
ggcgcgggct ggacagacag cgcctgctgc gcgaggagga ctttgagccc gacacgcaga    8400
cgggcatcag ccccgcgcgc gcgcacgtag ccgcggccga cctggtgacc gcctacgagc    8460
agacggtaaa ccaggagcgc aacttccaaa agagcttcaa caaccacgtg cgcacgctgg    8520
tggcgcgcga ggaggtgacc ctgggtctca tgcatctgtg ggacctggtg gaggcgatcg    8580
tgcagaaccc cagcagcaag cccctgaccg cgcagctgtt cctggtggtg cagcacagca    8640
gggacaacga ggccttcagg gaggcgctgc tgaacatcac cgagccggag gggcgctggc    8700
tcctggacct gataaacatc ctgcagagca tagtggtgca ggagcgcagc ctgagcctgg    8760
ccgagaaggt ggcggccatc aactactcta tgctgagcct gggcaagttc tacgcccgca    8820
agatctacaa gaccccctac gtgcccatag acaaggaggt gaagatagac agcttctaca    8880
tgcgcatggc gctgaaggtg ctgacccctga gcgacgacct gggagtgtac cgcaacgagc    8940
gcatccacaa ggccgtgagc gccagccggc ggcgcgagct gagcgaccgc gagctgatgc    9000
acagtctgca gcgcgcgctg accggcgcgg gcgagggcga cagggaggtc gagtcctact    9060
tcgacatggg ggccgacctg cactggcagc cgagccgccg cgccctggag gcggcggggg    9120
cgtacggcgg cccctggcg gccgatgacc aggaagagga ggactatgag ctagaggagg    9180
gcgagtacct ggaggactga cctggctggt ggtgttttgg tatagatgca agatccgaac    9240
gtggcggacc cggcggtccg ggcggcgctg caaagccagc cgtccggcat taactcctct    9300
gacgactggg ccgcggccat gggtcgcatc atggccctga ccgcgcgcaa ccccgaggct    9360
ttcaggcagc agcctcaggc caaccggctg gcggccatct tggaagcggt agtgcccgcg    9420
cgctccaacc ccacccacga gaaggtgctg ccatagtcaa acgcgctggc ggagagcagg    9480
gccatccgcg cggacgaggc cggactggtg tacgatgcgc tgctgcagcg ggtggcgcgg    9540
tacaacagcg gcaacgtgca gaccaacctg gaccgcctgg tgacggacgt gcgcgaggcc    9600
gtggcgcagc gcgagcgctt gcatcaggac ggtaacctgg gctcgctggt ggcgctaaac    9660
gccttcctca gcacccagcc ggccaacgta ccgcgggggc aggaggacta caccaacttt    9720
ttgagcgcgc tgcggctgat ggtgaccgag gtccctcaga gcgaggtgta ccagtcgggg    9780
cccgactact tcttccagac cagcagacag ggcttgcaaa ccgtgaacct gagccaggct    9840
ttcaagaacc tgcgggggct gtggggagtg aaggcgccca ccggcgaccg ggctacggtg    9900
tccagcctgc taacccccaa ctcgcgcctg ctgctgctgc tgatcgcgcc cttcacggac    9960
agcgggagcg tctcgcggga gacctatctg gccacctgc tgacgctgta ccgcgaggcc    10020
atcgggcagg cgcaggtgga cgagcacacc ttccaagaga tcaccagcgt gagccacgcg    10080
ctggggcagg aggacacggg cagcctgcag gcgaccctga actacctgct gaccaacagg    10140
cggcagaaga ttcccacgct gcacagcctg acccaggagg aggagcgcat cttgcgctac    10200
gtgcagcaga gcgtgagcct gaacctgatg cgcgacggcg tgacgcccag cgtggcgctg    10260
gacatgaccg cgcgcaacat ggaacgggc atgtacgcct cccaccggcc gtttatcaac    10320
cgcctgatgg actacttgca tcgggcggcg gccgtgaacc ccgagtactt cactaatgcc    10380
```

```
attctgaatc cccactggat gccccctccg ggtttctaca acggggactt tgaggtgccc   10440
gaggtcaacg acgggttcct ctgggatgac atggatgaca gtgtgttctc acccaacccg   10500
ctgcgcgccg cgtctctgcg attgaaggag ggctctgaca gggaaggacc gaggagtctg   10560
gcctcctccc tggctctggg agcggtgggc gccacgggcg cggcggcgcg gggcagtagc   10620
cccttcccca gcctggcaga ctctctgaac agcgggcggg tgagcaggcc ccgcttgcta   10680
ggcgaggagg agtatctgaa caactccctg ctgcagcccg cgaggacaa gaacgctcag   10740
cggcagcagt ttcccaacaa tgggatagag agcctggtgg acaagatgtc cagatggaag   10800
acgtatgcgc aggagtacaa ggagtgggag gaccgccagc cgcggccctt gccgccccct   10860
aggcagcgct ggcagcggcg cgcgtccaac cgccgctgga ggcaggggcc cgaggacgat   10920
gatgactctg cagatgacag cagcgtgttg gacctgggcg ggagcgggaa ccccttttcg   10980
cacctgcgcc cacgcctggg caagatgttt taaaagaaaa aaaaaataaa actcaccaag   11040
gccatggcga cgagcgttgg tttttttgttc ccttccttag tatgcggcgc gcggcgatgt   11100
tcgaggaggg gcctcccccc tcttacgaga gcgcgatggg gatttctcct gcggcgcccc   11160
tgcagcctcc ctacgtgcct cctcggtacc tgcaacctac agggggggaga aatagcatct   11220
gttactctga gctgcagccc ctgtacgata ccaccagact gtacctggtg gacaacaagt   11280
ccgcggacgt ggcctccctg aactaccaga acgaccacag cgattttttg accacggtga   11340
tccaaaacaa cgacttcacc ccaaccgagg ccagcaccca gaccataaac ctggataaca   11400
ggtcgaactg gggcggcgac ctgaagacca tcttgcacac caacatgccc aacgtgaacg   11460
agttcatgtt caccaactct tttaaggcgc gggtgatggt ggcgcgcgag caggggggagg   11520
cgaagtacga gtgggtggac ttcacgctgc ccgagggcaa ctactcagag accatgactc   11580
tcgacctgat gaacaatgcg atcgtggaac actatctgaa agtgggcagg cagaacgggg   11640
tgaaggaaag cgatatcggg gtcaagtttg acaccagaaa cttccgtctg ggctgggacc   11700
ccgtgaccgg gctggtcatg ccgggggtct acaccaacga ggcctttcat cccgacatag   11760
tgcttctgcc cggctgtggg gtggacttca cccagagccg gctgagcaac ctgctgggca   11820
ttcgcaagcg gcagccttttc caggagggtt tcaagatcac ctatgaggat ctgaaggggg   11880
gcaacattcc cgcgctcctt gatctggacg cctacgagga gagcttgaaa cccgaggaga   11940
gcgctggcga cagcggcgag agtggcgagg agcaagccgg cggcggtggc ggcgcgtcgg   12000
tagaaaacga aagtacgccc gcagtggcgg cggacgctgc ggaggtcgag ccggaggcca   12060
tgcagcagga cgcagaggag ggcgcacagg agggcgcgca aaggacatg aacgatgggg   12120
agatcagggg agacacattc gccacccggg gcgaagaaaa agaggcagag cggcggcgg   12180
cggcgacggc ggaggccgaa accgaggttg aggcagaggc agagcccgag accgaagtta   12240
tggaagacat gaatgatgga gaacgtaggg gcgacacgtt cgccacccgg ggcgaagaga   12300
aggcggcgga ggcagaagcc gcggctgagg aggcggctgc ggctgcggcc aagactgagg   12360
ctgcggctaa ggctgaggtc gaagccaatg ttgcggttga ggctcaggct gaggaggagg   12420
cggcggctga agcagttaag gaaaaggccc aggcagagca ggaagagaaa aaacctgtca   12480
ttcaacctct aaaagaagat agcaaaaagc gcagttacaa cgtcatcgag ggcagcacct   12540
ttacccagta ccgcagctgg tacctggcgt acaactacgg cgacccggtc aagggggtgc   12600
gctcgtggac cctgctctgc acgcggacg tcacctgcgg ctccgagcag atgtactggt   12660
cgctgccgaa catgatgcaa gacccggtga ccttccgctc cacgcggcag gttagcaact   12720
tcccggtggt gggcgccgaa ctgctgcccg tgcactccaa gagttttttac aacgagcagg   12780
```

```
ccgtctactc ccagctgatc cgccaggcca cctctctgac ccacgtgttc aatcgctttc   12840
ccgagaacca gattttggcg cgcccgccgg cccccaccat caccaccgtg agtgaaaacg   12900
ttcctgccct cacagatcac gggacgctac cgctgcgcaa cagcatctca ggagtccagc   12960
gagtgaccat tactgacgcc agacgccgga cctgcccta cgtttacaag gccttgggca    13020
tagtctcgcc gcgcgtcctc tccagtcgca cttttaaaa cacatctacc cacacgttcc    13080
aaaatcatgt ccgtactcat ctcacccagc aacaacaccg gctgggggct gcgcgcgccc   13140
agcaagatgt ttggaggggc gaggaagcgc tccgaccagc accctgtgcg cgtgcgcggc   13200
cactaccgcg cgcccggggg agcgcacaag gcgggcgca cagggcgcac cactgtggac    13260
gacgtcattg actccgtagt ggagcaagcg cgccactaca caccccggcgc gccgaccgcc   13320 cccgccgtgt ccaccgtgga ccaggcgatc gaaagcgtgg tacagggcgc gcggcactat   13380
gccaacctta aaagtcgccg ccgccgcgtg gcccgccgcc atcgccggag accccgggcc   13440
accgccgccg cgcgccttac taaggctctg ctcaggcgcg ccaggcgaac tggccaccgg   13500
gccgccatga gggccgcacg gcgggctgcc gctgccgcaa gcgtcgtggc cccgcgggca    13560
cgaaggcgcg cggccgctgc cgccgccgcc gccatttcca gcttggcctc gacgcggcgc   13620
ggtaacatat actgggtgcg cgactcggta accggcacgc gggtacccgt gcgctttcgc   13680
cccccgcgga attagcacaa gacaacatac acactgagtc tcctgctgtt gtgtatccca   13740
gcggcgaccg tcagcagcgg cgacatgtcc aagcgcaaaa ttaaagaaga gatgctccag   13800
gtcatcgcgc cggagatcta tgggcccccg aagaaggagg aggatgatta caagcccgc    13860 aagctaaagc gggtcaaaaa gaaaagaaa gatgatgatg acgaggcggt ggagtttgtc    13920
cgccgcatgg cacccaggcg ccccgtgcag tggaagggcc ggcgcgtgca gcgcgttttg   13980
cgccccggca ccgcggtggt cttcacgccc ggcgagcgct ccacgcgcac tttcaagcgg   14040
gtgtacgatg aggtgtacgg cgacgaggac ctgttggagc aggccaacca gcgctttggg   14100
gagtttgcat atgggaaacg gccccgcgag agtctaaaag gaggacctgct ggcgctaccg   14160 ctggacgagg gcaatcccac cccgagtctg aagccggtaa ccctgcaaca ggtgctgcct   14220
ttgagcgcgc ccagcgagca taagcgaggg ttgaagcgcg aaggcgggga cctggcgccc   14280
accgtgcagt tgatggtgcc caagcggcag aagctggagg acgtgctgga gaaatgaaa    14340 gtagagcccg ggatccagcc cgagatcaag gtccgcccca tcaagcaggt ggcgcccggc   14400
gtgggagtcc agaccgtgga cgttaggatt cccacggagg agatggaaac ccaaaccgcc   14460
actccctctt cggcggccag cgccaccacc ggcaccgctt cggtagaggt gcagacggac   14520
ccctggctac ccgccaccgc tgttgccgcc gccgccccc gttcgcgcgg gcgcaagaga   14580
aattatccag cggccagcgc gctcatgccc cagtacgcac tgcatccatc catcgtgccc   14640 accccggct accgcgggta ctcgtaccgc ccgcgcagat cagccggcac tcgcggccgc   14700
cgccgccgtg cgaccacaac cagcgccgc cgtcgccgcc gccgccagcc agtgctgacc    14760
cccgtgtctg taaggaaggt ggctcgctcg gggagcacgc tggtggtgcc cagagcgcgc   14820
taccacccca gcatcgttta aagccggtct ctgtatggtt cttgcagata tggccctcac   14880
ttgtcgcctc cgcttcccgg tgcgggata ccgaggaaga actcaccgcc gcagaggcat    14940
ggcgggcagc ggtctccgcg gcggccgtcg ccatcgccgg cgcgcaaaaa gcaggcgcat   15000
gcgcggcggt gtgctgcctc tgctaatccc gctaatcgcc gcggcgatcg gtgccgtacc   15060
cgggatcgcc tccgtggccc tgcaggcgtc ccagaaacgt tgactcttgc aaccttgcaa   15120
```

```
gcttgcattt tttggaggaa aaataaaaaa aagtctagac tctcacgctc gcttggtcct  15180
gtgactattt tgtagaaaaa aagatggaag acatcaactt tgcgtcgctg gccccgcgtc  15240
acggctcgcg cccgttcatg ggagactgga cagatatcgg caccagcaat atgagcggtg  15300
gcgccttcag ctggggcagt ctgtggagcg gccttaaaaa ttttggttcc accattaaga  15360
actatggcaa caaagcgtgg aacagcagca cgggccagat gctgagagac aagttgaaag  15420
agcagaactt ccaggagaag gtggcgcagg gcctggcctc tggcatcagc ggggtggtgg  15480
acatagctaa ccaggccgtg cagaaaaaga taaacagtca tctggacccc cgtcctcagg  15540
tggaggaaat gcctccagcg atggagacgg tgtctcccga gggcaaaggc gaaaagcgcc  15600
cgcggcccga cagagaagag accctggtgt cacacaccga ggagccgccc tcttacgagg  15660
aggcagtcaa ggccggcctg cccaccactc gccccatagc ccccatggcc accggtgtgg  15720
tgggccacag gcaacacact cccgcaacac tagatctgcc cccgccgtcc gagccgccgc  15780
gccagccaaa ggcggcgacg gtgcccgctc cctccacttc cgccgccaac agagtgcccc  15840
tgcgccgcgc cgcgagcggc ccccgggcct cgcgagttag cggcaactgg cagagcacac  15900
tgaacagcat cgtgggcctg ggagtgagga gtgtgaagcg ccgccgttgc tactgaatga  15960
gcaagctagc taacgtgttg tatgtgtgta tgcgtcctat gtcgccgcca gaggagctgt  16020
tgagccgccg gcgccgtctg cactccagcg aatttcaaga tggcgacccc atcgatgatg  16080
cctcagtggt cgtacatgca catctcgggc caggacgctt cggagtacct gagccccggg  16140
ctggtgcagt tcgcccgcgc cacagacacc tacttcaaca tgagtaacaa gttcaggaac  16200
cccactgtgg cgcccaccca cgatgtgacc acggaccggt cgcagcgcct gacgctgcgg  16260
ttcatccccg tggatcggga ggacaccgcc tactcttaca aggcgcggtt cacgctggcc  16320
gtgggcgaca accgcgtgct ggacatggcc tccacttact ttgacatcag gggggtgctg  16380
gacaggggcc ccaccttcaa gccctactcg ggtactgcct acaactccct ggcccccaag  16440
ggcgctccca attcttgcga gtgggaacaa gatgaaccag ctcaggcagc aatagctgaa  16500
gatgaagaag aacttgaaga agaacaagct caggacgaac aggcgcccac taagaaaacc  16560
catgtatacg cccaggcacc tctttctggt gaaaaaatta ctaaggatgg tttgcaaata  16620
ggtgtggatg ccacacaggc gggagataac cctatatatg ctgataaaac attccaaccc  16680
gaacctcaga taggtgagtc tcagtggaac gaggctgatg ccacagtagc aggaggcaga  16740
gtcttaaaaa agaccacccc tatgagacct tgctatggat cctatgccaa acctactaat  16800
gccaatggcg gtcaagggat catggtggcc aatgatcagg gagcgcttga atctaaagtt  16860
gagatgcaat tttctccac cacaacgtct cttaatgtaa gggaaggtga aaacaatctt  16920
cagccaaaag tagtgctata cagcgaagat gttaacttgg aatcccctga cactcatttg  16980
tcttacaaac ctaaaaagga tgacaccaac tctaaaatca tgttgggtca gcaagccatg  17040
cccaacagac ccaacctcat tgcttttagg gacaacttta ttggacttat gtactacaac  17100
agcacaggca acatgggagt gctggcagga caggcctccc agctaaacgc tgtggtagac  17160
ttgcaagaca gaaacacaga gctgtcatac caactgatgc ttgattccat tggagacaga  17220
tcaagatact tttccatgtg gaaccaggca gtggacagct atgacccaga tgtcagaatc  17280
attgaaaacc atggggttga agatgagctg cccaactatt gctttcccct gggcggtatt  17340
ggaattacag acacatacca gtgcataaaa ccaaccgcag ctgctaataa cactacatgg  17400
tctaaggatg aagaatttag tgatcgcaat gaaatagggg tgggaaacaa cttcgccatg  17460
gagatcaaca tccaggccaa cctctggagg aacttcctct atgcgaacgt ggggctctac  17520
```

```
ctgccagaca agctcaagta caaccccacc aacgtggaca tctctgacaa ccccaacacc    17580
tatgactaca tgaacaagcg tgtggtggct cccggcctgg tggactgctt tgtcaatgtg    17640
ggagccaggt ggtccctgga ctacatggac aacgtcaacc ccttcaacca ccaccgcaat    17700
gcgggtctgc gctaccgctc catgatcctg ggcaacgggc gctacgtgcc cttccacatt    17760
caggtgcccc agaagttctt tgccatcaag aacctcctcc tcctgccggg ctcctacact    17820
tacgagtgga acttcaggaa ggatgtcaac atggtcctgc agagctctct gggcaatgac    17880
cttagggtgg acggggccag catcaagttt gacagcgtca ccctctatgc taccttcttc    17940
cccatggctc acaacaccgc ctccacgctc gaggccatgc tgaggaacga caccaacgac    18000
cagtccttca tgactacct ctctggggcc aacatgctct accccatccc cgccaaggcc    18060
accaacgtgc ccatctccat tccctctcgc aactgggccg ccttcagagg ctgggccttt    18120
acccgcctta agaccaagga aaccccctcc ctgggctcgg ttttgaccc ctactttgtc    18180 tactcgggat ccatccccta cctggatggc accttctacc tcaaccacac ttttaagaag    18240
atatccatca tgtatgactc ctccgtcagc tggccgggca atgaccgcct gctcaccccc    18300
aatgagttcg aggtcaagcg cgccgtggac ggcgagggc acaacgtggc ccagtgcaac    18360
atgaccaagg actggttcct ggtgcagatg ctggccaact acaacatagg ctaccagggc    18420
ttctacatcc cagagagcta caaggacagg atgtactcct tcttcagaaa tttccaaccc    18480
atgagcaggc aggtggtgga cgagaccaaa tacaaggact atcaggccat ggcatcact    18540 caccagcaca caactcggg attcgtgggc tacctggctc ccaccatgcg cgaggggcag    18600
gcctaccccg ccaacttccc ctaccgttg ataggcaaaa ccgcggtcga cagcgtcacc    18660
cagaaaaagt tcctctgcga ccgcaccctc tggcgcatcc ccttctctag caacttcatg    18720
tccatgggtg cgctcacgga cctgggccag aacctgctct atgccaactc cgcccatgcg    18780
ctggacatga cttttgaggt ggaccccatg gacgagccca cccttctcta tattgtgttt    18840
gaagtgttcg acgtggtcag agtgcaccag ccgcaccgcg tgtcatcga accgtgtac    18900 ctgcgcacgc ccttctcggc cggcaacgcc accacctaag gagacagcgc cgccgcctgc    18960
atgacgggtt ccaccgagca agagctcagg gccatcgcca gagacctggg atgcggaccc    19020
tattttttgg gcacctatga caaacgcttc ccgggcttca tctcccgaga caagctcgcc    19080
tgcgccatcg tcaacacggc cgcgcgcgag accggggcg tgcactggct ggcctttggc    19140
tgggacccgc gctccaaaac ctgctacctc ttcgacccct ttggcttctc cgatcagcgc    19200
ctcagacaga tctatgagtt tgagtacgag gggctgctgc ccgcagcgc gcttgcctcc    19260 tcgcccgacc gctgcatcac ccttgagaag tccaccgaga ccgtgcaggg gccccactcg    19320
gccgcctgcg gtctcttctg ctgcatgttt ttgcacgcct ttgtgcgctg gccccagagt    19380
cccatggatc gcaaccccac catgaacttg ctcaaggag tgcccaacgc catgctccag    19440 agccccagg tccagcccac cctgcgccac aaccaggaac agctctaccg cttcctggag    19500
cgccactccc cctacttccg cagtcacagc gcgcacatcc gggggccac ctctttctgc    19560 cacttgcaag aaaacatgca agacggaaaa tgatgtacag ctcgcttttt aataaatgta    19620
aagactgtgc actttatttta tacacgggct cttttctggtt atttattcaa caccgccgtc    19680
gccatctaga aatcgaaagg gttctgccgc gcgtcgccgt gcgccacggg cagagacacg    19740
ttgcgatact ggaagcggct cgcccactta aactcgggca ccaccatgcg gggcagtggt    19800
tcctcgggga agttctcgcc ccacagggtg cgggtcagct gcagcgcgct caggaggtcg    19860
```

```
ggagccgaga tcttgaagtc gcagttgggg ccggaaccct gcgcgcgcga gttgcggtac  19920
acggggttgc agcactggaa caccagcagg gccggattat gcacgctggc cagcaggctc  19980
tcgtcgctga tcatgtcgct gtccagatcc tccgcgttgc tcagggcgaa cggggtcatc  20040
ttgcagacct gcctgcccag gaaaggcgga agcccgggct tgccgttgca gtcgcagcgc  20100
aggggcatca gcaggtgccc gcggcccgac tgcgcctgcg ggtacagcgc gcgcatgaag  20160
gcttcgatct gcctgaaagc cacctgcgtc ttggctccct ccgaaaagaa catcccacag  20220
gacttgctgg agaactggtt cgcgggacag ctggcatcgt gcaggcagca gcgcgcgtcg  20280
gtgttggcga tctgcaccac gttgcgaccc accggttct tcactatctt ggccttggaa  20340
gcctgctcct tcagcgcgcg ctggccgttc tcgctggtca catccatctc tatcacctgc  20400
tccttgttga tcatgtttgt accgtgcaga cacttcaggt cgccctccgt ctgggtgcag  20460
cggtgctccc acagcgcgca accggtgggc tcccaatttt tgtgggtcac ccccgcgtag  20520
gcctgcaggt aggcctgcaa gaagcgcccc atcatggcca caaaggtctt ctggctcgta  20580
aaggtcagct gcaggccgcg atgctcttcg ttcagccagg tcttgcagat ggcggccagc  20640
gcctcggtct gctcgggcag catcctaaaa tttgtcttca ggtcgttatc cacgtggtac  20700
ttgtccatca tggcgcgcgc cgcctccatg cccttctccc aggcggacac catgggcagg  20760 cttaggggg t ttatcacttc caccggcgag gacaccgtac tttcgatttc ttcttcctcc  20820
ccctcttccc ggcgcgcgcc cacgctgctg cgcgctctca ccgcctgcac caaggggtcg  20880
tcttcaggca agcgccgcac cgagcgcttg ccgcccttga cctgcttaat cagcaccggc  20940
gggttgctga agcccaccat ggtcagcgcc gcctgctctt cttcgtcttc gctgtctacc  21000
actatctctg gggaagggct tctccgctct cggcggcgc gcttctttttt tttcttggga  21060 gcggccgtga tggagtccgc cacggcgacg gaggtcgagg gcgtggggct gggggtgcgc  21120
ggtaccaggg cctcgtcgcc ctcggactct tcctctgact ccaggcggcg gcggagtcgc  21180
ttctttgggg gcgcgcgcgt cagcggcggc ggagacgggg acgggacgg ggacgggacg  21240 ccctccacag ggggtggtct tcgcgcagac ccgcggccgc gctcggggt cttctcgagc  21300 tggtcttggt cccgactggc cattgtatcc tcctcctcct aggcagagag acataaggag  21360
tctatcatgc aagtcgagaa ggaggagagc ttaaccaccc cctctgagac cgccgatgcg  21420
cccgccgtcg ccgtcgcccc cgctgccgcc gacgcgcccg ccacaccgag cgacaccccc  21480
gcggaccccc ccgccgacgc accccctgttc gaggaagcgg ccgtggagca ggacccgggc  21540
tttgtctcgg cagaggagga tttgcgagag gaggaggata aggagaagaa gccctcagtg  21600
ccaaaagatg ataaagagca agacgagcac gacgcagatg cacaccaggg tgaagtcggg  21660 cgggggggacg gagggcatga cggcgccgac tacctagacg aagggaacga cgtgctcttg  21720
aagcacctgc atcgtcagtg cgccattgtt tgcgacgctc tgcaggagcg cagcgaagtg  21780
cccctcagcg tggcggaggt cagccacgcc tacgagctca gcctcttctc ccccccgggtg  21840 cccccccgcc gccgcgaaaa cggcacatgc gagcccaacc cgcgcctcaa cttctacccc  21900
gcctttgtgg tacccgaggt cctggccacc tatcacatct tcttttcaaaa ttgcaagatc  21960 cccctctcgt gccgcgccaa ccgtagccgc gccgataaga tgctggccct gcgccagggc  22020
gaccacatac ctgatatcgc cgctttggaa gatgtaccaa agatcttcga gggtctgggt  22080
cgcaacgaga agcgggcagc aaactctctg caacaggaaa acagcgaaaa tgagagtcac  22140
accggggtac tggtggagct cgagggcgac aacgcccgcc tggcggtggt caagcgcagc  22200
atcgaggtca cccactttgc ctaccccgcg ctaaacctgc ccccccaaagt catgaacgcg  22260
```

```
gccatggacg ggctgatcat gcgccgcggc cggcccctcg ctccagatgc aaacttgcat    22320
gaggagaccg aggacggcca gcccgtggtc agcgacgagc agctggcgcg ctggctggag    22380
accgcggacc ccgccgaact ggaggagcgg cgcaagatga tgatggccgt ggtgctggtc    22440
accgtagagc tggagtgtct gcagcgcttc ttcggcgacc ccgagatgca gagaaaggtc    22500
gaggagaccc tgcactacac cttccgccag ggctacgtgc gccaggcttg caagatctcc    22560
aacgtggagc tcagcaacct ggtgtcctac ctgggcatct tgcatgagaa ccgcctcggg    22620
cagagcgtgc tgcactccac cctgcgcggg gaggcgcgcc gcgactacgt gcgcgactgc    22680
gtttacctct tcctctgcta cacctggcag acggccatgg gggtctggca gcagtgcctg    22740
gaggagcgca acctcaagga gctggagaag ctcctgcagc gcgcgctcaa agatctctgg    22800
acgggctaca cgagcgctc ggtggccgcc gcgctggccg acctcatctt ccccgagcgc    22860
ctgctcaaaa ccctccagca ggggctgccc gacttcacca gccaaagcat gttgcaaaac    22920
ttcaggaact ttatcctgga gcgttctggc atcctacccg ccacctgctg cgccctgccc    22980
agcgactttg tcccctcgt gtaccgcgag tgccccccgc cgctgtgggg tcactgctac    23040
ctgttccaac tggccaacta cctgtcctac cacgcggacc tcatggagga ctccagcggc    23100
gaggggctca tggagtgcca ctgccgctgc aacctctgca cgccccaccg ctccctggtc    23160
tgcaacaccc aactgctcag cgagagtcag attatcggta ccttcgagct acagggtccg    23220
tcctcctcag acgagaagtc cgcggctccg gggctaaaac tcactccggg gctgtggact    23280
tccgcctacc tgcgcaaatt tgtacctgaa gactaccacg cccacgagat caggttttac    23340
gaagaccaat cccgcccgcc caaggcggag ctgaccgcct gcgtcatcac ccagggcgag    23400
atcctaggcc aattgcaagc catccaaaaa gccgccaag acttttttgct gaagaagggt    23460 cgggggtgt atctggaccc ccagtcgggt gaggagctca cccggttcc cccgctgccg    23520 ccgccgcggg accttgcttc ccaggataag catcgccatg ctcccagaa agaagcagca    23580 gcggccgcca ctgccgccac cccacatgct ggaggaagag gaggaatact gggacagtca    23640
ggcagaggag gtttcggacg aggaggagcc ggagacggag atggaagagt ggggaggagga    23700 cagcttagac gaggaggctt ccgaagccga agaggcagac gcaacaccgt cacccctcggc    23760 cgcagccccc tcgcaggcgc ccccgaagtc cgctcccagc atcagcagca acagcagcgc    23820
tataacctcc gctcctccac cgccgcgacc cacggccgac cgcagaccca accgtagatg    23880
ggacaccacc ggaaccgggg ccggtaagtc ctccgggaga ggcaagcaag cgcagcgcca    23940
aggctaccgc tcgtggcgcg ctcacaagaa cgccatagtc gcttgcttgc aagactgcgg    24000
ggggaacatc tccttcgccc gccgcttcct gctcttccac cacggtgtgg ccttcccccg    24060
taacgtcctg cattactacc gtcatctcta cagcccctac tgcggcggca gtgagccaga    24120
gacggtcggc ggcggcggcg gcgcccgttt cggcgcctag aagacccag gcaagactt    24180 cagccaagaa actcgcggcg gccgcggcga acgcgtcgc ggggccctg cgcctgacgg    24240 tgaacgaacc cctgtcgacc cgcgaactga ggaaccgaat cttccccact ctctatgcca    24300
tcttccagca gagcagaggg caggatcagg aactgaaagt aaaaaacagg tctctgcgct    24360
ccctcacccg cagctgtctg tatcacaaga gcgaagacca gcttcggcgc acgctggagg    24420
acgctgaggc actcttcagc aaatactgcg cgctcactct taaggactag ctccgcgccc    24480
ttctcgaatt taggcgggaa cgcctacgtc atccagcgc cgccgtcatg agcaaggaca    24540
ttcccacgcc atacatgtgg agctatcagc cgcagatggg actcgcggcg ggcgcctccc    24600
```

```
aagactactc cacccgcatg aactggctca gtgccggccc acacatgatc tcacaggtta    24660
atgatatccg cacccatcga aaccaaatat tggtggagca ggcggcaatt accaccacgc    24720
cccgcaataa tcccaacccc agggagtggc ccgcgtccct ggtgtatcag gaaattcccg    24780
gccccaccac cgtactactt ccgcgtgatt cccaggccga agtccaaatg actaactcag    24840
gggcacagct cgcgggcggc tgtcgtcaca gggtgcggcc tcctcgccag ggtataactc    24900
acctggagat ccgaggcaga ggtattcagc tcaacgacga gtcggtgagc tcctcgctcg    24960
gtctcagacc tgacgggacc ttccagatag ccggagccgg ccgatcttcc ttcacgcccc    25020
gccaggcgta cctgactctg caaagctcgt cctcggcgcc gcgctcgggc ggcatcggga    25080
ctctccagtt cgtgcaggag tttgtgccct cggtctactt caacccettc tcgggctctc    25140 ccggtcgcta cccggaccag ttcatctcga actttgacgc cgcgagggac tcggtggacg    25200
gctacgactg aatgtcgggt ggacccggtg cagagcaact tcgcctgaag cacctcgacc    25260
actgccgccg ccctcagtgc tttgcccgct gtcagaccgg tgagttccag tacttttccc    25320
tgcccgactc gcacccggac ggcccggcgc acggggtgcg cttttttcatc ccgagtcagg    25380 tgcgctctac cctaatcagg gagtttaccg cccgtcccct actggcggag ttggaaaagg    25440
ggccttctat cctaaccatt gcctgcatct gctctaaccc tggattgcac caagatctttt   25500 gctgtcattt gtgtgctgag tataataaag gctgagatca gaatctactc gggctcctgt    25560
cgccatcctg tcaacgccac cgtccaagcc cggcccgatc agcccgaggt gaacctcacc    25620
tgcggtctgc accggcgcct gaggaaatac ctagcttggt actacaacag cactccettt    25680 gtggtttaca acagctttga ccaggacggg gtctcactga gggataacct ctcgaacctg    25740
agctactcca tcaggaagaa cagcacccte gagctacttc ctccttacct gcccgggact    25800
taccagtgtg tcaccggtcc ctgcacccac acccacctgt tgatcgtaaa cgactctctt    25860
ccgagaacag acctcaataa ctcctcttcg cagttcccca gaacaggagg tgagctcagg    25920
aaaccccggg taaagaaggg tggacgagag ttaacacttg tggggtttct ggtgtatgtg    25980
acgctggtgg tggctctttt gattaaggct tttccttcca tgtctgaact ctccctcttc    26040
ttttatgaac aactcgacta gtgctaacgg gaccctaccc aacgaatcgg gattgaatat    26100
cggtaaccag gttgcagttt cacttttgat taccttcata gtcctcttcc tgctagtgct    26160
gtcgcttctg tgcctgcgga tcgggggctg ctgcatccac gtttatatct ggtgctggct    26220
gtttagaagg ttcggagacc atcgcaggta gaataaacat gctgctgctt accctctttg    26280
tcctggcgct ggccgccagc tgccaagcct tttccgaggc tgactttata gagccccagt    26340
gtaatgtgac tttttaaagcc catgcacagc gttgtcatac tataatcaaa tgtgccaccg    26400
aacacgatga ataccttatc cagtataaag ataaatcaca caaagtggca cttgttgaca    26460
tctgaaaacc cgaagaccct ttggaataca atgtgaccgt tttccagggt gacctcttca    26520
aaatttacaa ttcactttc ccatttgacc agatgtgtga ctttgtcatg tacatggaaa    26580
agcagcacaa gctgtggcct ccgactcccc agggctgtgt ggaaaatcca ggctctttct    26640
gcatgatctc tctctgtgta actgtgctgg cactaatact cacgcttttg tatatcagat    26700
ttaaatcaag gcaaagcttc attgatgaaa agaaatgcc ttaatcgctt tcacgcttga    26760
ttgctaacac cgggtttta tccgcagaat gattggaatc accctactaa tcacctccct    26820
ccttgcgatt gcccatgggt tggaacgaat cgaagtccct gtgggggcca atgttaccct    26880 ggtgggcct gtcggcaatg ctacattaat gtgggaaaaa tatactaaaa atcaatgggt    26940
ctcttactgc actaacaaaa atagccacaa gcccagagcc atctgcgatg ggcaaaatct    27000
```

```
aaccttgatt gatgttcaat tgctggatgc gggctactat tatgggcagc tgggtacaat    27060
gattaattac tggagacccc acagagatta catgctccac gtagtaaagg gtcccttag    27120 cagcccaccc actaccacct ctactacccc cactaccacc actactccca ccaccagcac    27180
tgccgcccag cctcctcata gcagaacaac cactttatc aattccaagt cccactcccc    27240
ccacattgcc ggcgggccct ccgcctcaga ctccgaaacc accgagatct gcttctgcaa    27300
atgctctgac gccattgccc aggatttgga agatcacgag gaagatgagc atgacttcgc    27360
agatgcatgc caggcatcag agccagaagc gctgccggtg ccctcaaac agtatgcaga    27420 cccccacacc accccgacc ttcctccacc ttcccagaag ccaagtttcc tgggggaaaa    27480
tgaaactctg cctctctcca tactcgctct gacatctgtt gctatgttga ccgctctgct    27540
ggtgcttcta tgtctatat gctacctgat ctgctgcaga aagaaaaat ctcacggcca    27600 tgctcaccag cccctcatgc acttcccta ccctccagag ctgggcgacc acaaacttta    27660
agtctgcagt aactatctgc ccatcccttg tcagtcgaca gcgatgagcc ccactaatct    27720
aacggcctct ggacttacaa catcgtctct taatgagacc accgctcctc aagacctgta    27780
cgatggtgtc tccgcgctgg ttaaccagtg ggatcacctg gcatatggt ggctcctcat    27840 aggagcagtg accctgtgcc taatcctggt ctggatcatc tgctgcatca aaagcagaag    27900
acccaggcgg cggcccatct acaggccctt tgtcatcaca cctgaagatg atgatgacac    27960
cacttccagg ctgcagaggc taaagcagct actcttctct tttacagcat ggtaaattga    28020
atcatgcctc gcattttcat ctacttgtct ctccttccac ttttttctggg ctcttctaca    28080 ttggccgctg tgtcccacat cgaggtagac tgcctcacgc ccttcacagt ctacctgctt    28140
ttcggctttg tcatctgcac ctttgtctgc agcgttatca ctgtagtgat ctgcttcata    28200
cagtgcatcg actacgtctg cgtgcgggtg gcttacttta gacaccaccc ccagtatcgc    28260
aacagggaca tagcggctct cctaagactt gtttaaaatc atggccaaat taactgtgat    28320
tggtcttctg atcatctgct gcgtcctagc cgcgattggg actcaagctc ctaccaccac    28380
cagcgctccc agaaagagac atgtatcctg cagcttcaag cgtccctgga atataccca    28440 atgctttact gatgaacctg aaatctcttt ggcttggtac ttcagcgtca ccgcccttct    28500
tatcttctgc agtacggtta ttgcccttgc catctaccct tcccttgacc tgggctggaa    28560
tgctgtcaac tctatggaat atcccacctt cccagaacca gacctgccag acctggttgt    28620
tctaaacgcg tttcctcctc ctgctcccgt tcaaaatcag tttcgccctc cgtccccac    28680 gcccactgag gtcagctact ttaatctaac aggcggagat gactgaaaac ctagacctag    28740
aaatggacgg tctctgcagc gagcaacgca cactagagag gcgccggcaa aaagagctcg    28800
agcgtcttaa acaagagctc caagacgcgg tggccataca ccagtgcaaa aaaggtgtct    28860
tctgtctggt aaaacaggcc acgctcacct atgaaaaaac aggtgacacc caccgcctag    28920
gatacaagct gccacacag cgccaaaagt tcgccctcat gataggcgaa caacccatca    28980
ccgtgaccca gcactccgtg gagacagaag gctgcataca tgctccctgt agggcgctg    29040 actgcctcta caccttgatc aaaacccctct gcggtctcag agaccttatc cctttcaatt    29100
aatcataact gtaatcaata aaaaatcact tacttgaaat ctgatagcaa gcctctgtcc    29160
aattttttca gcaacacttc cttcccctcc tcccaactct ggtactctag gcgcctccta    29220 gctgcaaaact tcctccacag tctgaaggga atgtcagatt cctcctcctg tccctccgca    29280
cccacgatct tcatgttgtt gcagatgaaa cgcgcgagat cgtctgacga gaccttcaac    29340
```

```
cccgtgtacc cctacgatac cgagatcgct ccgacttctg tccctttcct tacccctccc   29400
tttgtgtcat ccgcaggaat gcaagaaaat ccagctgggg tgctgtccct gcacttgtca   29460
gagccccttt ccacccacaa tggggccctg actctaaaaa tgggggggcgg cctgaccctg   29520 gacaaggaag ggaatctcac ttcccaaaac atcaccagtg tcgatccccc tctcaaaaaa   29580
agcaagaaca acatcagcct tcagaccgcc gcacccctcg ccgtcagctc cggggcccta   29640 acacttttg ccactccccc cctagcggtc agtggtgaca accttactgt gcagtctcag   29700 gccctctca ctttggaaga ctcaaaacta actctggcca ccaaaggacc cctaactgtg   29760
tccgaaggca aacttgtcct agaaacagag gctcccctgc atgcaagtga cagcagcagc   29820
ctgggcctta gcgttacggc cccacttagc attaacaatg acagcctagg actagatctg   29880
caggcaccca ttgtctctca aaatggaaaa ctggctctaa atgtagcagg cccctagct   29940 gtggccaatg gcattaatgc tttgacagta ggcacaggca aaggtattgg tctaaatgaa   30000
accagcactc acttgcaagc aaagttggtc gcccccctag gctttgatac caatggcaac   30060
attaagctaa gcgttgcagg aggcatgaga ctaaataatg acacacttat actagatgta   30120
aactacccat ttgaagctca aggccaacta agtctaagag tgggccaggg tccgctgtat   30180
gtagattcta gcagccataa cctgaccatt agatgcctta gaggattata cataacatcg   30240
tctaataacc aaaccggtct agaggccaac ataaaactaa caaaaggcct tgtctatgat   30300
ggaaatgcca tagcagtcaa tgttggtcaa ggattgcaat acagcactac tgccacatcg   30360
gaaggtgtgt atcctataca gtctaagata ggtttgggaa tggaatatga taccaacgga   30420
gccatgatga caaaactagg ctctggacta agctttgaca attcaggagc cattgtagtg   30480
ggaaacaaaa atgatgacag gcttactctg tggactacac cagacccatc tcctaactgt   30540
agaatttatt ctgaaaaaga tactaaacta accttggtgc tgactaagtg tggcagccaa   30600
atcctaggca cagtatctgc ccttgctgtc agaggcagcc ttgcgcccat cactaatgca   30660
tccagcatag tccaaatatt tctaagattt gatgaaaatg gactattgat gagcaactca   30720
tcgctagacg gtgattactg gaattacaga aatggggact ccactaatag cacaccatat   30780
acaaatgcag taggctttat gcctaatcta gcagcctatc ctaaaggtca ggctacagct   30840
gcaaaaagca gtattgtaag ccaggtatac atggatggtg acactactaa acctataaca   30900
ctaaaaataa acttcaatgg cattgatgaa acaacagaaa ataccccctgt tagtaaatat   30960 tccatgacat tctcatggag ctggcccacc gcaagctaca taggccacac ttttgcaaca   31020 aactcttta ctttctccta catcgcccaa gaataaagaa agcacagaga tgcttgtttt   31080
gatttcaaaa ttgtgtgctt ttatttattt tcagcttaca gtatttccag tagtcattcg   31140
aataaagctt aatcaaactg catgagaacc cttccacata gcttaaatta gcaccagtgc   31200
aaatggagaa aagcctcgag gtcgttgcgc ggccgggatc ggtgatcacc gatccagaca   31260
tgataagata cattgatgag tttggacaaa ccacaactag aatgcagtga aaaaatgct   31320 ttatttgtga aatttgtgat gctattgctt tatttgtaac cattataagc tgcaataaac   31380
aagttcccgg atcgcgatcc ggcccgaggc tgtagccgac gatggtgcgc caggagagtt   31440
gttgattcat tgtttgcctc cctgctgcgg ttttcaccg aagttcatgc cagtccagcg   31500
tttttgcagc agaaaagccg ccgacttcgg tttgcggtcg cgagtgaaga tccctttctt   31560
gttaccgcca acgcgcaata tgccttgcga ggtcgcaaaa tcggcgaaat tccatacctg   31620
ttcaccgacg acggcgctga cgcgatcaaa gacgcggtga tacatatcca gcatgcaca   31680 ctgatactct tcactccaca tgtcggtgta cattgagtgc agcccggcta acgtatccac   31740
```

```
gccgtattcg gtgatgataa tcggctgatg cagtttctcc tgccaggcca gaagttcttt    31800
ttccagtacc ttctctgccg tttcaaatc gccgctttgg acataccatc cgtaataacg     31860
gttcaggcac agcacatcaa agagatcgct gatggtatcg gtgtgagcgt cgcagaacat    31920
tacattgacg caggtgatcg gacgcgtcgg gtcgagttta cgcgttgctt ccgccagtgg    31980
cgcgaaatat tcccgtgcac cttgcggacg ggtatccggt tcgttggcaa tactccacat    32040
caccacgctt gggtggtttt tgtcacgcgc tatcagctct ttaatcgcct gtaagtgcgc    32100
ttgctgagtt tccccgttga ctgcctcttc gctgtacagt tctttcggct tgttgcccgc    32160
ttcgaaacca atgcctaaag agaggttaaa gccgacagca gcagtttcat caatcaccac    32220
gatgccatgt tcatctgccc agtcgagcat ctcttcagcg taagggtaat gcgaggtacg    32280
gtaggagttg gccccaatcc agtccattaa tgcgtggtcg tgcaccatca gcacgttatc    32340
gaatcctttg ccacgcaagt ccgcatcttc atgacgacca aagccagtaa agtagaacgg    32400
tttgtggtta atcaggaact gttcgcccct cactgccact gaccggatgc cgacgcgaag    32460
cgggtagata tcacactctg tctggctttt ggctgtgacg cacagttcat agagataacc    32520
ttcacccggt tgccagaggt gcggattcac cacttgcaaa gtcccgctag tgccttgtcc    32580
agttgcaacc acctgttgat ccgcatcacg cagttcaacg ctgacatcac cattggccac    32640
cacctgccag tcaacagacg cgtggttaca gtcttgcgcg acatgcgtca ccacggtgat    32700
atcgtccacc caggtgttcg gcgtggtgta gagcattacg ctgcgatgga ttccggcata    32760
gttaaagaaa tcatggaagt aagactgctt tttcttgccg ttttcgtcgg taatcaccat    32820
tcccggcggg atagtctgcc agttcagttc gttgttcaca caaacggtga tacgtacact    32880
tttcccggca ataacatacg gcgtgacatc ggcttcaaat ggcgtatagc cgccctgatg    32940
ctccatcact tcctgattat tgacccacac tttgccgtaa tgagtgaccg catcgaaacg    33000
cagcacgata cgctggcctg cccaaccttt cggtataaag acttcgcgct gataccagac    33060
gttgcccgca taattacgaa tatctgcatc ggcgaactga tcgttaaaac tgcctggcac    33120
agcaattgcc cggctttctt gtaacgcgct ttcccaccaa cgctgatcaa ttccacagtt    33180
ttcgcgatcc agactgaatg cccacaggcc gtcgagtttt ttgatttcac gggttgggt    33240 ttctacagga cggaccatgc gttcgaccct tctcttcttt tttgggccca tgatggcaga    33300
tccgtatagt gagtcgtatt agctggttct ttccgcctca gaagccatag agcccaccgc    33360
atccccagca tgcctgctat tgtcttccca atcctccccc ttgctgtcct gccccacccc    33420
acccccagca atagaatgac acctactcag acaatgcgat gcaatttcct cattttatta    33480
ggaaaggaca gtgggagtgg caccttccag ggtcaaggaa ggcacggggg aggggcaaac    33540
aacagatggc tggcaactag aaggcacagt cgaggctgat cagcgagctc tagatgcatg    33600
ctcgagcggc cgcacgtcgt accggcaatt gccgcggcaa ttgccgacgc cgcgtaacta    33660
taacggtcct aaggtagcga gagggccaag tgccgaacga gtatatatag gaataaaaaa    33720
tgacgtaaat gtgtaaaggt cagaaaacgc ccagaaaaat acacagacca acgcccgaaa    33780
cgaaaacccg cgaaaaaata cccagaactt cctcaacaac cgccacttcc ggtttctcac    33840
ggtacgtcac ttccgcaaga aaagcaaaac tacatttccc acatgtgtaa aaacgaaacc    33900
ccgccccttg taactgccca caacttacat catcaaaaca taaactccta cgtcacccgc    33960
cccgcctctc cccgcccacc tcattatcat attggccaca atccaaaata aggtatatta    34020
ttgatgatg                                                            34029
```

AFFENADENOVIRUS (GORILLA) OR ADENOVIRAL VECTORS AND METHODS OF USE

CROSS-REFERENCE TO RELATED APPLICATIONS

This patent application is a continuation of U.S. patent application Ser. No. 15/650,289, filed Jul. 14, 2017, now U.S. Pat. No. 10,260,074, which is a continuation of U.S. patent application Ser. No. 14/992,152, filed Jan. 11, 2016, now U.S. Pat. No. 9,725,738, which is a divisional of U.S. patent application Ser. No. 14/349,421, filed Apr. 3, 2014, now U.S. Pat. No. 9,233,153, which is a U.S. National Phase of International Patent Application No. PCT/US2012/058956, filed Oct. 5, 2012, which claims the benefit of U.S. Provisional Patent Application No. 61/543,638, filed. Oct. 5, 2011, all of which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 285,442 Byte ASCII (Text) file named "742015_ST25.txt," created Feb. 22, 2019.

BACKGROUND OF THE INVENTION

In vivo delivery of proteins in biologically relevant forms and amounts has been an obstacle to drug and vaccine development for decades. One solution that has proven to be a successful alternative to traditional protein delivery approaches is the delivery of exogenous nucleic acid sequences for production of proteins in vivo. Gene transfer vectors ideally enter a wide variety of cell types, have the capacity to accept large nucleic acid sequences, are safe, and can be produced in quantities required for treating patients. Viral vectors are gene transfer vectors with these advantageous properties (see, e.g., Thomas et al., *Nature Review Genetics*, 4: 346-358 (2003)). Furthermore, while many viral vectors are engineered to infect a broad range of cell types, viral vectors also can be modified to target specific cell types, which can enhance the therapeutic efficacy of the vector (see, e.g., Kay et al., *Nature Medicine*, 7(1): 33-40 (2001).

Viral vectors that have been used with some success to deliver exogenous proteins to mammalian cells for therapeutic purposes include, for example, Retrovirus (see, e.g., Cavazzana-Calvo et al., *Science*, 288 (5466): 669-672 (2000)), Lentivirus (see, e.g., Cartier et al., *Science*, 326: 818-823 (2009)), Adeno-associated virus (AAV) (see, e.g., Mease et al., *Journal of Rheumatology*, 27(4): 692-703 (2010)), Herpes Simplex Virus (HSV) (see, e.g., Goins et al., *Gene Ther.*, 16(4): 558-569 (2009)), Vaccinia Virus (see, e.g., Mayrhofer et al., *J. Virol.*, 83(10): 5192-5203 (2009)), and Adenovirus (see, e.g., Lasaro and Ertl, *Molecular Therapy*, 17(8): 1333-1339 (2009)).

Despite their advantageous properties, widespread use of viral gene transfer vectors is hindered by several factors. In this respect, certain cells are not readily amenable to gene delivery by currently available viral vectors. For example, lymphocytes are impaired in the uptake of adenoviruses (Silver et al., *Virology*, 165: 377-387 (1988), and Horvath et al., *J. Virology*, 62(1): 341-345 (1988)). In addition, viral vectors that integrate into the host cell's genome (e.g., retroviral vectors) have the potential to cause insertion mutations in oncogenes (see, e.g., Cavazzana-Calvo et al., supra, and Hacein-Bey-Abina et al., *N. Engl. J. Med.*, 348: 255-256 (2003)).

The use of viral vectors for gene transfer also is impeded by the immunogenicity of viral vectors. A majority of the U.S. population has been exposed to wild-type forms of many of the viruses currently under development as gene transfer vectors (e.g., adenovirus). As a result, much of the U.S. population has developed pre-existing immunity to certain virus-based gene transfer vectors. Such vectors are quickly cleared from the bloodstream, thereby reducing the effectiveness of the vector in delivering biologically relevant amounts of a gene product. Moreover, the immunogenicity of certain viral vectors prevents efficient repeat dosing, which can be advantageous for "boosting" the immune system against pathogens when viral vectors are used in vaccine applications, thereby resulting in only a small fraction of a dose of the viral vector delivering its payload to host cells.

Thus, there remains a need for improved viral vectors that can be used to efficiently deliver genes to mammalian cells in vivo. The invention provides such viral vectors.

BRIEF SUMMARY OF THE INVENTION

The invention provides an adenovirus or adenoviral vector. The adenovirus or adenoviral vector comprises one or more of the nucleic acid sequences selected from the group consisting of (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5.

The invention provides an adenovirus or adenoviral vector comprising one or more of the nucleic acid sequences selected from the group consisting of (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10.

The invention provides an adenovirus or adenoviral vector comprising one or more of the nucleic acid sequences selected from the group consisting of (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

The invention provides an adenovirus or adenoviral vector comprising one or more of the amino acid sequences selected from the group consisting of (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15.

The invention provides an adenovirus or adenoviral vector comprising one or more of the nucleic acid sequences selected from the group consisting of (a) a nucleic acid sequence encoding the amino acid sequence of SEQ ID NO: 11, (b) a nucleic acid sequence encoding an amino acid sequence that is at least 99% identical to SEQ ID NO: 12, (c) a nucleic acid sequence encoding an amino acid sequence that is at least 82% identical to SEQ ID NO: 13, (d) a nucleic acid sequence encoding an amino acid sequence that is at least 80% identical to SEQ ID NO: 14, and (e) a nucleic acid sequence encoding an amino acid sequence that is at least 83% identical to SEQ ID NO: 15.

The invention provides an adenovirus or adenoviral vector comprising one or more of the amino acid sequences selected from the group consisting of (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20.

The invention provides an adenovirus or adenoviral vector comprising one or more of the nucleic acid sequences selected from the group consisting of (a) a nucleic acid sequence encoding the amino acid sequence of SEQ ID NO: 16, (b) a nucleic acid sequence encoding an amino acid sequence that is at least 99.78% identical to SEQ ID NO: 17, (c) a nucleic acid sequence encoding an amino acid sequence that is at least 97.8% identical to SEQ ID NO: 18, (d) a nucleic acid sequence encoding an amino acid that is at least 93.4% identical to SEQ ID NO: 19, and (e) a nucleic acid sequence encoding an amino acid sequence that is at least 98.2% identical to SEQ ID NO: 20.

The invention provides an adenovirus or adenoviral vector comprising one or more of the amino acid sequences selected from the group consisting of (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The invention provides an adenovirus or adenoviral vector comprising one or more of the nucleic acid sequences selected from the group consisting of (a) a nucleic acid sequence encoding an amino acid sequence comprising at least 89 contiguous amino acid residues of SEQ ID NO: 16, (b) a nucleic acid sequence encoding an amino acid sequence comprising at least 428 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 370 contiguous amino acid residues of SEQ ID NO: 19, and (e) a nucleic acid sequence encoding an amino acid sequence comprising at least 192 contiguous amino acid residues of SEQ ID NO: 20.

DETAILED DESCRIPTION OF THE INVENTION

Adenoviruses are generally associated with benign pathologies in humans, and the genomes of adenoviruses isolated from a variety of species, including humans, have been extensively studied. Adenovirus is a medium-sized (90-100 nm), nonenveloped icosohedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology*, 28: 782-83 (1966)). The hexon comprises three identical proteins, namely polypeptide II (Roberts et al., *Science*, 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell*, 67: 145-54 (1991), and Stewart et al., *EMBO J.*, 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e. "gene therapy"), or for use as antigen delivery systems for vaccine applications. For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.*, 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

The invention is predicated, at least in part, on the discovery and isolation of an adenovirus that has not previously been identified or isolated. The adenovirus described herein was isolated from a gorilla. There are four widely recognized gorilla subspecies within the two species of Eastern Gorilla (*Gorilla beringei*) and Western Gorilla (*Gorilla gorilla*). The Western Gorilla species includes the subspecies Western Lowland Gorilla (*Gorilla gorilla gorilla*) and Cross River Gorilla (*Gorilla gorilla diehli*). The Eastern Gorilla species includes the subspecies Mountain Gorilla (*Gorilla beringei beringei*) and Eastern Lowland Gorilla (*Gorilla beringei graueri*) (see, e.g., Wilson and Reeder, eds., *Mammalian Species of the World*, 3$^{rd}$ ed., Johns Hopkins University Press, Baltimore, Md. (2005)). The adenovirus of the invention was isolated from Mountain Gorilla (*Gorilla beringei beringei*).

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, or SEQ ID NO: 25, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, 5$^{th}$ ed., Knipe et al. (eds.), Lippincott Williams & Wilkins, Philadelphia, Pa. (2006)).

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gen. Virol.,* 44: 783-800 (1979); Horwitz M. S., "Adenoviridae and their replication" in *Virology,* 2nd ed., B. N. Fields et al. (eds.), Raven Press, Ltd., New York, pp. 1679-1721 (1990), Ghosh-Choudhury et al., *EMBO J.,* 6: 1733-1739 (1987), and van Oostrum et al, *J. Virol.,* 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.,* 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.,* 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7 and SEQ ID NO: 2. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.,* 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.,* 215: 567-88 (1990), Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions key to the life cycle of adenovirus. Nucleic acid sequences that encode all or a portion of an adenovirus fiber protein include, for example, SEQ ID NO: 10 and SEQ ID NO: 5. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene,* 69: 153-157 (1988)). The RGD tripeptide mediates binding to αv integrins and adenoviruses that have point mutations in the RGD sequence of the penton base are restricted in their ability to infect cells (Bai et al., *J. Virol.,* 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, Algorithms on Strings, Trees and Sequences, Cambridge University Press, Cambridge UK (1997)).

In one embodiment, the adenovirus or adenoviral vector comprises one or more of the following nucleic acid sequences: (a) the nucleic acid sequence of SEQ ID NO: 1, (b) a nucleic acid sequence that is at least 98.5% identical (e.g., at least 98.73%, at least 98.96%, at least 99.18%, at least 99.41%, at least 99.64%, at least 99.87%, or 100% identical) to SEQ ID NO: 2, (c) a nucleic acid sequence that is at least 90% identical (e.g., at least 92.94%, at least 95.88%, 98.82%, or 100% identical) to SEQ ID NO: 3, (d) a nucleic acid sequence that is at least 80% identical (e.g., at least 80.83%, at least 83.06%, at least 85.28%, at least 87.50%, at least 89.72%, at least 91.94%, at least 94.17%, at least 96.39%, at least 98.61%, or 100% identical) to SEQ ID NO: 4, and (e) a nucleic acid sequence that is at least 89% identical (e.g., at least 92.33%, at least 95.67%, at least 99%, or 100% identical) to SEQ ID NO: 5.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise the nucleic acid sequence of SEQ ID NO: 1. The adenovirus or adenoviral vector can comprise a nucleic acid sequence that is at least 98.5% identical to SEQ ID NO: 2 and a nucleic acid sequence that is at least 90% identical to SEQ ID NO: 3. The adenovirus or adenoviral vector can comprise the nucleic acid sequence of SEQ ID NO: 1, a nucleic acid sequence that is at least 90% identical to SEQ ID NO: 3, and a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, or (e) the nucleic acid sequence of SEQ ID NO: 5. The adenovirus or adenoviral vector can comprise (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, and (e) the nucleic acid sequence of SEQ ID NO: 5.

In another embodiment, the adenovirus or adenoviral vector comprises one or more of the following nucleic acid sequences: (a) a nucleic acid sequence that is at least 98.6% identical (e.g., at least 98.85%, at least 99.10%, at least 99.35%, at least 99.60%, or 100% identical) to SEQ ID NO: 6, (b) a nucleic acid sequence that is at least 99.06% identical (e.g., at least 99.09%, at least 99.12%, at least 99.15%, at least 99.19%, at least 99.22%, at least 99.25%, at least 99.28%, at least 99.31%, at least 99.34%, at least 99.38%, at least 99.41%, at least 99.44%, at least 99.47%, at least 99.50%, at least 99.53%, at least 99.57%, at least 99.60%, at least 99.63%, at least 99.66%, at least 99.69%, at least 99.72%, at least 99.75%, at least 99.79%, at least 99.82%, at least 99.85%, at least 99.88%, at least 99.91%, at least 99.94%, at least 99.98%, or 100% identical) to SEQ ID NO: 7, (c) a nucleic acid sequence that is at least 97.13% identical (e.g., at least 97.18%, at least 97.23%, at least 97.28%, at least 97.33%, at least 97.38%, at least 97.43%, at least 97.48%, at least 97.5% at least 97.54%, at least 97.59%, at least 97.6%, at least 97.64%, at least 97.69%, at least 97.7%, at least 97.74%, at least 97.79%, at least 97.8%, at least 97.84%, at least 97.89%, at least 97.9%, at least 97.94%, at least 97.99%, at least 98%, at least 98.04%, at least 98.09%, at least 98.1%, at least 98.14%, at least 98.19%, at least 98.2%, at least 98.24%, at least 98.30%, at least 98.35%, at least 98.40%, at least 98.45%, at least 98.50%, at least 98.55%, at least 98.60%, at least 98.70%, at least 98.75%, at least 98.80%, at least 98.85%, at least 98.90%, at least 98.95%, at least 99.00%, at least 99.06%, at least 99.11%, at least 99.16%, at least 99.2%, at least 99.21%, at least 99.26%, at least 99.3%, at least 99.31%, at least 99.36%, at least 99.4%, at least 99.41%, at least 99.46%, at least 99.5%, at least 99.51%, at least 99.56%, at least 99.6%, at least 99.61%, at least 99.66%, at least 99.7%, at least 99.71%, at least 99.76%, at least 99.8%, at least 99.81%, at least 99.87%, at least 99.9%, at least 99.92%, at least 99.95%, at least 99.97%, or 100% identical) to SEQ ID NO: 8, (d) a nucleic acid sequence that is at least 90.7% identical (e.g., at least 90.73%, at least 90.77%, at least 90.80%, at least 90.84%, at least 90.87%, at least 90.91%, at least 90.94%, at least 90.98%, at least 91.01%, at least 91.05%, at least 91.08%, at least 91.12%, at least 91.15%, at least 91.19%, at least 91.22%, at least 91.26%, at least 91.29%, at least 91.33%, at least 91.36%, at least 91.40%, at least 91.43%, at least 91.46%, at least 91.50%, at least 91.53%, at least 91.57%, at least 91.60%, at least 91.64%, at least 91.67%, at least 91.71%, at least 91.74%, at least 91.78%, at least 91.81%, at least 91.85%, at least 91.88%, at least 91.92%, at least 91.95%, at least 91.99%, at least 92.02%, at least 92.06%, at least 92.09%, at least 92.13%, at least 92.16%, at least 92.19%, at least 92.23%, at least 92.26%, at least 92.30%, at least 92.33%, at least 92.37%, at least 92.40%, at least 92.44%, at least 92.47%, at least 92.51%, at least 92.54%, at least 92.58%, at least 92.61%, at least 92.65%, at least 92.68%, at least 92.72%, at least 92.75%, at least 92.79%, at least 92.82%, at least 92.86%, at least 92.89%, at least 92.92%, at least 92.96%, at least 92.99%, at least 93.03%, at least 93.06%, at least 93.10%, at least 93.13%, at least 93.17%, at least 93.20%, at least 93.24%, at least 93.27%, at least 93.31%, at least 93.34%, at least 93.38%, at least 93.41%, at least 93.45%, at least 93.48%, at least 93.52%, at least 93.55%, at least 93.58%, at least 93.62%, at least 93.65%, at least 93.69%, at least 93.72%, at least 93.76%, at least 93.79%, at least 93.83%, at least 93.86%, at least 93.90%, at least 93.93%, at least 93.97%, at least 94.00%, at least 94.04%, at least 94.07%, at least 94.11%, at least 94.14%, at least 94.18%, at least 94.21%, at least 94.25%, at least 94.28%, at least 94.31%, at least 94.35%, at least 94.38%, at least 94.42%, at least 94.45%, at least 94.49%, at least 94.52%, at least 94.56%, at least 94.59%, at least 94.63%, at least 94.66%, at least 94.70%, at least 94.73%, at least 94.77%, at least 94.80%, at least 94.84%, at least 94.87%, at least 94.91%, at least 94.94%, at least 94.98%, at least 95.01%, at least 95.04%, at least 95.08%, at least 95.11%, at least 95.15%, at least 95.18%, at least 95.22%, at least 95.25%, at least 95.29%, at least 95.32%, at least 95.36%, at least 95.39%, at least 95.43%, at least 95.46%, at least 95.50%, at least 95.53%, at least 95.57%, at least 95.60%, at least 95.64%, at least 95.67%, at least 95.71%, at least 95.74%, at least 95.77%, at least 95.81%, at least 95.84%, at least 95.88%, at least 95.91%, at least 95.95%, at least 95.98%, at least 96.02%, at least 96.05%, at least 96.09%, at least 96.12%, at least 96.16%, at least 96.19%, at least 96.23%, at least 96.26%, at least 96.30%, at least 96.33%, at least 96.37%, at least 96.40%, at least 96.44%, at least 96.47%, at least 96.50%, at least 96.54%, at least 96.57%, at least 96.61%, at least 96.64%, at least 96.68%, at least 96.71%, at least 96.75%, at least 96.78%, at least 96.82%, at least 96.85%, at least 96.89%, at least 96.92%, at least 96.96%, at least 96.99%, at least 97.03%, at least 97.06%, at least 97.10%, at least 97.13%, at least 97.17%, at least 97.20%, at least 97.23%, at least 97.27%, at least 97.30%, at least 97.34%, at least 97.37%, at least 97.41%, at least 97.44%, at least 97.48%, at least 97.51%, at least 97.55%, at least 97.58%, at least 97.62%, at least 97.65%, at least 97.69%, at least 97.72%, at least 97.76%, at least 97.79%, at least 97.83%, at least 97.86%, at least 97.89%, at least 97.93%, at least 97.96%, at least 98.00%, at least 98.03%, at least 98.07%, at least 98.10%, at least 98.14%, at least 98.17%, at least 98.21%, at least 98.24%, at least 98.28%, at least 98.31%, at least 98.35%, at least 98.38%, at least 98.42%, at least 98.45%, at least 98.49%, at least 98.52%, at least 98.56%, at least 98.59%, at least 98.62%, at least 98.66%, at least 98.69%, at least 98.73%, at least 98.76%, at least 98.80%, at least 98.83%, at least 98.87%, at least 98.90%, at least 98.94%, at least 98.97%, at least 99.01%, at least 99.04%, at least 99.08%, at least 99.11%, at least 99.15%, at least 99.18%, at least 99.22%, at least 99.25%, at least 99.29%, at least 99.32%, at least 99.35%, at least 99.39%, at least 99.42%, at least 99.46%, at least 99.49%, at least 99.53%, at least 99.56%, at least 99.60%, at least 99.63%, at least 99.67%, at least 99.70%, at least 99.74%, at least 99.77%, at least 99.81%, at least 99.84%, at least 99.88%, at least 99.91%, at least 99.95%, at least 99.98%, or 100% identical) to SEQ ID NO: 9, and (e) a nucleic acid sequence that is at least 96.6% identical (e.g., at least 96.66%, at least 96.71%, at least 96.77%, at least 96.83%, at least 96.89%, at least 96.94%, at least 97.00%, at least 97.06%, at least 97.11%, at least 97.17%, at least 97.23%, at least 97.29%, at least 97.34%, at least 97.40%, at least 97.46%, at least 97.51%, at least 97.57%, at least 97.63%, at least 97.69%, at least 97.74%, at least 97.80%, at least 97.86%, at least 97.92%, at least 97.97%, at least 98.03%, at least 98.09%, at least 98.14%, at least 98.20%, at least 98.26%, at least 98.32%, at least 98.37%, at least 98.43%, at least 98.49%, at least 98.54%, at least 98.60%, at least 98.66%, at least 98.72%, at least 98.77%, at least 98.83%, at least 98.89%, at least 98.94%, at least 99.00%, at least 99.06%, at least 99.12%, at least 99.17%, at least 99.23%, at least 99.29%, at least 99.34%, at least 99.40%, at least 99.46%, at least 99.52%, at least 99.57%, at least 99.63%, at least 99.69%, at least 99.74%, at least at least 99.80%, at least 99.86%, at least 99.92%, at least 99.97%, or 100% identical) to SEQ ID NO: 10.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 98.6% identical to SEQ ID NO: 6. The adenovirus or adenoviral vector can comprise a nucleic acid sequence that is at least 99.06% identical to SEQ ID NO: 7 and a nucleic acid sequence that is at least 97.13% identical to SEQ ID NO: 8. The adenovirus or adenoviral vector can comprise a nucleic acid sequence that is at least 97.13% identical to SEQ ID NO: 8, a nucleic acid sequence that is at least 90.7% identical to SEQ ID NO: 9, and a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, or (e) the nucleic acid sequence of SEQ ID NO: 10. The adenovirus or adenoviral vector can comprise (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, and (e) the nucleic acid sequence of SEQ ID NO: 10.

In another embodiment, the adenovirus or adenoviral vector comprises one or more of the following nucleic acid sequences: (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, or (e) a nucleic acid sequence comprising at least 188 contiguous nucleotides of SEQ ID NO: 10.

The adenovirus or adenoviral vector can comprise a nucleic acid sequence comprising at least 121 (e.g., 125 or more, 130 or more, 150 or more, 200 or more, 250 or more, or 300 or more) contiguous nucleotides of SEQ ID NO: 6, but no more than 399 (e.g., 398 or less, 350 or less, or 275 or less) contiguous nucleotides of SEQ ID NO: 6. Preferably, the adenovirus or adenoviral vector comprises a nucleic acid sequence comprising 121 to 300 contiguous nucleotides (e.g., 125, 150, 175, 200, 250, or 275 contiguous nucleotides), 121 to 200 contiguous nucleotides (e.g., 130, 140, 145, 160, 165, 170, 180, 185, 190, 195, or 199 contiguous nucleotides), or 121 to 150 contiguous nucleotides (e.g., 122, 123, 124, 125, 126, 127, 128, 129, 130, 131, 132, 133, 134, 135, 136, 137, 138, 139, 140, 141, 142, 143, 144, 145, 146, 147, 148, or 149 contiguous nucleotides) of SEQ ID NO: 6, or a range defined by any two of the foregoing values.

The adenovirus or adenoviral vector can comprise a nucleic acid sequence comprising at least 462 (e.g., 470 or more, 500 or more, 600 or more, 700 or more, 800 or more, 900 or more, or 1,000 or more) contiguous nucleotides of SEQ ID NO: 7, but no more than 3168 (e.g., 3,100 or less, 3,000 or less, 2,500 or less, 2,000 or less, or 1,500 or less) contiguous nucleotides of SEQ ID NO: 7. Preferably, the adenovirus or adenoviral vector comprises a nucleic acid sequence comprising 462 to 2,000 contiguous nucleotides (e.g., 475, 500, 700, 1,000, 1,200, 1,500, or 1,700 contiguous nucleotides), 462 to 1,000 contiguous nucleotides (e.g., 490, 525, 575, 600, 650, 675, 725, 750, 800, 850, 900, or 950 contiguous nucleotides), or 462 to 800 contiguous nucleotides (e.g., 480, 485, 490, 495, 499, 510, 515, 530, 540, 550, 560, 565, 570, 580, 585, 590, 595, 615, 625, 630, 640, 660, 665, 670, 680, 685, 690, 695, 705, 715, 730, 740, 755, 760, 765, 770, 775, 780, 785, 790, 795, or 799 contiguous nucleotides) of SEQ ID NO: 7, or a range defined by any two of the foregoing values.

The adenovirus or adenoviral vector can comprise a nucleic acid sequence comprising at least 234 (e.g., 235 or more, 250 or more, 300 or more, 350 or more, 400 or more, 450 or more, or 500 or more) contiguous nucleotides of SEQ ID NO: 8, but no more than 1,974 (e.g., 1,900 or less, 1,800 or less, 1,500 or less, 1,200 or less, 1,000 or less, 850 or less, 800 or less, 750 or less, or 700 or less) contiguous nucleotides of SEQ ID NO: 8. Preferably, the adenovirus or adenoviral vector comprises a nucleic acid sequence comprising 234 to 1,500 contiguous nucleotides (e.g., 290, 300, 400, 500, 600, 700, 800, 900, 1,000, or 1,200 contiguous nucleotides), 234 to 1,000 contiguous nucleotides (e.g., 295, 350, 450, 550, 650, 750, 850, or 950 contiguous nucleotides), or 234 to 500 contiguous nucleotides (e.g., 290, 305, 310, 315, 325, 340, 345, 360, 365, 370, 375, 380, 385, 390, 395, 405, 425, 430, 440, 455, 460, 465, 470, 475, 480, 485, 490, 495, or 499 contiguous nucleotides) of SEQ ID NO: 8, or a range defined by any two of the foregoing values.

The adenovirus or adenoviral vector can comprise a nucleic acid sequence comprising at least 606 (e.g., 610 or more, 650 or more, 700 or more, 800 or more, or 1,000 or more) contiguous nucleotides of SEQ ID NO: 9, but no more than 2877 (2,800 or less, 2,500 or less, 2,000 or less, 1,800 or less, or 1,500 or less) contiguous nucleotides of SEQ ID NO: 9. Preferably, the adenovirus or adenoviral vector comprises a nucleic acid sequence comprising 606 to 2,000 contiguous nucleotides (e.g., 615, 650, 700, 800, 900, 1,000, 1,200, 1,500, 1,700, or 1,900 contiguous nucleotides), 606 to 1,000 contiguous nucleotides (e.g., 630, 645, 665, 675, 725, 750, 775, 825, 850, 875, 925, 950, or 975 contiguous nucleotides), or 606 to 800 contiguous nucleotides (e.g., 620, 635, 640, 655, 660, 670, 680, 685, 690, 695, 699, 705, 715, 730, 735, 740, 745, 755, 760, 765, 770, 785, 790, 795, or 799 contiguous nucleotides) of SEQ ID NO: 9, or a range defined by any two of the foregoing values.

The adenovirus or adenoviral vector can comprise a nucleic acid sequence comprising at least 188 (e.g., 189 or more, 200 or more, 300 or more, 500 or more, 700 or more, or 900 or more) contiguous nucleotides of SEQ ID NO: 10, but no more than 1,749 (1,700 or less, 1,500 or less, 1,200 or less, or 1,000 or less) contiguous nucleotides of SEQ ID NO: 10. Preferably, the adenovirus or adenoviral vector comprises a nucleic acid sequence comprising 188 to 1,500 contiguous nucleotides (e.g., 200, 400, 600, 800, 1,000, 1,200, or 1,400 contiguous nucleotides), 188 to 1,000 contiguous nucleotides (e.g., 195, 250, 350, 450, 550, 650, 750, 850, or 950 contiguous nucleotides), or 188 to 500 contiguous nucleotides (e.g., 190, 225, 230, 240, 255, 260, 265, 270, 275, 315, 325, 330, 340, 355, 360, 365, 370, 375, 380, 385, 390, 395, 415, 425, 430, 440, 455, 460, 465, 470, 475, 480, 485, 490, 495, or 499 contiguous nucleotides) of SEQ ID NO: 10, or a range defined by any two of the foregoing values.

The adenovirus or adenoviral vector can comprise one, two, three, four, or all five of the aforementioned sequences alone, or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence comprising at least 121 contiguous nucleotides of SEQ ID NO: 6. The adenovirus or adenoviral vector can comprise a nucleic acid sequence comprising at least 234 contiguous nucleotides of SEQ ID NO: 8, and a nucleic acid sequence comprising at least 188 contiguous nucleotides of SEQ ID NO: 10. The adenovirus or adenoviral vector can comprise a nucleic acid sequence comprising at least 462 contiguous nucleotides of SEQ ID NO: 7, a nucleic acid sequence comprising at least 606 contiguous nucleotides of SEQ ID NO: 9, and a nucleic acid sequence comprising at least 188 contiguous nucleotides of SEQ ID NO: 10. The adenovirus or adenoviral vector can comprise a nucleic acid sequence comprising at least 121 contiguous nucleotides of SEQ ID NO: 6, a nucleic acid sequence comprising at least 462 contiguous nucleotides of SEQ ID NO: 7, a nucleic acid sequence comprising at least 234 contiguous nucleotides of SEQ ID NO: 8, and a nucleic acid sequence comprising at least 606 contiguous nucleotides of SEQ ID NO: 9. The adenovirus or adenoviral vector can comprise (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

In another embodiment, the adenovirus or adenoviral vector comprises one or more of the following amino acid sequences: (a) the amino acid sequence of SEQ ID NO: 11, (b) an amino acid sequence that is at least 82% identical (e.g., at least 88.67%, at least 95.33%, or 100% identical) to SEQ ID NO: 13, (c) an amino acid sequence that is at least 80% identical (e.g., at least 81%, at least 82%, at least 83%, at least 83.06%, at least 84%, at least 85%, at least 85.28%, at least 86%, at least 87%, at least 87.5%, at least 88%, at least 88.67%, at least 89%, at least 89.72% at least 90%, at least 91%, at least 91.94%, at least 92%, at least 92.33%, at least 93%, at least 94%, at least 94.17%, at least 95%, at least 95.33%, at least 95.67%, at least 96%, at least 96.39%, at least 97%, at least 98%, at least 98.61%, at least 99%, at least 99.5%, or 100% identical) to SEQ ID NO: 14, and (d) an amino acid sequence that is at least 83% identical (e.g., at least 89.67%, at least 96.33%, or 100% identical) to SEQ ID NO: 15.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 11. The adenovirus or adenoviral vector can comprise an amino acid sequence of SEQ ID NO: 11, and an amino acid sequence that is at least 82% identical to SEQ ID NO: 13. The adenovirus or adenoviral vector can comprise the amino acid sequence of SEQ ID NO: 11, an amino acid sequence that is at least 82% identical to SEQ ID NO: 13, and an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, or (d) the amino acid sequence of SEQ ID NO: 15. The adenovirus or adenoviral vector can comprise (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, and (d) the amino acid sequence of SEQ ID NO: 15.

In another embodiment, the adenovirus or adenoviral vector comprises one or more of the following amino acid sequences: (a) the amino acid sequence of SEQ ID NO: 16, (b) an amino acid sequence that is at least 97.8% identical (e.g., at least 97.95%, at least 98.10%, at least 98.26%, at least 98.41%, at least 98.56%, at least 98.71%, at least 98.86%, at least 99.02%, at least 99.17%, at least 99.32%, at least 99.47%, at least 99.62%, at least 99.78%, or 100% identical) to SEQ ID NO: 18, (c) an amino acid sequence that is at least 93.4% identical (e.g., at least 93.50%, at least 93.61%, at least 93.71%, at least 93.82%, at least 93.92%, at least 94.03%, at least 94.13%, at least 94.23%, at least 94.34%, at least 94.44%, at least 94.55%, at least 94.65%, at least 94.76%, at least 94.86%, at least 94.96%, at least 95.07%, at least 95.17%, at least 95.28%, at least 95.38%, at least 95.49%, at least 95.59%, at least 95.69%, at least 95.80%, at least 95.90%, at least 96.01%, at least 96.11%, at least 96.22%, at least 96.32%, at least 96.42%, at least 96.53%, at least 96.63%, at least 96.74%, at least 96.84%, at least 96.95%, at least 97.05%, at least 97.15%, at least 97.26%, at least 97.36%, at least 97.47%, at least 97.57%, at least 97.68%, at least 97.78%, at least 97.88%, at least 97.99%, at least 98.09%, at least 98.20%, at least 98.30%, at least 98.41%, at least 98.51%, at least 98.61%, at least 98.72%, at least 98.82%, at least 98.93%, at least 99.03%, at least 99.14%, at least 99.24%, at least 99.34%, at least 99.45%, at least 99.55%, at least 99.66%, at least 99.76%, at least 99.87%, at least 99.97%, or 100% identical) to SEQ ID NO: 19, and (d) an amino acid sequence that is at least 98.2% identical (e.g., at least 98.37%, at least 98.54%, at least 98.71%, at least 98.89%, at least 99.06%, at least 99.23%, at least 99.40%, at least 99.57%, at least 99.74%, at least 99.92%, or 100% identical) to SEQ ID NO: 20.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 16. The adenovirus or adenoviral vector can comprise the amino acid sequence of SEQ ID NO: 16, and an amino acid sequence that is at least 93.4% identical to SEQ ID NO: 19. The adenovirus or adenoviral vector can comprise the amino acid sequence of SEQ ID NO: 16, an amino acid sequence that is at least 93.4% identical to SEQ ID NO: 19, and an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, or (d) the amino acid sequence of SEQ ID NO: 20. The adenovirus or adenoviral vector can comprise (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, and (d) the amino acid sequence of SEQ ID NO: 20.

In another embodiment, the adenovirus or adenoviral vector comprises one or more of the following amino acid sequences: (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The adenovirus or adenoviral vector can comprise an amino acid sequence comprising at least 89 (e.g., 90 or more, 100 or more, or 110 or more) contiguous amino acid residues of SEQ ID NO: 16, but no more than 133 (e.g., 130 or less, 125 or less, 120 or less, or 115 or less) contiguous amino acid residues of SEQ ID NO: 16. Preferably, the adenovirus or adenoviral vector comprises an amino acid sequence comprising 89 to 130 contiguous amino acid residues (e.g., 90, 100, 110, 115, 120, or 125 contiguous amino acid residues) of SEQ ID NO: 16, 89 to 115 contiguous amino acid residues of SEQ ID NO: 16 (e.g., 95, 110, or 112 contiguous amino acid residues), or 89 to 100 contiguous amino acid residues (e.g., 89, 90, 91, 92, 93, 94, 95, 96, 97, 98, or 99 contiguous amino acid residues) of SEQ ID NO: 16, or a range defined by any two of the foregoing values.

The adenovirus or adenoviral vector can comprise an amino acid sequence comprising at least 247 (e.g., 250 or more, 275 or more, 300 or more, or 400 or more) contiguous amino acid residues of SEQ ID NO: 18, but no more than 658 (e.g., 650 or less, 550 or less, or 450 or less) contiguous amino acid residues of SEQ ID NO: 18. Preferably, the adenovirus or adenoviral vector comprises an acid sequence comprising 247 to 600 contiguous amino acid residues (e.g., 255, 275, 300, 400, or 500 contiguous amino acid residues) of SEQ ID NO: 18, 247 to 500 contiguous amino acid residues of SEQ ID NO: 18 (e.g., 325, 350, 375, 425, 450, or 475 contiguous amino acid residues), or 247 to 400 contiguous amino acid residues (e.g., 265, 280, 285, 290, 295, 360, 365, 380, 385, 390, 395, or 399 contiguous amino acid residues) of SEQ ID NO: 18, or a range defined by any two of the foregoing values.

The adenovirus or adenoviral vector can comprise an amino acid sequence comprising at least 370 (e.g., 380 or more, 400 or more, or 500 or more) contiguous amino acid residues of SEQ ID NO: 19, but no more than 959 (e.g., 950 or less, 900 or less, 800 or less, 700 or less, or 600 or less) contiguous amino acid residues of SEQ ID NO: 19. Preferably, the adenovirus or adenoviral vector comprises an acid sequence comprising 370 to 800 contiguous amino acid residues (e.g., 390, 400, 500, 600, or 700 contiguous amino acid residues) of SEQ ID NO: 19, 370 to 600 contiguous amino acid residues (e.g., 375, 385, 395, 425, 445, 450, 465, 475, 525, 545, 550, 565 or 575 contiguous amino acid residues) of SEQ ID NO: 19, or 370 to 500 contiguous amino acid residues (e.g., 385, 389, 395, 399, 415, 435, 440, 460, 470, 480, or 499 contiguous amino acid residues) of SEQ ID NO: 19, or a range defined by any two of the foregoing values.

The adenovirus or adenoviral vector can comprise an amino acid sequence comprising at least 192 (e.g., 193 or more, 200 or more, or 300 or more) contiguous amino acid residues of SEQ ID NO: 20, but no more than 583 (e.g., 580 or less, 550 or less, 500 or less, 450 or less, or 400 or less) contiguous amino acid residues of SEQ ID NO: 20. Preferably, the adenovirus or adenoviral vector comprises an acid sequence comprising 192 to 500 contiguous amino acid residues (e.g., 198, 200, 300, or 400 contiguous amino acid residues) of SEQ ID NO: 20, 192 to 300 contiguous amino acid residues (e.g., 194, 196, 200, 210, 220, 230, 240, 250, 260, 270, 280, or 290 contiguous amino acid residues) of SEQ ID NO: 20, or 192 to 250 contiguous amino acid residues (e.g., 195, 199, 215, 225, 235, or 245 contiguous amino acid residues) of SEQ ID NO: 20, or a range defined by any two of the foregoing values.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence comprising at least 89 contiguous amino acid residues of SEQ ID NO: 16. The adenovirus or adenoviral vector can comprise an amino acid sequence comprising at least 89 contiguous amino acid residues of SEQ ID NO: 16, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 192 contiguous amino acid residues of SEQ ID NO: 20. The adenovirus or adenoviral vector can comprise (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

In other embodiments, the adenovirus or adenoviral vector comprises one or more nucleic acid sequences that encode one or more of any of the aforementioned amino acid sequences, e.g., the amino acid sequences of any of SEQ ID NOs: 11-20 or any of the variants and/or portions thereof as described herein. For example, the adenovirus or adenoviral vector can comprise a nucleic acid sequence encoding an amino acid sequence that is at least 99.78% identical (e.g., at least 99.87%, at least 99.97%, or 100% identical) to SEQ ID NO: 17, or a nucleic acid sequence encoding an amino acid sequence that is at least 99% identical (e.g., at least 99.68% or 100% identical) to SEQ ID NO: 12.

The adenovirus or adenoviral vector can comprise the nucleic acid sequence of, for example, SEQ ID NO: 21, SEQ ID NO: 22, SEQ ID NO: 23, SEQ ID NO: 24, or SEQ ID NO: 25.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA*, 95: 965-976 (1998); Chen et al., *Proc. Natl. Acad. Sci. USA*, 94: 1645-1650 (1997); and Kochanek et al., *Hum. Gene Ther.*, 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 5 (NCBI reference sequence AP 000218) and ends with the open reading frame that encodes a protein with high homology to the 14.7K protein from the E3 region of human adenovirus 5 (NCBI reference sequence AP 000224.1). The E3 region may be deleted in whole or in part, or retained in whole or in part. The size of the deletion may be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the invention, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.*, 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.*, 71: 9206-9213 (1997)). Other suitable complementing cell lines to produce the replication-deficient adenovirus or adenoviral vector of the invention include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

The invention provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the invention, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the present invention and, of course, should not be construed as in any way limiting its scope.

EXAMPLE 1

This example demonstrates the immunogenicity of an adenoviral vector encoding a Respiratory Syncytial Virus (RSV) F protein in cotton rats.

A gorilla adenovirus having the nucleic acid sequence of SEQ ID NO: 22 was modified by genetic engineering to (1) be rendered replication-deficient by deletion of the E1 region, and (2) express the human Respiratory Syncytial Virus (RSV) Fusion (F) glycoprotein. Because RSV replicates in the cytoplasm of cells, the gene encoding the F protein was modified for expression in a cell nucleus by removing RNA processing signals (e.g., RNA splicing sites), and was codon-optimized for expression in a mammalian cell. The expression of the F protein from the adenoviral vector was verified by infection of HEK-293 cells in vitro, and by a Western blot assay using protein extracts of the infected cells and a commercially available anti-RSV polyclonal antibody (Pab7133P, Maine Biotechnology, Portland, Me.).

Cotton rats (*Sigmodon hispidus*) were injected in the tibialis muscle with a single administration of $10^7$ particle units (pu) of the E1-deleted adenoviral vector expressing the RSV F glycoprotein. The animals were then challenged 28 days later with live human RSV ($10^6$ particle forming units (pfu) administered intranasally). At 5 days post-challenge, the viral load of RSV in the lungs of the animals was measured. The animals that were immunized with the adenoviral vector expressing the F protein did not have detectable RSV in the lungs (limit of detection 70 pfu/gram of lung tissue).

The results of this example demonstrate that the inventive adenoviral vector encoding an RSV F protein is immunogenic in vivo and can confer complete protection against RSV infection in cotton rats.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of delivering a non-native nucleic acid sequence to mammalian cells in vivo, wherein the method comprises in vivo administration of an adenovirus or adenoviral vector comprising a non-native nucleic acid sequence encoding an immunogenic protein and one or more of the nucleic acid sequences selected from the group consisting of:
   (a) a nucleic acid sequence that is at least 98.5% identical to SEQ ID NO: 2,
   (b) a nucleic acid sequence that is at least 80% identical to SEQ ID NO: 4, and
   (c) a nucleic acid sequence that is at least 89% identical to SEQ ID NO: 5.

2. The method of claim 1, wherein the adenovirus or adenoviral vector further comprises the nucleic acid sequence of SEQ ID NO: 1.

3. The method of claim 1, wherein the adenovirus or adenoviral vector comprises a nucleic acid sequence that is at least 98.5% identical to SEQ ID NO: 2.

4. The method of claim 3, wherein the adenovirus or adenoviral vector comprises the nucleic acid sequence of SEQ ID NO: 2.

5. The method of claim 1, wherein the adenovirus or adenoviral vector further comprises a nucleic acid sequence that is at least 90% identical to SEQ ID NO: 3.

6. The method of claim 5, wherein the adenovirus or adenoviral vector comprises the nucleic acid sequence of SEQ ID NO: 3.

7. The method of claim 1, wherein the adenovirus or adenoviral vector comprises a nucleic acid sequence that is at least 80% identical to SEQ ID NO: 4.

8. The method of claim 7, wherein the adenovirus or adenoviral vector comprises the nucleic acid sequence of SEQ ID NO: 4.

9. The method of claim 1, wherein the adenovirus or adenoviral vector comprises a nucleic acid sequence that is at least 89% identical to SEQ ID NO: 5.

10. The method of claim 9, wherein the adenovirus or adenoviral vector comprises the nucleic acid sequence of SEQ ID NO: 5.

11. A method of delivering a non-native nucleic acid sequence to mammalian cells in vivo, wherein the method comprises in vivo administration of an adenovirus or adenoviral vector comprising a non-native nucleic acid sequence encoding an immunogenic protein and one or more of the amino acid sequences selected from the group consisting of:
   (a) an amino acid sequence that is at least 80% identical to SEQ ID NO: 14, and
   (b) an amino acid sequence that is at least 83% identical to SEQ ID NO: 15.

12. The method of claim 11, wherein the adenovirus or adenoviral vector further comprises the amino acid sequence of SEQ ID NO: 11.

13. The method of claim 11, wherein the adenovirus or adenoviral vector further comprises an amino acid sequence that is at least 82% identical to SEQ ID NO: 13.

14. The method of claim 13, wherein the adenovirus or adenoviral vector comprises the amino acid sequence of SEQ ID NO: 13.

15. The method of claim 11, wherein the adenovirus or adenoviral vector comprises an amino acid sequence that is at least 80% identical to SEQ ID NO: 14.

16. The method of claim 15, wherein the adenovirus or adenoviral vector comprises the amino acid sequence of SEQ ID NO: 14.

17. The method of claim 11, wherein the adenovirus or adenoviral vector comprises an amino acid sequence that is at least 83% identical to SEQ ID NO: 15.

18. The method of claim 17, wherein the adenovirus or adenoviral vector comprises the amino acid sequence of SEQ ID NO: 15.

19. A method of delivering a non-native nucleic acid sequence to mammalian cells in vivo, wherein the method comprises in vivo administration of an adenovirus or adenoviral vector comprising a non-native nucleic acid sequence encoding an immunogenic protein and one or more of the nucleic acid sequences selected from the group consisting of:
   (a) a nucleic acid sequence encoding an amino acid sequence that is at least 99.68% identical to SEQ ID NO: 12,
   (b) a nucleic acid sequence encoding an amino acid sequence that is at least 80% identical to SEQ ID NO: 14, and
   (c) a nucleic acid sequence encoding an amino acid sequence that is at least 83% identical to SEQ ID NO: 15.

20. The method of claim 19, wherein the adenovirus or adenoviral vector further comprises a nucleic acid sequence encoding the amino acid sequence of SEQ ID NO: 11.

21. The method of claim 19, wherein the adenovirus or adenoviral vector comprises a nucleic acid sequence encoding an amino acid sequence that is at least 99.68% identical to SEQ ID NO: 12.

22. The method of claim 21, wherein the adenovirus or adenoviral vector comprises a nucleic acid sequence encoding the amino acid sequence of SEQ ID NO: 12.

23. The method of claim 19, wherein the adenovirus or adenoviral vector further comprises a nucleic acid sequence encoding an amino acid sequence that is at least 82% identical to SEQ ID NO: 13.

24. The method of claim 23, wherein the adenovirus or adenoviral vector comprises a nucleic acid sequence encoding the amino acid sequence of SEQ ID NO: 13.

25. The method of claim 19, wherein the adenovirus or adenoviral vector comprises a nucleic acid sequence encoding an amino acid sequence that is at least 80% identical to SEQ ID NO: 14.

26. The method of claim 25, wherein the adenovirus or adenoviral vector comprises a nucleic acid sequence encoding the amino acid sequence of SEQ ID NO: 14.

27. The method of claim 19, wherein the adenovirus or adenoviral vector comprises a nucleic acid sequence encoding an amino acid sequence that is at least 83% identical to SEQ ID NO: 15.

28. The method of claim 27, wherein the adenovirus or adenoviral vector comprises a nucleic acid sequence encoding the amino acid sequence of SEQ ID NO: 15.

* * * * *